US009416180B1

(12) United States Patent
Clube

(10) Patent No.: US 9,416,180 B1
(45) Date of Patent: *Aug. 16, 2016

(54) PRECISION MEDICINE BY TARGETING VEGF-A VARIANTS FOR TREATMENT OF DIABETIC MACULAR EDEMA AND BRANCH RETINAL VEIN OCCLUSION

(71) Applicant: Kymab Limited, Cambridge (GB)

(72) Inventor: Jasper Rupert Clube, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,912

(22) Filed: Apr. 26, 2016

Related U.S. Application Data

(63) Continuation of application No. 14/331,730, filed on Jul. 15, 2014.

(51) Int. Cl.
*A61K 39/395* (2006.01)
*C07K 16/22* (2006.01)
*A61K 9/00* (2006.01)
*C12Q 1/68* (2006.01)

(52) U.S. Cl.
CPC .............. *C07K 16/22* (2013.01); *A61K 9/0019* (2013.01); *C12Q 1/6883* (2013.01); *C07K 2317/21* (2013.01); *C07K 2317/52* (2013.01); *C07K 2317/565* (2013.01); *C07K 2317/76* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,767,996 | B1 | 7/2004 | Gorman et al. |
| 7,704,500 | B2 | 4/2010 | Papadopoulos et al. |
| 9,062,105 | B1 | 6/2015 | Clube |
| 2012/0030144 | A1 | 2/2012 | Ramakrishnan |
| 2012/0064621 | A1 | 3/2012 | Papadopoulos et al. |

FOREIGN PATENT DOCUMENTS

| | | |
|---|---|---|
| WO | 2008/130704 A2 | 10/2008 |
| WO | 2011072263 A1 | 6/2011 |
| WO | 2013/041844 A2 | 3/2013 |
| WO | 2013/172933 A1 | 11/2013 |
| WO | 2014/109999 A1 | 7/2014 |
| WO | 2015/092393 A2 | 6/2015 |

OTHER PUBLICATIONS

Adebi et al., "Variants in the VEGFA gene and treatment outcome after anti-VEGF treatment for neovascular age-related macular degeneration2", Ophthalmology 120(1)115-21 (2013).

Augood et al., "Prevalence of agerelated maculopathy in older Europeans: the European Eye Study (EUREYE)", Arch Ophthalmol. 124:529e35 (2006).
Awata et al., "A common polymorphism in the 5'-untranslated region of the VEGF gene is associated with diabetic retinopathy in type 2 diabetes", Diabetes. 51(5):1635-9 (2002).
Dong et al., "Antagonism of PDGF-BB suppresses subretinal neovascularization and enhances the effects of blockin VEGF-A", Angiogenesis., 17(3):553-62 (2014).
Finger et al., "Predictors of anti-VEGF treatment response in neovascular age-related macular degeneration", Survey of Ophthalmology, 59(1):1-8 (2014).
Fong et al., "Role of the Flt-1 receptor tyrosine kinase in regulating the assembly of vascular endothelium", Nature, 376(6):66-70 (1995).
Franco et al., "Pericytes promote endothelial cell survival through induction of autocrine VEGF-A signaling and Bcl-w expression", Blood, 118(10): 2906-2917 (2011).
Gong et al., "Association of VEGF gene polymorphisms with diabetic retinopathy: a meta-analysis", PLoS One., 8(12):e84069 (2013).
Han et al., "The associations between VEGF gene polymorphisms and diabetic retinopathy susceptibility: a meta-analysis of 11 case-control studies", J Diabetes Res., 2014:805801 (2014).
Hermann et al., "Polymorphisms in vascular endothelial growth factor receptor 2 are associated with better response rates to ranibizumab treatment in age-related macular degeneration", Ophthalmology, 121(4):905-10. (2014).
Ikeda et al., "Characterization of the promoter region for flt-1 tyrosine kinase gene, a receptor for vascular endothelial growth factor", Growth Factors., 13:151-162 (1996).
Ito et al., "Cell biology and metabolism: Identification of vascular endothelial growth factor factor receptor-1 tyrosine phosphorylation sites and binding of SH2 domain-containing molecules", J. Biol. Chem., 273:23410-23418 (1998).
Jo et al. , "Inhibition of platelet-derived growth factor B signaling enhances the efficacy of anti-vascular endothelial growth factor therapy in multiple models of ocular neovascularisation", Am J Pathol., 168(6):2036-53 (2006).
Kondo et al., "Genomic organization of the flt-1 gene encoding for vascular endothelial growth factor (VEGF) receptor-1 suggest an intimate evolutionary relationship between the 7-Ig and the 5-Ig tyrosine kinase receptors", Gene, 208:297-305 (1998).
Kuo et al., "Genetic risk, ethnic variations and pharmacogenetic biomarkers in age-related macular degeneration and polypoidal choroidal vasculopathy", Expert Rev Ophthalmol., 8(2): 127-140 (2013).
Lu et al., "Two polymorphisms (rs699947, rs2010963) in the VEGF-A gene and diabetic retinopathy: an updated meta-analysis", BMC Ophthalmol., 13:56 (2013).
Mabry et al., "A dual-targeting PDGFRbeta/VEGF-A molecule assembled from stable antibody fragments demonstrates anti-angiogenic activity in vitro and in vivo", MAbs., 2(1):20-34 (2010).
Morishita et al., "Nucleic Acids, Protein Synthesis, and Molecular Genetics: A novel promoter for vascular endothelial growth factor receptor (flt-1) that confers endothelial-speicific gene expression", J Biol Chem, 270:27948-27953 (1995).
Neufeld et al., "Vascular endothelial growth factor VEGF) and its receptors", FASEB Journal., 13:11-22 (1999).
Ong et al., "Personalized Medicine in Ophthalmology: From Pharmacogenetic Biomarkers to Therapeutic and Dosage optimization", J. Pers. Med., 3:40-69 (2013).

(Continued)

*Primary Examiner* — Sharon Wen
(74) *Attorney, Agent, or Firm* — Nixon Peabody LLP; Leena H. Karttunen Contarino; Nicole D. Kling

(57) ABSTRACT

The invention relates to human targets of interest (TOI), anti-TOI ligands, kits compositions and method.

6 Claims, 5 Drawing Sheets

(56) References Cited

OTHER PUBLICATIONS

Qui et al., "VEGF 634G>C polymorphism and diabetic retinopathy risk: A meta-analysis", Gene, 518(2):310-315 (2013).
Rosnet et al., "Close physical linkage of the FLT1 and FLT3 genes on chromosome 13 in man and chromosome 5 in mouse", Oncogene, 8: 173-179 (1993).
Schneider et al., "The Role of Vascular Endothelial Growth Factor Genetic Variability in Cancer", Clin Cancer Res, 15(17):5297-5302 (2009).
Skobe et al., "Halting angiogenesis suppress carcinoma cell invasion", Nature Medicine 3:1222-1227 (1997).
Stickler et al., "The human G1m1 allotype associates with CD4+ T-cell responsiveness to a highly conserved IgG1 constant region peptide and confers an asparaginyl endopeptidase cleavage site", Nature, 12: 213-221 (2011).
Tong et al., "LOC387715/HTRA1 gene polymorphisms and susceptibility to age-related macular degeneration: A HuGE review and meta-analysis", Molecular Vision,16:1958-1981 (2010).
Yagi et al., "VEGF 936C>T is predictive of threshold retinopathy of prematurity in Japanese infants with a 30-week gestational age or less", Research and Reports in Neonatology, 1:5-11 (2011).
Zachary et al., "Vascular Endothelial Growth Factor: How it transmits its signal", Experimental Nephrology, 6:480-487 (1998).
WHO Drug Information, "Essential medicines and health products", accessed at: http://www.who.int/medicines/publications/druginformation/en/ on Mar. 9, 2016.
Lambert et al., "The PCSK9 decade", Journal of Lipid Research, 53: 2515-2524 (2012).
Ding et al., "Evidence for Positive Selection in the C-terminal DOmain of the Cholesterol Metabolism Gene PCSK9 Based on Phylogenetic Analysis in 14 Primate Species", PLoS One, 10: e1098 (2007).
Kotowski et al., "A Spectrum of PCSK9 Alleles Contributes to Plasma Levels of Low-Density Lipoprotein Cholesterol", The American Journal of Human Genetics, 78: 410-422 (2006).
Scartenzini et al., "The PCSK9 gene R46L variant is associated with lower plasma lipid levels and cardiovascular rish in healthy U.K. men", Clinical Science, 113: 435-441 (2007).
Raal et al., "Low-Density Lipoprotein Cholesterol-Lowering Effects of AMG 145, a Monoclonal Antibody to Proprotein Convertase Subtilisin/Kexin Type 9 Serine Protease in Patients with Heterozygous Familial Hyperchypercholesterolemia: the Reduction of LDL-C with PCSK9 Inhibition in Heterozygous Familial Hypercholesterolemia Disorder (Rutherford) randomized trial" Circulation, 126: 2408-2417 (2012).
Davignon et al., "The Influence of PCSK9 Polymorphisms on Serum Low-Density Lipoprotein Cholesterol and Risk of Atherosclerosis", Current Atherosclerosis Reports, 12: 308-315 (2010).
Hopkins et al., "Randomized Placebo-phase Clinical Trial With the Monoclonal Antibody Alirocumab Demonstrates Reductions in Low-density Lipoprotein Cholesterol in Patient With Proprotein Convertase Subtilisin/Kexi . . . ", Circulation, 128(22) (2013).
Yan et al., "Pharmacogenetics and pharmacogenomics in oncology therapeutic antibody development", Pharmacogenomics, 39: 565-568 (2005).
Galicia et al., "Polymorphisms in the IL-6 receptor (IL-6R) gene: strong evidence that serum levels of soluble IL-6R are genetically influenced", Genes and Immunity, 5: 513-516 (2004).
Wang et al., "Molecular Screening and Association of Analyses of the Interleukin 6 Receptor Gene Variants with Type 2 Diabetes, Diabetic Neuropathy, and Insulin Sensitivity", The Journal of Clinical Endocrinology & Metabolism, 90(2): (2005).
Wu et al., "A population genetics study of single nucleotide polymorphisms in the interleukin 4 receptor (IL4RA) gene", Genes and Immunity, 2(3): 128-134 (2001).
Li et al., "Possible association between polymorphisms of human vascular endothelial growth factor A gene and susceptibility to glioma in a Chinese population", Int J Cancer, 128(1): 166-175 (2011).

Variants:   f, c, m, e, h, p, q         f, c, m, e, h         f, c, m, e, h

Variants:       f, c, p, aj            f, c, p

Non-Synonymous FW1 residue change to Valine due to rs56069819 SNP is underlined)

E V Q L V E S G G G L V Q P G G S L R
L S C A A S G F T F S S Y A M S W V R
Q A P G K G L E W V S A I S G S G G S
T Y Y A D S V K G R F T I S R D N S K
N T L Y L Q M N S L R A E D T A V Y Y
C A K

VH3-23*04

(rs56069819 SNP is underlined)

gag gtg cag ctg gtg gag tct ggg gga ggc ttg gta cag cct ggg
ggg tcc ctg aga ctc tcc tgt gca gcc tct gga ttc acc ttt agc agc tat
gcc atg agc tgg gtc cgc cag gct cca ggg aag ggg ctg gag tgg
gtc tca gct att agt ggt agt ggt ggt agc aca tac tac gca gac tcc
gtg aag ggc cgg ttc acc atc tcc aga gac aat tcc aag aac acg ctg
tat ctg caa atg aac agc ctg aga gcc gag gac acg gcc gta tat tac
tgt gcg aaa ga FW1 Encoded by VH3-23*04

PRECISION MEDICINE BY TARGETING VEGF-A VARIANTS FOR TREATMENT OF DIABETIC MACULAR EDEMA AND BRANCH RETINAL VEIN OCCLUSION

CROSS-REFERENCE TO RELATED APPLICATIONS

This application is a continuation of co-pending U.S. application Ser. No. 14/331,730 filed Jul. 15, 2014, the entire content of which is incorporated by reference.

SEQUENCE LISTING

The instant application contains a Sequence Listing which has been submitted electronically in ASCII format and is hereby incorporated by reference in its entirety. Said ASCII copy, created on Jul. 14, 2014, is named 069496-080095_SL.txt and is 222,931 bytes in size.

TECHNICAL FIELD

The technology described herein relates to ligands, e.g., antibodies for the treatment of disease.

BACKGROUND

It is recognized that individual humans differ in their sequence and recently several individuals have had their genomes sequenced, for instance James Watson and Craig Venter. Comparison of the genome sequence of individuals has revealed differences in their sequences in both coding and non-coding parts of the genome. Some of these variations in humans are significant and contribute to phenotypic differences between individuals. In extreme cases these will result in genetic disease. The 1000 Genomes Project has the objective of cataloguing sequences in the human genome, involving sequencing the genomes of a very large sampling of individuals from diverse art-recognized human ethnic populations.

SUMMARY

Through the application of human genetic variation analysis and rationally-designed sequence selection the present invention provides for improved human patient diagnosis and therapy. Importantly, the invention enables tailored medicines that address individual human patient genotypes or phenotypes.

The inventor's analysis of large numbers of naturally-occurring genomic human TOI sequences reveals that there is significant variation across diverse human populations and provides for the ability for correlation between individual human patients and tailored medical and diagnostic approaches addressing the target. The technical applications of these findings, as per the present invention, thus contribute to better treatment, prophylaxis and diagnosis in humans and provides for patient benefit by enabling personalized medicines and therapies. This provides advantages of better prescribing, less wastage of medications and improved chances of drug efficacy and better diagnosis in patients.

Furthermore, the inventor surprisingly realised that some rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention and better serving patients in those populations.

With this, the inventor realised that there is significant industrial and medical application for the invention in terms of guiding the choice of an anti-TOI ligand for administration to human patients for therapy and/or prophylaxis of TOI-mediated or associated diseases and conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical mis-prescription and waste.

To this end, the invention provides:—

In a First Configuration

A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%;
wherein
b. Before step (a) said human has been or is genotyped as positive for said nucleotide sequence or phenotyped as positive for said TOI variant.

In a Second Configuration

A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%; wherein
b. before step (a) the ligand has been or is determined as capable of binding to said TOI variant.

In a Third Configuration

A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent said disease or condition, wherein the TOI in said human is a variant encoded by a nucleotide sequence having a cumulative human allele frequency of more than 50% and/or having a total human genotype frequency of more than 50%; wherein
b. Before step (a) said human has been or is genotyped as negative for a variant nucleotide sequence having a cumulative human allele frequency of less than 50% and/or having a total human genotype frequency of less than 50%; or phenotyped as negative for a TOI variant encoded by a nucleotide sequence having a cumulative human allele frequency of less than 50% and/or having a total human genotype frequency of less than 50%.

In a Fourth Configuration

An anti-human TOI ligand for use in a method of treating and/or preventing a TOI-mediated disease or condition in a human, wherein the TOI is present in humans as different polymorphic variants and wherein the genome of said human comprises a TOI nucleotide sequence having a cumulative human allele frequency of less than 50% and/or a total human genotype frequency of less than 50%, the method comprising administering the ligand to the human.

In a Fifth Configuration

A ligand that binds a human TOI comprising an amino acid sequence encoded by a TOI nucleotide sequence having a cumulative human allele frequency of less than 50% and/or a total human genotype frequency of less than 50%, for use in a method comprising the step of using the ligand to target said TOI in a human to treat and/or prevent a disease or condition mediated by TOI, the method comprising administering the ligand to the human.

In a Sixth Configuration

A pharmaceutical composition or kit for treating or preventing a condition or disease mediated by a TOI.

In a Seventh Configuration

A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody binding site that binds in the screening step.

In a Eighth Configuration

A method of producing an anti-human TOI antibody, the method comprising immunising a non-human vertebrate (eg, a mouse or a rat) with a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody that binds a TOI comprising an amino acid sequence encoded by a TOI nucleotide sequence having a cumulative human allele frequency of less than 50% and/or a total human genotype frequency of less than 50%, and optionally producing a TOI-binding fragment or derivative of the isolated antibody.

In a Ninth Configuration

A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof; and/or the nucleic acid comprises a nucleotide sequence that comprises at least 10 contiguous nucleotides of a TOI nucleotide sequence having a cumulative human allele frequency of less than 50% and/or a total human genotype frequency of less than 50% or is an antisense sequence thereof.

In a Tenth Configuration

Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.

In a Eleventh Configuration

Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.

In a Twelfth Configuration

A method of targeting a TOI for treating and/or preventing a TOI-mediated disease or condition in a human, the method comprising administering an anti-TOI ligand to a human comprising a TOI nucleotide sequence selected having a cumulative human allele frequency of less than 50% and/or a total human genotype frequency of less than 50%, whereby a TOI encoded by said nucleotide sequence is targeted.

In a Thirteenth Configuration

A method of TOI genotyping a nucleic acid sample of a human, the method comprising identifying in the sample the presence of a TOI nucleotide sequence having a cumulative human allele frequency of less than 50% and/or having a total human genotype frequency of less than 50%.

In a Fourteenth Configuration

A method of TOI typing a protein sample of a human, the method comprising identifying in the sample the presence of a TOI amino acid sequence encoded by a TOI nucleotide sequence having a cumulative human allele frequency of less than 50% and/or having a total human genotype frequency of less than 50%.

In an example, the TOI is a human TOI selected from the group consisting of PCSK9, VEGF-A and IL6 receptor.

A Fifteenth Configuration provides a ligand, method, use, kit or composition of the invention, wherein
(i) the ligand (eg, antibody or fragment) comprises
  (a) a variable domain that is encoded by a human V region nucleotide sequence, wherein the V nucleotide sequence is derived from recombination of human VH, D and JH gene segments or human VL and JL gene segments; or
  (b) a constant region domain encoded by a C region gene segment;
Wherein a first gene segment of said gene segments of (a), or said C region gene segment of (b) comprises a first single nucleotide polymorphism (SNP) encoding a first amino acid polymorphism; and
  (ii) the genome of said human comprises said first SNP or wherein said human expresses (a') an antibody variable domain comprising said first amino acid polymorphism or (b') an antibody constant domain comprising said first amino acid polymorphism.

A Sixteenth Configuration provides the ligand, method, use, kit or composition of the invention, wherein the ligand comprises or consists of an antibody or fragment that comprises a human antibody variable domain derived from the recombination of a human V gene segment and a human J gene segment (and optionally a human D gene segment when the variable domains are VH domains); and wherein the genome of the human comprises said human V gene segment and/or the human expresses antibodies comprising antibody variable domains derived from the recombination of said human V gene segment and a human J gene segment (and optionally a human D gene segment).

A Sixteenth Configuration provides the ligand, method, use, kit or composition of the invention, wherein the ligand (eg, comprising or consisting of an antibody or fragment or an Fc-fused human PCSK9 receptor) comprises a human heavy chain constant domain encoded by a first constant region nucleotide sequence; and wherein the genome of the human comprises a heavy chain constant region nucleotide sequence that is identical to said first constant region nucleotide sequence and/or the human expresses antibodies comprising said human constant domain.

A Seventeenth Configuration provides the ligand, method, use, kit or composition of the invention, wherein the ligand (eg, comprising or consisting of an antibody or fragment or an Fc-fused TOI receptor) comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu.

A Eighteenth Configuration provides the ligand, method, use, kit or composition of the invention, wherein the ligand (eg, comprising or consisting of an antibody or fragment or an Fc-fused TOI receptor) comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid.

A Ninteenth Configuration provides the ligand, method, use, kit or composition of the invention, wherein the ligand (eg, comprising or consisting of an antibody or fragment or an Fc-fused TOI receptor) comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys.

A Twentieth Configuration provides the ligand, method, use, kit or composition of the invention, wherein the ligand comprises or consists of an antibody or fragment, wherein the antibody or fragment comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV146*01.

A Twenty-First Configuration provides the ligand, method, use, kit or composition of the invention, wherein the ligand comprises or consists of an antibody or fragment, wherein the antibody or fragment comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3 depicts frameworks and CDRs encoded by VH3-23*04 as obtained from the IMGT database (available on the World Wide Web at www.IMGT.org). FIG. 3 discloses the nucleotide sequences as SEQ ID NOS 68, 68, 68, 70, 70, 70, 71, 73, 75, 39 and 76, respectively, in order of appearance. FIG. 3 discloses the coded amino acid sequences as SEQ ID NOS 69, 69, 69, 69, 69, 69, 72, 74, 74, 38 and 77, respectively, in order of appearance.

FIG. 4 depicts sequences of VH3-23*04. The portion of VH3-23*04 comprising the FW1 residue change of rs56069819 (SEQ ID NO: 38). The portion of the nucleic acid sequence encoding rs56069819 is depicted (SEQ ID NO: 39). The FW1 encoded by VH3-23*04 is depicted (SEQ ID NO: 40).

DETAILED DESCRIPTION

Figure 1:
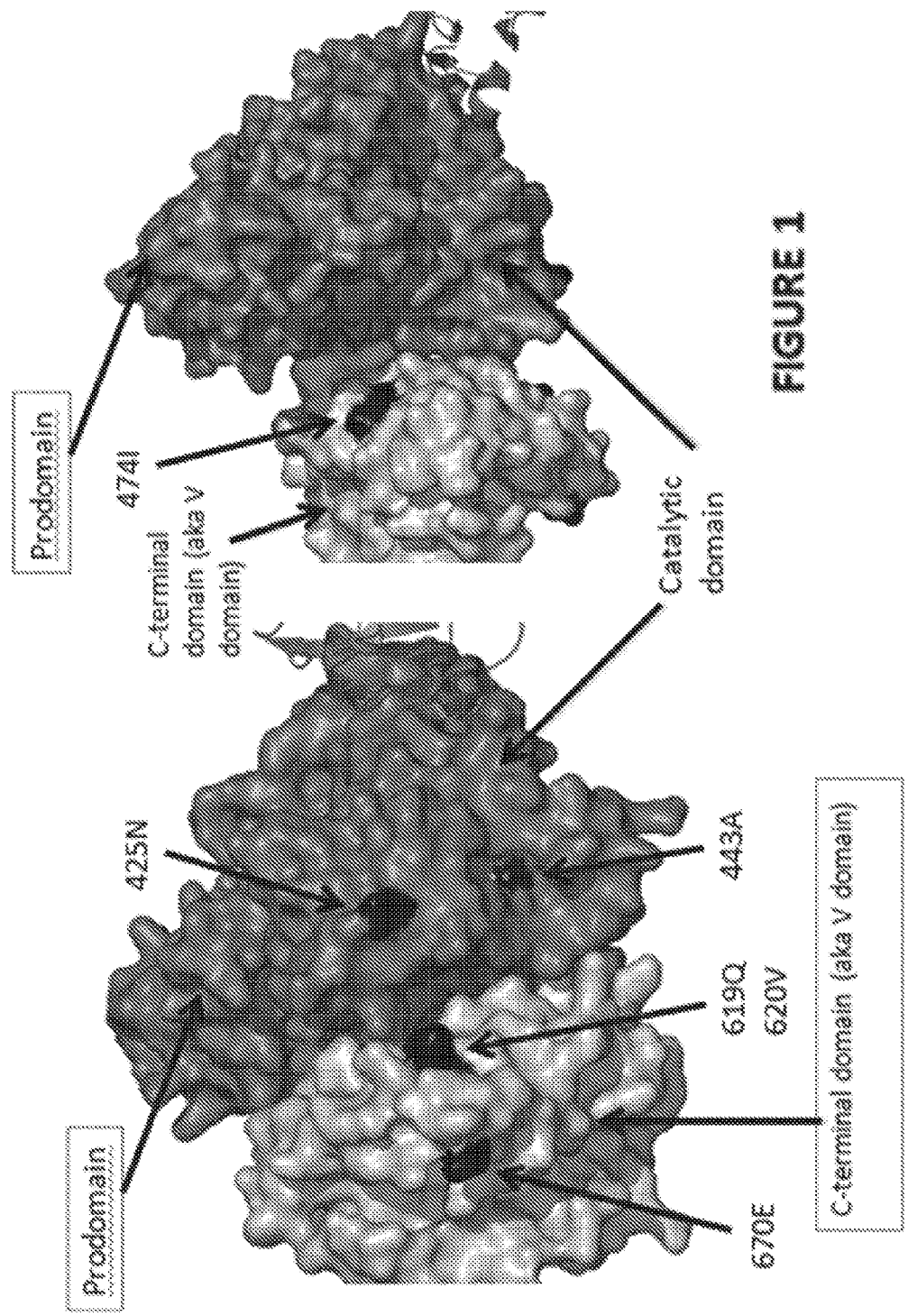
FIG. 1 shows in silico modeling of PCSK9 surface variant residues.

The skilled person will know that SNPs or other changes that translate into amino acid variation can cause variability in conformation or activity of human targets to be addressed. This has spawned great interest in personalized medicine where genotyping and knowledge of protein and nucleotide variability is used to tailor medicines and diagnosis of patients more effectively. The present invention provides for tailored pharmaceuticals and testing that specifically addresses rarer variant forms of a human target of interest (TOI).

The present invention harnesses the power of human genetic variation analysis and rationally-designed sequence selection. The technical applications of these approaches, as per the present invention, contribute to better treatment, prophylaxis and diagnosis in humans and provides for patient benefit by providing choice and enabling personalized medicines and therapies. This provides advantages of better prescribing, less wastage of medications and improved chances of drug efficacy and better diagnosis in patients.

As sources of genomic sequence variation data, the skilled person will be aware of the available databases and resources (including updates thereof) provided by the following:—
1. HapMap (The International HapMap Consortium. 2003; available on the World Wide Web at hapmap.ncbi.nlm.nih.gov/index.html.en). The HapMap Project is an international project that aims to compare the genetic sequences of different individuals to identify chromosomal regions containing shared genetic variants. The HapMap www site provides tools to identify chromosomal regions and the variant therein, with options to drill down to population level frequency data.
2. 1000 Genomes Project (The 1000 Genomes Project Consortium 2010; available on the World Wide Web at 1000genomes.org/). This resource provides complete genomic sequence for at least 2500 unidentified individuals from one of 25 distinct population groups.
3. Japanese SNP Database (H. Haga et al. 2002; available on the World Wide Web at snp.ims.u-tokyo.ac.jp/index.html). Based on a study identifying 190,562 human genetic variants.

The present invention involves the identification and cataloguing of naturally-occurring human genomic target sequence variants, including those found to be relatively low-frequency or rare variants that segregate with specific human ethnic populations and in many individual humans.

An aspect of the invention is based on rational design of sequence selection addressing the desirability to tailor medicaments and diagnostics to rarer, but yet still significant groups of human individuals that suffer from, or have the potential to suffer from (ie, who are at risk of), a disease or condition mediated or associated with the target of interest. In devising this rational design of the present aspect of the invention, the inventor included considerations of the spread of prevalence of naturally-occurring target variant sequences across multiple, diverse human ethnic populations, as well as the importance of addressing such populations where many individuals are likely to display a genotype and/or phenotype of one or more of the variants being analysed. As part of this design, the inventor saw the importance of adopting the art-recognised classifications of human ethnic populations, and in this respect the inventor based the analysis and design on the recognised human ethnic populations adopted by the 1000 Genomes Project, since this is a resource that is, and will continue to be, widely adopted by the scientific and medical community.

Thus, in this aspect of the invention, the inventor designed the following variant sequence selection criteria, these being criteria that the inventor realised would provide for useful medical drugs and diagnostics to tailored need in the human population.

Selection Criteria
Three or four of the following:—
Naturally-occurring human target variant sequences having a cumulative human allele frequency of 35% or less;
Naturally-occurring human target variant sequences having a total human genotype frequency of 40% or less;
Naturally-occurring human target variant sequences found in many different human ethnic populations (using the standard categorisation of the 1000 Genomes Project; see Table 4 below); and
Naturally-occurring human target variant sequences found in many individuals distributed across such many different ethnic populations.

The inventor's selection included, as a consideration, selection for nucleotide variation that produced amino acid variation in corresponding TOI forms (ie, non-synonymous variations), as opposed to silent variations that do not alter amino acid residues in the target protein.

In an embodiment, the cumulative human allele frequency is 30, 25, 20, 15, 10 or 5% or less, eg, in the range from 1 to 20% or 1 to 15% or 1 to 10%.

In an embodiment, the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

In an embodiment, the naturally-occurring human target variant sequences are found in at least 9, 10, 11, 12, 13, 14, 15, 16, 17, 18, 19 or 20 different human ethnic populations (using the standard categorisation of the 1000 Genomes Project).

In an embodiment, the naturally-occurring human target variant sequences are found in at least 20, 25, 30, 35, 40, 45, 50, 55, 60, 65, 70, 75, 80, 85, 90, 95, 100, 105, 110, 115, 120, 130, 140 or 150 individuals distributed across such many different ethnic populations.

In an example, the following criteria are applied:—
Naturally-occurring human target variant sequences having a cumulative human allele frequency of 15% or less;
Naturally-occurring human target variant sequences having a total human genotype frequency of 20% or less;
Naturally-occurring human target variant sequences found in at least 5 different human ethnic populations (using the standard categorisation of the 1000 Genomes Project); and
Naturally-occurring human target variant sequences found in many individuals distributed across such many different ethnic populations.

In an example, the criteria are applied with reference to one or more human genomic sequence databases as described herein. For example, the criteria are those as applied to the 1000 Genomes database.

For example in any aspect example, embodiment or configuration of the invention, the 1000 Genomes database release 13. For example, the 1000 Genomes database in its most recent version as at 1 Oct. 2013.

Optionally, further sequence analysis and 3D in silico modelling (eg, see FIG. 1) can also be used as an additional selection criterion: variants whose variant amino acid residues (versus the most common form of human TOI) are surface-exposed on the target are desirable for selection, since the inventor saw these as contributing to determining the topography of the target and potentially contributing to how and where ligand binding on the target occurs.

The following bioinformatics protocol is envisaged to indentify human sequences for use in the present invention:
(a) Identify a genomic region containing a target sequence of interest (target genomic region') and calculate the genomic coordinates, using coordinates that match the sequence assembly build used by either the 1000

Genomes Project or International HapMap project (or another selected human gene database of choice).

(b) Identify genomic variants mapped to the genomic region previously identified in (a). Retrieve allele frequencies for variants for each super population and preferably sub-population where such data is available. The VWC tools for the 1000 Genomes Project can be used for this step.

(c) Filter list of genomic variants from target genomic region to contain only variants classed as either 'non-synonymous' single nucleotide polymorphisms (SNPs) or genomic 'insertions or deletions' (indels). Filter further to include those that are present in exonic sequences only. "Non-synonymous" refers to nucleotide variation that produces amino acid variation (ie, excluding silent mutations).

(d) Correlate population frequency data for each of the identified variants for each of the super populations (for example 'European Ancestry', 'East Asian ancestry', 'West African ancestry', 'Americas', and 'South Asian ancestry') to identify those variants that segregate with less than two super-populations. Further correlate all identified variants with each of the sub-populations (for example, 'European ancestry' super-population might be subdivided into groups such as 'CEU—Utah residents with Northern or Western European ancestry', 'TSI Toscani in Italia' and 'British from England and Scotland') and produce a second score for rarity of variants within a super-population.

(e) Collect one or more sequences that show segregation to specific sub-populations for use in the present invention, eg, according to selection criteria as described herein.

Human Populations

Optionally the ethnic populations are selected from those identified in the 1000 Genomes Project database. In this respect, see Table 4 which provides details of the ethnic populations on which the 1000 Genomes Project database is based.

N A Rosenberg et al (Science 20 Dec. 2002: vol. 298 no. 5602 2342-2343) studied the genetic structure of human populations of differing geographical ancestry. In total, 52 populations were sampled, these being populations with:

African Ancestry (Mbuti Pygmies, Biaka Pygmies, San peoples, and speakers of Niger-Kordofanian languages (Bantu, Yoruba or Mandenka populations), Eurasian Ancestry (European ancestry (Orcadian, Adygel, Basque, French, Russians, Italians, Sardinian, Tuscan), Middle Eastern ancestry (Mozabite, Bedouin, Druze, Palestinians), Central/South Asian ancestry (Balochl, Brahul, Makrani, Sindhi, Pathan, Burusho, Hazara, Uygur, Kalash)), East Asian Ancestry (Han, Dal, Daur, Hezhen, Lahu, Miao, Orogen, She, Tujia, Tu, Xibo, Yi, Mongola, Naxi, Cambodian, Japanese, Yakut), Oceanic ancestry (Melanesian, Papuan); or Americas Ancestry (Karitiana, Surui, Colombian, Maya, Pima).

The International HapMap Project, Nature, 2003 Dec. 18; 426(6968):789-96, discloses that goal of the HapMap Project: to determine the common patterns of DNA sequence variation in the human genome by determining the genotypes of one million or more sequence variants, their frequencies and the degree of association between them in DNA samples from populations with ancestry from parts of Africa, Asia and Europe. The relevant human populations of differing geographical ancestry include Yoruba, Japanese, Chinese, Northern European and Western European populations. More specifically:—

Utah population with Northern or Western European ancestry (samples collected in 1980 by the Centre d'Etude du Polymorphisme Humain (CEPH));

population with ancestry of Yoruba people from Ibadan, Nigeria;

population with Japanese ancestry; and population with ancestry of Han Chinese from China.

The authors, citing earlier publications, suggest that ancestral geography is a reasonable basis for sampling human populations.

A suitable sample of human populations used in the present invention is as follows:—

(a) European ancestry (b) Northern European ancestry; Western European ancestry; Toscani ancestry; British ancestry, Finnish ancestry or Iberian ancestry.

(c) More specifically, population of Utah residents with Northern and/or Western European ancestry; Toscani population in Italia; British population in England and/or Scotland; Finnish population in Finland; or Iberian population in Spain.

(a) East Asian ancestry (b) Japanese ancestry; Chinese ancestry or Vietnamese ancestry.

(c) More specifically, Japanese population in Toyko, Japan; Han Chinese population in Beijing, China; Chinese Dai population in Xishuangbanna; Kinh population in Ho Chi Minh City, Vietnam; or Chinese population in Denver, Colo., USA.

(a) West African ancestry (b) Yoruba ancestry; Luhya ancestry; Gambian ancestry; or Malawian ancestry.

(c) More specifically, Yoruba population in Ibadan, Nigeria; Luhya population in Webuye, Kenya; Gambian population in Western Division, The Gambia; or Malawian population in Blantyre, Malawi.

(a) Population of The Americas (b) Native American ancestry; Afro-Caribbean ancestry; Mexican ancestry; Puerto Rican ancestry; Columbian ancestry; or Peruvian ancestry.

(c) More specifically, population of African Ancestry in Southwest US; population of African American in Jackson, Miss.; population of African Caribbean in Barbados; population of Mexican Ancestry in Los Angeles, Calif.; population of Puerto Rican in Puerto Rico; population of Colombian in Medellin, Colombia; or population of Peruvian in Lima, Peru.

(a) South Asian ancestry (b) Ahom ancestry; Kayadtha ancestry; Reddy ancestry; Maratha; or Punjabi ancestry.

(c) More specifically, Ahom population in the State of Assam, India; Kayadtha population in Calcutta, India; Reddy population in Hyderabad, India; Maratha population in Bombay, India; or Punjabi population in Lahore, Pakistan.

In any configuration of the invention, in one embodiment, each human population is selected from a population marked "(a)" above.

In any configuration of the invention, in another embodiment, each human population is selected from a population marked "(b)" above.

In any configuration of the invention, in another embodiment, each human population is selected from a population marked "(c)" above.

In one embodiment the ethnic populations are selected from the group consisting of an ethnic population with European ancestry, an ethnic population with East Asian, an ethnic population with West African ancestry, an ethnic population with Americas ancestry and an ethnic population with South Asian ancestry.

In one embodiment the ethnic populations are selected from the group consisting of an ethnic population with Northern European ancestry; or an ethnic population with Western European ancestry; or an ethnic population with Toscani ancestry; or an ethnic population with British ancestry; or an ethnic population with Icelandic ancestry; or an ethnic population with Finnish ancestry; or an ethnic population with Iberian ancestry; or an ethnic population with Japanese ancestry; or an ethnic population with Chinese ancestry; or an ethnic population Vietnamese ancestry; or an ethnic population with Yoruba ancestry; or an ethnic population with Luhya ancestry; or an ethnic population with Gambian ancestry; or an ethnic population with Malawian ancestry; or an ethnic population with Native American ancestry; or an ethnic population with Afro-Caribbean ancestry; or an ethnic population with Mexican ancestry; or an ethnic population with Puerto Rican ancestry; or an ethnic population with Columbian ancestry; or an ethnic population with Peruvian ancestry; or an ethnic population with Ahom ancestry; or an ethnic population with Kayadtha ancestry; or an ethnic population with Reddy ancestry; or an ethnic population with Maratha; or an ethnic population with Punjabi ancestry.

Anti-Target Ligands

The invention provides useful anti-target ligands for addressing humans suffering from or likely to suffer from a disease or condition mediated or associated with the TOI. For example, the ligand specifically binds to the TOI variant as per the invention. The ligand may inhibit or antagonise the activity of the target, eg, the ligand neutralises the target. The skilled person will be familiar with neutralising ligands in general, such as antibodies or antibody fragments, and can readily test suitable ligands for specific binding and/or neutralisation of a target in vitro or in an in vivo assay.

An antibody "fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

In an embodiment, the ligand of the invention is or comprises an antibody or antibody fragment, for example an antibody or fragment comprising human variable regions (and optionally also human constant regions). Anti-TOI or TOI-binding or targeting antibodies and fragments can be prepared according to any known method, eg, using transgenic mice (eg, the Kymouse™ or Velocimouse™, or Omnimouse™, Xenomouse™, HuMab Mouse™ or MeMo Mouse™), rats (eg, the Omnirat™), camelids, sharks, rabbits, chickens or other non-human animals immunised with the TOI followed optionally by humanisation of the constant regions and/or variable regions to produce human or humanised antibodies. In an example, display technologies can be used, such as yeast, phage or ribosome display, as will be apparent to the skilled person. Standard affinity maturation, eg, using a display technology, can be performed in a further step after isolation of an antibody lead from a transgenic animal, phage display library or other library. Representative examples of suitable technologies are described in US20120093818 (Amgen, Inc), which is incorporated herein by reference, eg, the methods set out in paragraphs [0309] to [0346]. Although this is with reference to PCSK9, the antibody-generating methods can be applied to other TOIs as per the broadest scopes of the present invention.

Generally, a VELOCIMMUNE™ or other mouse or rat can be challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimaeric antibodies or the variable domains of the light and heavy chains may be isolated directly from antigen-specific lymphocytes.

Initially, high affinity chimaeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4 (for example, SEQ ID NO: 751, 752, 753 in US2011/0065902, which sequences are incorporated herein by reference for use in the ligands of the present invention). While the constant region selected may vary according to specific use, high affinity antigen-binding and target specificity characteristics reside in the variable region.

In an example, the ligand of the invention is or comprises a nucleic acid, eg, RNA, eg, siRNA that hybridises under stringent condition to the TOI variant sequence, eg, hybridises a nucleotide sequence comprising one or more nucleotides that are variant (versus the most common TOI sequence, eg, with reference to the 1000 Genomes Project database).

Target binding ability, specificity and affinity (Kd, $K_{off}$ and/or $K_{on}$) can be determined by any routine method in the art, eg, by surface plasmon resonance (SPR). The term "Kd", as used herein, is intended to refer to the equilibrium dissociation constant of a particular antibody-antigen interaction.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the ligand (eg, antibody) is determined using SPR by
1. Coupling anti-mouse (or other relevant human, rat or non-human vertebrate antibody constant region species-matched) IgG (eg, Biacore™ BR-1008-38) to a biosensor chip (eg, GLM chip) such as by primary amine coupling;

2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

In an example, the ligand of the invention is contained in a medical container, eg, a vial, syringe, IV container or an injection device (eg, an intraocular or intravitreal injection device). In an example, the ligand is in vitro, eg, in a sterile container. In an example, the invention provides a kit comprising the ligand of the invention, packaging and instructions for use in treating or preventing or diagnosing in a human a disease or condition mediated by the TOI. In an example, the instructions indicate that the human should be genotyped for a TOI variant sequence of the invention before administering the ligand to the human. In an example, the instructions indicate that the human should be phenotyped for a TOI variant of the invention before administering the ligand to the human. In an example, the human is of Chinese (eg, Han) ethnicity and the instructions are in Chinese (eg, Mandarin). In an example, the instructions comprise directions to administer alirocumab or evolocumab to said human.

The invention relates to the concepts set out in the following clauses.

Clause 1 A method of treating or preventing a disease or condition in a human, wherein the disease or condition is mediated by a Target of Interest (TOI), wherein the TOI is present in humans as different polymorphic variants, the method comprising
   a. Administering to the human an anti-TOI ligand to target a TOI variant in the human and treat or prevent (eg, by at least 40, 50, 60, 70, 80, 90 or 95%) said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%; wherein
     Before step (a) said human has been or is genotyped as positive for said nucleotide sequence or phenotyped as positive for said TOI variant, or the method comprises before step (a) genotyping the human as positive for said nucleotide sequence or phenotyping the human as positive for said TOI variant.

In any aspect, configuration, example, embodiment, clause or concept herein, frequencies may be determined using bioinformatics.

In any aspect, configuration, example, embodiment, clause or concept herein, frequencies may be determined by reference to a database comprising at least 1000 or 2000 human sequences.

In any aspect, configuration, example, embodiment, clause or concept herein "heterozygous human genotype frequency" means the cumulative frequency of all genotypes in the sample or database or in humans having one occurrence of the rare variant allele and one occurrence of another allele (heterozygous state), eg, genotype in 1000 Genomes database.

In any aspect, configuration, example, embodiment, clause or concept herein "homozygous human genotype frequency" means the cumulative frequency of two occurrences of the variant allele (homozygous state), eg, genotype in 1000 Genomes Project database.

In any aspect, configuration, example, embodiment, clause or concept herein "total human genotype frequency" means the total of heterozygous plus homozygous human genotype frequencies.

In any aspect, configuration, example, embodiment, clause or concept herein "cumulative human allele frequency" refers to the total of all occurrences of the variant allele in the sample or database or in humans, eg, in the 1000 Genomes Project database.

Clause 2: The method of clause 1, wherein before step (a) the ligand has been or is determined as being capable of binding to said TOI variant, eg, with an affinity (Kd) disclosed below.

In an example, the ligand is (or has been determined as) a neutraliser of the TOI. In an example, determination is carried out in a human (eg, in a clinical trial). In an example, determination is carried out in a non-human, eg, in a mouse, rat, rabbit, pig, dog, sheep or non-human primate (eg, Cynomolgous monkey, rhesus monkey or baboon).

Clause 3: A method of treating or preventing a disease or condition in a human, wherein the disease or condition is mediated by a Target of Interest (TOI), wherein the TOI is present in humans as different polymorphic variants, the method comprising
   a. Administering to the human an anti-TOI ligand to target a TOI variant in the human and treat or prevent (eg, by at least 40, 50, 60, 70, 80, 90 or 95%) said disease or condition, wherein the TOI in said human is encoded by a nucleotide sequence having a cumulative human allele frequency of less than 50% and/or wherein the TOI in said human is encoded by a nucleotide sequence having a total human genotype frequency of less than 50%; wherein
   b. Before step (a) the ligand has been or is determined as capable of binding to said TOI variant, eg, with an affinity (Kd) disclosed below.

In an example, the ligand is (or has been determined as) a neutraliser of the TOI. In an example, determination is carried out in a human (eg, in a clinical trial). In an example, determination is carried out in a non-human, eg, in a mouse, rat, rabbit, pig, dog, sheep or non-human primate (eg, Cynomolgous monkey, rhesus monkey or baboon).

Clause 4: The method of clause 3, wherein the genome of said human comprises a nucleotide sequence encoding said TOI variant; and before step (a) said nucleotide sequence has been or is determined as having a cumulative human allele frequency of less than 50% and/or having a total human genotype frequency of less than 50%.

The TOI variant is not the most frequent.

Clause 5: The method of clause 3 or 4, wherein said human has been or is genotyped as positive for said variant nucleotide sequence before step (a), or the method comprises genotyping the human as positive for said variant nucleotide sequence before step (a).

Clause 6: The method of any preceding clause, wherein the human has been or is phenotyped as positive for said TOI variant before step (a), or the method comprises phenotyping the human as positive for said variant nucleotide sequence before step (a).

Clause 7: The method of any preceding clause, wherein said frequency is less than 10 or 15% (eg, from 1 to 10%).

In an embodiment, the cumulative human allele frequency is 30, 25, 20, 15, 10 or 5% or less, eg, in the range from 1 to 20% or 1 to 15% or 1 to 10%.

In an embodiment, the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 8: The method of any preceding clause, wherein the ligand is capable of binding to two or more different TOI variants, each being encoded by a nucleotide sequence having a cumulative human allele frequency of less than 50% (eg, from 1 to 10%) and/or having a total human genotype frequency of less than 50% (eg, from 1 to 20%).

In an embodiment, the cumulative human allele frequency of each TOI variant is 30, 25, 20, 15, 10 or 5% or less, eg, in the range from 1 to 20% or 1 to 15% or 1 to 10%.

In an embodiment, the total human genotype frequency of each TOI variant is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 9: A method of treating or preventing a disease or condition in a human, wherein the disease or condition is mediated by a Target of Interest (TOI), wherein the TOI is present in humans as different polymorphic variants, the method comprising a. Administering to the human an anti-TOI ligand to target a TOI variant in the human and treat or prevent (eg, by at least 40, 50, 60, 70, 80, 90 or 95%) said disease or condition, wherein the TOI in said human is a variant encoded by a nucleotide sequence having a cumulative human allele frequency of more than 50% (eg, the highest frequency) and/or having a total human genotype frequency of more than 50% (eg, the highest frequency); wherein b. Before step (a) said human has been or is genotyped as negative for a variant nucleotide sequence having a cumulative human allele frequency of less than 50% and/or having a total human genotype frequency of less than 50%; or phenotyped as negative for a TOI variant encoded by a nucleotide sequence having a cumulative human allele frequency of less than 50% and/or having a total human genotype frequency of less than 50%; or Before step (a) said the method comprises genotyping the human as negative for a variant nucleotide sequence having a cumulative human allele frequency of less than 50% and/or having a total human genotype frequency of less than 50%; or phenotyping the human as negative for a TOI variant encoded by a nucleotide sequence having a cumulative human allele frequency of less than 50% and/or having a total human genotype frequency of less than 50%.

In an embodiment, in (a) the cumulative human allele frequency is 55, 60, 65, 70, 75, 80, 85 or 90 or more but less than 95, 96, 97, 98, 99 or 100% (eg, in the range from 51 to 80%).

In an embodiment, in (a) the total human genotype frequency is 55, 60, 65, 70, 75, 80, 85 or 90 or more but less than 95, 96, 97, 98, 99 or 100% (eg, in the range from 51 to 80%).

In an embodiment, in (b) the cumulative human allele frequency is 30, 25, 20, 15, 10 or 5% or less, eg, in the range from 1 to 20% or 1 to 15% or 1 to 10%.

In an embodiment, in (b) the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 10: The method of clause 9, wherein before step (a), the human has been or is phenotyped as positive for the most frequent TOI variant or genotyped for the nucleotide sequence thereof.

In an embodiment, before step (a) the human has been or is genotyped as positive for TOI variant nucleotide sequence having a cumulative human allele frequency of 55, 60, 65, 70, 75, 80, 85 or 90 or more but less than 95, 96, 97, 98, 99 or 100% (eg, in the range from 51 to 80%) or phenotyped for the TOI variant thereof.

In an embodiment, before step (a) the human has been or is genotyped as positive for TOI variant nucleotide sequence having a total human genotype frequency of 55, 60, 65, 70, 75, 80, 85 or 90 or more but less than 95, 96, 97, 98, 99 or 100% (eg, in the range from 51 to 80%) or phenotyped for the TOI variant thereof.

Clause 11: The method of clause 9 or 10, wherein before step (a) the ligand has been or is determined as being capable of binding to the most frequent TOI variant.

Clause 12: The method of clause 9, 10 or 11, wherein before step (a) the ligand has been or is determined as being substantially incapable of neutralising or inhibiting said TOI variant recited in step (b).

By "substantially incapable or neutralising or inhibiting" is meant: Neutralisation or inhibition less than 50, 25, 10, 5 or 0.5% inhibition or neutralisation of the most frequent TOI variant.

Clause 13: The method of any one of clauses 9 to 12, wherein the ligand is capable of binding to the most frequent TOI variant.

Clause 14: The method of any one of clauses 9 to 13, wherein the ligand is capable of binding to two or more different TOI variants, each being encoded by a nucleotide sequence having a cumulative human allele frequency of more than 50%.

In an embodiment, each TOI variant is encoded by a nucleotide sequence having a cumulative human allele frequency of 55, 60, 65, 70, 75, 80, 85 or 90 or more but less than 95, 96, 97, 98, 99 or 100% (eg, in the range from 51 to 80%).

In an embodiment, each TOI variant is encoded by a nucleotide sequence having a total human genotype frequency of 55, 60, 65, 70, 75, 80, 85 or 90 or more but less than 95, 96, 97, 98, 99 or 100% (eg, in the range from 51 to 80%).

Clause 15: The method of any preceding clause, wherein said variant nucleotide sequence recited in step (a) has been or is determined as being present in at least 2 different human ethnic populations, eg, at least 2, 3, 4, 5, 6, 7, 8 or 9 different human ethnic populations in Table 4.

Clause 16: The method of any preceding clause, wherein said human frequency is the frequency in a database of naturally-occurring sequences sampled from at least 15, 20 or 25 different human ethnic populations and comprising at least 1000 sequences. In an embodiment, the database is the 1000 Genomes Project database as described herein.

Clause 17: An anti-human TOI ligand for use in a method of treating and/or preventing a TOI-mediated disease or condition in a human, wherein the TOI is present in humans as different polymorphic variants and wherein the genome of said human comprises a TOI nucleotide sequence having a cumulative human allele frequency of less than 50% and/or a total human genotype frequency of less than 50%, the method comprising administering the ligand to the human.

In the alternative, clause 17 provides an anti-human TOI ligand for use in a method according to any one of clauses 1 to 16, the method comprising administering the ligand to the human.

In an embodiment, the cumulative human allele frequency is 30, 25, 20, 15, 10 or 5% or less, eg, in the range from 1 to 20% or 1 to 15% or 1 to 10%.

In an embodiment, the total human genotype frequency is 35, 30, 25, 20, 15, 10 or 5% or less, eg, in the range from 1 to 25%, 1 to 20%, 1 to 15%, 1 to about 15%, 1 to 10%, 1 to about 10% or 1 to 5% or 1 to about 5%.

Clause 18: The ligand of clause 17, wherein the ligand has been or is determined as capable of binding the human TOI encoded by said nucleotide sequence.

In the alternative, clause 18 provides a ligand that binds a human TOI comprising an amino acid sequence encoded by a TOI nucleotide sequence having a cumulative human allele frequency of less than 50% and/or a total human genotype frequency of less than 50%, for use in a method comprising the step of using the ligand to target said TOI in a human to treat and/or prevent a disease or condition mediated by TOI, the method comprising administering the ligand to the human.

Clause 19: A ligand that binds a human TOI comprising an amino acid sequence encoded by a TOI nucleotide sequence having a cumulative human allele frequency of less than 50% and/or a total human genotype frequency of less than 50%, for use in a method according to any one of clauses 1 to 16, the method comprising administering the ligand to the human.

Clause 20: The ligand of any one of clauses 17 to 19, wherein the human has been or is genotyped as positive for said TOI nucleotide sequence having a cumulative human allele frequency of less than 50%.

The ligand of any one of clauses 17 to 19, wherein the human has been or is genotyped as positive for said TOI nucleotide sequence having a total human genotype frequency of less than 50%.

Clause 21: The ligand of any one of clauses 17 to 20, wherein the human has been or is phenotyped as positive for a TOI encoded by a nucleotide sequence having a cumulative human allele frequency of less than 50% and/or having a total human genotype frequency of less than 50%.

Clause 22: The ligand of any one of clauses 17 to 21, wherein the human has been or is genotyped as heterozygous for a TOI nucleotide sequence having a cumulative human allele frequency of less than 50% and/or having a total human genotype frequency of less than 50%; optionally wherein the human has been or is genotyped as comprising a TOI nucleotide sequence having a cumulative human allele frequency of less than 50% and a TOI nucleotide sequence having a cumulative human allele frequency of more than 50% (eg, having the highest cumulative human allele frequency) and/or having a total human genotype frequency of more than 50% (eg, having the highest total human genotype frequency).

Clause 23: The ligand of any one of clauses 17 to 22, wherein the genome of the human has been or is genotyped as homozygous for a TOI nucleotide sequence having a cumulative human allele frequency of less than 50% and/or having a total human genotype frequency of less than 50%.

Clause 24: The ligand of any one of clauses 17 to 23, wherein the ligand comprises an antibody binding site that binds a human TOI comprising an amino acid sequence encoded by a TOI nucleotide sequence having a cumulative human allele frequency of less than 50% and/or having a total human genotype frequency of less than 50%; and optionally has been or is determined as capable of such binding.

Clause 25: The ligand of clause 24, wherein the ligand is an antibody or antibody fragment.

Clause 26: The ligand of any one of clauses 17 to 23, wherein the ligand comprises a nucleotide sequence that specifically hybridises to a TOI nucleotide sequence having a cumulative human allele frequency of less than 50% and/or having a total human genotype frequency of less than 50% or an RNA transcript thereof; and/or the ligand comprises a nucleotide sequence that comprises at least 10 contiguous nucleotides of a nucleotide sequence having a cumulative human allele frequency of less than 50% and/or having a total human genotype frequency of less than 50% or is an antisense sequence thereof.

In an embodiment, the ligand comprises a nucleotide sequence that comprises at least 10, 11, 12, 13, 14, 15, 20, 25, 30, 35, 40, 45, 50 or 100 contiguous nucleotides of a nucleotide sequence having a cumulative human allele frequency of less than 50% and/or having a total human genotype frequency of less than 50% or is an antisense sequence thereof.

Clause 27: The ligand of any one of clauses 17 to 26, wherein the genome of said human comprises a nucleotide sequence having a cumulative human allele frequency of less than 50% and the sequence is found in at least 2 different ethnic populations (eg, found in at least 9, 10, 11, 12, 13, 14, 15, 16, 17, 18, 19 or 20 different human ethnic populations (for example as per the populations in Table 4)). In an example, numbers are with reference to the 1000 Genomes Project database.

The ligand of any one of clauses 17 to 26, wherein the genome of said human comprises a nucleotide sequence having a cumulative human allele frequency of less than 50% and the sequence is found in at least 20 individuals distributed across at least 2 said different ethnic populations (eg, found in at least in at least 20, 25, 30, 35, 40, 45, 50, 55, 60, 65, 70, 75, 80, 85, 90, 95, 100, 105, 110, 115, 120, 130, 140 or 150 individuals distributed across such many different ethnic populations). In an example, numbers are with reference to the 1000 Genomes Project database.

Clause 28: A pharmaceutical composition or kit for treating or preventing a condition or disease mediated by a TOI as recited in any preceding clause, the composition or kit comprising a ligand of any one of clauses 17 to 27; and optionally in combination with a label or instructions for use to treat and/or prevent said disease or condition in a human; optionally wherein the label or instructions comprise a marketing authorisation number (eg, an FDA or EMA authorisation number); optionally wherein the kit comprises an injection pen or IV container that comprises the ligand.

In an example, the label or instructions cover or describe use for a human comprising a TOI variant encoded by a nucleotide sequence as recited in clause 17.

Clause 29: A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody binding site that binds in the screening step.

In an embodiment of any aspect herein, the antibody, fragment or binding site is recombinant.

In the alternative, clause 29 provides: A method of producing an anti-human TOI antibody, the method comprising immunising a non-human vertebrate (eg, a mouse or a rat) with a TOI comprising an amino acid sequence encoded by a nucleotide sequence having a cumulative human allele frequency of less than 50% and/or a total human genotype frequency of less than 50%, or to a peptide thereof that comprises an amino acid variation from the corresponding sequence encoded by the TOI-encoding nucleotide sequence having the highest cumulative human allele frequency and/or the highest total human genotype frequency, and isolating an antibody that binds a TOI comprising an amino acid sequence encoded by a TOI nucleotide sequence having a cumulative human allele frequency of less than 50% and/or a total human genotype frequency of less than 50%, and optionally producing a TOI-binding fragment or derivative of the isolated antibody.

The term "isolated" with reference to a ligand, antibody or protein, for example in any aspect, configuration, example or embodiment, means that a subject ligand, antibody, protein etc (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated" ligand, antibody, protein etc constitutes at least about 5%, at least about 10%, at least about 25%, or at least about 50% of a given sample. Genomic DNA, cDNA, mRNA or other RNA, of synthetic origin, or any combination thereof can encode such an isolated ligand, antibody protein etc. Preferably, the isolated ligand, antibody protein etc is substantially free from proteins or polypeptides or other contaminants that are found in its natural environment that would interfere with its therapeutic, diagnostic, prophylactic, research or other use.

For example, an "isolated" antibody is one that has been identified, separated and/or recovered from a component of its production environment (eg, naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

Immunoconjugates

The invention encompasses the ligand (eg, antibody) conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-TOI (eg, anti-PCSK9) mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Clause 30: The method of clause 29, comprising the step of obtaining a nucleic acid encoding the antibody, fragment, derivative or binding site and optionally inserting the nucleic acid in an expression vector.

Clause 31: A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof and/or the nucleic acid comprises a nucleotide sequence that comprises at least 10 (eg, at least 10, 11, 12, 13, 14, 15, 20, 25, 30, 35, 40, 45, 50 or 100) contiguous nucleotides of a TOI nucleotide sequence having a cumulative human allele frequency of less than 50% and/or a total human genotype frequency of less than 50% or is an antisense sequence thereof.

For example, the nucleic acid hybridises to a region immediately flanking a nucleotide that is variant compared to the corresponding nucleotide of the TOI nucleotide sequence having the highest cumulative human allele frequency and/or the highest total human genotype frequency. In an example, the nucleic acid hybridises to at two or more such variant nucleotides.

Specific hybridisation is under stringent conditions, as will be apparent to the skilled person, eg, conditions of 5×SSC, 5×Denhardt's reagent, and 0.5% SDS at 65° C.

Clause 32: A kit for TOI genotyping or phenotyping a human, wherein the kit comprises a ligand according to any one of clauses 17 to 27 or an antibody, fragment or derivative produced by the method of any one of clauses 29 to 31.

For example, the ligand specifically binds to an epitope comprising an amino acid that is variant compared to the corresponding amino acid of the TOI encoded by a nucleotide sequence having the highest cumulative human allele frequency and/or the highest total human genotype frequency. In an example, the ligand specifically binds to an epitope comprising two or more such variant amino acids. In an example, specific binding means binding with an affinity (Kd) of 1 mM, 100 nM, 10 nM or 1 nM or less, eg, as determined by SPR.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Clause 33: Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.

Clause 34: Use of an anti-TOI ligand that binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.

The use of clause 33 or 34, wherein the ligand, human, disease or condition is according to any one of clauses 1 to 27.

Clause 35: A method of targeting a TOI for treating and/or preventing a TOI-mediated disease or condition in a human, the method comprising administering an anti-TOI ligand to a human comprising a TOI nucleotide sequence selected having a cumulative human allele frequency of less than 50% and/or a total human genotype frequency of less than 50%, whereby a TOI encoded by said nucleotide sequence is targeted.

Clause 36: The method of clause 35, wherein the method comprises targeting a human TOI comprising an amino acid sequence with said ligand to treat and/or prevent said disease or condition in said human, wherein said amino acid sequence is encoded by a nucleotide sequence having a cumulative human allele frequency of less than 50% and/or a total human genotype frequency of less than 50%.

Clause 37: A method of TOI genotyping a nucleic acid sample of a human, the method comprising identifying in the sample the presence of a TOI nucleotide sequence having a cumulative human allele frequency of less than 50% and/or having a total human genotype frequency of less than 50%.

In an example, the method comprises obtaining a TOI nucleic acid sample from the human and then carrying out the identifying step.

Clause 38: A method of TOI typing a protein sample of a human, the method comprising identifying in the sample the presence of a TOI amino acid sequence encoded by a TOI nucleotide sequence having a cumulative human allele frequency of less than 50% and/or having a total human genotype frequency of less than 50%.

In an example, the method comprises obtaining a TOI protein sample from the human and then carrying out the identifying step.

Clause 39: The method of clause 37 or 38, comprising obtaining a sample of serum, blood, faeces, hair, urine or saliva from a human, whereby the nucleic acid or protein sample is obtained for use in the step of identifying said sequence.

Clause 40: The method of any one of clauses 37 to 39, comprising using a ligand according to any one of clauses 17 to 27 to carry out said identifying step.

Clause 41: A diagnostic kit comprising a ligand that is capable of binding a human TOI comprising an amino acid sequence encoded by a TOI nucleotide sequence having a cumulative human allele frequency of less than 50% and/or a total human genotype frequency of less than 50% and instructions for carrying out the method of clause 38 or 39.

Clause 42: A diagnostic kit comprising a nucleic acid probe comprising a nucleotide sequence that specifically hybridises a TOI nucleotide sequence having a cumulative human allele frequency of less than 50% and/or a total human genotype frequency of less than 50% or an RNA transcript thereof and instructions for carrying out the method of clause 38 or 39.

Clause 43: The method, ligand, composition, kit or use of any preceding clause, wherein the TOI is encoded by a nucleotide sequence having a cumulative human allele frequency from 1 to 10% and/or a total human genotype frequency from 1 to about 15% or from 1 to 15%.

Clause 44: The method, ligand, composition, kit or use of any preceding clause wherein the TOI is a human TOI selected from Table 5; optionally for treating and/or preventing a corresponding disease or condition as set out in Table 5.

For example, the TOI is human PCSK9, eg, a mature, cleaved, autocatalysed or active PCSK9. In an example, the disease is a cardiovascular disease such as hyperlipidaemia.

Ligands of the invention are useful, for instance, in specific binding assays, for genotyping or phenotyping humans, affinity purification of the TOI and in screening assays to identify other antagonists of TOI activity. Some of the ligands of the invention are useful for inhibiting binding of TOI to a congnate human receptor or protein, or inhibiting TOI-mediated activities.

The invention encompasses anti-TOI (eg, PCSK9) antibody ligands having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In an example, the invention features a pharmaceutical composition comprising a ligand of the invention, wherein the ligand is or comprises a recombinant human antibody or fragment thereof which specifically binds the TOI (eg, a rare variant as described herein) and a pharmaceutically acceptable carrier. In one embodiment, the invention features a composition which is a combination of an antibody ligand or antigen-binding fragment of an antibody of the invention, and a second therapeutic agent. The second therapeutic agent may be any of an anti-inflammatory agent, an anti-angiogenesis agent, a painkiller, a diuretic, a chemotherapeutic agent, an anti-neoplastic agent, a vasodilator, a vasoconstrictor, a statin, a beta blocker, a nutrient, an adjuvant, an anti-obesity agent and an anti-diabetes agent.

"Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to an carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

In an example, the invention features a method for inhibiting TOI activity using the anti-TOI ligand of the invention (eg, an antibody or antigen-binding portion of the antibody of the invention), wherein the therapeutic method comprises administering a therapeutically effective amount of a pharmaceutical composition comprising the ligand. The disorder treated is any disease or condition which is improved, ameliorated, inhibited or prevented by removal, inhibition or reduction of TOI activity.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "specifically binds," or the like, means that a ligand, eg, an antibody or antigen-binding fragment thereof, forms a complex with an antigen that is relatively stable under physiologic conditions. Specific binding can be characterized by an equilibrium dissociation constant of at least about $1 \times 10^{-6}$M or less (e.g., a smaller KD denotes a tighter binding). Methods for determining whether two molecules specifically bind are well known in the art and include, for example, equilibrium dialysis, surface plasmon resonance, and the like. An isolated antibody that specifically binds a human TOI may, however, exhibit cross-reactivity to other antigens such as a TOI molecule from another species. Moreover, multi-specific antibodies (e.g., bispecifics) that bind to human TOI and one or more additional antigens are nonetheless considered antibodies that "specifically bind" TOI, as used herein.

Genotyping & Phenotyping

The skilled person will be familiar with techniques that can be used for accurate genotyping and application to the invention. These include the following.
1 Hybridization-based methods
1.1 Dynamic allele-specific hybridization
1.2 Molecular beacons
1.3 SNP microarrays
2 Enzyme-based methods
2.1 Restriction fragment length polymorphism
2.2 PCR-based methods
2.3 Flap endonuclease
2.4 Primer extension
2.5 5'-nuclease
2.6 Oligonucleotide Ligation Assay
3 Other post-amplification methods based on physical properties of DNA
3.1 Single strand conformation polymorphism
3.2 Temperature gradient gel electrophoresis
3.3 Denaturing high performance liquid chromatography
3.4 High-resolution melting of the entire amplicon
3.5 Use of DNA mismatch-binding proteins
3.6 SNPlex (SNPlex™ is a proprietary genotyping platform sold by Applied Biosystems).

Next-generation sequencing technologies such as pyrosequencing is also useful.

Reference is also made to GB2444410A and the genotyping method disclosed therein, which is incorporated herein by reference in its entirety.

Miniaturized assays, such as microarrays with oligonucleotide reagents immobilized on small surfaces, are frequently proposed for large-scale mutation analysis and high-throughput genotyping (Large-scale identification, mapping, and genotyping of single-nucleotide polymorphisms in the human genome (Wang D G, Fan J B, Siao C J, Berno A, Young P, Sapolsky R, Ghandour G, Perkins N, Winchester E, Spencer J, Kruglyak L, Stein L, Hsie L, Topaloglou T, Hubbell E, Robinson E, Mittmann M, Morris M S, Shen N, Kilburn D, Rioux J, Nusbaum C, Rozen S, Hudson T J, Lipshutz R, Chee M, Lander E S, Science. 1998 May 15; 280(5366):1077-82). Other high-throughput methods discriminate alleles by differential hybridization, primer extension, ligation and cleavage of an allele-specific probe (Review Accessing genetic variation: genotyping single nucleotide polymorphisms, Syvanen A C, Nat Rev Genet. 2001 December; 2(12):930-42; Review Techniques patents for SNP genotyping, Twyman R M, Primrose S B, Pharmacogenomics. 2003 January; 4(1): 67-79).

An approach for a fully automated, large-scale SNP analysis is the 'homogeneous' assay, i.e. a single-phase assay without separation steps, permitting continual monitoring during amplification. The TaqMan™ assay (Applied Biosystems), originally designed for quantitative real-time PCR, is a homogeneous, single-step assay also used in determination of mutation status of DNA (see, eg, A. A. Komar (ed.), Single Nucleotide Polymorphisms, Methods in Molecular Biology 578, DOI 10.1007/978-1-60327-411-1_19, Humana Press, a part of Springer Science+Business Media, LLC; and Single Nucleotide Polymorphisms, Methods in Molecular Biology™ Volume 578, 2009, pp 293-306, The TaqMan Method for SNP Genotyping, Gong-Qing Shen et al). The TaqMan SNP Genotyping Assay exploits the 5'-exonuclease activity of AmpliTaq Gold™ DNA polymerase to cleave a doubly labeled probe hybridized to the SNP-containing sequence of ssDNA. Cleavage separates a 5'-fluorophore from a 3'-quencher leading to detectable fluorescent signal. The use of two allele-specific probes carrying different fluorophores permits SNP determination in the same tube without any post-PCR processing. Genotype is determined from the ratio of intensities of the two fluorescent probes at the end of amplification. Thus, rather than taking advantage of the full set of real-time PCR data as in quantitative studies, only end-point data are used.

TaqMan SNP genotyping in a high-throughput, automated manner is facilitated by the use of validated Pre-made TaqMan® Genotyping assays, but Custom TaqMan® Assays may also be used (High-throughput genotyping with single nucleotide polymorphisms, Ranade K, Chang M S, Ting C T, Pei D, Hsiao C F, Olivier M, Pesich R, Hebert J, Chen Y D, Dzau V J, Curb D, Olshen R, Risch N, Cox D R, Botstein D, Genome Res. 2001 July; 11(7):1262-8; Assessment of two flexible and compatible SNP genotyping platforms: TaqMan SNP Genotyping Assays and the SNPlex Genotyping System, De la Vega F M, Lazaruk K D, Rhodes M D, Wenz M E I, Mutat Res. 2005 Jun. 3; 573 (1-2):111-35). The results of the assay can be automatically determined by genotyping software provided with real-time thermal cyclers (e.g. IQ software of Bio-Rad, Sequence Detection Software of Applied Biosystems).

Single nucleotide polymorphisms (SNPs) can be determined using TaqMan™ real-time PCR assays (Applied Biosystems) and commercial software that assigns genotypes based on reporter probe signals at the end of amplification. An algorithm for automatic genotype calling of SNPs using the full course of TaqMan real-time data is available for use (A. Callegaro et al, Nucleic Acids Res. 2006; 34 (7): e56, Published online 2006 April 14. doi: 10.1093/nar/gkl185, PMCID: PMC1440877). The algorithm is unique in that it classifies samples according to the behavior of blanks (no DNA samples), which cluster with heterozygous samples. This method of classification eliminates the need for positive controls and permits accurate genotyping even in the absence of a genotype class, for example when one allele is rare.

The skilled person will be familiar with techniques that can be used for accurate phenotyping and application to the invention. These include the use of amino acid sequencing of isolated target protein and comparison of sequences from different variants (eg, with the most common variant). An antibody that specifically and selectively binds in the area of a SNP under stringent conditions can also be used to identify a particular variant. In another method, the genotype is determined and a corresponding amino acid sequence (phenotype) determined, eg, by in silico translation.

Therapeutic Administration and Formulations

The invention provides therapeutic compositions comprising the anti-TOI ligand, eg, antibodies or antigen-binding fragments thereof, of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the ligand, eg, antibody, of the present invention is used for treating various conditions and diseases associated with the TOI in an adult patient, it is advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the ligand or pharmaceutical composition of the invention, for example a ligand provided by e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The ligand or composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The ligand or pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the ligand or pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a ligand or pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPENT™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the ligand(s). Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Exemplary TOIs

For example in any configuration, aspect, concept, example or configuration of the invention, the or each TOI is selected from the group consisting of ABCF1; ACVR1; ACVR1B; ACVR2; ACVR2B; ACVRL1; ADORA2A; Aggrecan; AGR2; AICDA; AW1; AIG1; AKAP1; AKAP2; AIYIH; amyloid-beta; AMHR2; ANGPT1; ANGPT2; ANGPTL3; ANGPTL4; ANPEP; APC; APOC1; AR; Axl; AZGP1 (zinc-a-glycoprotein); B7.1; B7.2; BAD; BAFF; BAG1; BAI1; BCL2; BCL6; BDNF; BLNK; BLR1 (MDR15); B1yS; BMP1; BMP2; BMP3B (GDF1O); BMP4; BMP6; BMP8; BMPR1A; BMPR1B; BMPR2; BPAG1 (plectin); BRCA1; C19orfl0 (IL27w); C3; C4A; C5; C5R1; CANT1; CASP1; CASP4; CAV1; CB1; CCBP2 (D6/JAB61); CCL1 (I-309); CCL11 (eotaxin); CCL13 (MCP-4); CCL15 (MIP-id); CCL16 (HCC-4); CCL17 (TARC); CCL18 (PARC); CCL19 (MIP-3b); CCL2 (MCP-1); MCAF; CCL2O (MIP-3a); CCL21 (MIP-2); SLC; exodus-2; CCL22 (MDC/STC-1); CCL23 (MPIF-1); CCL24 (MPIF-2 I eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD7, CD164; CD19; CD1C; CD2O; CD200; CD-22; CD24; CD28; CD3; CD37; CD38; CD3E; CD3G; CD3Z; CD4; CD4O; CD4OL; CD44; CD45RB; CD52; CD69; CD72; CD74; CD79A; CD79B; CD8; CD8O; CD81; CD83; CD86; CD96; CD207; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKNIC; CDKN2A (p16INK4a); CDKN2B; CDKN2C; CDKN3; CEBPB; CELSR3; CER1; CHGA; CHGB; Chitinase; CHRNG; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COL1A1; COL4A3; COL6A1; CR2; CRP; CSF1 (M-CSF); CRLF2; CSF2 (GM-CSF); CSF3 (GCSF); CTLA4; CTNNB1 (b-catenin); CTSB (cathepsin B); CX3CL1 (SCYDi); CX3CR1 (V28); CXCR6; CXCL1 (GRO1); CXCL1O (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78 I LIX); CXCL6 (GCP-2); CXCL9 (MIG); CXCR3 (GPR9/CKR-L2); CXCR4; CXCR6 (TYMSTR ISTRL33 I Bonzo); CYB5; CYC1; CYSLTR1; DAB2IP; DAND5; DES; DKFZp451J0118; DNCL1; DPP4; E2F1; ECGF1; EDG1; EFNAI; EFNA3; EFNB2; EGF; EGFR; ELAC2; ENG; ENO1; ENO2; ENO3; EphA4; EPHB4; EPO; ERBB2 (Her-2); EREG; ERK8; ESR1; ESR2; F3 (TF); FADD; FasL; FASN; FCER1A; FCER2; FCGR3A; FCRL4; FGF; FGF1 (aFGF); FGF1O; FGF11; FGF12; FGF12B; FGF13; FGF14; FGF16; FGF17; FGF18; FGF19; FGF2 (bFGF); FGF2O; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; Galectin-3; GALNAC4S-65T; GATA3; GDF5; GFI1; GGT1; GHR; GM-CSF; GNAS1; GNRH1; GPR2 (CCR1O); GPR31; GPR44; GPR81 (FKSG8O); GPR87; GPR137C; GRCC10 (C10); GRP; GSN (Gelsolin); GSTP1; HAVCR1; HAVCR2; HDAC4; EDAC5; HDAC7A; HDAC9; hepcidin; hemojuvelin; HGF; HIF1A; HIP1; histamine and histamine receptors; HLA-A; HLA-DRA; HM74; HMOX1; HUMCYT2A; ICEBERG; ICOS; 1D2; IFN-α; IFNA1; IFNA2; IFNA4; IFNA5; IFNA6; IFNA7; IFNB1; IFN-gamma; TFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; 1L13; IL13RA1; IL13RA2; 1L14; 1L15; IL15RA; IL16; 1L17; IL17B; IL17C; IL17R; 1L18; IL18BP; IL18R1; IL18RAP; 1L19; IL1A; IL1B; IL1F1O; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; 1L2; 1L20; IL2ORA; IL21R; 1L22; 1L22R; 1L22RA2; 1L23; 1L24; 1L25; 1L26; 1L27; IL28A; IL28B; 1L29; IL2RA; IL2RB; IL2RG; 1L3; 1L30; IL3RA; 1L4; IL4R; 1L5; IL5RA; 1L6; IL6 receptor; IL6ST (glycoprotein 130); 1L7; TL7R; 1L8; IL8RA; IL8RB; IL8RB; 1L9; IL9R; ILK; INHA; INHBA; INSL3; INSL4; IRAK1; IRAK2; ITGA1; ITGA2; 1TGA3; ITGA6 (a6 integrin); ITGAV; ITGB3; ITGB4 (b 4 integrin); JAG1; JAK1; JAK3; JUN; K6HF; KAI1; KDR; MTLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAG3; LAMAS; LEP (leptin); LIGHT; Lingo-p75; Lingo-Troy; LPS; LRP5; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MK167 (Ki-67); MMP2; MMP9; MS4A1; MSMB; MT3 (metallothionectin-ifi); MTSS 1; MUC 1 (mucin); MYC; MYD88; NCK2; neurocan; Na$_v$1.7; Na$_v$1.8; NFKB 1; NFKB2; NGFB (NGF); NGFR; NgR-Lingo; NgR-Nogo66 (Nogo); NgR-p75; NgR-Troy; NME1 (NM23A); NOXS; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPG; OPRD1; OX4OL; OX40; P2RX7; PAP; PART1; PATE;

PAWR; PCA3; PCNA; PCSK9, PD-1, PD-L1; PDGFA; PDGFB; PECAM1; PF4 (CXCL4); PGF; PGR; phosphacan; PIAS2; Placental Growth Factor (PIGF); PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; ROR1; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINIA3; SERPINB5 (maspin); SERPINE1 (PAT-i); SERPINF1; SHBG; SLA2; SLC2A2; SLC33A1; SLC43A1; SLIT2; SPP1; SPRR1B (Spri); ST6GAL1; STAB1; STATE; STEAP; STEAP2; TB4R2; TBX21; TCP1O; TDGF1; TEK; TGFA; TGFB1; TGFB1l1; TGFB2; TGFB3; TGFBI; TGFBR1; TGFBR2; TGFBR3; TH1L; THBS1 (thrombospondin-1); THBS2; THBS4; THPO; TIE (Tie-i); TIM3; TMP3; tissue factor; TLR1O; TLR2; TLR3; TLR4; TLR5; TLR6; TLR7; TLR8; TLR9; TMPRSS6; TNF; TNF-α; TNFAIP2 (B94); TNFAIP3; TNFRSF1 1A; TNFRSF1A; TNFRSF1B; TNFRSF21; TNFRSF5; TNFRSF6 (Fas); TNFRSF7; TNFRSF8; TNFRSF9; TNFSF1O (TRAIL); TNFSF1 1 (TRANCE); TNFSF12 (APO3L); TNFSF13 (April); TNFSF13B; TNFSF14 (HVEM-L); TNFSF1 5 (VEGI); TNFSF1 8; TNFSF4 (0X40 ligand); TNFSF5 (CD4O ligand); TNFSF6 (FasL); TNFSF7 (CD27 ligand); TNFSF8 (CD3O ligand); TNFSF9 (4-1BB ligand); TOLLIP; Toll-like receptors; TOP2A (topoisomerase lia); TP53; TPM1; TPM2; TRADD; TRAF1; TRAF2; TRAF3; TRAF4; TRAF5; TRAF6; TRAIL; TREM1; TREM2; TRPC6; TSLP; TWEAK; VEGFA; VEGFB; VEGFC; versican; VHL C5; VLA-4; Wnt7A; XCL1 (lymphotactin); XCL2 (SCM-1b); XCR1 (GPR5/CCXCR1); YY1; and ZFPM2.

In an example, the TOI is a human TOI selected from Table 5.
  In an example, the TOI is OX40 ligand.
  In an example, the TOI is OX40.
  In an example, the TOI is PCSK9.
  In an example, the TOI is IL6 receptor (IL-6R).
  In an example, the TOI is LIGHT.
  In an example, the TOI is VEGF-A.
  In an example, the TOI is TNF alpha.
  In an example, the TOI is PIGF.
  In an example, the TOI is IGF1R.
  In an example, the TOI is OPG.
  In an example, the TOI is ICOS.
  In an example, the TOI is NGF.
  In an example, the TOI is BMP6.
  In an example, the TOI is ferroportin.
  In an example, the TOI is TMPRSS6.
  In an example, the TOI is hemojuvelin.
  In an example, the TOI is VEGF receptor.
  In an example, the TOI is PDGF receptor.
  In an example, the TOI is stem cell factor receptor.
  In an example, the TOI is hepcidin.
  In an example, the TOI is IL-4 receptor alpha.
  In an example, the TOI is sclerostin.
  In an example, the TOI is IL-13 receptor.
  In an example, the TOI is CD7.
  In an example, the TOI is delta-like ligand-4 (D114).
  In an example, the TOI is HGF.
  In an example, the TOI is angiopoietin-2 (Ang2).
  In an example, the TOI is GDF8.
  In an example, the TOI is ERBB3.
  In an example, the TOI is IL-17 receptor.
  In an example, the TOI is CD40.
  In an example, the TOI is CD40 ligand.
  In an example, the TOI is EGFR.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", or "reduction" are all used herein to mean a decrease by a statistically significant amount. In some embodiments, "reduce," "reduction" or "decrease" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" does not encompass a complete reduction as compared to a reference level. A decrease can be preferably down to a level accepted as within the range of normal for an individual without a given disorder. However, for example, for the purposes of lowering or reducing cholesterol level, for example, a reduction by about 5-10 points can be considered a "decrease" or "reduction."

In certain aspects of all embodiments of the invention, the term "inhibition" is used. Inhibition refers and refers to decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more including 100% inhibition as compared to a reference level. "Complete inhibition" refers to a 100% inhibition as compared to a reference level.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. For the removal of doubt, "substantially" can refer to at least a 90% extent or degree of a characteristic or property of interest, e.g. at least 90%, at least 92%, at least 95%, at least 98%, at least 99% or greater.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. In some embodiments, the subject is a mammal, e.g., a primate, e.g., a human. The terms, "individual," "patient" and "subject" are used interchangeably herein. In some embodiments, the subject can be a non-human vertebrate, e.g. a primate, a rodent, a mouse, a rat, a pig, a sheep, a zebrafish, a frog, etc.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease or condition, e.g., a cardiovascular condition. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" or "human in need" of treatment for a particular condition can be a subject having that condition, such as increased cholesterol levels, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids with natural amino acids. When referring to "modified polypeptides" one refers to polypeptides that include modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins with the specified sequence. One can also use peptide homologs, peptide orthologs, peptide paralogs, peptide fragments and other equivalents, variants, fragments, and analogs of the peptides as these terms are understood by one of ordinary skill in the art.

As used herein, the term "nucleic acid" or "nucleic acid sequence" refers to any molecule, preferably a polymeric molecule, incorporating units of ribonucleic acid, deoxyribonucleic acid. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA. In some aspects one can also use analogs of nucleic acids.

As used herein, the term "nucleic acid probe" refers to an isolated oligonucleotide molecule having a nucleic acid sequence which can hybridize to a target nucleic acid sequence, e.g. specifically hybridize to the target sequence. In some embodiments, a nucleic acid probe can further comprise a detectable label. In some embodiments, a nucleic acid probe can be attached to a solid surface. In some embodiments, a nucleic acid from is from about 5 nt to about 100 nt in length.

As used herein, the term "siRNA" refers to a nucleic acid that forms an RNA molecule comprising two individual strands of RNA which are substantially complementary to each other. Typically, the siRNA is at least about 15-40 nucleotides in length (e.g., each complementary sequence of the double stranded siRNA is about 15-40 nucleotides in length, and the double stranded siRNA is about 15-40 base pairs in length, preferably about 19-25 base nucleotides, e.g., 19, 20, 21, 22, 23, 24, or 25 nucleotides in length). In some embodiments, a siRNA can be blunt-ended. In some embodiments, a siRNA can comprise a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. The siRNA molecules can also comprise a 3' hydroxyl group. In some embodiments, the siRNA can comprise a 5' phosphate group. A siRNA has the ability to reduce or inhibit expression of a gene or target RNA when the siRNA is present or expressed in the same cell as the target gene, e.g. the target RNA. siRNA-dependent post-transcriptional silencing of gene expression involves cutting the target RNA molecule at a site guided by the siRNA.

As used herein, "PCSK9" or "proprotein convertase subtilisin/kexin type 9" refers to a serine protease involved in regulating the levels of the low density lipoprotein receptor (LDLR) protein (Horton et al., 2007; Seidah and Prat, 2007). PCSK9 has been shown to directly interact with the LDLR protein, be endocytosed along with the LDLR, and co-immunofluoresce with the LDLR throughout the endosomal pathway (Lagace et al., 2006). PCSK9 is a prohormone-proprotein convertase in the subtilisin (S8) family of serine proteases (Seidah et al., 2003). The sequence of PCSK9 for a variety of species is known, e.g., human PCSK9 (NCBI Gene ID No: 255738). Nucleotide and polypeptide sequences for a number of PCSK9 isoforms are provided herein, e.g., SEQ ID NOs: 1-37.

PCSK9 exists as both a pro-form and a mature form. Autocatalysis of the PCSK9 proform occurs between Gln152 and Ser153 (VFAQ|SIP (SEQ ID NO: 67)) (Naureckiene et al., 2003), and has been shown to be required for its secretion from cells (Seidah et al., 2003). The inactive form prior to this cleavage can be referred to herein as the "inactive", "proform", or "unprocessed" form of PCSK9. The C-terminal fragment generated by the autocatalysis event can be referred to herein as the "mature," "cleaved", "processed" or "active" PCSK9. Examples of pro-form and mature PCSK9 isoforms are provided herein, see, e.g. SEQ ID NOs: 1-27.

As used herein, the "catalytic domain" of PCSK9 refers to the portion of a PCSK9 polypeptide corresponding to positions 153 to 449 of PCSK9, e.g. of SEQ ID NO: 1. As used herein, the "C-terminal domain" of PCSK9 refers to the portion of a PCSK9 polypeptide corresponding to positions 450-692 of PCSK9, e.g., of SEQ ID NO: 1.

As used herein, a disease or condition "mediated by PCSK9" refers to a disease or condition which is caused by or characterized by a change in PCSK9, e.g. a change in expression level, a change in activity, and/or the presence of a variant or mutation of PCSK9. Non-limiting examples of such diseases or conditions can include, for example, a lipid disorder, hyperlipoproteinemia, hyperlipidemia; dyslipidemia; hypercholesterolemia, a heart attack, a stroke, coronary heart disease, atherosclerosis, peripheral vascular disease, claudication, type II diabetes, high blood pressure, and a cardiovascular disease or condition. In an example, the disease or condition is an inflammatory or autoimmune disease or condition. Methods of identifying and/or diagnosing such diseases and conditions are well known to medical practitioners of ordinary skill.

A subject at risk of having or developing a disease or condition mediated by PCSK9 can be a subject exhibiting one or more signs or symptoms of such a disease or condition or having one or more risk factors for such a disease or condition, e.g. being overweight, having elevated cholesterol level, comprising one or more genetic polymorphisms known to predispose to the disease or condition, e.g., elevated cholesterol level, such as having a mutation in the LDLR (encoding low-density lipoprotein receptor) or APOB (encoding apolipoprotein B) or in the PCSK9 gene and/or having a family history of such a disease or condition.

As used herein, "ligand" refers to a molecule which can bind, e.g., specifically bind, to a second molecule or receptor. In some embodiments, a ligand can be, e.g., an antibody, antibody fragment, antibody portion, and/or affibody.

The term "variant" as used herein refers to a peptide or nucleic acid that differs from the polypeptide or nucleic acid (eg, the most common one in humans, eg, most frequent in a database as disclosed herein, such as the 1000 Genomes Project database) by one or more amino acid or nucleic acid deletions, additions, yet retains one or more specific functions or biological activities of the naturally occurring molecule. Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

Variants of PCSK9 are provided elsewhere herein. Variants of PCSK9 can include the forms described herein as a, f, c, r, p, m, e h, aj, and q. Sequences of these variants are provided herein, see, e.g, SEQ ID NOs: 1-27 and in Table 1, 2 or 6.

In some aspects, one can use "synthetic variants", "recombinant variants", or "chemically modified" polynucleotide variants or polypeptide variants isolated or generated using methods well known in the art. "Modified variants" can include conservative or non-conservative amino acid changes, as described below. Polynucleotide changes can result in amino acid substitutions, additions, deletions, fusions and truncations in the polypeptide encoded by the reference sequence. Some aspects use include insertion variants, deletion variants or substituted variants with substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. MoI Biol, 1999, 217, 721-739 and Taylor et al, J. Theor. Biol. 119(1986); 205-218 and S. French and B. Robson, J. MoI. Evol. 19 (1983) 171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanized using routine technology.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody fragment" refers to a polypeptide that includes at least one immunoglobulin variable domain or immunoglobulin variable domain sequence and which specifically binds a given antigen. An antibody fragment can comprise an antibody or a polypeptide comprising an antigen-binding domain of an antibody. In some embodiments, an antibody fragment can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody fragment" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). VH refers to the variable domain of the heavy chain. VL refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature.

D domain or region refers to the diversity domain or region of an antibody chain. J domain or region refers to the joining domain or region of an antibody chain.

An antibody "gene segment", e.g. a VH gene segment, D gene segment, or JH gene segment refers to oligonucleotide having a nucleic acid sequence that encodes that portion of an antibody, e.g. a VH gene segment is an oligonucleotide comprising a nucleic acid sequence that encodes a polypeptide VH domain.

The VH and VL regions can be further subdivided into regions of hypervariability, termed "complementarity determining regions" ("CDR"), interspersed with regions that are more conserved, termed "framework regions" ("FR"). The extent of the framework region and CDRS has been precisely defined (see, IMGT or Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRS and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "antibody binding site" refers to a polypeptide or domain that comprises one or more CDRS of an antibody and is capable of binding an antigen. For example, the polypeptide comprises a CDR3 (eg, HCDR3). For example the polypeptide comprises CDRs 1 and 2 (eg, HCDR1 and 2) or CDRS 1-3 of a variable domain of an antibody (eg, HCDRs1-3). In an example, the antibody binding site is provided by a single variable domain (eg, a VH or VL domain). In another example, the binding site comprises a VH/VL pair or two or more of such pairs.

As used herein, the term "specific binding" refers to a chemical interaction between two molecules, compounds, cells and/or particles wherein the first entity binds to the second, target entity with greater specificity and affinity than it binds to a third entity which is a non-target. For example, in an diagnostic test the specific binding of a ligand can distinguish between two variant PCSK9 proteins as described herein. In some embodiments, specific binding can refer to an affinity of the first entity for the second target entity which is at least 10 times, at least 50 times, at least 100 times, at least 500 times, at least 1000 times or greater than the affinity for the third nontarget entity. In the context of oligonucleotide strands which interact via hybridization, specific binding can be "specific hybridization."

Additionally, and as described herein, a recombinant human(ized) antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a target molecule.

The term "immunizing" refers to the step or steps of administering one or more antigens to an animal so that antibodies can be raised in the animal Generally, immunizing comprises injecting the antigen or antigens into the animal. Immunization can involve one or more administrations of the antigen or antigens. Suitable methods are prime-boost and RIMMS procedures as known to the skilled person in the art.

As used herein, an "affibody" refers to a relatively small synthetic protein molecule that has high binding affinity for a target protein (e.g. for PCSK9 or a variant thereof). Affibodies are composed of a three-helix bundle domain derived from the IgG-binding domain of staphylococcal protein A. The protein domain consists of a 58 amino acid sequence, with 13 randomized amino acids affording a range of affibody variants. Despite being significantly smaller than an antibody (an affibody weighs about 6 kDa while an antibody commonly weighs about 150 kDa), an affibody molecule works like an antibody since its binding site is approximately equivalent in surface area to the binding site of an antibody.

Figure 3:
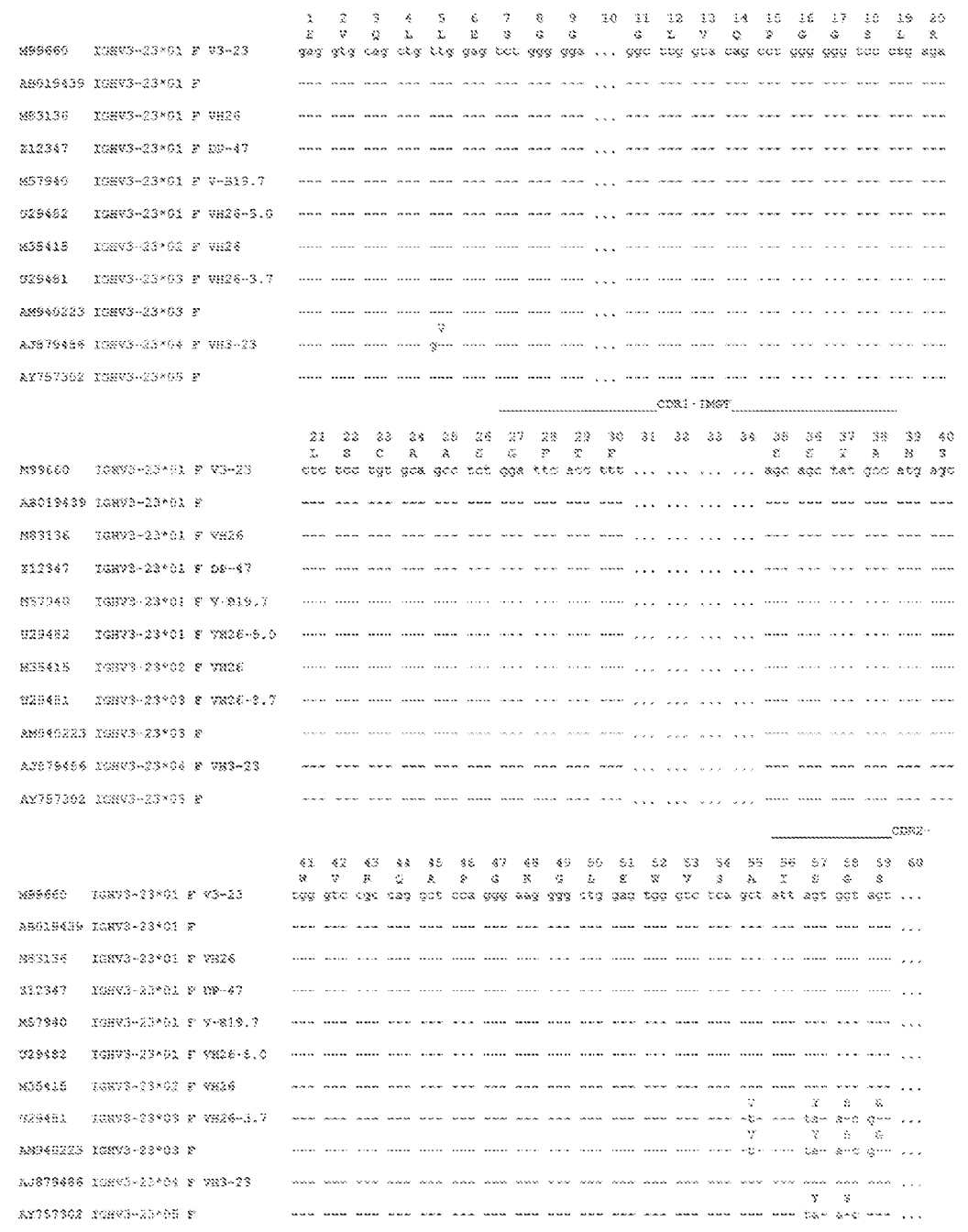
Figure 3:
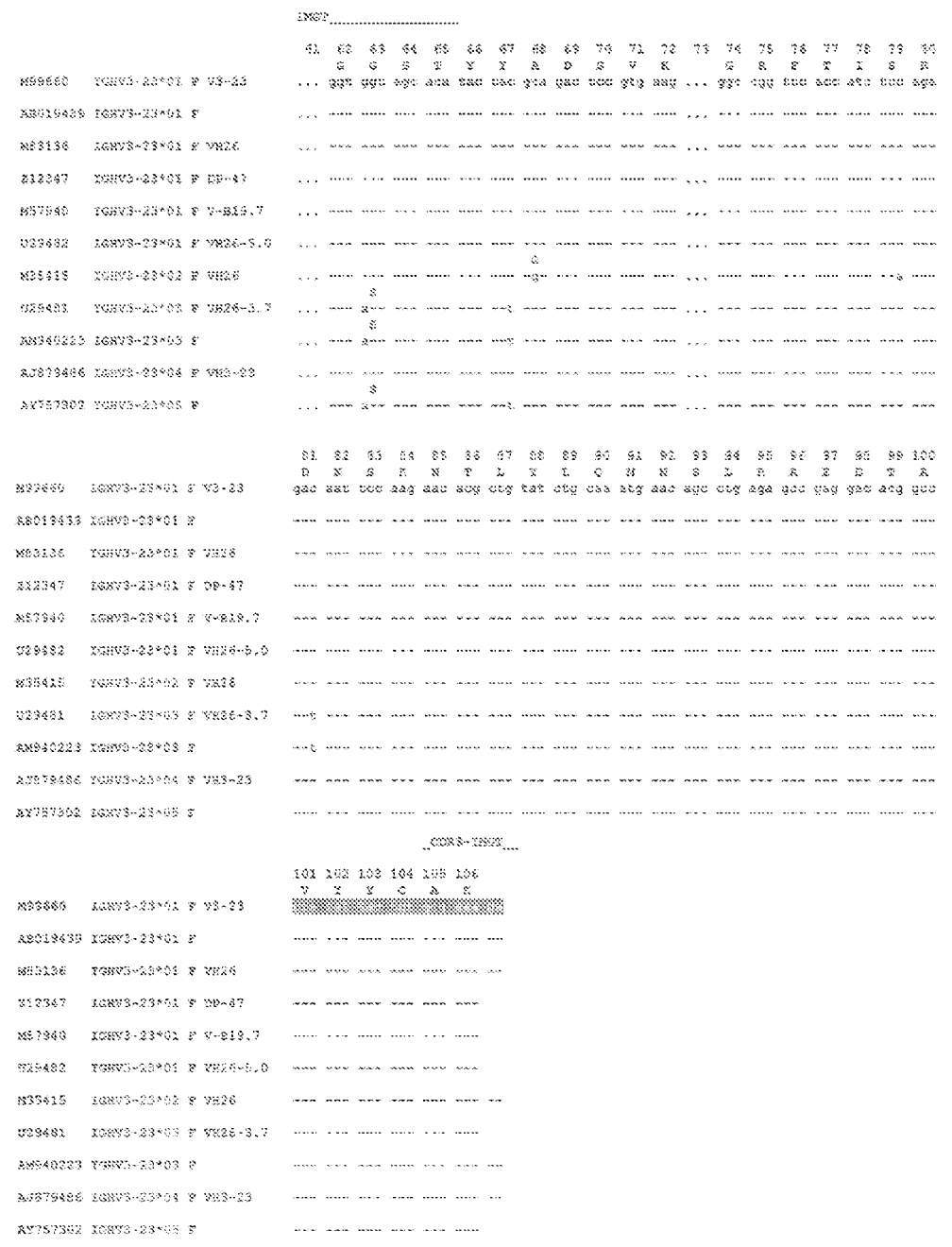

As used herein, "VH3-23*04" refers to a human VH domain variant comprising the polypeptide sequence of SEQ ID NO: 38. As opposed to the reference sequence, VH3-23*04 has a valine residue instead of a leucine residue (see FIGS. 3 and 4; L24V, numbering including signal sequence; valine at position 5 shown in FIG. 4) as a result of the presence of the rs56069819 SNP in the nucleic acid sequence encoding the VH domain. As used herein, "rs56069819" refers to a mutation or variant in a VH gene segment from adenosine to cytosine (or thymine to guanine, depending upon the strand of DNA which is being read), resulting in the VH domain encoding VH3-23*04. Rs56069819 is depicted in FIG. 4 and SEQ ID NO: 39, which demonstrate the T→G mutation (it is noted that the dbSNP entry for RS5606819 depicts the other strand, which comprises the A→C mutation). Further description of VH3-23*04 can be found, e.g., in US Patent Publication 2013/0071405; which is incorporated by reference herein in its entirety.

As used herein, "determine" or "determining" refers to ascertaining, e.g., by a quantitative or qualitative analysis. As used herein, "has been determined" can refer to ascertaining on the basis of previously obtained information or simultaneously obtained information.

In some aspects of all embodiments of the invention selecting can include automation such as a computer implemented software program that upon input of the relevant data such as ethnicity or a panel of SNP data can make the determination based on the instructions set forth herein.

As used herein, "assaying" refers to assessing, evaluating, quantifying, measuring, or characterizing an analyte, e.g., measuring the level of an analyte in a sample, identifying an analyte, or detecting the presence or absence of an analyte in a sample. In some embodiments, assaying refers to detecting a presence or absence of the analyte of interest. In some embodiments, assaying refers to quantifying an amount of an analyte, e.g., providing a measure of concentration or degree of analyte abundance. In some embodiments, assaying refers to enumerating the number of molecules of analyte present in a sample and/or specimen, e.g., to determine an analyte copy number.

As used herein "multiplex" refers to the carrying out of a method or process simultaneously and in the same reaction vessel on two or more, typically three or more, different target sequences, e.g. on two or more isoforms of PCSK9, or PCSK9 and an additional target. A multiplex analysis typically includes analysis of 10-50; 10-100; 10-1000, 10-5000, 10-10000 reactions in a multiplex format, such as a multiwall, an array, or a multichannel reaction.

Often the analysis or multiplex analysis is also automated using robotics and typically software executed by a computer and may include a robotic handling of samples, automatic or robotic selection of positive or negative results, assaying for presence of absence of a target, such as a nucleic acid polymorphism or a protein variant.

The term "biological sample" or "test sample" as used herein denotes a sample taken or isolated from a biological organism, e.g., a sample from a subject. Exemplary biological samples include, but are not limited to, a biofluid sample; serum; plasma; urine; saliva; hair, epithelial cells, skin, a tumor biopsy and/or tissue sample etc. The term also includes a mixture of the above-mentioned samples. The term "test sample" or "biological sample" also includes untreated or pretreated (or pre-processed) biological samples. For the analysis of nucleic acids, the biological sample should typically comprise at least one cell comprising nucleic acids.

The test sample can be obtained by removing a sample of cells from a subject, but can also be accomplished by using previously isolated cells (e.g. isolated at a prior time point and isolated by the same or another person). In addition, the test sample can be freshly collected or a previously collected, refrigerated, frozen or otherwise preserved sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

As used herein, "genotyping" refers to a process of determining the specific allelic composition of a cell and/or subject at one or more position within the genome, e.g. by determining the nucleic acid sequence at that position. Genotyping refers to a nucleic acid analysis and/or analysis at the nucleic acid level. As used herein, "phenotyping" refers a process of determining the identity and/or composition of an expression product of a cell and/or subject, e.g. by determining the polypeptide sequence of an expression product. Phenotyping refers to a protein analysis and/or analysis at the protein level.

As used herein, the term "nucleic acid amplification" refers to the production of additional copies of a nucleic acid sequence and is typically carried out using polymerase chain reaction (PCR) or ligase chain reaction (LCR) technologies well known in the art (Dieffenbach, C. W. and G. S. Dveksler (1995) PCR Primer, a Laboratory Manual, Cold Spring Harbor Press, Plainview, N. Y.). Other methods for amplification are also contemplated in aspects of the invention.

The term "allele-specific amplification" refers to a reaction (e.g., PCR reaction) in which at least one of the primers (e.g., allele-specific primer) is chosen from a polymorphic area of gene (e.g., single nucleotide polymorphism), with the polymorphism located at or near the primer's 3'-end. A mismatched primer will not initiate amplification, whereas a matched primer will initiate amplification. The appearance of an amplification product is indicative of the presence of the polymorphism.

As used herein, "sequencing" refers to the determination of the exact order of nucleotide bases in a strand of DNA (deoxyribonucleic acid) or RNA (ribonucleic acid) or the exact order of amino acids residues or peptides in a protein. Nucleic acid sequencing can be done using Sanger sequencing or next-generation high-throughput sequencing.

As used herein "next-generation sequencing" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina): SOLiD technology (Applied Biosystems); Ion semiconductor sequencing (ION Torrent); DNA nanoball sequencing (Complete Genomics); and technologies available from Pacific Biosciences, Intelligen Bio-systems, Oxford Nanopore Technologies, and Helicos Biosciences. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. No. 7,282,337; U.S. Pat. No. 7,279,563; U.S. Pat. No. 7,226,720; U.S. Pat. No. 7,220,549; U.S. Pat. No. 7,169,560; U.S. Pat. No. 6,818,395; U.S. Pat. No. 6,911,345; US Pub. Nos. 2006/0252077; 2007/0070349; and 20070070349; which are incorporated by reference herein in their entireties).

As used herein, "nucleic acid hybridization" refers to the pairing of complementary RNA and DNA strands as well as the pairing of complementary DNA single strands. In some embodiments, nucleic acid hybridization can refer to a method of determining a nucleic acid sequence and/or identity by hybridizing a nucleic acid sample with a probe, e.g. Northern or Southern blot analysis or microarray analysis.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

As used herein, "contacting" refers to any suitable means for delivering, or exposing, an agent to at least one complex, enzyme, or cell. Exemplary delivery methods include, but are not limited to, direct delivery to cell culture medium, perfusion, injection, or other delivery method well known to one skilled in the art.

As used herein, "obtain" refers to any method of acquiring, securing, procuring, or coming into the possession of, e.g. a sample. Obtaining a biological sample from a subject can comprise physical removing a sample from a subject (e.g. drawing blood or taking a hair or saliva sample) without or without active participation from the subject; receiving a sample from a subject (e.g. the subject collects a saliva or hair sample themselves and provides it, e.g. in a container provided for the purpose); or procuring a sample from a storage facility, medical facility, or medical provider. Obtain from the human or subject, refers to an active step of, e.g., drawing blood or taking a tissue or cell sample.

As used herein, "cholesterol level" refers to a level of one or more of total cholesterol, LDL cholesterol, HDL cholesterol, and/or triglycerides. Cholesterol levels can be the level of cholesterol in the blood of a subject.

As used herein in reference to cholesterol levels, "maintain" refers to preventing the level from worsening (e.g. increasing). In some embodiments, maintaining a particular level refers to a process that results in the cholesterol level not increasing by more than 10% over time. Maintaining may also refer to maintaining a previously achieved level. For example, if a human has received statin treatment, one can maintain the cholesterol level achieved using the statin treatment.

In some embodiments, the subject treated according to the methods described herein has previously had their cholesterol level reduced. As used herein, "previously reduced" indicates that at a prior point in time, the subject experienced a decrease in cholesterol levels. The decrease can be due to administration of a pharmaceutical composition (e.g. administration of a composition as described herein or another composition, e.g. a statin) or due to another cause, e.g. a change in diet and/or exercise.

An existing treatment for high cholesterol levels is the administration of a statin. As referred to herein, a "statin" (also known as HMG-CoA reductase inhibitors) are inhibitors of the enzyme HMG-coA reductase, which mediates cholesterol production in the liver. Statins, by competitively binding HMG-CoA reductase, prevent the binding of HMG-CoA to the enzyme and thereby inhibit the activity of the reductase (e.g. the production of mevalonate). Non-limiting examples of statins can include atorvastatin (LIPITOR™), fluvastatin (LESCOL™), lovastatin (MEVACOR™, ALTOCOR™), pitavastatin (LIVALO™), pravastatin (PRAVACHOL™) rosuvastatin (CRESTOR™), and simvastatin (ZOCOR™). Statins can be administered in combination with other agents, e.g. the combination of ezetimibe and simvastatin.

Some subjects are, or become, resistant to statin treatment. As used herein, "resistant to statin treatment" or "reduced responsiveness to statin treatment" refers to a subject exhibiting a statistically significantly lower response to the administration of a statin as compared to a reference level. The reference level can be, e.g., the average response for a population of subjects or the level of the individual subject at an earlier date. A response to statin treatment is readily measured by one of skill in the art, e.g., measurement of cholesterol levels, changes in cholesterol levels, and/or HMG-CoA reductase activity.

As used herein, the term "detectable label" refers to a molecule or moiety that can be detected, e.g. measured and/or determined to be present or absent. Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detectable label can be a fluorescent compound. When the fluorescently label is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^{3}H$, $^{125}I$, $^{35}S$, $^{14}C$, $^{32}P$, and $^{33}P$. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use as a detectable label can include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g, the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, a "buffer" refers to a chemical agent that is able to absorb a certain quantity of acid or base without undergoing a strong variation in pH.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labeling, etc.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

As used herein, a "solid surface" refers to an object suitable for the attachment of biomolecules. Non-limiting examples of a solid surface can include a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid surface can include many different materials including, but not limited to, polymers, plastics, resins, polysaccharides, silicon or silica based materials, carbon, metals, inorganic glasses, and membranes.

As used herein, "classification" of a subject, e.g., classification of the subject's ancestry refers to determining if the subject has biological ancestors who originated in a particular geographical area, and are therefore likely to have particular genetic variants found in the populations which have historically occupied that area. Classification can comprise, e.g. obtaining information on the subject's family, interviewing the subject or a family member regarding their biological family's ancestry, and/or genetic testing. Classification can be on the basis used for the 1000 Genomes Project, as will be familiar to the skilled person in the art. In some embodiments, the subject can be classified as being of a particular ancestry if at least the subject's genome comprises a substantial number of different alleles in common with other humans of that ancestry (eg, determined by reference to the 1000 Genomes Project database), for example, at least 10, 20, 30, 40, 50 or 100 or more alleles in common. Abbreviations for particular ancestral groups are provided in Table 4.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, aspects, examples, clauses and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

Some embodiments of the technology described herein can be defined according to any of the following numbered paragraphs:

1. A method of treating or preventing a disease or condition in a human, wherein the disease or condition is mediated by a Target of Interest (TOI), wherein the TOI is present in humans as different polymorphic variants, the method comprising
   a. selecting a human that is positive for the TOI polymorphic variant, wherein the TOI in said human is encoded by a nucleotide sequence comprising an allele having a cumulative human allele frequency of less than 50% and/or wherein the TOI in said human is encoded by a nucleotide sequence comprising an allele having total human genotype frequency of less than 50%; and
   b. administering to the human an anti-TOI ligand to target the TOI in the human to treat or prevent said disease or condition.

In an alternative where the TOI is human PCSK9, paragraph 1 provides:—
   A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation as defined herein (eg, I474V or E670G) in SEQ ID NO: 1, wherein the antibody comprises a VH domain derived from the recombination of a human VH segment, a human D gene segment and a human JH segment, the human VH segment encoding a valine at the amino acid corresponding to position 5 of SEQ ID NO: 40 and wherein said human comprises (i) a VH gene segment encoding the framework 1 of SEQ ID NO: 40 and (ii) a nucleotide sequence encoding a proprotein convertase subtilisin/kexin type 9 (PCSK9) that comprises a C-terminal domain comprising said mutation in SEQ ID NO: 1.

In an alternative where the TOI is human PCSK9, paragraph 1 provides:—A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation as defined herein (eg, I474V or E670G) in SEQ ID NO: 1, wherein the antibody comprises a VL domain derived from the recombination of a human VL segment and a human JL segment, the human VL segment is a Vλ or Vκ disclosed herein and wherein said human comprises (i) said VL gene segment and (ii) a nucleotide sequence encoding a proprotein convertase subtilisin/kexin type 9 (PCSK9) that comprises a C-terminal domain comprising said mutation in SEQ ID NO: 1.

In an alternative where the TOI is human PCSK9, paragraph 1 provides:—
   A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation as defined herein (eg, I474V or E670G) in SEQ ID NO: 1, wherein the antibody comprises a C domain encoded by a human CH, Cλ or Cκ gene segment disclosed herein and wherein said human comprises (i) said C gene segment and (ii) a nucleotide sequence encoding a proprotein convertase subtilisin/kexin type 9 (PCSK9) that comprises a C-terminal domain comprising said mutation in SEQ ID NO: 1.

2. The method of paragraph 1, wherein before step (a) the ligand has been or is determined as being capable of specifically binding to said TOI variant.
3. The method of paragraph 1 or 2, comprising determining that the human is positive for the TOI polymorphic variant, optionally wherein the step of determining comprises determining that the human is positive for a nucleotide variant encoding said TOI variant.
4. The method of paragraph 3, wherein the step of determining comprises assaying a biological sample obtained from said human for a nucleotide polymorphism encoding said TOI polymorphic variant.
5. The method of paragraph 3 or 4, wherein the step of determining comprises assaying a biological sample obtained from said human for a protein corresponding to the TOI polymorphic variant.
6. The method of any preceding paragraph, wherein said frequency is less than 15%.
7. The method of any preceding paragraph, wherein said frequency is less than 10%.
8. The method of any preceding paragraph, wherein the ligand is capable of specifically binding to two or more different TOI variants, each being encoded by a nucleotide sequence comprising an allele having a cumulative human allele frequency of less than 50% and/or having a total human genotype frequency of less than 50%.
9. A method of treating or preventing a disease or condition in a human, wherein the disease or condition is mediated by a Target of Interest (TOI), wherein the TOI is present in humans as different polymorphic variants, the method comprising
   a. selecting a human that is negative for a variant nucleotide sequence comprising an allele having a cumulative human allele frequency of less than 50% and/or having a total human genotype frequency of less than 50%; or that the human is negative for a TOI variant encoded by a nucleotide sequence comprising the allele having a cumulative human allele frequency of less than 50% and/or having a total human genotype frequency of less than 50%; and
   b. administering to the human an anti-TOI ligand to target the TOI variant in the human and treat or prevent said disease or condition, wherein the TOI in said human is a variant encoded by a nucleotide sequence comprising an allele having a cumulative human allele frequency of more than 50% and/or having a total human genotype frequency of more than 50%.
10. The method of paragraph 9, comprising determining that the human is positive for the TOI polymorphic variant, optionally wherein the determining comprises that the human has been or is phenotyped as positive for the most frequent TOI variant or genotyped for the nucleotide sequence thereof.
11. The method of paragraph 10, wherein determining comprises assaying for the nucleotide sequence to determine the presence of said allele.
12. The method of paragraph 11, wherein the assaying comprises nucleic acid amplification.

13. The method of paragraph 11 or 12, wherein the assaying comprises hybridization, sequencing, or next generation sequencing.
14. The method of any of paragraphs 11-13, further comprising the step of obtaining a biological sample from the human.
15. The method of any one of paragraphs 9-14, wherein the ligand has been or is determined as being capable of specifically binding to the most frequent TOI variant.
16. The method of any one of paragraphs 9-15, wherein the ligand has been or is determined as being substantially incapable of neutralising or inhibiting said TOI variant.
17. The method of any one of paragraphs 9-16, wherein the ligand is capable of specifically binding to the most frequent TOI variant.
18. The method of any one of paragraphs 9-17, wherein the ligand is capable of specifically binding to two or more different TOI variants, each being encoded by a nucleotide sequence comprising an allele having a cumulative human allele frequency of more than 50%.
19. The method of any preceding paragraph, wherein said TOI polymorphic variant has been or is determined as being present in at least two different human ethnic populations.
20. The method of any preceding paragraph, wherein said cumulative human allele frequency is the frequency in a database of naturally-occurring sequences sampled from at least 15 different human ethnic populations and comprising at least 1000 sequences.
21. The method of any of the preceding paragraphs, wherein the ligand is an antibody, antibody fragment or an affibody.
22. The method of any of the preceding paragraphs, wherein the ligand comprises a nucleotide sequence that specifically hybridises to a TOI nucleotide sequence comprising an allele having a cumulative human allele frequency of less than 50% and/or having a total human genotype frequency of less than 50% or an RNA transcript thereof; and/or the ligand comprises a nucleotide sequence that comprises at least 10 contiguous nucleotides of a nucleotide sequence having a cumulative human allele frequency of less than 50% and/or having a total human genotype frequency of less than 50% or is an antisense sequence thereof.
23. The method of any of the preceding paragraphs, wherein the genome of said human comprises an allele having a cumulative human allele frequency of less than 50% and the allele is found in at least 2 different ethnic populations.
24. A composition comprising a ligand capable of binding a target of interest encoded by a nucleotide sequence comprising an allele having a cumulative human allele frequency of less than 50% and the allele is found in at least 2 different ethnic populations and optionally a pharmaceutically acceptable carrier and optionally a label or instructions for use to treat and/or prevent said disease or condition in a human; optionally wherein the label or instructions comprise a marketing authorisation number issued by a regulatory authority.
25. A kit for treating or preventing a condition or disease mediated by a target of interest as recited in any preceding paragraph, the kit comprising a ligand capable of specifically binding a target of interest encoded by a nucleotide sequence comprising an allele having a cumulative human allele frequency of less than 50% and the allele is found in at least 2 different ethnic populations; and optionally in combination with a label or instructions for use to treat and/or prevent said disease or condition in a human; optionally wherein the label or instructions comprise a marketing authorisation number issued by a regulatory agency; optionally wherein the kit comprises an injection pen or IV container that comprises the ligand.
26. The composition of paragraph 24 or the kit of paragraph 25, wherein the regulatory agency is FDA or EMA.
27. A method of producing an anti-human TOI antibody binding site, the method comprising obtaining a plurality of anti-TOI antibody binding sites, screening the antibody binding sites for binding to a TOI comprising an amino acid sequence encoded by a nucleotide sequence comprising an allele having a cumulative human allele frequency of less than 50% and/or a total human genotype frequency of less than 50%, or to a peptide thereof that comprises an amino acid variation from the corresponding sequence encoded by the TOI-encoding nucleotide sequence comprising an allele having the highest cumulative human allele frequency and/or the highest total human genotype frequency, and isolating an antibody binding site that binds in the screening step.
28. A method of producing an anti-human TOI antibody, the method comprising immunising a non-human vertebrate with a TOI comprising an amino acid sequence encoded by a nucleotide sequence comprising an allele having a cumulative human allele frequency of less than 50% and/or a total human genotype frequency of less than 50%, or to a peptide thereof that comprises an amino acid variation from the corresponding sequence encoded by the TOI-encoding nucleotide sequence comprising an allele having the highest cumulative human allele frequency and/or the highest total human genotype frequency, and isolating an antibody that binds a TOI comprising an amino acid sequence encoded by a TOI nucleotide sequence comprising an allele having a cumulative human allele frequency of less than 50% and/or a total human genotype frequency of less than 50%, and optionally producing a TOI-binding fragment or derivative of the isolated antibody.
29. The method of paragraph 28, wherein the non-human vertebrate is a mouse or a rat.
30. The method of paragraph 29 or 30, comprising the step of obtaining a nucleic acid encoding the antibody, fragment, derivative or binding site and optionally inserting the nucleic acid in an expression vector.
31. A kit for TOI genotyping a human, wherein the kit comprises a nucleic acid comprising a nucleotide sequence that specifically hybridises to a TOI nucleotide sequence selected having a cumulative human allele frequency of less than 50% and/or a total human genotype frequency of less than 50% or an RNA transcript thereof; and/or the nucleic acid comprises a nucleotide sequence that comprises at least 10 contiguous nucleotides of a TOI nucleotide sequence having a cumulative human allele frequency of less than 50% and/or a total human genotype frequency of less than 50% or is an antisense sequence thereof
32. A kit for TOI genotyping or phenotyping a human, wherein the kit comprises a ligand capable of binding a target of interest encoded by a nucleotide sequence comprising an allele having a cumulative human allele frequency of less than 50% or an antibody, fragment or derivative produced by the method of any one of paragraphs 28 to 30.
33. The kit of paragraph 32, wherein the allele is found in at least 2 different ethnic populations.
34. Use of an anti-TOI ligand that specifically binds a human TOI comprising an amino acid sequence encoded by a TOI nucleotide sequence having a cumulative human allele frequency of less than 50% and/or a total human genotype frequency of less than 50%, in the manufacture of a medicament for treating and/or preventing a TOI-mediated disease or condition in a human whose genome comprises a TOI nucleotide sequence having a cumulative human allele frequency of less than 50% and/or having a total human genotype frequency of less than 50%.
35. Use of an anti-TOI ligand that specifically binds a human TOI comprising an amino acid sequence encoded by a TOI nucleotide sequence having a cumulative human allele frequency of less than 50% and/or a total human genotype frequency of less than 50%, in the manufacture of a medicament for targeting said TOI in a human to treat and/or prevent a disease or condition mediated by TOI.
36. A method of targeting a Target of Interest (TOI) for treating and/or preventing a TOI-mediated disease or condition in a human, the method comprising administering an anti-TOI ligand to a human comprising a TOI nucleotide sequence comprising an allele selected as having a cumulative human allele frequency of less than 50% and/or a total human genotype frequency of less than 50%, whereby a TOI encoded by said nucleotide sequence is targeted.
37. The method of paragraph 36, wherein the method comprises targeting a human TOI comprising an amino acid sequence with said ligand to treat and/or prevent said disease or condition in said human, wherein said amino acid sequence is encoded by a nucleotide sequence comprising an allele having a cumulative human allele frequency of less than 50% and/or a total human genotype frequency of less than 50%.
38. A method of Target of Interest (TOI) genotyping a nucleic acid sample of a human, the method comprising assaying in the sample the presence of a TOI nucleotide sequence comprising an allele having a cumulative human allele frequency of less than 50% and/or having a total human genotype frequency of less than 50%.
39. A method of Target of Interest (TOI) typing a protein sample of a human, the method comprising assaying the sample the presence of a TOI amino acid sequence encoded by a TOI nucleotide sequence comprising an allele having a cumulative human allele frequency of less than 50% and/or having a total human genotype frequency of less than 50%.
40. The method of paragraph 38 or 39, comprising obtaining a sample of serum, blood, faeces, hair, urine or saliva from a human, whereby the nucleic acid or protein sample is obtained for use in the step of assaying said sequence.
41. The method of any one of paragraphs 38-40, comprising using a ligand capable of targeting a nucleic acid sequence comprising an allele having a cumulative human allele frequency of less than 50% and/or having a total human genotype frequency of less than 50% or a ligand capable of specifically binding the TOI encoded by said nucleic acid sequence to carry out said identifying step.
42. A diagnostic kit comprising a ligand that is capable of binding a human Target of Interest (TOI) comprising an amino acid sequence encoded by a TOI nucleotide sequence comprising an allele having a cumulative human allele frequency of less than 50% and/or a total human genotype frequency of less than 50% and instructions for carrying out the method of any one of paragraphs 38-41.
43. The diagnostic kit wherein the ligand is selected from an antibody, antibody fragment, antibody portion, affybody, oligonucleotide, modified oligonucleotide, antisense oligonucleotide, siRNA, and microRNA.
44. A diagnostic kit comprising a nucleic acid probe comprising a nucleotide sequence that specifically hybridises a Target of Interest (TOI) nucleotide sequence comprising an allele having a cumulative human allele frequency of less than 50% and/or a total human genotype frequency of less than 50% or an RNA transcript thereof and instructions for carrying out the method of paragraph 38 or 39.
45. The method, ligand, composition, kit or use of any preceding paragraph, wherein the TOI is encoded by a nucleotide sequence having a cumulative human allele frequency from 1 to 10% and/or a total human genotype frequency from 1 to about 15% or from 1 to 15%.
46. The method, ligand, composition, kit or use of any preceding paragraph wherein the TOI is a human TOI selected from Table 5; optionally for treating and/or preventing a corresponding disease or condition as set out in Table 5.
47. A method of treating or preventing a disease or condition in a human, wherein the disease or condition is mediated by a Target of Interest (TOI), wherein the TOI is present in humans as different polymorphic variants, the method comprising administering to the human determined to be positive for the TOI polymorphic variant, wherein the TOI in said human is encoded by a nucleotide sequence comprising an allele having a cumulative human allele frequency of less than 50% and/or wherein the TOI in said human is encoded by a nucleotide sequence comprising an allele having total human genotype frequency of less than 50% an anti-TOI ligand to target the TOI in the human to treat or prevent said disease or condition.
48. The method of paragraph 47, wherein the anti-TOI ligand is selected from an antibody, an antibody portion, an antibody fragment, an affibody, an antisense oligonucleotide, an siRNA, and a microRNA.

Additional Tailoring of Ligands to Genotype and/or Phenotype of the Human Patient As described herein, the present invention contemplates ligands (eg, antibodies and fragments) whose binding site specificities have been matched to one or more variant human TOIs (eg, PCSK9 or IL6R). Additionally or alternatively (and as further illustrated in the non-limiting Examples below), an optional aspect of the invention provides for matching of other features of the ligand to the patient's genotype or phenotype. In this respect, for example, the invention includes the ability to match amino acid sequence variation in a human patient to one or more ligand sequences or domains outside of the binding sites. For example, where the ligand comprises or consists of a human TOI-binding antibody or an anti-human TOI receptor Fc fusion, this aspect of the invention provides for more tailored matching of one or more constant region domains (eg, the Fc) to the patient genotype or phenotype. Additionally or alternatively, it is contemplated that sequence variation in the binding site can be similarly matched to the patient's genotype or phenotype. The present inventor has done this by considering the SNP occurrences in sequences encoding one or more parts of the ligand, eg, SNP occurrences in one, more or all of the gene segments from which the variable domain(s) and/or constant region domain(s) are derived. The inventor realised that it would be desirable to match the ligand to one or more corresponding variant SNPs found in the patient to be treated therapeutically and/or prophylactically. Matching could involve designing the ligand specifically for a patient of known phenotype and/or genotype, or matching could involve choosing a ligand by determining that there is correspondence between variation in the patient's phenotype or genotype with the variation in the ligand amino acid and/or corresponding nucleotides.

A key consideration for the inventor was the desire to promote compatibility of the ligand with the patient's body, and in particular, the possible patient immune system responses to administered ligands. For example, it has been observed that human patients receiving human or humanised antibody drugs may mount an immune response against the incoming antibody (a so-called HAHA response) which results in the patient producing anti-drug antibodies as a result of the patient's immune system recognising the drug as foreign. For example, studies have suggested that some patients receiving HUMIRA™ (adalimumab), currently the biggest selling antibody medicine, mount a HAHA immune response against the medicine, and this may impact treatment adversely. Reference is made to JAMA. 2011; 305(14):1460-1468. doi:10.1001/jama.2011.406: "Development of Antidrug Antibodies Against Adalimumab and Association With Disease Activity and Treatment Failure During Long-term Follow-up", GM Bartelds et al. The authors concluded that results of this study showed that development of antidrug antibodies was associated with a negative outcome of adalimumab treatment in human RA patients. It was reported that not only did patients with anti-adalimumab antibodies discontinue treatment more often and earlier than patients without anti-adalimumab antibodies, they also had a higher disease activity during treatment and only rarely came into remission. In addition, reportedly the data showed that two-thirds of the anti-adalimumab antibody-positive patients developed these antibodies in the first 28 weeks of treatment and that the presence of anti-adalimumab antibodies substantially influenced serum adalimumab concentrations.

This HAHA theme is, therefore, a significant concern and this has been considered by the regulatory authorities. For example, the European Medicines Agency (EMA) has issued a "Guideline on immunogenicity assessment of monoclonal antibodies intended for in vivo clinical use" (available on the world wide web at ema.europa.eu/docs/en_GB/document_library/Scientific_guideline/2012/06/WC500128688.pdf; EMA/CHMP/BMWP/86289/2010, addendum to EMEA/CHMP/BMWP/14327/2006), which came into force on 1$^{st}$ December 2012. As such, it is good practice for researchers to identify and assess risk of anti-antibody drug occurrence and effects.

The present aspect of the invention, by more closely tailoring the ligand itself (as well as its specificity) to the patient, helps to address these considerations when designing and administering anti-human TOI medicines for treating and/or preventing human TOI-related diseases and conditions.

The inventor also considered the desirability to tailor the variation in the ligand constant region (eg, for an antibody or Fc-containing ligand), mindful that then the constant region being administered to the patient would be tuned to the various components, such as patient's Fc receptors, that would interact with the constant region in the patient. Good Fc/Fc receptor interactions can be important for drug recycling (via the FcRn) to provide for useful half-lives in vivo or for use in cell killing, eg, for cancer indications. In this way it is possible, therefore, to tune the effector function of the constant region (eg, Fc) to the patient more closely, to promote efficacy. For example, more efficacious drugs are desirable for better patient treatment and may provide the possibility of lowered dosing and/or dosing frequencies.

Thus, in examples of this aspect, the invention provides the following (set out as clauses):—

1. The ligand, method, use, kit or composition of the invention, wherein
    (i) the ligand (eg, antibody or fragment) comprises
        (c) a variable domain that is encoded by a human V region nucleotide sequence, wherein the V nucleotide sequence is derived from recombination of human VH, D and JH gene segments or human VL and JL gene segments; or
        (d) a constant region domain encoded by a C region gene segment;
        Wherein a first gene segment of said gene segments of (a), or said C region gene segment of (b) comprises a first single nucleotide polymorphism (SNP) encoding a first amino acid polymorphism; and
        (ii) the genome of said human comprises said first SNP or wherein said human expresses (a') an antibody variable domain comprising said first amino acid polymorphism or (b') an antibody constant domain comprising said first amino acid polymorphism.

2. The ligand, method, use, kit or composition of clause 1, wherein blood of said human comprises substantially no antibodies that specifically bind to the domain comprising said first amino acid polymorphism as determined in an in vitro binding assay.

3. The ligand, method, use, kit or composition of clause 2, wherein SPR is used to carry out said assay.
    In an alternative, ELISA is used.

4. The ligand, method, use, kit or composition of any one of clauses 1 to 3, wherein the genome of said human comprises said first gene segment (when (a) applies) or said C region gene segment (when (b) applies).

5. The ligand, method, use, kit or composition of any one of clauses 1 to 4, wherein said first segment or a second segment of said segments of (a), or said C region gene segment of (b), comprises a second SNP encoding a second amino acid polymorphism; and wherein the genome of said human comprises said second SNP or wherein said human expresses (a'') an antibody variable domain comprising said second amino acid polymorphism or (b'') an antibody constant region domain comprising said first and second amino acid polymorphisms.

6. The ligand, method, use, kit or composition of clause 5, wherein said human expresses an antibody variable domain comprising said first and second amino acid polymorphisms.

7. The ligand, method, use, kit or composition of clause 5 or 6, wherein the first and second SNPs of said genome are comprised by the same antibody gene segment.
    For example, the first and second SNPs of the genome are comprised by an IGHG1*01 gene segment and said first segment of (a) is an IGHG1*01 gene segment.
    For example, the first and second SNPs of the genome are comprised by an IGHG2*01 gene segment and said first segment of (a) is an IGHG2*01 gene segment.

8. The ligand, method, use, kit or composition of any one of clauses 1 to 7, wherein each SNP is a variable region gene segment SNP.

9. The ligand, method, use, kit or composition of any one of clauses 1 to 7, wherein each SNP is a constant region gene segment SNP, eg each SNP is a gamma-1 constant region gene segment SNP, or a gamma-2 constant region gene segment SNP, or a gamma-3 constant region gene segment SNP or a gamma-4 constant region gene segment SNP.

10. The ligand, method, use, kit or composition of clause 9, wherein the first SNP is a CH1, CH2, CH3 or CH4 gene segment SNP and/or the second SNP is a CH1, CH2, CH3 or CH4 gene segment SNP.

11. The ligand, method, use, kit or composition of any one of clauses 1 to 8, wherein each SNP is a variable domain SNP, eg, a VH domain SNP, or a Vκ domain SNP, or a Vλ SNP.

12. The ligand, method, use, kit or composition of any one of clauses 1 to 11, wherein said constant region domain of (b) is comprised by an antibody Fc region.

13. The ligand, method, use, kit or composition of any one of clauses 1 to 12, wherein the ligand (eg, antibody or fragment) has been determined to specifically bind one or more human TOI variants as disclosed herein, for example, with a KD of 1 nM or less (eg, 100 or 10 pM or less) as determined by SPR.
14. The ligand, method, use, kit or composition of the invention (eg, according to any one of clauses 1 to 13), wherein the ligand comprises or consists of an antibody or fragment that comprises a human antibody variable domain derived from the recombination of a human V gene segment and a human J gene segment (and optionally a human D gene segment when the variable domains are VH domains); and wherein the genome of the human comprises said human V gene segment and/or the human expresses antibodies comprising antibody variable domains derived from the recombination of said human V gene segment and a human J gene segment (and optionally a human D gene segment).
   In an example, the V gene segment is any of the V gene segments disclosed in WO2013041844, a 1000 Genomes database and/or www.imgt.org, the disclosures of which (including disclosure relating to sequence) is explicitly incorporated herein by reference for use in the present invention.
15. The ligand, method, use, kit or composition of the invention (eg, according to any one of clauses 1 to 14), wherein the ligand (eg, comprising or consisting of an antibody or fragment or an Fc-fused human TOI receptor) comprises a human heavy chain constant domain encoded by a first constant region nucleotide sequence; and wherein the genome of the human comprises a heavy chain constant region nucleotide sequence that is identical to said first constant region nucleotide sequence and/or the human expresses antibodies comprising said human constant domain.
16. The ligand, method, use, kit or composition of the invention (eg, according to any one of clauses 1 to 15), wherein the ligand (eg, comprising or consisting of an antibody or fragment or an Fc-fused human TOI receptor) comprises a human gamma heavy chain CH1 domain encoded by a CH1 nucleotide sequence; and wherein the genome of the human comprises a gamma heavy chain constant region nucleotide sequence that is identical to said CH1 nucleotide sequence and/or the human expresses antibodies comprising said human gamma CH1 domain.
17. The ligand, method, use, kit or composition of the invention (eg, according to any one of clauses 1 to 16), wherein the ligand (eg, comprising or consisting of an antibody or fragment or an Fc-fused human TOI receptor) comprises a human gamma heavy chain CH2 domain encoded by a CH2 nucleotide sequence; and wherein the genome of the human comprises a gamma heavy chain constant region nucleotide sequence that is identical to said CH2 nucleotide sequence and/or the human expresses antibodies comprising said human gamma CH2 domain.
18. The ligand, method, use, kit or composition of the invention (eg, according to any one of clauses 1 to 17), wherein the ligand (eg, comprising or consisting of an antibody or fragment or an Fc-fused human TOI receptor) comprises a human gamma heavy chain CH3 domain encoded by a CH3 nucleotide sequence; and wherein the genome of the human comprises a gamma heavy chain constant region nucleotide sequence that is identical to said CH3 nucleotide sequence and/or the human expresses antibodies comprising said human gamma CH3 domain.
19. The ligand, method, use, kit or composition of the invention (eg, according to any one of clauses 1 to 18), wherein the ligand (eg, comprising or consisting of an antibody or fragment or an Fc-fused human TOI receptor) comprises a human gamma heavy chain CH4 domain encoded by a CH4 nucleotide sequence; and wherein the genome of the human comprises a gamma heavy chain constant region nucleotide sequence that is identical to said CH4 nucleotide sequence and/or the human expresses antibodies comprising said human gamma CH4 domain.
20. The ligand, method, use, kit or composition of the invention (eg, according to any one of clauses 1 to 19), wherein the ligand (eg, comprising or consisting of an antibody or fragment or an Fc-fused human TOI receptor) comprises a human gamma heavy chain Fc region encoded by a Fc nucleotide sequence; and wherein the genome of the human comprises a gamma heavy chain constant region nucleotide sequence that is identical to said Fc nucleotide sequence and/or the human expresses antibodies comprising said human gamma Fc region.
21. The ligand, method, use, kit or composition of any one of clauses 16 to 20, wherein said human gamma heavy chain is a human gamma-1 heavy chain
22. The ligand, method, use, kit or composition of any one of clauses 16 to 20, wherein said human gamma heavy chain is a human gamma-2 heavy chain
23. The ligand, method, use, kit or composition of any one of clauses 16 to 20, wherein ligand comprises a human IGHG1*01 gamma-1 heavy chain constant region.
24. The ligand, method, use, kit or composition of any one of clauses 16 to 20, wherein ligand comprises a human IGHG2*01 gamma-1 heavy chain constant region.
25. The ligand, method, use, kit or composition of any one of clauses 15 to 24, wherein the human has been or is genotyped as positive for said heavy chain constant region nucleotide sequence.
26. The ligand, method, use, kit or composition of clause 23, wherein the human has been or is genotyped as positive for human IGHG1*01 nucleotide sequence.
27. The ligand, method, use, kit or composition of clause 24, wherein the human has been or is genotyped as positive for human IGHG2*01 nucleotide sequence.
28. The ligand, method, use, kit or composition of any one of clauses 16 to 24, wherein the human has been or is phenotyped as positive for said gamma heavy chain constant domain, CH1, CH2, CH3, CH4 or Fc.
29. The ligand, method, use, kit or composition of clause 28, (i) when dependent from clause 23, wherein the human has been or is phenotyped as positive for a human IGHG1*01 gamma heavy chain constant domain, CH1, CH2, CH3, CH4 or Fc or (ii) when dependent from clause 24, wherein the human has been phenotyped as positive for a human IGHG2*01 gamma heavy chain constant domain, CH1, CH2, CH3, CH4 or Fc.
30. The method or use of any one of clauses 16 to 24 and 26 to 29, comprising genotyping the human as positive for said gamma heavy chain constant region nucleotide sequence, eg, positive for said gamma heavy chain constant domain, CH1, CH2, CH3, CH4 or Fc nucleotide sequence; positive for said human IGHG1*01 gamma heavy chain constant region, CH1, CH2, CH3, CH4 or Fc nucleotide sequence; or positive for said human IGHG2*01 gamma heavy chain constant region, CH1, CH2, CH3, CH4 or Fc nucleotide sequence.
31. The method or use of any one of clauses 16 to 24 and 26 to 30, comprising phenotyping the human as positive for said gamma heavy chain constant region, eg, positive for said gamma heavy chain constant domain, CH1, CH2, CH3, CH4 or Fc; positive for said human IGHG1*01 gamma heavy chain constant domain, CH1, CH2, CH3, CH4 or Fc; or positive for said human IGHG2*01 gamma heavy chain constant domain, CH1, CH2, CH3, CH4 or Fc.

Examples of Tailored Ligands

The inventor analysed amino acid variability and distribution amongst large representative human samples. The result of the analysis for example antibody gene segments is shown in Table 9.

In a first example, the inventor identified the possibility of addressing the rarer IGH-gamma-1 SNPs 204D (observed cumulative frequency of 0.296) and 206L (observed cumulative frequency of 0.283) individually or in combination. These residues are part of the CH3 domain, and as such they form part of antibody Fc regions. Thus, matching of these CH3 variations with the patient is especially beneficial for reasons as discussed above. Thus, this example provides aspects set out in the following clauses.

32. The ligand, method, use, kit or composition of the invention (eg, according to any one of clauses 1 to 31), wherein the ligand (eg, comprising or consisting of an antibody or fragment or an Fc-fused TOI receptor) comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu.

The skilled person will be familiar with techniques for determining genome sequences of a human, eg, by using a sample containing genomic DNA and/or RNA, sequencing and comparing using bioinformatics or other computer tools to compare the sampled sequence with sequences of human alleles (eg, as shown in the IMGT, 100 genomes or other database as disclosed herein). In an example, the sample is a blood or saliva or cheek swab sample.

33. The ligand, method, use, kit or composition of clause 32, wherein the ligand comprises a human gamma-1 heavy chain constant region that comprises an Asp corresponding to position 204 of SEQ ID NO: 42 and a Leu corresponding to position 206 of SEQ ID NO: 42.

34. The ligand, method, use, kit or composition of clause 32 or 33, wherein the genome of the human comprises a gamma-1 heavy chain constant region nucleotide sequence that encodes such an Asp and Leu or the human expresses antibodies comprising human gamma-1 constant regions comprising such an Asp and Leu.

35. The ligand, method, use, kit or composition of clause 32, 33 or 34, wherein the ligand comprises a human IGHG1*01 gamma-1 heavy chain constant region, eg, an Fc, CH1, CH2 and/or CH3 domain encoded by human IGHG1*01.

36. The ligand, method, use, kit or composition of any one of clauses 32 to 35, wherein the genome of the human comprises a human IGHG1*01 nucleotide sequence or the human expresses antibodies comprising human constant domains encoded by a human IGHG1*01 nucleotide sequence.

37. The ligand, method, use, kit or composition of any one of clauses 32 to 36, wherein the ligand comprises a hinge region encoded by human IGHG1*01.

38. The ligand, method, use, kit or composition of any one of clauses 32 to 37, wherein the ligand comprises or consists of an antibody, wherein the antibody comprises heavy chains that comprise SEQ ID NO: 61.

39. The ligand, method, use, kit or composition of any one of clauses 32 to 38, wherein the human is of European ancestry.

As shown in Table 9, 204D and 206L are found in such humans.

40. The ligand, method, use, kit or composition of any one of clauses 32 to 39, wherein the human has been or is genotyped as positive for said Asp and/or Leu.

41. The ligand, method, use, kit or composition of any one of clauses 32 to 40, wherein the human has been or is genotyped as positive for human IGHG1*01.

42. The ligand, method, use, kit or composition of any one of clauses 32 to 41, wherein the human has been or is phenotyped as positive for a human IGHG1*01 CH3.

43. The method or use of any one of clauses 32 to 42, comprising selecting a said human whose genome comprises a codon(s) encoding said Asp and/or Leu; comprises human IGHG1*01; or comprises a human IGHG1*01 CH3.

44. The method or use of any one of clauses 32 to 43, comprising selecting a said human whose phenotype comprises said Asp and/or Leu; a human IGHG1*01 region; or a human IGHG1*01 CH3.

44a. The ligand, method, use, kit or composition of any one of clauses 32 to 44, wherein the human expresses antibodies comprising human gamma-1 constant regions comprising such an Asp and Leu.

In a second example, the inventor identified the possibility of addressing IGH-gamma-2 SNPs. This included consideration of Fc region variation—in this respect, the inventor focused on positions 161 and 257 which are in the Fc region. Thus, this example provides aspects set out in the following clauses.

45. The ligand, method, use, kit or composition of the invention (eg, according to any one of clauses 1 to 31), wherein the ligand (eg, comprising or consisting of an antibody or fragment or an Fc-fused TOI receptor) comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid.

46. The ligand, method, use, kit or composition of clause 45, wherein the ligand comprises a human gamma-2 heavy chain constant region that comprises (i) a Pro corresponding to position 72 of SEQ ID NO: 44, an Asn corresponding to position 75 of SEQ ID NO: 44, a Phe corresponding to position 76 of SEQ ID NO: 44 and optionally (ii) a Val corresponding to position 161 of SEQ ID NO: 44 and/or an Ala corresponding to position 257 of SEQ ID NO: 44; and wherein the genome of the human comprises a gamma-2 heavy chain constant region nucleotide sequence that encodes such amino acids of (i) or the human expresses antibodies comprising human gamma-2 constant regions comprising such amino acids of (i).

This example focuses on CH1 variation.

47. The ligand, method, use, kit or composition of clause 45 or 46, wherein the ligand comprises a human gamma-2 heavy chain constant region that comprises (i) a Val corresponding to position 161 of SEQ ID NO: 44 and an Ala corresponding to position 257 of SEQ ID NO: 44 and optionally (ii) an amino acid selected from the group consisting of a Pro corresponding to position 72 of SEQ ID NO: 44, an Asn corresponding to position 75 of SEQ ID NO: 44 and a Phe corresponding to position 76 of SEQ ID NO: 44; and wherein the genome of the human comprises a gamma-2 heavy chain constant region nucleotide sequence that encodes such amino acids of (i) or the human expresses antibodies comprising human gamma-2 constant regions comprising such amino acids of (i).

This example focuses on Fc variation.

48. The ligand, method, use, kit or composition of any one of clauses 45 to 47, wherein the ligand comprises a human IGHG2*01 gamma-2 heavy chain constant region, eg, an Fc, CH1, CH2 and/or CH3 domain encoded by human IGHG2*01.

49. The ligand, method, use, kit or composition of any one of clauses 45 to 48, wherein the genome of the human comprises a human IGHG2*01 nucleotide sequence or the human expresses antibodies comprising human constant domains encoded by a human IGHG2*01 nucleotide sequence.

50. The ligand, method, use, kit or composition of any one of clauses 45 to 49, wherein the ligand comprises a hinge region encoded by human IGHG2*01.

51. The ligand, method, use, kit or composition of any one of clauses 45 to 50, wherein the ligand comprises or consists of an antibody, wherein the antibody comprises heavy chains that comprise SEQ ID NO: 63 or 65.

52. The ligand, method, use, kit or composition of any one of clauses 45 to 51, wherein the human is of European, African American, or European American ancestry.

53. The ligand, method, use, kit or composition of any one of clauses 45 to 52, wherein the human has been or is genotyped as positive for one, more or all of said Pro, Asn, Phe, Val and Ala.

54. The ligand, method, use, kit or composition of any one of clauses 45 to 53, wherein the human has been or is genotyped as positive for human IGHG2*01.

55. The ligand, method, use, kit or composition of any one of clauses 45 to 54, wherein the human has been or is phenotyped as positive for a human IGHG2*01 CH1.

56. The ligand, method, use, kit or composition of any one of clauses 45 to 55, wherein the human has been or is phenotyped as positive for a human IGHG2*01 CH2.

57. The ligand, method, use, kit or composition of any one of clauses 45 to 56, wherein the human has been or is phenotyped as positive for a human IGHG2*01 CH3.

58. The method or use of any one of clauses 45 to 57, comprising selecting a said human whose genome comprises a codon(s) encoding one, more or all of said Pro, Asn, Phe, Val and Ala; comprises human IGHG2*01; or comprises a human IGHG2*01 CH1, CH2 and/or CH3.

59. The method or use of any one of clauses 45 to 58, comprising selecting a said human whose phenotype comprises one, more or all of said Pro, Asn, Phe, Val and Ala; a human IGHG2*01 region; or a human IGHG2*01 CH1, CH2 and/or CH3.

60. The ligand, method, use, kit or composition of any one of clauses 45 to 59, wherein the human expresses antibodies comprising human gamma-2 constant regions comprising such a Pro, Asn, Phe, Val and Ala.

In a third example, the inventor addressed human kappa constant region variation. Thus, the present aspect of the invention also provides the following.

61. The ligand, method, use, kit or composition of the invention (eg, according to any one of clauses 1 to 60), wherein the ligand (eg, comprising or consisting of an antibody or fragment or an Fc-fused TOI receptor) comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys.

62. The ligand, method, use, kit or composition of clause 61, wherein the ligand comprises a human kappa light chain constant region that comprises a Val corresponding to position 84 of SEQ ID NO: 50 and a Cys corresponding to position 87 of SEQ ID NO: 50.

63. The ligand, method, use, kit or composition of clause 61 or 62, wherein the genome of the human comprises a kappa light chain constant region nucleotide sequence that encodes such a Val and Cys or the human expresses antibodies comprising human kappa constant regions comprising such a Val and Cys.

64. The ligand, method, use, kit or composition of any one of clauses 61 to 63, wherein the antibody or fragment comprises a human IGKC*01 kappa light chain constant region.

65. The ligand, method, use, kit or composition of any one of clauses 61 to 64, wherein the ligand comprises or consists of an antibody, wherein the antibody comprises light chains that comprise SEQ ID NO: 62 or 66.

66. The ligand, method, use, kit or composition of any one of clauses 61 to 65, wherein the ligand comprises or consists of an antibody, wherein the antibody comprises a light chain variable domain derived from recombination of a human Vκ gene segment and a human Jκ gene segment, wherein the Jκ gene segment is IGKJ2*01 (SEQ ID NO: 57).

67. The ligand, method, use, kit or composition of any one of clauses 61 to 66, wherein the human has been or is phenotyped as positive for said Val and/or Cys.

68. The ligand, method, use, kit or composition of any one of clauses 61 to 67, wherein the human has been or is genotyped as positive for human IGKC*01.

69. The ligand, method, use, kit or composition of any one of clauses 61 to 68, wherein the human has been or is phenotyped as positive for a human IGKC*01 domain.

70. The method or use of any one of clauses 61 to 69, comprising selecting a said human whose genome comprises a codon(s) encoding said Val and/or Cys; or comprises human IGKC*01.

71. The method or use of any one of clauses 61 to 70, comprising selecting a said human whose phenotype comprises such a Val and/or Cys; or comprises a human IGKC*01 domain.

72. The ligand, method, use, kit or composition of any one of clauses 61 to 71, wherein the human expresses antibodies comprising human kappa constant domains comprising such a Val and Cys, eg, expresses human IGKC*01 constant domains.

In a fourth example, the inventor addressed human lambda constant region variation. Thus, this example provides aspects set out in the following clauses.

73. The ligand, method, use, kit or composition of the invention (eg, according to any one of clauses 1 to 60), wherein the ligand (eg, comprising or consisting of an antibody or fragment or an Fc-fused TOI receptor) comprises a human IGLC2*01 light chain constant region; and wherein the genome of the human comprises a human IGLC2*01 nucleotide sequence or the human expresses antibodies comprising human light chain IGLC2*01 constant regions.

74. The ligand, method, use, kit or composition of clause 73, wherein the antibody comprises light chains that comprise SEQ ID NO: 64.
75. The ligand, method, use, kit or composition of clause 73 or 74, wherein the human has been or is genotyped as positive for human IGLC2*01.
76. The ligand, method, use, kit or composition of any one of clauses 73 to 75, wherein the human has been or is phenotyped as positive for a human IGLC2*01 domain.
77. The method or use of any one of clauses 73 to 76, comprising selecting a said human whose genome comprises human IGLC2*01.
78. The method or use of any one of clauses 73 to 77, comprising selecting a said human whose phenotype comprises a human IGLC2*01 domain.
79. The ligand, method, use, kit or composition of any one of clauses 73 to 78, wherein the human expresses antibodies comprising human lambda IGLC2*01 constant domains.

In a fifth example, the inventor addressed human heavy chain variable region variation. Thus, this example provides aspects set out in the following clauses.

80. The ligand, method, use, kit or composition of the invention (eg, according to any one of clauses 1 to 79), wherein the ligand comprises or consists of an antibody or fragment, wherein the antibody or fragment comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV1-46*01.
81. The ligand, method, use, kit or composition of clause 80, wherein the antibody or fragment comprises a one more or all of a CH1 domain, CH2 domain, CH3 domain, hinge or Fc encoded by human IGHG2*01.
82. The ligand, method, use, kit or composition of clause 80 or 81, wherein the antibody or fragment comprises heavy chains that comprise SEQ ID NO: 63 or 65.
83. The ligand, method, use, kit or composition of any one of clauses 80 to 82, wherein the human has been or is genotyped as positive for said selected VH gene segment, positive for human IGHV1-18*01 or IGVH1-46*01.
84. The method or use of any of clauses 80 to 83, comprising genotyping the human as positive for said selected VH gene segment, eg, positive for human IGHV1-18*01 or IGVH1-46*01.

In a sixth example, the inventor addressed human light chain variable region variation. Thus, this example provides aspects set out in the following clauses.

85. The ligand, method, use, kit or composition of the invention (eg, according to any one of clauses 1 to 84), wherein the ligand comprises or consists of an antibody or fragment, wherein the antibody or fragment comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.
86. The ligand, method, use, kit or composition of clause 85, wherein the antibody comprises light chains that comprise SEQ ID NO: 62, 64 or 66.
87. The ligand, method, use, kit or composition of clause 85 or 86, wherein the antibody or fragment comprises a light chain variable domain derived from recombination of a human Vκ gene segment and a human Jκ gene segment, wherein the Jκ gene segment is IGKJ2*01 (SEQ ID NO: 57; wherein (i) or (iii) applies.
88. The ligand, method, use, kit or composition of any one of clauses 85 to 87, wherein the human has been or is genotyped as positive for said selected VL gene segment, eg, positive for human IGKV4-1*01, IGLV2-14*01 or IGKV1-13*02.
89. The method or use of clause 88, comprising genotyping the human as positive for said selected VL gene segment, eg, genotyping the human as positive for human IGKV4-1*01, IGLV2-14*01 or IGKV1-13*02.
90. The ligand, method, use, kit or composition of any one of clauses 1 to 89, wherein the ligand (eg, antibody or fragment) binds said human TOI with a dissociation constant (Kd) of 1 nM or less as determined by SPR, (eg, 100, 10 or 1 pM or less).

EXAMPLES

Example 1

Rare PCSK9 Variants

Proprotein convertase subtilisin kexin type 9 (PCSK9) is a serine protease involved in regulating the levels of the low density lipoprotein receptor (LDLR) protein (Horton et al., 2007; Seidah and Prat, 2007). In vitro experiments have shown that adding PCSK9 to HepG2 cells lowers the levels of cell surface LDLR (Benjannet et al., 2004; Lagace et al., 2006; Maxwell et al., 2005; Park et al., 2004). Experiments with mice have shown that increasing PCSK9 protein levels decreases levels of LDLR protein in the liver (Benjannet et al., 2004; Lagace et al., 2006; Maxwell et al., 2005; Park et al., 2004), while PCSK9 knockout mice have increased levels of LDLR in the liver (Rashid et al., 2005). Additionally, various human PCSK9 mutations that result in either increased or decreased levels of plasma LDL have been identified (Kotowski et al., 2006; Zhao et al., 2006). PCSK9 has been shown to directly interact with the LDLR protein, be endocytosed along with the LDLR, and co-immunofluoresce with the LDLR throughout the endosomal pathway (Lagace et al., 2006).

PCSK9 is a prohormone-proprotein convertase in the subtilisin (S8) family of serine proteases (Seidah et al., 2003). Humans have nine prohormone-proprotein convertases that can be divided between the S8A and S8B subfamilies (Rawlings et al., 2006). Furin, PC1/PC3, PC2, PACE4, PC4, PC5/PC6 and PC7/PC8/LPC/SPC7 are classified in subfamily S8B. Crystal and NMR structures of different domains from mouse furin and PC1 reveal subtilisin-like pro- and catalytic domains, and a P domain directly C-terminal to the catalytic domain (Henrich et al., 2003; Tangrea et al., 2002). Based on the amino acid sequence similarity within this subfamily, all seven members are predicted to have similar structures (Henrich et al., 2005). SKI-1/S1P and PCSK9 are classified in subfamily S8A. Sequence comparisons with these proteins also suggest the presence of subtilisin-like pro- and catalytic domains (Sakai et al., 1998; Seidah et al., 2003; Seidah et al., 1999). In these proteins the amino acid sequence C-terminal to the catalytic domain is more variable and does not suggest the presence of a P domain.

Prohormone-proprotein convertases are expressed as zymogens and they mature through a multi step process. The function of the pro-domain in this process is two-fold. The pro-domain first acts as a chaperone and is required for proper folding of the catalytic domain (Ikemura et al., 1987). Once the catalytic domain is folded, autocatalysis occurs between the pro-domain and catalytic domain. Following this initial cleavage reaction, the pro-domain remains bound to the catalytic domain where it then acts as an inhibitor of catalytic activity (Fu et al., 2000). When conditions are correct, maturation proceeds with a second autocatalytic event at a site within the pro-domain (Anderson et al., 1997). After this second cleavage event occurs the pro-domain and catalytic domain dissociate, giving rise to an active protease.

Autocatalysis of the PCSK9 zymogen occurs between Gln152 and Ser153 (VFAQ|SIP (SEQ ID NO: 67)) (Naureckiene et al., 2003), and has been shown to be required for its secretion from cells (Seidah et al., 2003). A second autocatalytic event at a site within PCSK9's pro-domain has not been observed. Purified PCSK9 is made up of two species that can be separated by non-reducing SDS-PAGE; the pro-domain at 17 Kd, and the catalytic plus C-terminal domains at 65 Kd. PCSK9 has not been isolated without its inhibitory pro-domain, and measurements of PCSK9's catalytic activity have been variable (Naureckiene et al., 2003; Seidah et al., 2003).

In certain embodiments, a PCSK9 polypeptide includes terminal residues, such as, but not limited to, leader sequence residues, targeting residues, amino terminal methionine residues, lysine residues, tag residues and/or fusion protein residues. "PCSK9" has also been referred to as FH3, NARC1, HCHOLA3, proprotein convertase subtilisin/kexin type 9, and neural apoptosis regulated convertase 1. The PCSK9 gene encodes a proprotein convertase protein that belongs to the proteinase K subfamily of the secretory subtilase family. The term "PCSK9" denotes both the proprotein and the product generated following autocatalysis of the proprotein. When only the autocatalyzed product is being referred to (such as for an antigen binding protein or ligand that binds to the cleaved PCSK9), the protein can be referred to as the "mature," "cleaved", "processed" or "active" PCSK9. When only the inactive form is being referred to, the protein can be referred to as the "inactive", "pro-form", or "unprocessed" form of PCSK9. The term PCSK9 also encompasses PCSK9 molecules incorporating post-translational modifications of the PCSK9 amino acid sequence, such as PCSK9 sequences that have been glycosylated, PCSK9 sequences from which its signal sequence has been cleaved, PCSK9 sequence from which its pro domain has been cleaved from the catalytic domain but not separated from the catalytic domain (see, e.g., FIGS. 1A and 1B of US20120093818A1; which is incorporated by reference herein in its entirety).

The present invention provides anti-PCSK9 ligands; and PCSK9-binding or targeting ligands as described herein. The ligands have a variety of utilities. Some of the ligands, for instance, are useful in specific binding assays, for genotyping or phenotyping humans, affinity purification of PCSK9, in particular human PCSK9 or its ligands and in screening assays to identify other antagonists of PCSK9 activity. Some of the ligands of the invention are useful for inhibiting binding of PCSK9 to LDLR, or inhibiting PCSK9-mediated activities.

Anti-PCSK9 ligands (eg, antibodies and anti-sense RNA) have been developed based on targeting and neutralising so-called "wild-type" human PCSK9, which is a commonly-occurring form (see, eg, US20120093818A1 and US20110065902A1; each of which is incorporated by reference herein in its entirety). While such therapies are useful for human patients harbouring this form of human PCSK9, the inventor considered it useful to investigate the possibility of targeting much rarer—but still naturally-occurring—forms of PCSK9 amongst human populations. In this way, the inventor arrived at insight into the natural occurrences and distributions of rarer human PCSK9 forms that can serve as useful targets (at the protein or nucleic acid level) for human treatment, prophylaxis and diagnosis pertinent to diseases and conditions mediated or associated with PCSK9 activity. This particularly provides for tailored therapies, prophylaxis and diagnosis in humans that are devoid of the common PCSK9 gene or protein (ie, the form a or a' as used in US20120093818A1 and US20110065902A1 to generate antibodies).

The skilled person will know that SNPs or other changes that translate into amino acid variation can cause variability in activity and/or conformation of human targets to be addressed. This has spawned great interest in personalized medicine where genotyping and knowledge of protein and nucleotide variability is used to more effectively tailor medicines and diagnosis of patients. The invention, therefore, provides for tailored pharmaceuticals and testing that specifically addresses rarer PCSK9 polymorphic variant forms. Such forms or "alleles" (at the nucleotide level), in many of the examples determined by the inventor, comprise multiple changes at the nucleotide and amino acid levels from the corresponding common form nucleotide and amino acids sequences, ie, there are multiple non-synonymous changes at the nucleotide level that translate into multiple corresponding changes in the protein target in humans.

Furthermore, the inventor surprisingly realised that the rarer natural forms, although present in humans at much lower frequencies than the common form, nevertheless are represented in multiple and ethnically-diverse human populations and usually with many human examples per represented ethnic population. Thus, the inventor realised that targeting such rarer forms would provide for effective treatment, prophylaxis or diagnosis across many human ethnic populations, thereby extending the utility of the present invention.

With this realisation, the inventor realised that there is significant industrial and medical application for the invention in terms of guiding the choice of anti-PCSK9 ligand for administration to human patients for therapy and/or prophylaxis of PCSK9-mediated or associated diseases or conditions. In this way, the patient receives drugs and ligands that are tailored to their needs—as determined by the patient's genetic or phenotypic makeup. Hand-in-hand with this, the invention provides for the genotyping and/or phenotyping of patients in connection with such treatment, thereby allowing a proper match of drug to patient. This increases the chances of medical efficacy, reduces the likelihood of inferior treatment using drugs or ligands that are not matched to the patient (eg, poor efficacy and/or side-effects) and avoids pharmaceutical mis-prescription and waste.

In developing this thinking, the present inventor decided to determine a set of human PCSK9 variants on the basis of the following criteria, these being criteria that the inventor realised would provide for useful medical drugs and diagnostics to tailored need in the human population. The inventor selected variants having at least 3 of the 4 following criteria:—

PCSK9 variants having a cumulative human allele frequency in the range from 1 to 10%;

PCSK9 variants having a total human genotype frequency in the range from 1 to about 15%;

PCSK9 variants found in many different human ethnic populations (using the standard categorisation of the 1000 Genomes Project, which is an accepted standard in the art; see Table 4 below); and PCSK9 variants found in many individuals distributed across such many different ethnic populations.

On the basis of these criteria, the inventor identified the variants listed in Table 1 below (excluding form a).

The inventor's selection included, as a consideration, selection for nucleotide variation that produced amino acid variation in corresponding PCSK9 forms (ie, non-synonymous variations), as opposed to silent variations that do not alter amino acid residues in the target protein.

TABLE 1

Human PCSK9 variants distributed over several human ethnic populations & having a total human genotype frequency in the range of 1 to about 15%

(a) Amino acid variability, population distributions and frequencies

| Variant Form | Amino Acid Position & Variation | | | | | | | Human Populations | No. Individs[1] | No. Unique Pops[2] | Het Freq[3] | Hom Freq[4] (Het + Hom freq[5]) | Cum Freq[6] |
|---|---|---|---|---|---|---|---|---|---|---|---|---|---|
| Form a | 46R | 53A | 425N | 443A | 474I | 619Q | 670E | ASW, YRI, GBR, TSI, CLM, CHB, LWK, CHS, MXL, JPT, PUR, IBS, FIN, CEU | 939 | 14 | 0.3951 | 0.4506 (0.8457) | 0.64815 |
| | 46L | 53V | 425S | 443T | 474V | 619P | 670G | | | | | | |
| f | | | | | x | | | ASW, YRI, GBR, TSI, CLM, LWK, MXL, JPT, PUR, IBS, FIN, CEU | 180 | 12 | 0.153 | 0.009 (0.162) | 0.0855 |
| c | | | | | | | x | ASW, YRI, GBR, TSI, CLM, CHB, LWK, CHS, JPT, PUR, FIN, CEU | 153 | 12 | 0.1296 | 0.0081 (0.1377) | 0.0729 |
| r | | | | | x | x | | | | | 0.0234 | 0.009 (0.0324) | 0.0292 |
| p | | x | | | x | | | ASW, GBR, TSI, CLM, JPT, PUR, IBS, FIN, CEU | 49 | 9 | 0.0441 | (0.0441) | 0.0221 |
| m | | | | x | | | | LWK, ASW, YRI, CLM | 29 | 4 | 0.0225 | (0.0225) | 0.0149 |
| e | | | x | | x | | | LWK, ASW, YRI | 15 | 3 | 0.0135 | (0.0135) | 0.0068 |
| h | | | | x | | x | | LWK, ASW, YRI | 10 | 3 | 0.009 | (0.009) | 0.0045 |
| aj | X | | | | x | | | PUR, TSI, FIN, CEU | 9 | 4 | 0.0081 | (0.0081) | 0.0041 |
| q | | x | | | | | x | CHS, ASW, JPT, PUR, CHB | 7 | 5 | 0.0063 | (0.0063) | 0.0032 |

Table Footnotes:

"x" in a box indicates that the amino acid for the variant form is different from the amino acid at that position in form a, the variant amino acid being shown in "Amino Acid Position & Variation" of the table and the form a amino acid being shown in the first row of the table; amino acids at all other positions of each variant form are identical to those found in form a.

Amino acid numbering is per the numbering shown for the pro-form in Table 2 below.

[1]Number of individuals in 1000 Genomes database found to have the allele;

[2]Number of unique human ethnic populations in 1000 Genomes database in which the allele was found to occur;

[3]Heterozygous human genotype frequency, ie, cumulative frequency of all genotypes having one occurrence of the variant allele and one occurrence of another allele (heterozygous state), eg, ac genotype in 1000 Genomes database;

[4]Homozygous human genotype frequency, ie, cumulative frequency of two occurrences of the variant allele (homozygous state), eg, cc genotype in 1000 Genomes database; and

[5]Total human genotype frequency, ie, total of heterozygous plus homozygous human genotype frequencies.

[6]Cumulative human allele frequency of all occurrences of the variant allele in 1000 Genomes database.

Form a' is identical to form a with the exception that form a' has a glycine (G) at position 620 (see US20120093818 (Amgen, Inc); form a has E at this position.

TABLE 1-continued

Human PCSK9 variants distributed over several human ethnic populations & having a total human genotype frequency in the range of 1 to about 15%

(b) Nucleotide Sequence Variations of Selected Alleles

| Allele a | G | C | A | G | A | A | A |
|---|---|---|---|---|---|---|---|
| | | | | Nucleotide Position[1] | | | |
| Variant Allele | 1:55505647 | 1:55505668 | 1:55523802 | 1:55523855 | 1:55524237 | 1:55527222 | 1:55529187 |
| | | | | Non-Synonymous Nucleotide Variation[2] | | | |
| | T | T | G | A | G | C | G |
| | | | | Variant ID[3] | | | |
| | rs11591147 | rs11583680 | rs28362261 | rs28362263 | rs562556 | rs28362277 | rs505151 |
| | | | | Corresponding Amino Acid Variation | | | |
| | 46L | 53V | 425S | 443T | 474V | 619P | 670G |
| f | | | | | X | | |
| c | | | | | | | X |
| r | | | | | X | | X |
| p | | X | | | X | | |
| m | | | | X | | | |
| e | | | X | | X | | |
| h | | | | X | | X | |
| aj | X | | | | X | | |
| q | | X | | | | | X |

"x" in a box indicates that a variant allele comprises the non-synonymous nucleotide variation indicated in the 5th row.

Table Footnotes:

[1]Notation is chromosome number (all positions are on human chromosome 1):coordinate number (Ensembl release 73 - September 2013, Genome assembly: GRCh37 (GCA_000001405.13));

[2]Nucleotide change (compared to allele a nucleotide shown in first row) giving rise to an amino acid change in the variant form (compared to amino acid of allele a); and

[3]NCBI dbSNP reference number (NCBI dbSNP Build 138 released on Apr 25, 2013).

TABLE 2

Sequences (a) Human PCSK9 Form a Amino Acid Sequence (SEQ ID NO:1) - "Pro-form" with Signal Sequence

```
                                              46        53
MGTVSSRRSWWPLPLLLLLLLLLGPAGARAQEDEDGDYEELVLALRSEEDGLAEAPEHGTTATFHRCAKDP

WRLPGTYVVVLKEETHLSQSERTARRLQAQAARRGYLTKILHVFHGLLPGFLVKMSGDLLELALKLPH

VDYIEEDSSVFAQsipwnleritppryradeyqppggslvevylldtsiqsdhreiegrvmvtdfenvpeedgtrfhrqaskcdshg thiagvvsgrdagvakgasmrslrvlncqgkgtvsgtliglefirksqlvqpvgplvvllplaggysrvlnaacqrlaragvvlvtaagnfrddacly
spasapevitvgatnaqdqpvtlgtlgtnfgrcvdlfapgediigassdcstcfvsqsgtsqaaahvagiaammlsaepeltlaelrqrlihfsak 425       443                 474
dvineawfpedqrvltpnlvaalppsthGAGWQLFCRTVWSAHSGPTRMATAIARCAPDEELLSCSSFSRSGKRRGERM

EAQGGKLVCRAHNAFGGEGVYAIARCCLLPQANCSVHTAPPAEASMGTRVHCHQQGHVLTGCSSHWEVEDLGT 619 620
HKPPVLRPRGQPNQCVGHREASIHASCCHAPGLECKVKEHGIPAPQEQVTVACEEGWTLTGCSALPGTSHVLGAY

670
AVDNTCVVRSRDVSTTGSTSEEAVTAVAICCRSRHLAQASQELQ
```

*Italics* = signal sequence 1-30

`Courier` = pro peptide 31-152 lower case = catalytic domain 153-449
UPPER CASE = C-terminal domain 450-692
Underlined = residues changed from allele a in other sequences (aa residue number shown)
The pro-form is the sequence from amino acid number 31 to (and including) amino acid number 692 of SEQ ID NO: 1.
The mature form is the sequence from amino acid number 153 to (and including) amino acid number 692 of SEQ ID NO: 12

TABLE 2-continued

Sequences (b) Human PCSK9 Form a Amino Acid Sequence (SEQ ID NO:3) - "Mature-form"
(Numbering and notation as per SEQ ID NO:1 above has been retained)

sipwnleritppryradeyqppdggslvevylldtsiqsdhreiegrvmvtdfenvpeedgtrfhrqaskcdshg
thlagvvsgrdagvakgasmrslrvlncqgkgtvsgtliglefirksqlvqpvgplvvllplaggysrvlnaacqrlaragvvlvtaagnfrddacly
spasapevitvgatnaqdqpvtlgtlgnfgrcvdifapgediigassdcstcfvsqsgtsqaaahvagiaammlsaepeltlaelrqrlihfsak 425      443       474
dvineawfpedqrvltpnlvaalppsthGAGWQLFCRTVWSAHSGPTRMATAIARCAPDEELLSCSSFSRSGKRRGERM

EAQGGKLVCRAHNAFGGEGVYAIARCCLLPQANCSVHTAPPAEASMGTRVHCHQQGHVLTGCSSHWEVEDLGT 619 620
HKPPVLRPRGQPNQCVGHREASIHASCCHAPGLECKVKEHGIPAPQEQVTVACEEGWTLTGCSALPGTSHVLGAY

570
AVDNTCVVRSRDVSTTGSTSEEAVTAVAICCRSRHLAQASQELQ (c) Human PCSK9 Allele a Nucleotide Sequence (SEQ ID NO: 28) - Encoding "Pro-form" Plus Signal Sequence

*ATGGGCACCGTCAGCTCCAGGCGGTCCTGGTGGCCGCTGCCACTGCTGCTGCTGCTGCTGCTGCTCCTGGGTC*

R46L CGT to CTT
*CCGCGGGCGCCCGTGCG*CAGGAGGACGAGGACGGCGACTACGAGGAGCTGGTGCTAGCCTTGCGTTCCG

A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCGACCTGCTGGAGCTGGCCTTGAAGTTGCCC

CATGTCGACTACATCGAGGAGGACTCCTCTGTCTTTGCCCAGagcatcccgtggaacctggagcggattaccctcca cggtaccgggcggatgaataccagccccccgacggaggcagcctggtggaggtgtatctcctagacaccagcatacagagtgaccaccgggaa
atcgagggcagggtcatggtcaccgacttcgagaatgtgcccgaggaggacgggacccgcttccacagacaggccagcaagtgtgacagtcat
ggcacccacctggcagggggtggtcagcggccgggatgccggcgtggccaaggggtgccagcatgcgcagcctgcgcgtgctcaactgccaaggg
aagggcacggttagcggcaccctcataggcctggagtttattcggaaaagccagctggtccagcctgtgggccactggtggtgctgctgctgcccct
ggcgggtgggtacagccgcgtcctcaacgccgcctgccagccgcctggcgagggctggggtcgtgctggtcaccgctgccggcaacttccgggac
gatgccctgcctctactccccagcctcagctcccgaggtcatcacagttggggccaccaatgcccaagaccagccggtgaccctggggactttggg
gaccaacttggccgctgtgtggacctctttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT                   A443T GCC to ACC
atccacttctctgccaaagatgtcatcaatgaggcctggttccctgaggaccagcgggtactgaccccccaacctggtggccgccctgcccccccag cacccatGGGGCAGGTTGGCAGCTGTTTTGCAGGACTGTATGGTCAGCACACTCGGGGCCTACACGGATGGCC I474V ATC to GTC
ACAGCCATCGCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGG
GTGTCTACGCCATTGCCAGGTGCTGCCTGCTACCCCAGGCCAACTGCAGCGTCCACACAGCTCCACCAGCTGA
GGCCAGCATGGGGACCCGTGTCCACTGCCACCAACAGGGCCACGTCCTCACAGGCTGCAGCTCCCACTGGGA
GGTGGAGGACCTTGGCACCCACAAGCCGCCTGTGCTGAGGCCACGAGGTCAGCCCAACCAGTGCGTGGGCC
ACAGGGAGGCCAGCATCCACGCTTCCTGCTGCCATGCCCCAGGTCTGGAATGCAAAGTCAAGGAGCATGGAA Q619P CAG to CCG E620G GAG to GGG
TCCCGGCCCCTCAGGAGCAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTGTAGTCAGGAGCCGGGACGTCAGCA

TABLE 2-continued

Sequences

E670G GAG to GGG
CTACAGGCAGCACCAGCGAA<u>GAG</u>GCCGTGACAGCCGTTGCCATCTGCTGCCGGAGCCGGCACCTGGCGCAG

GCCTCCCAGGAGCTCCAGTGAC

*Italics* = nucleotide sequence encoding signal sequence (nucleotides 1-90)

`Courier` = nucleotide sequence encoding pro peptide (nucleotides 91-456)

lower case = nucleotide sequence encoding catalytic domain (nucleotides 457-1346)
UPPER CASE = nucleotide sequence encoding C-terminal domain (nucleotides 1347-2076)
<u>Underlined</u> = allelic variations from allele a in other sequences (aa residue number changes and codon changes shown)
The pro-form is encoded by nucleotide sequence from nucleotide 91 to (and including) nucleotide 2076.
The mature form is encoded by nucleotide sequence from nucleotide 457 to (and including) nucleotide 2076.

Variant Allele Nucleotide Sequences
Thus,
(i) The nucleotide sequence of allele f is identical to SEQ ID NO: 28 except that the nucleotide sequence of allele f comprises a GTC codon instead of an ATC codon at the position labelled "I474V" in SEQ ID NO: 28;
(ii) The nucleotide sequence of allele c is identical to SEQ ID NO: 28 except that the nucleotide sequence of allele c comprises a GGG codon instead of an GAG codon at the position labelled "E670G" in SEQ ID NO: 28;
(iii) The nucleotide sequence of allele r is identical to SEQ ID NO: 28 except that the nucleotide sequence of allele r comprises a GTC codon instead of an ATC codon at the position labelled "I474V" in SEQ ID NO: 28; and a GGG codon instead of an GAG codon at the position labelled "E670G" in SEQ ID NO: 28;
(iv) The nucleotide sequence of allele p is identical to SEQ ID NO: 28 except that the nucleotide sequence of allele p comprises a GTC codon instead of a GCC codon at the position labelled "A53V" in SEQ ID NO: 28; and a GTC codon instead of an ATC codon at the position labelled "I474V" in SEQ ID NO: 28;
(v) The nucleotide sequence of allele m is identical to SEQ ID NO: 28 except that the nucleotide sequence of allele m comprises a ACC codon instead of a GCC codon at the position labelled "A443T" in SEQ ID NO: 28;
(vi) The nucleotide sequence of allele e is identical to SEQ ID NO: 28 except that the nucleotide sequence of allele e comprises a AGT codon instead of an AAT codon at the position labelled "N425S" in SEQ ID NO: 28; and a GTC codon instead of an ATC codon at the position labelled "I474V" in SEQ ID NO: 28;
(vii) The nucleotide sequence of allele h is identical to SEQ ID NO: 28 except that the nucleotide sequence of allele h comprises a ACC codon instead of a GCC codon at the position labelled "A443T" in SEQ ID NO: 28; and a CCG codon instead of a CAG codon at the position labelled "Q619P" in SEQ ID NO: 28;
(viii) The nucleotide sequence of allele aj is identical to SEQ ID NO: 28 except that the nucleotide sequence of allele aj comprises a CTT codon instead of an CGT codon at the position labelled "R46L" in SEQ ID NO: 28; and a GTC codon instead of an ATC codon at the position labelled "I474V" in SEQ ID NO: 28; and
(ix) The nucleotide sequence of allele q is identical to SEQ ID NO: 28 except that the nucleotide sequence of allele q comprises a GTC codon instead of a GCC codon at the position labelled "A53V" in SEQ ID NO: 28; and a GGG codon instead of an GAG codon at the position labelled "E670G" in SEQ ID NO: 28.

Variant Pro-Form Amino Acid Sequences
(Numbering is as Per SEQ ID NO: 1 Recited Above)
(A) The amino acid sequence of form f is identical to the amino acid sequence from amino acid number 31 to (and including) amino acid number 692 of SEQ ID NO: 1 except that the amino acid sequence of form f comprises a valine at position 474;
(B) The amino acid sequence of form c is identical to the amino acid sequence from amino acid number 31 to (and including) amino acid number 692 of SEQ ID NO: 1 except that the amino acid sequence of form c comprises a glycine at position 670;
(C) The amino acid sequence of form r is identical to the amino acid sequence from amino acid number 31 to (and including) amino acid number 692 of SEQ ID NO: 1 except that the amino acid sequence of form r comprises a valine at position 474 and a glycine at position 670;
(D) The amino acid sequence of form p is identical the amino acid sequence from amino acid number 31 to (and including) amino acid number 692 of SEQ ID NO: 1 except that the amino acid sequence of form p comprises a valine at position 53 and a valine at position 474;
(E) The amino acid sequence of form m is identical to the amino acid sequence from amino acid number 31 to (and including) amino acid number 692 of SEQ ID NO: 1 except that the amino acid sequence of form m comprises a threonine at position 443;
(F) The amino acid sequence of form e is identical to the amino acid sequence from amino acid number 31 to (and including) amino acid number 692 of SEQ ID NO: 1 except that the amino acid sequence of form e comprises a serine at position 425 and a valine at position 474;
(G) The amino acid sequence of form h is identical to the amino acid sequence from amino acid number 31 to (and including) amino acid number 692 of SEQ ID NO: 1 except that the amino acid sequence of form h comprises a threonine at position 443 and a proline at position 619;
(H) The amino acid sequence of form aj is identical to the amino acid sequence from amino acid number 31 to (and including) amino acid number 692 of SEQ ID NO: 1 except that the amino acid sequence of form aj comprises a leucine at position 46 and a valine at position 474; and
(I) The amino acid sequence of form q is identical to the amino acid sequence from amino acid number 31 to (and including) amino acid number 692 of SEQ ID NO: 1 except that the amino acid sequence of form q comprises a valine at position 53 and a glycine at position 670.

Variant Mature Form Amino Acid Sequences
(Numbering is as Per SEQ ID NO: 1 Recited Above)

(A') The amino acid sequence of form f is identical to SEQ ID NO: 2 except that the amino acid sequence of form f comprises a valine at position 474;
(B') The amino acid sequence of form c is identical to SEQ ID NO: 2 except that the amino acid sequence of form c comprises a glycine at position 670;
(C') The amino acid sequence of form r is identical to SEQ ID NO: 2 except that the amino acid sequence of form r comprises a valine at position 474 and a glycine at position 670;
(D') The amino acid sequence of form p is identical to SEQ ID NO: 2 except that the amino acid sequence of form p comprises a valine at position 474;
(E') The amino acid sequence of form m is identical to SEQ ID NO: 2 except that the amino acid sequence of form m comprises a threonine at position 443;
(F') The amino acid sequence of form e is identical to SEQ ID NO: 2 except that the amino acid sequence of form e comprises a serine at position 425 and a valine at position 474;
(G') The amino acid sequence of form h is identical to SEQ ID NO: 2 except that the amino acid sequence of form h comprises a threonine at position 443 and a proline at position 619;
(H') The amino acid sequence of form aj is identical to SEQ ID NO: 2 except that the amino acid sequence of form aj comprises valine at position 474; and
(I') The amino acid sequence of form q is identical to SEQ ID NO: 2 except that the amino acid sequence of form q comprises a glycine at position 670.

The mature form of p is identical to the mature form of f and aj.

The mature form of c is identical to the mature form of q.

Further sequence analysis and 3D in silico modelling (see FIG. 1) revealed that selected variants also fulfilled the following selection criteria:—

PCSK9 variants whose variant amino acid residues (versus the common form of human PCSK9) are found in the mature form of the target (ie, outside the pro-domain); and PCSK9 variants whose variant amino acid residues (versus the common form of human PCSK9) are surface-exposed on the target, which the inventor saw as contributing to determining the topography of the target and potentially contributing to how and where ligand binding on the target occurs.

As shown in FIG. 1, identified positions 425, 443, 474, 619 and 670 (found in the selected variants of the invention) are all surface-exposed and outside of the pro-domain. Variant positions 425 and 443 are surface-exposed on the catalytic domain, while variant positions 474, 619 and 670 are surface-exposed on the C-terminal domain.

In a first example, the invention addresses the need to treat humans having naturally-occurring rarer natural PCSK9 alleles, genotypes and phenotypes (rarer protein forms). In this respect, the invention provides the following aspects:

In a First Aspect:

An anti-human PCSK9 ligand for use in a method of treating and/or preventing a PCSK9-mediated disease or condition in a human whose genome comprises a nucleotide sequence selected from the group consisting of SEQ ID NOs: 29-37, wherein the method comprises administering the ligand to the human.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Second Aspect:

The ligand of aspect 1, wherein the ligand has been or is determined as capable of binding a human PCSK9 selected from the group consisting forms f, c, r, p, m, e, h, aj and q.

In an example of any aspect, the ligand binds (or has been determined to bind) two, three, four or more human PCSK9 selected from the group consisting forms f, c, r, p, m, e, h, aj and q.

In an example of any aspect, the ligand comprises a protein domain that specifically binds to PCSK9, eg, a human PCSK9 selected from the group consisting forms f, c, r, p, m, e, h, aj and q.

The term "specifically binds," or the like, means that a ligand, eg, an antibody or antigen-binding fragment thereof, forms a complex with an antigen that is relatively stable under physiologic conditions. Specific binding can be characterized by an equilibrium dissociation constant of at least about $1 \times 10^{-6}$M or less (e.g., a smaller KD denotes a tighter binding). Methods for determining whether two molecules specifically bind are well known in the art and include, for example, equilibrium dialysis, surface plasmon resonance, and the like. An isolated antibody that specifically binds a human PCSK9 may, however, exhibit cross-reactivity to other antigens such as a PCSK9 molecule from another specie. Moreover, multi-specific antibodies (e.g., bispecifics) that bind to human PCSK9 and one or more additional antigens are nonetheless considered antibodies that "specifically bind" PCSK9, as used herein.

In an example of any aspect, the ligand comprises or consists of a protein that mimics the EGFA domain of the LDL receptor and specifically binds to PCSK9, eg, a human PCSK9 selected from the group consisting forms f c, r, p, m, e, h, aj and q.

In an example of any aspect, the ligand antagonises PCSK9, eg, a human PCSK9 selected from the group consisting forms f c, r, p, m, e, h, aj and q.

In an example of any aspect, the method comprises (before administering the ligand) the step of determining that the ligand is capable of binding a human PCSK9 selected from the group consisting forms f c, r, p, m, e, h, aj and q.

In an example of any aspect, binding is determined by SPR. In an example of any aspect, binding is determined by ELISA.

In an example of any aspect, said forms are the mature forms.

In an example of any aspect, said forms are the pro-forms.

In a Third Aspect:

A ligand that binds a human PCSK9 comprising an amino acid sequence selected from the group consisting of SEQ ID NOs: 4-27 for use in a method comprising the step of using the ligand to target said PCSK9 in a human to treat and/or prevent a disease or condition mediated by PCSK9, the method comprising administering the ligand to the human.

In an example, the disease or condition is mediated by a human PCSK9 comprising an amino acid sequence selected from the group consisting of SEQ ID NOs: 4-27.

In an example, the amino acid sequence selected from the group consisting of SEQ ID NOs: 4-23, 26 and 27; or selected from the group consisting of SEQ ID NOs: 4-14 and 18-27; or selected from the group consisting of SEQ ID NOs: 4-14, 18-23, 26 and 27. These are naturally-occurring sequences that do not comprise 46L and which meet the criteria set out above. These groups comprise variants that are associated with elevated LDL-C.

In an example, the amino acid sequence is SEQ ID NO: 18, 19 or 20, that comprises a 425S, which is associated with elevated LDL-C (Pisciotta et al 2006).

In an example, the amino acid sequence selected from the group consisting of SEQ ID NOs: 10, 11, 12, 26 and 27, that comprise 670G which is a marker for severity of coronary atherosclerosis (Chen et al 2005).

In an example, the amino acid sequence selected from the group consisting of SEQ ID NOs: 10-14 and 18-27; or selected from the group consisting of SEQ ID NOs: 10-14, 18-23, 26 and 27. These are sequences that have a naturally-occurring combination of differences from SEQ ID NOs: 1-3 (form a) and which meet the criteria set out above.

In an example, the amino acid sequence is SEQ ID NO: 4.
In an example, the amino acid sequence is SEQ ID NO: 5.
In an example, the amino acid sequence is SEQ ID NO: 6.
In an example, the amino acid sequence is SEQ ID NO: 7.
In an example, the amino acid sequence is SEQ ID NO: 8.
In an example, the amino acid sequence is SEQ ID NO: 9.
In an example, the amino acid sequence is SEQ ID NO: 10.
In an example, the amino acid sequence is SEQ ID NO: 11.
In an example, the amino acid sequence is SEQ ID NO: 12.
In an example, the amino acid sequence is SEQ ID NO: 13.
In an example, the amino acid sequence is SEQ ID NO: 14.
In an example, the amino acid sequence is SEQ ID NO: 15.
In an example, the amino acid sequence is SEQ ID NO: 16.
In an example, the amino acid sequence is SEQ ID NO: 17.
In an example, the amino acid sequence is SEQ ID NO: 18.
In an example, the amino acid sequence is SEQ ID NO: 19.
In an example, the amino acid sequence is SEQ ID NO: 20.
In an example, the amino acid sequence is SEQ ID NO: 21.
In an example, the amino acid sequence is SEQ ID NO: 22.
In an example, the amino acid sequence is SEQ ID NO: 23.
In an example, the amino acid sequence is SEQ ID NO: 24.
In an example, the amino acid sequence is SEQ ID NO: 25.
In an example, the amino acid sequence is SEQ ID NO: 26.
In an example, the amino acid sequence is SEQ ID NO: 27.

In a Fourth Aspect:

The ligand of aspect 3, wherein the genome of the human comprises a nucleotide sequence selected from the group consisting of SEQ ID NOs: 29-37.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Fifth Aspect:

The ligand of any preceding aspect, wherein the human has been or is genotyped as positive for a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.

In an example, the nucleotide sequence is SEQ ID NO: 37.

In a Sixth Aspect:

The ligand of any preceding aspect, wherein the human has been or is phenotyped as positive for a human PCSK9 selected from the group consisting of forms f c, r, p, m, e, h, aj and q or at least the catalytic or C-terminal domain thereof.

In an example, said forms are the mature forms.

In an example, said forms are the pro-forms.

In a Seventh Aspect:

The ligand of any preceding aspect, wherein the method comprises genotyping the human as positive for a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In an Eighth Aspect:

The ligand of any preceding aspect, wherein the method comprises phenotyping the human has positive for a human PCSK9 selected from the group consisting of forms f c, r, p, m, e, h, aj and q or at least the catalytic or C-terminal domain thereof.

In an example, said forms are the mature forms.

In an example, said forms are the pro-forms.

In a Ninth Aspect:

The ligand of any preceding aspect, wherein the human has been or is genotyped as heterozygous for a nucleotide sequence selected from the group consisting of SEQ ID NOs: 29-37 or at least the catalytic domain- or C-terminal domain-encoding sequence thereof optionally wherein the human has been or is genotyped as comprising the nucleotide sequence of SEQ ID NO: 28 or at least the catalytic domain- or C-terminal domain-encoding sequence thereof and a nucleotide sequence selected from the group consisting of SEQ ID NOs: 29-37 or at least the catalytic domain- or C-terminal domain-encoding sequence thereof.

"Heterozygous" here means that in the human's genotype one allele comprises a nucleotide sequence selected from the group consisting of SEQ ID NOs: 29-37 or at least the catalytic domain- or C-terminal domain-encoding sequence thereof and other allele can be any PCSK9 (eg, form a, a' or an allele comprising a nucleotide sequence selected from the group consisting of SEQ ID NOs: 29-37 or at least the catalytic domain- or C-terminal domain-encoding sequence thereof).

In an example, the method comprises (before administering the ligand) genotyping the human as heterozygous for a nucleotide sequence selected from the group consisting of SEQ ID NOs: 29-37 or at least the catalytic domain- or C-terminal domain-encoding sequence thereof; optionally also genotyping the human as comprising the nucleotide sequence of SEQ ID NO: 28 or at least the catalytic domain- or C-terminal domain-encoding sequence thereof and a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37.

These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Tenth Aspect:

The ligand of any one of aspects 1 to 9, wherein the genome of the human has been or is genotyped as homozygous for a nucleotide sequence selected from the group consisting of SEQ ID NOs: 29-37 or at least the catalytic domain- or C-terminal domain-encoding sequence thereof.

"Homozygous" here means that in the human's genotype each allele comprises the same nucleotide sequence selected from the group consisting of SEQ ID NOs: 29-37 or at least the catalytic domain- or C-terminal domain-encoding sequence thereof.

In an example, the method comprises genotyping the human as homozygous for a nucleotide sequence selected from the group consisting of SEQ ID NOs: 29-37 or at least the catalytic domain- or C-terminal domain-encoding sequence thereof.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In an Eleventh Aspect:

The ligand of any preceding aspect, wherein the ligand comprises an antibody binding site that binds a human PCSK9 comprising an amino acid sequence selected from the group consisting of SEQ ID NOs: 4-27 and optionally has been or is determined as capable of such binding.

In an example, the method comprises (before administering the ligand) the step of determining that the ligand is capable of binding to said human PCSK9.

In an example, the binding is specific binding. In an example, the ligand binds (or has been determined as binding) to the PCSK9 with an affinity (Kd) of 1 mM, 100 nM, 10 nM or 1 nM or less. In an embodiment, the affinity is no less than 10, 100 or 1000 fM.

In an example, binding or affinity is determined by SPR or ELISA.

In an example, the disease or condition is mediated by a human PCSK9 comprising an amino acid sequence selected from the group consisting of SEQ ID NOs: 4-27.

In an example, the amino acid sequence selected from the group consisting of SEQ ID NOs: 4-23, 26 and 27; or selected from the group consisting of SEQ ID NOs: 4-14 and 18-27; or selected from the group consisting of SEQ ID NOs: 4-14, 18-23, 26 and 27. These are naturally-occurring sequences that do not comprise 46L and which meet the criteria set out above. These groups comprise variants that are associated with elevated LDL-C.

In an example, the amino acid sequence is SEQ ID NO: 18, 19 or 20, that comprises a 425S, which is associated with elevated LDL-C (Pisciotta et al 2006).

In an example, the amino acid sequence selected from the group consisting of SEQ ID NOs: 10, 11, 12, 26 and 27, that comprise 670G which is a marker for severity of coronary atherosclerosis (Chen et al 2005).

In an example, the amino acid sequence selected from the group consisting of SEQ ID NOs: 10-14 and 18-27; or selected from the group consisting of SEQ ID NOs: 10-14, 18-23, 26 and 27. These are sequences that have a naturally-occurring combination of differences from SEQ ID NOs: 1-3 (form a) and which meet the criteria set out above In an example, the amino acid sequence is SEQ ID NO: 4.
In an example, the amino acid sequence is SEQ ID NO: 5.
In an example, the amino acid sequence is SEQ ID NO: 6.
In an example, the amino acid sequence is SEQ ID NO: 7.
In an example, the amino acid sequence is SEQ ID NO: 8.
In an example, the amino acid sequence is SEQ ID NO: 9.
In an example, the amino acid sequence is SEQ ID NO: 10.
In an example, the amino acid sequence is SEQ ID NO: 11.
In an example, the amino acid sequence is SEQ ID NO: 12.
In an example, the amino acid sequence is SEQ ID NO: 13.
In an example, the amino acid sequence is SEQ ID NO: 14.
In an example, the amino acid sequence is SEQ ID NO: 15.
In an example, the amino acid sequence is SEQ ID NO: 16.
In an example, the amino acid sequence is SEQ ID NO: 17.
In an example, the amino acid sequence is SEQ ID NO: 18.
In an example, the amino acid sequence is SEQ ID NO: 19.
In an example, the amino acid sequence is SEQ ID NO: 20.
In an example, the amino acid sequence is SEQ ID NO: 21.
In an example, the amino acid sequence is SEQ ID NO: 22.
In an example, the amino acid sequence is SEQ ID NO: 23.
In an example, the amino acid sequence is SEQ ID NO: 24.
In an example, the amino acid sequence is SEQ ID NO: 25.
In an example, the amino acid sequence is SEQ ID NO: 26.
In an example, the amino acid sequence is SEQ ID NO: 27.

In a Twelfth Aspect:

The ligand of aspect 11, wherein the ligand is an antibody or antibody fragment. For example, the antibody or antibody fragment is a PCSK9 antagonist, eg, neutralises PCSK9.

Examples of such antibodies are disclosed, for instance, in WO 2008/057457, WO2008/057458, WO 2008/057459, WO 2008/063382, WO 2008/133647, WO 2009/100297, WO 2009/100318, WO 2011/037791, WO 2011/053759, WO 2011/053783, WO 2008/125623, WO 2011/072263, WO 2009/055783, WO 2010/029513, WO 2011/11 1007, WO 2010/077854, the disclosures and sequences of such antibodies being incorporated herein for use in the invention in their entireties by reference. One specific example is AMG 145 (Amgen), LY3015014 (Eli Lilly) or alirocumab. Advantageously, the ligand is or comprises alirocumab. Alternatively, the ligand is or comprises evolocumab.

In an example, the ligand is SAR236553/REGN727 (Sanofi Aventis/Regeneron) or a PCSK9-binding derivative thereof.

In an example, the ligand comprises or consists of a neutralizing antibody that binds to the PCSK9, wherein the antibody binds to PCSK9 and reduces the likelihood that PCSK9 binds to LDLR.

The ligand of aspect 11, wherein the ligand is a PCSK9 antagonist, eg, neutralises PCSK9.

In an example of any aspect of the invention, the ligand comprises or consists a ligand selected from evolocumab, 1D05-IgG2 (Merck & Co.), ALN-PCS02 (Alnylam), RN316 (Pfizer-Rinat), LY3015014 (Eli Lilly) and alirocumab (SAR236553/REGN727; Sanofi Aventis/Regeneron).

In Thirteenth Aspect:

The ligand of any one of aspects 1 to 10, wherein (i) the ligand comprises a sequence of contiguous nucleotides that specifically hybridises to a nucleotide sequence selected from the group consisting of SEQ ID NOs: 29-37 or at least the catalytic domain- or C-terminal domain-encoding sequence thereof, or specifically hybridises to an antisense sequence or an RNA transcript of said sequence, wherein said sequence of contiguous nucleotides hybridises to at least one nucleotide present in said selected sequence which is not present in SEQ ID NO: 28 or hybridises to an antisense sequence or an RNA transcript thereof respectively; and/or (ii) the ligand comprises a sequence of at least 10 contiguous nucleotides of a nucleotide sequence selected from the group consisting of SEQ ID NOs: 29-37 or is an antisense sequence or RNA version of said contiguous nucleotides, wherein said sequence of contiguous nucleotides comprises at least one nucleotide present in said selected sequence which is not present in SEQ ID NO: 28.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In an embodiment, the ligand comprises at least 10, 11, 12, 13, 14, 15, 20, 25, 30, 35, 40, 45, 50 or 100 contiguous nucleotides of said nucleotide sequence.

In a Fourteenth Aspect:

The ligand of any preceding aspect, wherein said disease or condition is hyperlipidaemia, hypercholesterolaemia (eg, familial hypercholesterolaemia), heart attack, stroke, coronary heart disease, atherosclerosis or a cardiovascular disease or condition.

The ligand of any preceding aspect, wherein the disease or condition is hypercholesterolemia, hyperlipidemia, hypercholesterolemia, dyslipidemia, cholestatic liver disease, nephrotic syndrome, hypothyroidism, obesity, atherosclerosis or a cardiovascular disease.

In an example, said disease or condition is hypercholesterolaemia. The term "hypercholesterolaemia," as used herein, refers to a condition in which cholesterol levels are elevated above a desired level. In some embodiments, this denotes that serum cholesterol levels are elevated. In some embodiments, the desired level takes into account various "risk factors" that are known to one of skill in the art (and are described or referenced in US20120093818).

The ligand of any preceding aspect, wherein the human is identified as heterozygous for Familial Hypercholesterolemia, statin intolerant, statin uncontrolled, or at risk for developing hypercholesterolemia, dyslipidemia, cholestatic liver disease, nephrotic syndrome, hypothyroidism, obesity, atherosclerosis or a cardiovascular disease.

In a Fifteenth Aspect:

The ligand of any preceding aspect, wherein said disease or condition is associated with elevated LDL cholesterol.

Cholesterol levels are measured in milligrams (mg) of cholesterol per deciliter (dL) of blood in the United States and some other countries. Canada and most European countries measure cholesterol in millimoles (mmol) per liter (L) of blood. Below are general guideline ideal ranges and elevated ranges.

| Total cholesterol (U.S. and some other countries) | Total cholesterol* (Canada and most of Europe) | |
| --- | --- | --- |
| Below 200 mg/dL | Below 5.2 mmol/L | Ideal |
| 200-239 mg/dL | 5.2-6.2 mmol/L | Borderline high |
| 240 mg/dL and above | Above 6.2 mmol/L | High |
| LDL cholesterol (U.S. and some other countries) | LDL cholesterol* (Canada and most of Europe) | |
| 100-129 mg/dL | 2.6-3.3 mmol/L | Ideal |
| 130-159 mg/dL | 3.4-4.1 mmol/L | Borderline high |
| 160-189 mg/dL | 4.1-4.9 mmol/L | High |
| 190 mg/dL and above | Above 4.9 mmol/L | Very high |

*Canadian and European guidelines differ slightly from U.S. guidelines. These conversions are based on U.S. guidelines.

Elevated LDL cholesterol is, therefore, 160 mg/dL or above (4.1 mmol/L or above).

In a Sixteenth Aspect:

The ligand of any preceding aspect, wherein the ligand inhibits human PCSK9 binding to human LDL receptor and optionally has been or is determined as capable of such inhibition.

In an example, the method comprises (before administering the ligand) determining that the ligand is capable of such inhibition.

Inhibition determination is eg, inhibition in a blood or serum sample, at rtp, at ph7, at 37 degrees centigrade and/or under the physiological conditions of a human body.

In a Seventeeth Aspect:

The ligand of any preceding aspect, wherein the human is resistant or substantially resistant to statin (eg, avorstatin and/or fluvastatin) treatment of said disease or condition.

In an Eighteenth Aspect:

The ligand of any preceding aspect, wherein the ligand is for treating and/or preventing a PCSK9-mediated disease or condition in a human
(i) whose genome comprises SEQ ID NO: 29 and wherein the human is of ASW, YRI, GBR, TSI, CLM, LWK, MXL, JPT, PUR, IBS, FIN or CEU ancestry; or
(ii) whose genome comprises SEQ ID NO: 30 and wherein the human is of ASW, YRI, GBR, TSI, CLM, CHB, LWK, CHS, JPT, PUR, FIN or CEU ancestry; or
(iii) whose genome comprises SEQ ID NO: 32 and wherein the human is of ASW, GBR, TSI, CLM, JPT, PUR, IBS, FIN or CEU ancestry; or
(iv) whose genome comprises SEQ ID NO: 33 and wherein the human is of LWK, ASW, YRI or CLM ancestry; or
(v) whose genome comprises SEQ ID NO: 34 and wherein the human is of LWK, ASW or YRI ancestry; or
(vi) whose genome comprises SEQ ID NO: 35 and wherein the human is of PUR, TSI, FIN or CEU ancestry; or
(vii) whose genome comprises SEQ ID NO: 36 and wherein the human is of LWK, ASW or YRI ancestry; or (viii) whose genome comprises SEQ ID NO: 37 and wherein the human is of CHS, ASW, JPT, PUR or CHB ancestry.

In a Ninteenth Aspect:

The ligand of any preceding aspect, wherein the ligand is for treating and/or preventing a PCSK9-mediated disease or condition in a human
(i) that expresses PCSK9 form f and wherein the human is of ASW, YRI, GBR, TSI, CLM, LWK, MXL, JPT, PUR, IBS, FIN or CEU ancestry; or
(ii) that expresses PCSK9 form c and wherein the human is of ASW, YRI, GBR, TSI, CLM, CHB, LWK, CHS, JPT, PUR, FIN or CEU ancestry; or
(iii) that expresses PCSK9 form p and wherein the human is of ASW, GBR, TSI, CLM, JPT, PUR, IBS, FIN or CEU ancestry; or
(iv) that expresses PCSK9 form m and wherein the human is of LWK, ASW, YRI or CLM ancestry; or
(v) that expresses PCSK9 form e and wherein the human is of LWK, ASW or YRI ancestry; or
(vi) that expresses PCSK9 form h and wherein the human is of PUR, TSI, FIN or CEU ancestry; or
(vii) that expresses PCSK9 form aj and wherein the human is of LWK, ASW or YRI ancestry; or
(viii) that expresses PCSK9 form q and wherein the human is of CHS, ASW, JPT, PUR or CHB ancestry.

In an example, said forms are the mature forms.
In an example, said forms are the pro-forms.

In a Twentieth Aspect:

A pharmaceutical composition or kit for treating and/or preventing a PCSK9-mediated condition or disease (eg, as recited in aspect 14 or 15), the composition or kit comprising a ligand of any preceding aspect and optionally a statin (eg, cerovastatin, atorvastatin, simvastatin, pitavastin, rosuvastatin, fluvastatin, lovastatin or pravastatin); and optionally in combination with a label or instructions for use to treat and/or prevent said disease or condition in a human (eg, covering treatment of a human as recited in aspect 18 or 19); optionally wherein the label or instructions comprise a marketing authorisation number (eg, an FDA or EMA authorisation number); optionally wherein the label or instructions comprise directions to administer alirocumab or evolocumab to said human; optionally wherein the kit comprises an IV or injection device that comprises the ligand (and, eg, also a statin).

In a Twenty-First Aspect:

A method of producing an anti-human PCSK9 antibody binding site, the method comprising obtaining a plurality of anti-PCSK9 antibody binding sites, screening the antibody binding sites for binding to a human PCSK9 selected from the group consisting of forms f c, r, p, m, e, h, aj and q or a catalytic or C-terminal domain or a peptide thereof that comprises amino acid variation from the corresponding sequence of SEQ ID NO: 1, 2 or 3 and isolating an antibody binding site that binds in the screening step, and optionally producing a form f c, r, p, m, e, h, aj or q PCSK9-binding fragment or derivative of the isolated antibody.

In an example, said forms are the mature forms.
In an example, said forms are the pro-forms.

In an example of this and the next aspect, the plurality of binding sites comprises or consists of a plurality of 4-chain antibodies or fragments thereof, eg, dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (eg, a rodent, eg, a mouse or rat, eg, a Velocimouse™, Kymouse™, Xenomouse™, Aliva Mouse™, HuMab Mouse™, Omnimouse™, Omnirat™ or MeMo Mouse™) with a PCSK9 epitope and isolation of a repertoire of antibody-producing cells (eg, a B-cell, plasma cell or plasmablast repertoire) and/or a repertoire of isolated antibodies.

In an example, the method comprises selecting one or more antibody binding sites that each specifically binds to a human PCSK9 epitope comprising amino acid variation from the corresponding sequence of SEQ ID NO: 1, 2 or 3.

In a Twenty-Second Aspect:

A method of producing an anti-human PCSK9 antibody, the method comprising immunising a non-human vertebrate (eg, a mouse or a rat) with a human PCSK9 comprising an amino acid sequence selected from the group consisting of the amino acid sequences of forms f c, r, p, m, e, h, aj and q or a catalytic or C-terminal domain or a peptide thereof that comprises amino acid variation from the corresponding sequence of SEQ ID NO: 1, 2 or 3 and isolating an antibody that binds a human PCSK9 comprising selected from the group consisting of forms f c, r, p, m, e, h, aj and q or a catalytic or C-terminal domain or a peptide thereof that comprises amino acid variation from the corresponding sequence of SEQ ID NO: 1, 2 or 3, and optionally producing a form f c, r, p, m, e, h, aj or q PCSK9-binding fragment or derivative of the isolated antibody.

In an example, said forms are the mature forms.
In an example, said forms are the pro-forms.

In a Twenty-Third Aspect:

The method of aspect 21 or 22, comprising the step of obtaining a nucleic acid encoding the antibody, fragment, derivative or binding site and optionally inserting the nucleic acid in an expression vector.

For example, the method comprises isolating a cell (eg, B-cell, plasmablast, plasma cell or memory cell) comprising the nucleic acid, wherein the cell is obtained from a non-human vertebrate that has been immunised with the PCSK9 epitope.

In a Twenty-Fourth Aspect:

A kit for PCSK9 genotyping a human, wherein the kit comprises a nucleic acid (i) comprising a sequence of 10 or more (eg, 10, 15, 20, 30, 40, 50, 60, 70, 80, 90, 100 or more) contiguous nucleotides that specifically hybridises to a nucleotide sequence selected from the group consisting of SEQ ID NOs: 29-37 or at least the catalytic domain- or C-terminal domain-encoding sequence thereof, or specifically hybridises to an antisense sequence or an RNA transcript of said sequence, wherein said sequence of contiguous nucleotides hybridises to at least one nucleotide present in said selected sequence which is not present in SEQ ID NO: 28 or hybridises to an antisense sequence or an RNA transcript thereof; and/or (ii) comprising a sequence of at least 10 or more (eg, 10, 15, 20, 30, 40, 50, 60, 70, 80, 90, 100 or more) nucleotides of a nucleotide sequence selected from the group consisting of SEQ ID NOs: 29-37 or comprising an antisense sequence or RNA version of said contiguous nucleotides, wherein said sequence of contiguous nucleotides comprises at least one nucleotide present in said selected sequence which is not present in SEQ ID NO: 28.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Twenty-Fifth Aspect:

A kit for PCSK9 genotyping or phenotyping a human, wherein the kit comprises a ligand according to any one of aspects 1 to 19 or an antibody, fragment or derivative produced by the method of any one of aspects 21 to 23.

In a Twenty-Sixth Aspect:

Use of an anti-PCSK9 ligand that binds a human PCSK9 selected from the group consisting of forms f c, r, p, m, e, h, aj and q in the manufacture of a medicament for treating and/or preventing a PCSK9-mediated disease or condition in a human whose genome comprises a nucleotide sequence selected from the group consisting of SEQ ID NOs: 29-37, optionally for treating and/or preventing a PCSK9-mediated disease or condition in a human as recited in aspect 18 or 19.

In an example, said forms are the mature forms.
In an example, said forms are the pro-forms.

In a Twenty-Seventh Aspect:

Use of an anti-PCSK9 ligand that binds a human PCSK9 selected from the group consisting of forms f c, r, p, m, e, h, aj and q in the manufacture of a medicament for targeting said PCSK9 in a human to treat and/or prevent a disease or condition mediated by PCSK9, optionally for targeting PCSK9 in a human as recited in aspect 18 or 19.

In an example, said forms are the mature forms.
In an example, said forms are the pro-forms.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

The ligand can be any anti-PCSK9 ligand disclosed herein.

In a Twenty-Eight Aspect:

The use of aspect 26 or 27, wherein the ligand, human, disease or condition is according to any one of aspects 1 to 19.

In a Twenty-Ninth Aspect:

A method of targeting a PCSK9 for treating and/or preventing a PCSK9-mediated disease or condition in a human, the method comprising administering an anti-PCSK9 ligand to a human comprising a nucleotide sequence selected from the group consisting SEQ ID NOs: 29-37, whereby a PCSK9 encoded by said nucleotide sequence is targeted.

The ligand can be any anti-PCSK9 ligand disclosed herein.

In a Thirtieth Aspect:

The method of aspect 29, wherein the method comprises targeting a human PCSK9 selected from the group consisting of forms f c, r, p, m, e, h, aj and q with said ligand to treat and/or prevent said disease or condition in said human.

In an example, said forms are the mature forms.
In an example, said forms are the pro-forms.

In a Thirty-First Aspect:

A method of treating and/or preventing a disease or condition mediated by PCSK9 in a human, the method comprising targeting a human PCSK9 selected from the group consisting of forms f, c, r, p, m, e, h, aj and q by administering to the human a ligand that binds said PCSK9 thereby treating and/or preventing said disease or condition in the human.

In an example, said forms are the mature forms.
In an example, said forms are the pro-forms.

The ligand can be any anti-PCSK9 ligand disclosed herein.

In a Thirty-Second Aspect:

The method of aspect 31, wherein the genome of the human comprises a nucleotide sequence selected from the group consisting of SEQ ID NOs: 29-37.

In an example, the nucleotide sequence is selected from the group consisting of SEQ ID NOs: 29-35 and 37; or selected from the group consisting of SEQ ID NOs: 29-32 and 34-37; or selected from the group consisting of SEQ ID NOs: 29-32, 34, 35 and 37. These are naturally-occurring allele (haplotype) sequences that do not encode 46L and which meet the criteria set out above. These groups comprise variants that are associated with elevated LDL-C.

In an example, the nucleotide sequence is SEQ ID NO: 34, that encodes a 425S, which is associated with elevated LDL-C (Pisciotta et al 2006).

In an example, the nucleotide sequence selected from the group consisting of SEQ ID NOs: 31 and 37, that encode 670G which is a marker for severity of coronary atherosclerosis (Chen et al 2005).

In an example, the nucleotide sequence selected from the group consisting of SEQ ID NOs: 31, 32, 34, 35, 36 and 37; or selected from the group consisting of SEQ ID NOs: 31, 32, 34, 35 and 37. These are allele (haplotype) sequences that have a naturally-occurring combination of differences from SEQ ID NO: 28 (form a) and which meet the criteria set out above.

In an example, the nucleotide sequence is SEQ ID NO: 29.
In an example, the nucleotide sequence is SEQ ID NO: 30.
In an example, the nucleotide sequence is SEQ ID NO: 31.
In an example, the nucleotide sequence is SEQ ID NO: 32.
In an example, the nucleotide sequence is SEQ ID NO: 33.
In an example, the nucleotide sequence is SEQ ID NO: 34.
In an example, the nucleotide sequence is SEQ ID NO: 35.
In an example, the nucleotide sequence is SEQ ID NO: 36.
In an example, the nucleotide sequence is SEQ ID NO: 37.

In a Thirty-Third Aspect:
The method of any one of aspects 29 to 32, wherein the human has been or is genotyped as positive for a nucleotide sequence selected from the group consisting of SEQ ID NOs: 29-37 or the catalytic- or C-terminal domain-encoding sequence thereof.

In a Thirty-Fourth Aspect:
The method of any one of aspects 29 to 33, wherein the human has been or is phenotyped as positive for a human PCSK9 selected from the group consisting of forms f c, r, p, m, e, h, aj and q.

In an example, said forms are the mature forms.
In an example, said forms are the pro-forms.

In a Thirty-Fifth Aspect:
The method of any one of aspects 29 to 34, wherein the method comprises genotyping the human as positive for a nucleotide sequence selected from the group consisting of SEQ ID NOs: 29-37 or the catalytic- or C-terminal domain-encoding sequence thereof.

In a Thirty-Sixth Aspect:
The method of any one of aspects 29 to 35, wherein the method comprises phenotyping the human as positive for a human PCSK9 sequence selected from the group consisting of forms f c, r, p, m, e, h, aj and q.

In an example, said forms are the mature forms.
In an example, said forms are the pro-forms.

In a Thirty-Seventh Aspect:
The method of any one of aspects 29 to 36, wherein the human has been or is genotyped as heterozygous for a nucleotide sequence selected from the group consisting of SEQ ID NOs: 29-37 or the catalytic- or C-terminal domain-encoding sequence thereof; optionally wherein the human has been or is genotyped as comprising the nucleotide sequence of SEQ ID NO: 28 or the catalytic- or C-terminal domain-encoding sequence thereof and a nucleotide sequence selected from the group consisting of SEQ ID NOs: 29-37 or the catalytic- or C-terminal domain-encoding sequence thereof.

In a Thirty-Eighth Aspect:
The method of any one of aspects 29 to 37, wherein the genome of the human has been or is genotyped as homozygous for a nucleotide sequence selected from the group consisting of SEQ ID NOs: 29-37 or the catalytic- or C-terminal domain-encoding sequence thereof.

In a Thirty-Ninth Aspect:
The method of any one of aspects 29 to 38, wherein the method comprises genotyping the human for a nucleotide sequence selected from the group consisting of SEQ ID NOs: 29-37 or the catalytic- or C-terminal domain-encoding sequence thereof before administering the ligand to the human, wherein the ligand is determined to be capable of binding to a PCSK9 encoded by said selected sequence.

In a Fortieth Aspect:
The method of any one of aspects 29 to 39, wherein the ligand, human, disease or condition is according to any one of aspects 1 to 19.

In a Forty-First Aspect:
A method according to any one of aspects 29 to 40 for treating and/or preventing a condition or disease as recited in aspect 14 or 15, the method comprising administering said ligand and a statin (eg, cerovastatin, atorvastatin, simvastatin, pitavastin, rosuvastatin, fluvastatin, lovastatin or pravastatin) to the human.

In a Forty-Second Aspect:
The method of aspect 41, wherein the ligand and statin are administered separately.

In a Forty-Third Aspect:
The method of aspect 41, wherein the ligand and statin are administered simultaneously.

In a Forty-Fourth Aspect:
The method of any one of aspects 29 to 43, wherein the ligand is administered by subcutaneous injection.

In a Forty-Fifth Aspect:
A method of PCSK9 genotyping a nucleic acid sample of a human, the method comprising identifying in the sample the presence of a nucleotide sequence selected from the group consisting of SEQ ID NOs: 29-37 or the catalytic- or C-terminal domain-encoding sequence thereof.

In a Forty-Sixth Aspect:
A method of PCSK9 typing a protein sample of a human, the method comprising identifying in the sample the presence of a human PCSK9 selected from the group consisting of forms f c, r, p, m, e, h, aj and q.

In an example, said forms are the mature forms.
In an example, said forms are the pro-forms.

In a Forty-Seventh Aspect:
The method of aspect 45 or 46, comprising obtaining a sample of serum, blood, faeces, hair, tissue, cells, urine or saliva from a human, whereby the nucleic acid or protein sample is obtained and used in the step of identifying said sequence.

In a Forty-Eighth Aspect:
The method of any one of aspects 45 to 47, comprising using a ligand according to any one of aspects 1 to 19 to carry out said identifying step.

In a Forty-Ninth Aspect:
A method of treating and/or preventing in a human patient a cardiovascular disease or condition, or a disease or condition that is associated with elevated LDL cholesterol (eg, hypercholesterolaemia), wherein the patient is receiving or has previously received statin treatment for said disease or condition, the method comprising typing the patient using a method of any one of aspects 45 to 48 and administering a ligand according to one of aspects 1 to 19 whereby the human is treated or said disease or condition is prevented; optionally also reducing or stopping statin treatment.

In an example, said reducing or stopping comprises reducing the dose and/or dosing frequency of statin.

In a Fiftieth Aspect:
A diagnostic, therapeutic or prophylactic kit comprising a ligand that is capable of binding to or has been or is determined as capable of binding to an amino acid sequence selected from SEQ ID NOs: 4-27 and instructions for carrying out the method of any one of aspects 46 to 49 and/or a label or instructions indicating or covering administration of the ligand to a human as defined in any one of aspects 1 to 19.

In a Fifty-First Aspect:
A diagnostic, therapeutic or prophylactic kit comprising a nucleic acid probe comprising a nucleotide sequence that specifically hybridises to a nucleotide sequence selected from the group consisting of SEQ ID NOs: 29-37 or an antisense sequence or RNA transcript thereof and instructions for carrying out the method of aspect 45, 47 or 48.

In examples of the present invention, the ligand specifically binds to human PCSK9, eg, one or more of the rare PCSK9 variants disclosed herein (eg, one, two, three, more or all mature forms f c, r, p, m, e, h, aj and q) and optionally also the a and/or a' form. For example, the ligand specifically binds to mature form f and/or c as well as form a. Determination of such binding can be performed by any antibody binding test as known in the art, eg, by surface plasmon resonance Binding to each such form is, for example, respectively with a Kd of at least 1 mM, 100 nM, 1 nM, 100 pM, 10 pM or 1 pM.

In an example, the ligand binds form a and a PCSK9 selected from the group consisting of forms f c, r, p, m, e, h, aj and q, wherein the ligand binding to said selected form is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form f, wherein the ligand binding to form f is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form c, wherein the ligand binding to form c is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form r, wherein the ligand binding to form r is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form p, wherein the ligand binding to form p is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form m, wherein the ligand binding to form m is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form e, wherein the ligand binding to form e is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form h, wherein the ligand binding to form h is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form aj, wherein the ligand binding to form aj is with a Kd (determined by SPR) that is at least 60, 70, 80, 90 or 95% of the Kd for binding to form a. In an embodiment, both forms are mature forms. In an embodiment, both forms are pro-forms.

In an example, the ligand binds form a and form q, wherein the ligand binding to form q is with a Kd (determined by SPR) that is at least 60, 70, 80, 90 or 95% of the Kd for binding to form a. In an embodiment, both forms are mature forms. In an embodiment, both forms are pro-forms.

In examples of the present invention, the ligand neutralises human PCSK9, eg, one or more of the rare PCSK9 variants disclosed herein (eg, one, two, three, more or all mature forms f c, r, p, m, e, h, aj and q) and optionally also the a and/or a' form. For example, the ligand neutralises mature form f and/or c as well as form a. Determination of neutralisation can be performed, for example, by any neutralisation assay method disclosed in US20120093818A1 (Amgen, Inc) or US20110065902A1 (Regeneron Pharmaceuticals, Inc). Ligands of the invention that bind or target PCSK9 are useful, for example, for therapeutic and prophylactic applications disclosed in US20120093818A1 and US20110065902A1, these specific disclosures being incorporated herein by reference for use in the present invention and for possible inclusion in claims herein.

In embodiments where the ligand is used for therapeutic applications, an antigen binding protein can inhibit, interfere with or modulate one or more biological activities of a PCSK9 (eg, one or more of the rare variants disclosed herein and optionally also the a and/or a' form). In one embodiment, ligand binds specifically to human PCSK9 (eg, one or more of the rare variants disclosed herein and optionally also the a and/or a' form) and/or substantially inhibits binding of human PCSK9 (eg, said one or more of the rare variants disclosed herein and optionally also the a and/or a' form) to LDLR by at least 20%, eg, 20%-40%, 40-60%, 60-80%, 80-85%, or more (for example, by measuring binding in an in vitro competitive binding assay). In an example, the ligand is an antibody.

In an embodiment, the ligand has a Kd of less (binding more tightly) than $10^{-7}$, $10^{-8}$, $10^{-9}$, $10^{-10}$, $10^{-11}$, $10^{-12}$, $10^{-13}$ M for binding to one, two or more of the rare variants disclosed herein and optionally also the a and/or a' form. In an example, Kd is determined using SPR.

In an embodiment, the ligand has an IC50 for blocking the binding of LDLR to one or more of the rare PCSK9 variants disclosed herein (and optionally also the a and/or a' form) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

In an embodiment, the ligand has an IC50 for blocking the binding of LDLR to the a and/or a' form of PCSK9 that is no more than 1000, 100, 90, 80, 70, 60, 50, 40, 30, 20 or 10-fold more (ie, more inhibitory) than the IC50 for blocking the binding of LDLR to one or more of the rare PCSK9 variants disclosed herein (eg, one or more PCSK9 proteins comprising a sequence selected from SEQ ID NOs: 4 to 27). Additionally or alternatively, for example, the ligand has an IC50 for blocking the binding of LDLR to (i) the a and/or a' form of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, eg, in the range of 1 mM to 1 pM (eg, 1 mM to 100 pM; 10 nM to 100 pM; 1 nM to 10 pM; or 100 pM to 1 pM) and (ii) one or more PCSK9 proteins comprising a sequence selected from SEQ ID NOs: 4 to 27 of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, eg, in the range of 1 mM to 1 pM (eg, 1 mM to 100 pM; 10 nM to 100 pM; 1 nM to 10 pM; or 100 pM to 1 pM).

In an embodiment, the ligand binds to the a and/or a' form of PCSK9 with a binding affinity (Kd) that is greater than up to 10%, greater than up to 20%, greater than up to 40%, greater than up to 50%, greater than up to 55%, greater than up to 60%, greater than up to 65%, greater than up to 70%, greater than up to 75%, greater than up to 80%, greater than up to 85%, greater than up to 90%, greater than up to 95% or greater than up to 100% (ie, is double) relative to binding to a PCSK9 comprising a sequence selected from SEQ ID NOs: 4 to 27. Such binding measurements can be made using a variety of binding assays known in the art, eg, using surface plasmon resonance (SPR), such as by Biacore™ or using the ProteOn XPR36™ (Bio-Rad®), or using KinExA® (Sapidyne Instruments, Inc).

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the ligand which is an antibody is determined using SPR by
1. Coupling anti-mouse (or other relevant vertebrate) IgG (eg, Biacore BR-1008-38) to a biosensor chip (eg, GLM chip) such as by primary amine coupling;
2. Exposing the anti-mouse IgG (vertebrate antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

In an embodiment, assaying or testing of a ligand of the invention is carried out at or substantially at pH7 (eg, for in vitro tests and assays) and at or substantially at rtp.

One example of an IgG2 heavy chain constant domain of an anti-PCSK9 antibody of the present invention has the amino acid sequence as shown in SEQ ID NO: 154, FIG. 3KK of US20120093818A1, which sequence is incorporated herein by reference.

One example of an IgG4 heavy chain constant domain of an anti-PCSK9 antibody of the present invention has the amino acid sequence as shown in SEQ ID NO: 155, FIG. 3KK of US20120093818A1, which sequence is incorporated herein by reference.

One example of a kappa light chain constant domain of an anti-PCSK9 antibody has the amino acid sequence as shown in SEQ ID NO: 157, FIG. 3KK which sequence is incorporated herein by reference.

One example of a lambda light chain constant domain of an anti-PCSK9 antibody has the amino acid sequence as shown in SEQ ID NO: 156, FIG. 3KK of US20120093818A1, which sequence is incorporated herein by reference.

In examples of the present invention, the ligand binds mature PCSK9, eg, a mature form of one or more of the rare variants disclosed herein and optionally also the a and/or a' form.

In examples of the present invention, the ligand binds the catalytic domain of PCSK9, eg, of a mature form of one or more of the rare variants disclosed herein and optionally also the a and/or a' form.

In examples of the present invention, the ligand binds the prodomain of PCSK9, eg, of a mature form of one or more of the rare variants disclosed herein and optionally also the a and/or a' form.

In some embodiments, the ligand binds to the V domain of PCSK9, eg, of a mature form of one or more of the rare variants disclosed herein and optionally also the a and/or a' form. In some embodiments, the ligand binds to the V domain of PCSK9 (eg, of a mature form of one or more of the rare variants disclosed herein and optionally also the a and/or a' form) and prevents (or reduces, eg, by at least 10%) PCSK9 from binding to LDLR. In some embodiments, the ligand binds to the V domain of PCSK9 (eg, of a mature form of one or more of the rare variants disclosed herein and optionally also the a and/or a' form), and while it does not prevent (or reduce) the binding of PCSK9 to LDLR, the ligand prevents or reduces (eg, by at least 10%) the adverse activities mediated through PCSK9 on LDLR.

In examples of the present invention, the ligand is or comprises a fully human antibody. In an example, the ligand comprises human variable regions or humanised variable regions.

In an example, the ligand of the invention specifically binds to an epitope of a human PCSK9 selected from the group consisting of forms f c, r, p, m, e, h, aj and q, wherein the epitope comprises at least one amino acid that is not found in form a. For example, the amino acid is selected from the group consisting of 46L, 53V, 425S, 443T, 474V, 619P and 670G (numbering as used in SEQ ID NO:1). For example, the amino acid is selected from the group consisting of 425S, 443T, 474V, 619P and 670G (numbering as used in SEQ ID NO:1). For example, the amino acid is selected from the group consisting of 425S and 443T (numbering as used in SEQ ID NO:1). For example, the amino acid is selected from the group consisting of 474V, 619P and 670G (numbering as used in SEQ ID NO:1). In an example, the PCSK9 form is the mature form. In an example, the PCSK9 form is the pro-form. In an example, the ligand also specifically binds to form a and/or a'. In an embodiment, the ligand specifically binds to an epitope of form f PCSK9, wherein the epitope comprises at least one amino acid that is not found in form a. In an embodiment, the ligand specifically binds to an epitope of form c PCSK9, wherein the epitope comprises at least one amino acid that is not found in form a. In an embodiment, the ligand specifically binds to an epitope of form r PCSK9, wherein the epitope comprises at least one amino acid that is not found in form a. In an embodiment, the ligand specifically binds to an epitope of form p PCSK9, wherein the epitope comprises at least one amino acid that is not found in form a. In an embodiment, the ligand specifically binds to an epitope of form m PCSK9, wherein the epitope comprises at least one amino acid that is not found in form a. In an embodiment, the ligand specifically binds to an epitope of form e PCSK9, wherein the epitope comprises at least one amino acid that is not found in form a. In an embodiment, the ligand specifically binds to an epitope of form h PCSK9, wherein the epitope comprises at least one amino acid that is not found in form a. In an embodiment, the ligand specifically binds to an epitope of form aj PCSK9, wherein the epitope comprises at least one amino acid that is not found in form a. In an embodiment, the ligand specifically binds to an epitope of form q PCSK9, wherein the epitope comprises at least one amino acid that is not found in form a.

In an embodiment, ligand binds specifically to the pro-domain of a human PCSK9 selected from the group consisting of forms f c, r, p, m, e, h, aj and q. In an example, the ligand also specifically binds to the pro-domain of form a and/or a'. In an embodiment, the ligand specifically binds to the pro-domain of form f PCSK9, wherein the epitope comprises at least one amino acid that is not found in form a. In an embodiment, the ligand specifically binds to the pro-domain of form c PCSK9, wherein the epitope comprises at least one amino acid that is not found in form a. In an embodiment, the ligand specifically binds to the pro-domain of form r PCSK9, wherein the epitope comprises at least one amino acid that is not found in form a. In an embodiment, the ligand specifically binds to the pro-domain of form p PCSK9, wherein the epitope comprises at least one amino acid that is not found in form a. In an embodiment, the ligand specifically binds to the pro-domain of form m PCSK9, wherein the epitope comprises at least one amino acid that is not found in form a. In an embodiment, the ligand specifically binds to the pro-domain of form e PCSK9, wherein the epitope comprises at least one amino acid that is not found in form a. In an embodiment, the ligand specifically binds to the pro-domain of form h PCSK9, wherein the epitope comprises at least one amino acid that is not found in form a. In an embodiment, the ligand specifically binds to the pro-domain of form aj PCSK9, wherein the epitope comprises at least one amino acid that is not found in form a. In an embodiment, the ligand specifically binds to the pro-domain of form q PCSK9, wherein the epitope comprises at least one amino acid that is not found in form a.

In an embodiment, ligand binds specifically to the catalytic domain of a human PCSK9 selected from the group consisting of forms f c, r, p, m, e, h, aj and q. In an example, the ligand also specifically binds to the catalytic domain of form a and/or a'. In an embodiment, the ligand specifically binds to the catalytic domain of form f PCSK9, wherein the epitope comprises at least one amino acid that is not found in form a. In an embodiment, the ligand specifically binds to the catalytic domain of form c PCSK9, wherein the epitope comprises at least one amino acid that is not found in form a. In an embodiment, the ligand specifically binds to the catalytic domain of form r PCSK9, wherein the epitope comprises at least one amino acid that is not found in form a. In an embodiment, the ligand specifically binds to the catalytic domain of form p PCSK9, wherein the epitope comprises at least one amino acid that is not found in form a. In an embodiment, the ligand specifically binds to the catalytic domain of form m PCSK9, wherein the epitope comprises at least one amino acid that is not found in form a. In an embodiment, the ligand specifically binds to the catalytic domain of form e PCSK9, wherein the epitope comprises at least one amino acid that is not found in form a. In an embodiment, the ligand specifically binds to the catalytic domain of form h PCSK9, wherein the epitope comprises at least one amino acid that is not found in form a. In an embodiment, the ligand specifically binds to the catalytic domain of form aj PCSK9, wherein the epitope comprises at least one amino acid that is not found in form a. In an embodiment, the ligand specifically binds to the catalytic domain of form q PCSK9, wherein the epitope comprises at least one amino acid that is not found in form a.

In an embodiment, ligand binds specifically to the C-terminal domain of a human PCSK9 selected from the group consisting of forms f c, r, p, m, e, h, aj and q. In an example, the ligand also specifically binds to the C-terminal domain of form a and/or a'. In an embodiment, the ligand specifically binds to the C-terminal domain of form f PCSK9, wherein the epitope comprises at least one amino acid that is not found in form a. In an embodiment, the ligand specifically binds to the C-terminal domain of form c PCSK9, wherein the epitope comprises at least one amino acid that is not found in form a. In an embodiment, the ligand specifically binds to the C-terminal domain of form r PCSK9, wherein the epitope comprises at least one amino acid that is not found in form a. In an embodiment, the ligand specifically binds to the C-terminal domain of form p PCSK9, wherein the epitope comprises at least one amino acid that is not found in form a. In an embodiment, the ligand specifically binds to the C-terminal domain of form m PCSK9, wherein the epitope comprises at least one amino acid that is not found in form a. In an embodiment, the ligand specifically binds to the C-terminal domain of form e PCSK9, wherein the epitope comprises at least one amino acid that is not found in form a. In an embodiment, the ligand specifically binds to the C-terminal domain of form h PCSK9, wherein the epitope comprises at least one amino acid that is not found in form a. In an embodiment, the ligand specifically binds to the C-terminal domain of form aj PCSK9, wherein the epitope comprises at least one amino acid that is not found in form a. In an embodiment, the ligand specifically binds to the C-terminal domain of form q PCSK9, wherein the epitope comprises at least one amino acid that is not found in form a.

In an embodiment, ligand binds specifically to the substrate-binding groove of a human PCSK9 selected from the group consisting of forms f c, r, p, m, e, h, aj and q (see Cunningham et al., Nat Struct Mol Biol. 2007 May; 14(5): 413-9. Epub 2007 Apr. 15, "Structural and biophysical studies of PCSK9 and its mutants linked to familial hypercholesterolemia", incorporated herein in its entirety by reference). In an example, the ligand also specifically binds to the substrate-binding groove of form a and/or a'. In an embodiment, the ligand specifically binds to the Substrate-binding groove of form f PCSK9, wherein the epitope comprises at least one amino acid that is not found in form a. In an embodiment, the ligand specifically binds to the Substrate-binding groove of form c PCSK9, wherein the epitope comprises at least one amino acid that is not found in form a. In an embodiment, the ligand specifically binds to the Substrate-binding groove of form r PCSK9, wherein the epitope comprises at least one amino acid that is not found in form a. In an embodiment, the ligand specifically binds to the Substrate-binding groove of form p PCSK9, wherein the epitope comprises at least one amino acid that is not found in form a. In an embodiment, the ligand specifically binds to the Substrate-binding groove of form m PCSK9, wherein the epitope comprises at least one amino acid that is not found in form a. In an embodiment, the ligand specifically binds to the Substrate-binding groove of form e PCSK9, wherein the epitope comprises at least one amino acid that is not found in form a. In an embodiment, the ligand specifically binds to the Substrate-binding groove of form h PCSK9, wherein the epitope comprises at least one amino acid that is not found in form a. In an embodiment, the ligand specifically binds to the Substrate-binding groove of form aj PCSK9, wherein the epitope comprises at least one amino acid that is not found in form a. In an embodiment, the ligand specifically binds to the Substrate-binding groove of form q PCSK9, wherein the epitope comprises at least one amino acid that is not found in form a.

Reference is made to US20120093818A1 (Amgen, Inc), the entire disclosure of which is incorporated herein. This patent application discloses relevant ligands for use in the present invention, as well as examples and methods of producing and testing ligands that can be used with reference to the present invention.

In an example, the ligand is or comprises an antibody disclosed in Table 2 of US20120093818A1 (Amgen, Inc) or is a PCSK9-binding derivative thereof.

In an embodiment, the PCSK9-binding ligand of the invention is selected from the antigen binding proteins disclosed in US20120093818A1 (Amgen, Inc), eg, in paragraphs [0009] to and [0058] to [0063] of US20120093818A1; all of these disclosures (including the sequences of such proteins) are incorporated herein by reference as though explicitly recited herein and for possible inclusion in one or more claims or for use in the present invention.

In this paragraph SEQ ID NOs are those as appearing in US20120093818A1 (Amgen, Inc) and these sequences are incorporated herein by reference as though explicitly recited herein and for possible inclusion in one or more claims or for use in the present invention. In some aspects, the ligand of the invention comprises an isolated antigen binding protein that binds PCSK9 comprising: A) one or more heavy chain complementary determining regions (CDRHs) selected from the group consisting of: (i) a CDRH1 from a CDRH1 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (ii) a CDRH2 from a CDRH2 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; (iii) a CDRH3 from a CDRH3 in a sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60; and (iv) a CDRH of (i), (ii), and (iii) that contains one or more amino acid substitutions, deletions or insertions of no more than 4 amino acids; B) one or more light chain complementary determining regions (CDRLs) selected from the group consisting of: (i) a CDRL1 from a CDRL1 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (ii) a CDRL2 from a CDRL2 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; (iii) a CDRL3 from a CDRL3 in a sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46; and (iv) a CDRL of (i), (ii) and (iii) that contains one or more amino acid substitutions, deletions or insertions of no more than 4 amino acids; or C) one or more heavy chain CDRHs of A) and one or more light chain CDRLs of B). In some embodiments, the isolated antigen binding protein comprises at least one CDRH of A) and at least one CDRL of B). In some embodiments, the isolated antigen binding protein comprises at least two CDRH of A) and at least two CDRL of B). In some embodiments, the isolated antigen binding protein comprises said CDRH1, CDRH2, CDRH3, CDRL1, CDRL2 and CDRL3. In some embodiments, the CDRH of A) is selected from at least one of the group consisting of: (i) a CDRH1 amino acid sequence selected from the CDRH1 in a sequence selected from the group consisting of SEQ ID NO: 67, 79, 89, and 49; (ii) a CDRH2 amino acid sequence selected from the CDRH2 in a sequence selected from the group consisting of SEQ ID NO: 67, 79, 89, and 49; (iii) a CDRH3 amino acid sequence selected from the CDRH3 in a sequence selected from the group consisting of SEQ ID NO: 67, 79, 89, and 49; and (iv) a CDRH of (i), (ii) and (iii) that contains one or more amino acid substitutions, deletions or insertions of no more than 2 amino acids. In addition, the CDRL of B) is selected from at least one of the group consisting of: (i) a CDRL1 amino acid sequence selected from the CDRL1 in a sequence selected from the group consisting of SEQ ID NO: 12, 35, 32, and 23; (ii) a CDRL2 amino acid sequence selected from the CDRL2 in a sequence selected from the group consisting of SEQ ID NO: 12, 35, 32, and 23; (iii) a CDRL3 amino acid sequence selected from the CDRL3 in a sequence selected from the group consisting of SEQ ID NO: 12, 35, 32, and 23; and (iv) a CDRL of (i), (ii) and (iii) that contains one or more amino acid substitutions, deletions or insertions of no more than 2 amino acids; or C) one or more heavy chain CDRHs of A) and one or more light chain CDRLs of B. In some embodiments, the CDRH of A) is selected from at least one of the group consisting of: (i) a CDRH1 amino acid sequence of the CDRH1 amino acid sequence in SEQ ID NO: 67; (ii) a CDRH2 amino acid sequence of the CDRH2 amino acid sequence in SEQ ID NO: 67; (iii) a CDRH3 amino acid sequence of the CDRH3 amino acid sequence in SEQ ID NO: 67; and (iv) a CDRH of (i), (ii) and (iii) that contains one or more amino acid substitutions, deletions or insertions of no more than 2 amino acids; said CDRL of B) is selected from at least one of the group consisting of: (i) a CDRL1 amino acid sequence of the CDRL1 amino acid sequence in SEQ ID NO: 12; (ii) a CDRL2 amino acid sequence of the CDRL2 amino acid sequence in SEQ ID NO: 12; (iii) a CDRL3 amino acid sequence of the CDRL3 amino acid sequence in SEQ ID NO: 12; and (iv) a CDRL of (i), (ii) and (iii) that contains one or more amino acid substitutions, deletions or insertions of no more than 2 amino acids; or C) one or more heavy chain CDRHs of A) and one or more light chain CDRLs of B). In some embodiments, the antigen binding protein comprises A) a CDRH1 of the CDRH1 sequence in SEQ ID NO: 67, a CDRH2 of the CDRH2 sequence in SEQ ID NO: 67, and a CDRH3 of the CDRH3 sequence in SEQ ID NO: 67, and B) a CDRL1 of the CDRL1 sequence in SEQ ID NO: 12, a CDRL2 of the CDRL2 sequence in SEQ ID NO: 12, and a CDRL3 of the CDRL3 sequence in SEQ ID NO: 12. In some embodiments, the antigen binding protein comprises a heavy chain variable region (VH) having at least 80% sequence identity with an amino acid sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or a light chain variable region (VL) having at least 80% sequence identity with an amino acid sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, the VH has at least 90% sequence identity with an amino acid sequence selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or the VL has at least 90% sequence identity with an amino acid sequence selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46. In some embodiments, the VH is selected from the group consisting of SEQ ID NO: 74, 85, 71, 72, 67, 87, 58, 52, 51, 53, 48, 54, 55, 56, 49, 57, 50, 91, 64, 62, 89, 65, 79, 80, 76, 77, 78, 83, 69, 81, and 60, and/or the VL is selected from the group consisting of SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, and 46.

In an example of any aspect of the invention, the PCSK9-targeting or binding ligand comprises or consists of AMG145 or 31H4, 16F12, 11F1, 8A3 or 21B12 disclosed in US20120093818A1 (Amgen, Inc) or an antibody comprising the variable domains of AMG145, 31H4, 16F12, 11F1, 8A3 or 21B12, the disclosures of which (including sequences) are incorporated herein by reference as though explicitly recited herein and for possible inclusion in one or more claims or for use in the present invention. Preferably, the PCSK9-targeting or binding ligand comprises or consists of AMG145.

In an example, the AMG145 or other ligand of the invention is glycosylated, eg, has human glycosylation (eg, produced by a CHO, Cos or Hek293 cell). In an example, the ligand of the invention is produced in CHO.

Reference is made to US20110065902A1 (Regeneron Pharmaceuticals, Inc), the entire disclosure of which is incorporated herein. This patent application discloses relevant ligands for use in the present invention, as well as examples and methods of producing and testing ligands and determining medical efficacy that can be used with reference to the present invention.

Reference is made to the following PCT applications, the entire disclosures of which are incorporated herein. These disclose relevant ligands for use in the present invention, as well as examples and methods of producing and testing ligands and determining medical efficacy that can be used with reference to the present invention.
WO2008057457
WO2008057458
WO2008057459
WO2008063382
WO2008133647
WO2009100297
WO2009100318
WO2011037791
WO2011053759
WO2011053783
WO2008125623
WO2011072263
WO2009055783
WO2010029513
WO2011111007
WO2010077854

Antibody ligands to PCSK9 are described in, for example, WO 2008/057457, WO 2008/057458, WO 2008/057459, WO 2008/063382, WO 2008/125623, and US 2008/0008697; each of which is incorporated by reference herein in its entirety.

In an example, the ligand is or comprises an antibody disclosed in the Examples of US20110065902A1 (eg, 316P or 300N) or is a PCSK9-binding derivative thereof. All of these disclosures (including the sequences of such proteins and corresponding nucleotide sequences) are incorporated herein by reference as though explicitly recited herein and for possible inclusion in one or more claims or for use in the present invention. In an embodiment, the ligand is or comprises the variable domains of antibody 316P or 300N disclosed in US20110065902A1 or is (or comprises) such antibody or a PCSK9-binding derivative thereof.

In an embodiment, the ligand is or comprises the variable domains of antibody alirocumab or SAR236553/REGN727 (Sanofi Aventis/Regeneron) or is (or comprises) such antibody or a PCSK9-binding derivative thereof. In an example, the alirocumab is glycosylated, eg, has human glycosylation (eg, produced by a CHO, Cos or Hek293 cell). Preferably, the ligand is alirocumab or SAR236553/REGN727.

In an embodiment, the ligand is or comprises the variable domains of antibody evolocumab or is (or comprises) such antibody or a PCSK9-binding derivative thereof. In an example, the antibody is glycosylated, eg, has human glycosylation (eg, produced by a CHO, Cos or Hek293 cell). Preferably, the ligand is evolocumab.

In an embodiment, the ligand is selected from evolocumab, 1D05-IgG2 (Merck & Co.), ALN-PCS02 (Alnylam), RN316 (Pfizer-Rinat) and alirocumab.

In an embodiment, the ligand is selected from the following (sequences and definitions as per US2011/0065902, incorporated herein by reference):—
1. An antibody or antigen-binding fragment thereof which specifically binds hPCSK9, wherein the antibody or antigen-binding fragment comprises the heavy and light chain CDRs of a HCVR/LCVR amino acid sequence pair having SEQ ID NOs: 218/226.
2. The antibody or antigen-binding fragment of concept 1 comprising heavy and light chain CDR amino acid sequences having SEQ ID NOs: 220, 222, 224, 228, 230 and 232.
3. The antibody or antigen-binding fragment of concept 2 comprising an HCVR having the amino acid sequence of SEQ ID NO: 218 and an LCVR having the amino acid sequence of SEQ ID NO: 226.
4. An antibody or antigen-binding fragment thereof which binds to the same epitope on hPCSK9 as an antibody comprising heavy and light chain CDR amino acid sequences having SEQ ID NOs: 220, 222, 224, 228, 230 and 232.
5. An antibody or antigen-binding fragment thereof which competes for binding to hPCSK9 with an antibody comprising heavy and light chain CDR amino acid sequences having SEQ ID NOs: 220, 222, 224, 228, 230 and 232.

In an embodiment, the ligand is selected from the following (sequences and definitions as per US2012/0093818, incorporated herein by reference):—
1. An isolated neutralizing antigen binding protein that binds to a PCSK9 protein comprising the amino acid sequence of SEQ ID NO: 1, wherein the neutralizing antigen binding protein decreases the LDLR lowering effect of PCSK9 on LDLR, wherein the antigen binding protein comprises a light chain comprising an amino acid sequence of SEQ ID NO: 46, and wherein the antigen binding protein comprises a heavy chain comprising an amino acid sequence of SEQ ID NO: 60.
2. The isolated neutralizing antigen binding protein of concept 2, wherein the antigen binding protein is a LDLR non-competitive neutralizing antigen binding protein.
3. The isolated neutralizing antigen binding protein of concept 2, wherein the antigen binding protein is a LDLR competitive neutralizing antigen binding protein.
4. An antigen binding protein that selectively binds to PCSK9, wherein said antigen binding protein binds to PCSK9 with a Kd that is less than 100 pM.
5. An antigen binding protein that binds to a PCSK 9 protein of SEQ ID NO: 303 in a first manner, wherein the antigen binding protein binds to a variant of PCSK9 in a second manner, wherein said PCSK9 variant has at least one point mutation at a position selected from the group consisting of: 207, 208, 185, 181, 439, 513, 538, 539, 132, 351, 390, 413, 582, 162, 164, 167, 123, 129, 311, 313, 337, 519, 521, and 554 of SEQ ID NO: 303, wherein the first manner comprises a first EC50, a first Bmax, or a first EC50 and a first Bmax, wherein the second manner comprises a second EC50, a second Bmax, or a second EC50 and a second Bmax, and wherein a value for the first manner is different from a value for the second manner, and wherein the antigen binding protein comprises a light chain comprising an amino acid sequence of SEQ ID NO: 46, and wherein the antigen binding protein comprises a heavy chain comprising an amino acid sequence of SEQ ID NO: 60.

6. The antigen binding protein of concept 6, wherein the first manner comprises a first Bmax, wherein the second manner comprises a second Bmax that is different from the first Bmax, and wherein said PCSK9 variant has at least one point mutation selected from the group consisting of: D162R, R164E, E167R, S123R, E129R, A311R, D313R, D337R, R519E, H521R, and Q554R.

7. The antigen binding protein of concept 6, wherein the antigen binding protein binds to PCSK9 at a location that overlaps with a location that LDLR binds to PCSK9.

8. A method of making an antigen binding protein that binds to a PCSK9 protein comprising the amino acid sequence of SEQ ID NO: 1, wherein the antigen binding protein decreases the LDLR lowering effect of PCSK9 on LDLR, said method comprising: providing a host cell comprising a nucleic acid sequence that encodes the antigen binding protein; and maintaining the host cell under conditions in which the antigen binding protein is expressed, wherein the antigen binding protein comprises a light chain comprising an amino acid sequence of SEQ ID NO: 46, and wherein the antigen binding protein comprises a heavy chain comprising an amino acid sequence of SEQ ID NO: 60.

9. A method for treating or preventing a condition associated with elevated serum cholesterol levels in a subject, said method comprising administering to a subject in need thereof an effective amount of an isolated neutralizing antigen binding protein simultaneously or sequentially with an agent that elevates the availability of LDLR protein, wherein the isolated antigen binding protein binds to a PCSK9 protein comprising the amino acid sequence of SEQ ID NO: 1, wherein the neutralizing antigen binding protein decreases the LDLR lowering effect of PCSK9 on LDLR, wherein the antigen binding protein comprises a light chain comprising an amino acid sequence of SEQ ID NO: 46, and wherein the antigen binding protein comprises a heavy chain comprising an amino acid sequence of SEQ ID NO: 60.

10. The method of concept 10, wherein the agent that elevates the availability of LDLR protein comprises a statin.

11. An antigen binding protein that binds to PCSK9, wherein when the antigen binding protein is bound to PCSK9, the antibody is positioned 8 angstroms or less from at least one of the following residues of PCSK9: S153, S188, I189, Q190, S191, D192, R194, E197, G198, R199, V200, D224, R237, D238, K243, S373, D374, S376, T377, F379, 1154, T187, H193, E195, I196, M201, V202, C223, T228, S235, G236, A239, G244, M247, I369, S372, C375, or C378, wherein the antigen binding protein comprises a light chain comprising an amino acid sequence of SEQ ID NO: 46, and wherein the antigen binding protein comprises a heavy chain comprising an amino acid sequence of SEQ ID NO: 60.

The ligand can be used for the treatment, therapy, prophylaxis and/or diagnosis of one or more diseases or conditions or susceptibility thereto, wherein such diseases or conditions comprise those disclosed in US20120093818A1 (Amgen, Inc) and US20110065902A1 (Regeneron Pharmaceuticals, Inc), eg, a disease or condition disclosed in paragraphs [0375] to [0383] of US20120093818A1, which disclosure is incorporated herein by reference in its entirety for inclusion in one more claims herein.

The ligand can be administered to a human characterised as described in US20120093818A1 (Amgen, Inc) or US20110065902A1.

The ligand can be administered in a form or combination disclosed in US20120093818A1 (Amgen, Inc) or US20110065902A1, which disclosure is incorporated herein by reference. For example, the ligand with a drug, excipient, diluent or carrier as described in US20120093818A1 (Amgen, Inc) or US20110065902A1 (eg, as disclose in paragraphs [0384] to [0412] of US20120093818A1), which disclosure is incorporated herein by reference, and the present invention also relates to the corresponding pharmaceutical compositions comprising the combination of a ligand of the invention and such a further agent.

The ligand can be used in a method of diagnosis as set out in US20120093818A1 (Amgen, Inc) or US20110065902A1, eg, in paragraphs [0413] to [0415] of US20120093818A1 which disclosure is incorporated herein by reference.

Diagnostic Applications

In some embodiments, the ligand of the invention is a diagnostic tool. The ligand can be used to assay the amount of PCSK9 present in a sample and/or subject. As will be appreciated by one of skill in the art, such ligands need not be neutralizing ligands. In some embodiments, the diagnostic ligand is not a neutralizing ligand. In some embodiments, the diagnostic ligand binds to a different epitope than a neutralizing ligand binds to. In some embodiments, the two ligands do not compete with one another.

In some embodiments, the ligands of the invention are used or provided in an assay kit and/or method for the detection of PCSK9 in mammalian tissues or cells in order to screen/diagnose for a disease or disorder associated with changes in levels of PCSK9. The kit comprises a ligand that binds PCSK9 and means for indicating the binding of the ligand with PCSK9, if present, and optionally PCSK9 protein levels. Various means for indicating the presence of a ligand can be used. For example, fluorophores, other molecular probes, or enzymes can be linked to the ligand and the presence of the ligand can be observed in a variety of ways. The method for screening for such disorders can involve the use of the kit, or simply the use of one of the disclosed ligands and the determination of whether the ligand binds to PCSK9 in a sample. As will be appreciated by one of skill in the art, high or elevated levels of PCSK9 will result in larger amounts of the ligand binding to PCSK9 in the sample. Thus, degree of ligand binding can be used to determine how much PCSK9 is in a sample. Subjects or samples with an amount of PCSK9 that is greater than a predetermined amount (e.g., an amount or range that a person without a PCSK9 related disorder would have) can be characterized as having a PCSK9 mediated disorder. In some embodiments, the invention provides a method wherein the ligand is administered to a subject taking a statin, in order to determine if the statin has increased the amount of PCSK9 in the subject.

In some embodiments, the ligand is a non-neutralizing ligand and is used to determine the amount of PCSK9 in a subject receiving an ABP and/or statin treatment.

In some embodiments, the ligand of the invention can specifically bind human PCSK9 (eg, one, two or more rare variant forms disclosed herein) and is characterized by at least one of: (i) capable of reducing serum total cholesterol at least about 25-35% and sustaining the reduction over at least a 24 day period relative to a predose level; (ii) capable of reducing serum LDL cholesterol at least about 65-80% and sustaining the reduction over at least a 24 day period relative to a predose level; (iii) capable of reducing serum LDL cholesterol at least about 40-70% and sustaining the reduction over at least a 60 or 90 day period relative to a predose level; (iv) capable of reducing serum triglyceride at least about 25-40% relative to predose level; (v) does not reduce serum HDL cholesterol or reduces serum HDL cholesterol no more than 5% relative to predose level. In some embodiments, an isolated nucleic acid molecule is provided and it encodes the ligand. In some embodiments an expression vector is provided and comprises the nucleic acid molecule. In some embodiments, a pharmaceutical composition is provided and it can comprise the ligand and a pharmaceutically acceptable carrier. In some embodiments, a method is provided for treating a disease or condition which is ameliorated, improved, inhibited or prevented with a PCSK9 antagonist ligand of the invention. The method can comprise administering a therapeutic amount of the pharmaceutical composition or ligand to a subject in need thereof. In some embodiments, the subject is a human subject suffering from hypercholesterolemia, hyperlipidemia, indicated for LDL apheresis, identified as heterozygous for Familial Hypercholesterolemia, statin intolerant, statin uncontrolled, at risk for developing hypercholesterolemia, dyslipidemia, cholestatic liver disease, nephrotic syndrome, hypothyroidism, obesity, atherosclerosis and cardiovascular diseases. In some embodiments, a method of providing a treatment or therapy is provided to a subject. In some embodiments, the method comprises reducing serum cholesterol at least about 40-70% over at least 60 to 90 days. In some embodiments, a method of receiving treatment or therapy is provided, the method can comprise receiving a ligand thereof at a frequency of once every 60 to 90 days.

In one aspect, the invention provides a ligand of the invention which is or comprises an human antibody or antigen-binding fragment of a human antibody that specifically binds and inhibits human proprotein convertase subtilisin/kexin type 9 (hPCSK9, eg, one, two or more rare variant forms disclosed herein and optionally form a and/or form a'), characterized by the ability to reduce serum LDL cholesterol in a human by 40-80% over a 24, 60 or 90 day period relative to predose levels, with little or no reduction in serum HDL cholesterol and/or with little or no measurable effect on liver function, as determined by ALT and AST measurements.

In one embodiment, the ligand of the invention comprises an antibody or antigen-binding fragment of an antibody that specifically binds hPCSK9 and is characterized by at least one of:
(i) capable of reducing serum total cholesterol at least about 25-35% and sustaining the reduction over at least a 24 day period relative to a predose level, preferably the reduction in serum total cholesterol is at least about 30-40%;
(ii) capable of reducing serum LDL cholesterol at least about 65-80% and sustaining the reduction over at least a 24 day period relative to a predose level;
(iii) capable of reducing serum triglyceride at least about 25-40% relative to predose level;
(iv) does not reduce serum HDL cholesterol or reduces serum HDL cholesterol no more than 5% relative to predose level.

See US2011/0065902 for definitions of these terms and optional features, the disclosure of which is incorporated herein by reference in its entirety.

In one embodiment, the invention comprises an antibody or antigen-binding fragment of an antibody that specifically binds hPCSK9 and is characterized by at least one of:
(i) capable of reducing serum LDL cholesterol at least about 40-70% and sustaining the reduction over at least a 60 or 90 day period relative to a predose level;
(ii) capable of reducing serum triglyceride at least about 25-40% relative to predose level;
(iii) does not reduce serum HDL cholesterol or reduces serum HDL cholesterol no more than 5% relative to predose level.

In one embodiment, the antibody or antigen-binding fragment is characterized as exhibiting an enhanced binding affinity (KD) for hPCSK9 at pH 5.5 relative to the KD at pH 7.4, as measured by plasmon surface resonance. In a specific embodiment, the antibody or fragment thereof exhibits at least a 20-fold, at least a 40-fold or at least a 50-fold enhanced affinity for PCSK9 at an acidic pH relative to a neutral pH, as measured by surface plasmon resonance In one embodiment, the antibody or antigen-binding fragment is characterized as not exhibiting an enhanced binding affinity for PCSK9 at an acidic pH relative to a neutral pH, as measured by surface plasmon resonance. In a specific embodiment, the antibody or fragment thereof exhibits a decreased binding affinity at an acidic pH.

In another embodiment, the antibody or antigen-binding fragment binds human, human GOF mutation D374Y, cynomolgus monkey, rhesus monkey, mouse, rat and hamster PCSK9.

In one embodiment, the antibody or antigen-binding fragment binds human and monkey PCSK9, but does not bind mouse, rat or hamster PCSK9.

In one embodiment, the invention comprises an antibody or antigen-binding fragment of an antibody comprising one or more of a heavy chain variable region (HCVR), light chain variable region (LCVR), HCDR1, HCDR2, HCDR3 disclosed in any of paragraphs [023]-[037] of US2011/0065902, the disclosures of which are incorporated herein by reference.

In a related embodiment, the invention comprises an antibody or antigen-binding fragment of an antibody which specifically binds hPCSK9, wherein the antibody or fragment comprises heavy and light chain CDR domains contained within heavy and light chain sequence pairs selected from the group consisting of SEQ ID NO (using the sequence numbering in US2011/0065902): 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, 502/504, 506/514, 522/524, 526/528, 530/538, 546/548, 550/552, 554/562, 570/572, 574/576, 578/586, 594/596, 598/600, 602/610, 618/620, 622/624, 626/634, 642/644, 646/648, 650/658, 666/668, 670/672, 674/682, 690/692, 694/696, 698/706, 714/716, 718/720, 722/730, 738/740 and 742/744. In one embodiment, the CDR sequences are contained within HCVR and LCVR selected from the amino acid sequence pairs of SEQ ID NO: 50/58, 66/68, 70/72, 74/82, 90/92, 94/96, 122/130, 138/140, 142/144, 218/226, 234/236, 238/240, 242/250, 258/260, 262/264, 314/322, 330/332 and 334/336. In more specific embodiments, the CDR sequences are comprised within HCVR/LCVR sequences selected from SEQ ID NO: 90/92 or 218/226.

In an example, the invention features a pharmaceutical composition comprising a ligand of the invention, wherein the ligand comprises or consists of a recombinant human antibody or fragment thereof which specifically binds hPCSK9 and a pharmaceutically acceptable carrier. In one embodiment, the invention features a composition which is a combination of a ligand of the invention (eg, an antibody or antigen-binding fragment of an antibody), and a second therapeutic agent. The second therapeutic agent may be any agent that is advantageously combined with the ligand of the invention, for example, an agent capable of inducing a cellular depletion of cholesterol synthesis by inhibiting 3-hydroxy-3-methylglutaryl (HMG)-coenzyme A (CoA) reductase, such as, for example, cerovastatin, atorvastatin, simvastatin, pitavastin, rosuvastatin, fluvastatin, lovastatin, pravastatin, etc; capable of inhibiting cholesterol uptake and or bile acid re-absorption; capable of increasing lipoprotein catabolism (such as niacin); and/or activators of the LXR transcription factor that plays a role in cholesterol elimination such as 22-hydroxycholesterol.

In an example, the invention provides a method for inhibiting hPCSK9 activity using the anti-PCSK9 ligand of the invention (eg, an antibody or antigen-binding portion of the antibody of the invention), wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of PCSK9 activity. Specific populations treatable by the therapeutic methods of the invention include subjects indicated for LDL apheresis, subjects with PCSK9-activating mutations (gain of function mutations, "GOF"), subjects with heterozygous Familial Hypercholesterolemia (heFH); subjects with primary hypercholesterolemia who are statin intolerant or statin uncontrolled; and subjects at risk for developing hypercholesterolemia who may be preventably treated. Other indications include dyslipidemia associated with secondary causes such as Type 2 diabetes mellitus, cholestatic liver diseases (primary biliary cirrhosis), nephrotic syndrome, hypothyroidism, obesity; and the prevention and treatment of atherosclerosis and cardiovascular diseases.

In specific embodiments of the method of the invention, the ligand of the invention (eg, anti-hPCSK9 antibody or antibody fragment of the invention) is useful to reduce elevated total cholesterol, non-HDL cholesterol, LDL cholesterol, and/or apolipoprotein B (apolipoprotein B100).

The ligand (eg, antibody or antigen-binding fragment) of the invention may be used alone or in combination with a second agent, for example, an HMG-CoA reductase inhibitor and/or another lipid lowering drug.

Treatment Population

The invention provides therapeutic methods for treating a human patient in need of a composition or ligand of the invention. While modifications in lifestyle and conventional drug treatment are often successful in reducing cholesterol levels, not all patients are able to achieve the recommended target cholesterol levels with such approaches. Various conditions, such as familial hypercholesterolemia (FH), appear to be resistant to lowering of LDL-C levels in spite of aggressive use of conventional therapy. Homozygous and heterozygous familial hypercholesterolemia (hoFH, heFH) is a condition associated with premature atherosclerotic vascular disease. However, patients diagnosed with hoFH are largely unresponsive to conventional drug therapy and have limited treatment options. Specifically, treatment with statins, which reduce LDL-C by inhibiting cholesterol synthesis and upregulating the hepatic LDL receptor, may have little effect in patients whose LDL receptors are non-existent or defective. A mean LDL-C reduction of only less than about 20% has been recently reported in patients with genotype-confirmed hoFH treated with the maximal dose of statins. The addition of ezetimibe 10 mg/day to this regimen resulted in a total reduction of LDL-C levels of 27%, which is still far from optimal. Likewise, many patients are statin non-responsive, poorly controlled with statin therapy, or cannot tolerate statin therapy; in general, these patients are unable to achieve cholesterol control with alternative treatments. There is a large unmet medical need for new treatments that can address the short-comings of current treatment options.

Specific populations treatable by the therapeutic methods of the invention include patients indicated for LDL apheresis, subjects with PCSK9-activating (GOF) mutations, heterozygous Familial Hypercholesterolemia (heFH); subjects with primary hypercholesterolemia who are statin intolerant or statin uncontrolled; and subjects at risk for developing hypercholesterolemia who may be preventably treated.

Therapeutic Administration and Formulations

The invention provides therapeutic compositions comprising the anti-PCSK9 ligands, antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the ligand, eg, antibody, of the present invention is used for treating various conditions and diseases associated with PCSK9, including hypercholesterolemia, disorders associated with LDL and apolipoprotein B, and lipid metabolism disorders, and the like, in an adult patient, it is advantageous to intravenously administer the ligand or antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, thus the composition invention provides the ligand by e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

The invention provides therapeutic methods in which the ligand, eg, antibody or antibody fragment, of the invention is useful to treat hypercholesterolemia associated with a variety of conditions involving hPCSK9. The anti-PCSK9 ligands, eg, antibodies or antibody fragments, of the invention are particularly useful for the treatment of hypercholesterolemia and the like. Combination therapies may include the anti-PCSK9 ligand of the invention with, for example, one or more of any agent that (1) induces a cellular depletion of cholesterol synthesis by inhibiting 3-hydroxy-3-methylglutaryl (HMG)-coenzyme A (CoA) reductase, such as cerivastatin, atorvastatin, simvastatin, pitavastatin, rosuvastatin, fluvastatin, lovastatin, pravastatin; (2) inhibits cholesterol uptake and or bile acid re-absorption; (3) increase lipoprotein catabolism (such as niacin); and activators of the LXR transcription factor that plays a role in cholesterol elimination such as 22-hydroxycholesterol or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor).

Tailoring Antibodies to Rare PCSK9 Variant Profile

As outline above, the invention includes the possibility to tailor treatment of humans further by selecting antibody-based ligands with variable domains based on gene segments commonly found in humans of the ethnic populations where the variant PCSK9 forms are found to meet the selection criteria of the invention. An example is provided below for ligands comprising antibody VH domains derived from recombination of human VH3-23.

The inventor analysed the frequencies and distribution of various human VH3-23 alleles and realised the desirability of using ligands based on human VH3-23 alleles comprising SNP rs56069819. This SNP corresponds to a change from leucine at position 24 in the encoded protein sequence to a valine at that position (L24V change) and the SNP is at coordinate 106725482 on human chromosome 14.

Figure 2:
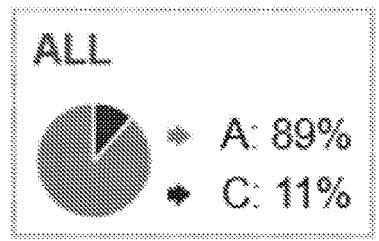
FIG. 2 depicts the cumulative allele frequency distribution across the 1000 Genomes Project database of human VH3-23 alleles comprising SNP rs56069819 (such alleles denoted "C" and the most frequent allele (which does not comprise this SNP) denoted "A"). The figure shows that VH3-23 alleles comprising SNP rs56069819 are present at a cumulative frequency of 11% across all human ethnic populations taken as a whole, whereas in certain specific human ethnic sub-populations (ASW, LWK, YRI, CEU and GBR) such alleles are present at an above-average cumulative frequency. Indicated in the figure are those human PCSK9 variant forms (marked "Variants") that are found in the various sub-populations with above-average occurrence of human VH3-23 alleles comprising SNP rs56069819.
Figure 2:
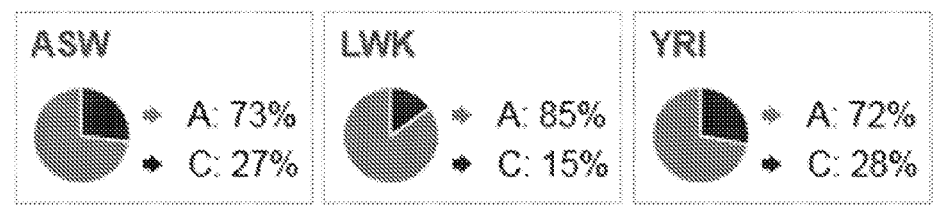
Figure 2:
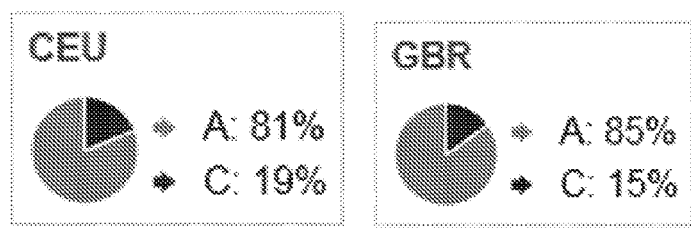

FIG. 2 shows the cumulative allele frequency distribution across the 1000 Genomes Project database of human VH3-23 alleles comprising SNP rs56069819 (such alleles denoted "C" and the most frequent allele (which does not comprise this SNP) denoted "A"). The figure shows that VH3-23 alleles comprising SNP rs56069819 are present at a cumulative frequency of 11% across all human ethnic populations taken as a whole, whereas in certain specific human ethnic sub-populations (ASW, LWK, YRI, CEU and GBR) such alleles are present at an above-average cumulative frequency. Indicated in the figure are those human PCSK9 variant forms (marked "Variants") that are found in the various sub-populations with above-average occurrence of human VH3-23 alleles comprising SNP rs56069819. Table 7 shows the VH3-23 variants and the SNPs that they comprise, as well as their cumulative allele frequencies as found in the 1000 Genomes Project database.

Notably, human VH3-23 alleles comprising SNP rs56069819 were found in the CEU population at a frequency that is almost double the frequency of 11% for all populations. For the ASW and YRI populations the frequency was over a quarter of the population. Thus, the invention advantageously enables one to select a ligand comprising an antibody or antibody fragment, wherein the antibody or fragment comprises a VH domain derived from the recombination of a human VH gene segment, a human D gene segment and a human JH gene segment, the VH gene segment comprising a nucleotide sequence that comprises SNP rs56069819 (db-SNP numbering, build number as recited above).

In an example, one can tailor the treatment further by selecting such a ligand that specifically binds to a human PCSK9 selected from forms: f c, m, e, h, p, q and aj, such forms being those appearing in human populations ASW, LWK, YRI, CEU and GBR.

In an example, the VH gene segment is VH3-23*04, which is a commonly found variant that comprises SNP rs56069819 in human populations ASW, LWK, YRI, CEU and GBR.

In an example, the ligand is for treating and/or preventing a PCSK9-mediated disease or condition in a human that expresses a human PCSK9 selected from forms: f c, m, e, h, p, q and aj.

In an example, the ligand is for treating and/or preventing a PCSK9-mediated disease or condition in a human of ASW, LWK, YRI, CEU or GBR ancestry.

In an embodiment, the ligand is for treating and/or preventing a PCSK9-mediated disease or condition in a human of ASW ancestry, wherein the human expresses a PCSK9 selected from f c, m, e, h, p and q or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of LWK ancestry, wherein the human expresses a PCSK9 selected from f c, m, e and h or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of YRI ancestry, wherein the human expresses a PCSK9 selected from f c, m, e and h or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of CEU ancestry, wherein the human expresses a PCSK9 selected from f c, p and aj or the human comprises a corresponding nucleotide or amino acid sequence as set out in Table 6. Optionally this ligand comprises a VH domain derived from recombination of human VH3-23*04.

In an embodiment, the ligand is for treating and/or preventing a PCSK9-mediated disease or condition in a human of GBR ancestry, wherein the human expresses a PCSK9 selected from f, c and p or the human comprises a corresponding nucleotide or amino acid sequence as set out in Table 6. Optionally this ligand comprises a VH domain derived from recombination of human VH3-23*04.

In an example, the ligand is alirocumab.

In other embodiments, as explained more fully above, the invention provides for ligands which are tailored to the human recipient's genotype and/or phenotype based on alternative human VH gene segments, or on Vκ, Vλ, or constant region gene segments (see further Table 9 for representative variants).

For example, the ligand of the invention comprises or consists of an antibody that comprises a VH domain that is derived from the recombination of a human VH gene segment, a human D gene segment and a human JH gene segment, wherein the VH gene segment is selected from the group consisting of (i) IGHV1-18*01 and the genome of the human comprises a human IGHV1-18*01 nucleotide sequence or the human expresses antibodies comprising variable domains derived from the recombination of human IGHV1-18*01; or (ii) IGVH1-46*01 and the genome of the human comprises a human IGHV1-46*01 nucleotide sequence or the human expresses antibodies comprising variable domains derived from the recombination of human IGHV1-46*01.

For example, the ligand of the invention comprises or consists of an antibody that comprises a VL domain that is derived from the recombination of a human VL gene segment and a human JL gene segment, wherein the VL gene segment is selected from the group consisting of (i) IGKV4-1*01 and the genome of the human comprises a human IGKV4-1*01 nucleotide sequence or the human expresses antibodies comprising variable domains derived from the recombination of human IGKV4-1*01; (ii) IGLV2-14*01 and the genome of the human comprises a human IGLV2-14*01 nucleotide sequence or the human expresses antibodies comprising variable domains derived from the recombination of human IGLV2-14*01; or (iii) IGKV1-13*02 and the genome of the human comprises a human IGKV1-13*02 nucleotide sequence or the human expresses antibodies comprising variable domains derived from the recombination of human IGKV1-13*02.

For example, the inventor identified the possibility of addressing the rarer IGH-gamma-1 SNPs 204D (observed cumulative frequency of 0.296) and 206L (observed cumulative frequency of 0.283) individually or in combination. These residues are part of the CH3 domain, and as such they form part of antibody Fc regions. Thus, matching of these CH3 variations with the patient is especially beneficial for reasons as discussed above. Thus, in this example the ligand of the invention comprises or consists of an antibody that comprises a human gamma-1 heavy chain constant region that comprises an Asp corresponding to position 204 of SEQ ID NO: 42 or a Leu corresponding to position 206 of SEQ ID NO: 42 and wherein the genome of the human comprises a gamma-1 heavy chain constant region nucleotide sequence that encodes such an Asp or Leu or the human expresses antibodies comprising human gamma-1 constant regions comprising such an Asp or Leu. An example of such a ligand is alirocumab.

In another example, the inventor identified the possibility of addressing IGH-gamma-2 SNPs. This included consideration of Fc region variation—in this respect, the inventor focused on positions 161 and 257 which are in the Fc region. Thus, in this example the ligand of the invention comprises or consists of an antibody that comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44; and wherein the genome of the human comprises a gamma-2 heavy chain constant region nucleotide sequence that encodes such a selected amino acid or the human expresses antibodies comprising human gamma-2 constant regions comprising such a selected amino acid. An example of such a ligand is evolocumab or bococizumab.

In another example, the inventor addressed human kappa constant region variation. Thus, in this example the ligand of the invention comprises or consists of an antibody that comprises a human kappa light chain constant region that comprises a Val corresponding to position 84 of SEQ ID NO: 50 or a Cys corresponding to position 87 of SEQ ID NO: 50; and wherein the genome of the human comprises a kappa light chain constant region nucleotide sequence that encodes such a Val or Cys or the human expresses antibodies comprising human kappa light chain constant regions comprising such a Val or Cys. An example of such a ligand is alirocumab or bococizumab.

In another example, the inventor addressed human lambda constant region variation. Thus, in this example the ligand of the invention comprises or consists of an antibody that comprises a human IGLC2*01 light chain constant region; and wherein the genome of the human comprises a human IGLC2*01 nucleotide sequence or the human expresses antibodies comprising human light chain IGLC2*01 constant regions. An example of such a ligand is evolocumab.

Further exemplary ligands are in the paragraphs 1-17 as follows.

1. An antibody or antibody fragment for use in a method of reducing cholesterol level or maintaining previously reduced cholesterol level in a human in need thereof, wherein the antibody or fragment comprises a human gamma heavy chain constant region that comprises a first amino acid that is encoded by a human gamma heavy chain constant region gene segment SNP, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said PCSK9 amino acid sequence and comprises a human gamma heavy chain constant region gene segment comprising said SNP, or the human expresses antibodies comprising human gamma constant regions comprising said first amino acid.

In an alternative, paragraph 1 provides:—

An antibody or antibody fragment for use in a method of reducing cholesterol level or maintaining previously reduced cholesterol level in a human in need thereof, wherein the antibody or fragment comprises a human gamma-1 heavy chain constant region that comprises an Asp corresponding to position 204 of SEQ ID NO: 42 or a Leu corresponding to position 206 of SEQ ID NO: 42, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises an IGHG1*01 human heavy chain constant region gene segment, or the human expresses antibodies comprising human gamma-1 constant regions comprising such an Asp and Leu.

In an embodiment, said mutation is I474V. In another embodiment, said mutation is E670G.

An example provides:—

An antibody or antibody fragment for use in a method of reducing cholesterol level or maintaining previously reduced cholesterol level in a human in need thereof, wherein the antibody or fragment comprises a human gamma-1 heavy chain constant region that comprises an Asp corresponding to position 204 of SEQ ID NO: 42 and a Leu corresponding to position 206 of SEQ ID NO: 42, and the antibody or fragment specifically binds a proprotein convertase subtilisin/kexin type 9 (PCSK9) amino acid sequence that comprises a C-terminal domain comprising a mutation I474V in SEQ ID NO:1, wherein the human comprises a nucleotide sequence encoding said amino acid sequence and comprises an IGHG1*01 human heavy chain constant region gene segment. Optionally, the antibody or fragment comprises an IGHG1*01 human heavy chain constant region.

Another example provides:—

An antibody or antibody fragment for use in a method of reducing cholesterol level or maintaining previously reduced cholesterol level in a human in need thereof, wherein the antibody or fragment comprises a human gamma-1 heavy chain constant region that comprises an Asp corresponding to position 204 of SEQ ID NO: 42 and a Leu corresponding to position 206 of SEQ ID NO: 42, and the antibody or fragment specifically binds a proprotein convertase subtilisin/kexin type 9 (PCSK9) amino acid sequence that comprises a C-terminal domain comprising a mutation E670G in SEQ ID NO:1, wherein the human comprises a nucleotide sequence encoding said amino acid sequence and comprises an IGHG1*01 human heavy chain constant region gene segment. Optionally, the antibody or fragment comprises an IGHG1*01 human heavy chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the antibody comprises a human gamma-1 heavy chain constant region that comprises an Asp corresponding to position 204 of SEQ ID NO: 42 and a Leu corresponding to position 206 of SEQ ID NO: 42.

3. The antibody or antibody fragment of paragraph 1 or 2, wherein the antibody comprises an IGHG1*01 human heavy chain constant region.

4. The antibody or antibody fragment of any one of paragraphs 1 to 3, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

5. The antibody or antibody fragment of any one of paragraphs 1 to 4, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

6. The antibody or antibody fragment of paragraph 5, wherein the step of determining comprises assaying a biological sample from the human for a nucleotide sequence encoding the PCSK9 that comprises the C-terminal domain comprising the mutation I474V or E670G in SEQ ID NO: 1.
7. The antibody or antibody fragment of paragraph 6, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.
8. The antibody or antibody fragment of paragraph 6 or 7, wherein the assaying comprises nucleic acid amplification and optionally one or more methods selected from sequencing, next generation sequencing, nucleic acid hybridization, and allele-specific amplification and/or wherein the assaying is performed in a multiplex format.
9. The antibody or antibody fragment of any one of paragraphs 1 to 8, wherein said antibody or antibody fragment is for administration to a human that is or has been further determined to be substantially resistant to statin treatment.
10. The antibody or antibody fragment of any one of paragraphs 1 to 9, wherein antibody or antibody fragment is for administration to a human that is receiving or has received statin treatment or has reduced responsiveness to statin treatment.
11. The antibody or antibody fragment of paragraph 9 or 10, wherein said antibody or antibody fragment is for administration to the human separately or simultaneously with said statin treatment.
12. The antibody or antibody fragment of any one of paragraphs 6 to 10, wherein said biological sample comprises serum, blood, faeces, tissue, a cell, urine and/or saliva of said human.
13. The antibody or antibody fragment of any one of paragraphs 1 to 12, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.
14. The antibody or antibody fragment of any one of paragraphs 1 to 13, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
15. The antibody or antibody fragment of any one of paragraphs 1 to 14, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The antibody or antibody fragment of any one of paragraphs 1 to 15, wherein the nucleotide sequence is SEQ ID NO: 29 or 30.
17. The antibody or antibody fragment of any one of paragraphs 1 to 16, wherein said antibody or antibody fragment is for administration by intravenous or subcutaneous administration and/or is comprised in an injectable preparation.

Further exemplary methods are in the paragraphs 1-18 as follows.
1. A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human gamma-1 heavy chain constant region that comprises an Asp corresponding to position 204 of SEQ ID NO: 42 or a Leu corresponding to position 206 of SEQ ID NO: 42 and wherein said human comprises (i) an IGHG1*01 human heavy chain constant region gene segment, or the human expresses antibodies comprising human gamma-1 heavy chain constant regions comprising such an Asp and Leu and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

An example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises a IGHG1*01 human heavy chain constant region.

Another example provides:—

A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGHG1*01 human heavy chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-1 heavy chain constant region that comprises an Asp corresponding to position 204 of SEQ ID NO: 42 and a Leu corresponding to position 206 of SEQ ID NO: 42 and wherein said human comprises (i) an IGHG1*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The method of paragraph 1, comprising, before said administering, selecting a human comprising said nucleotide sequence of (ii), wherein the human is the human of paragraph 1.

3. The method of paragraph 1 or 2, wherein the antibody comprises a human gamma-1 heavy chain constant region that comprises an Asp corresponding to position 204 of SEQ ID NO: 42 and a Leu corresponding to position 206 of SEQ ID NO: 42.

4. The method of paragraph 1, 2 or 3, wherein the antibody comprises an IGHG1*01 human heavy chain constant region.

5. The method of any one of paragraphs 1 to 4, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

6. The method of any one of paragraphs 1 to 5, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

7. The method of paragraph 6, wherein the step of determining comprises assaying a biological sample from the human for a nucleotide sequence encoding the PCSK9 that comprises the C-terminal domain comprising the mutation I474V or E670G in SEQ ID NO: 1.

8. The method of paragraph 7, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.

9. The method of paragraph 7 or 8, wherein the assaying comprises nucleic acid amplification and optionally one or more methods selected from sequencing, next generation sequencing, nucleic acid hybridization, and allele-specific amplification and/or wherein the assaying is performed in a multiplex format.

10. The method of any one of paragraphs 1 to 9, wherein said human is or has been further determined to be substantially resistant to statin treatment.

11. The method of any one of paragraphs 1 to 10, wherein said human is receiving or has received statin treatment or has reduced responsiveness to statin treatment.

12. The method of paragraph 10 or 11, wherein said antibody or antibody fragment is administered to the human separately or simultaneously with said statin treatment.

13. The method of any one of paragraphs 7 to 9, wherein said biological sample comprises serum, blood, faeces, tissue, a cell, urine and/or saliva of said human.

14. The method of any one of paragraphs 1 to 13, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

15. The method of any one of paragraphs 1 to 14, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The method of any one of paragraphs 1 to 15, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
17. The method of any one of paragraphs 1 to 16, wherein the nucleotide sequence is SEQ ID NO: 29 or 30.
18. The method of any one of paragraphs 1 to 17, wherein said antibody or antibody fragment is administered by intravenous or subcutaneous administration and/or is comprised in an injectable preparation.

Further exemplary ligands are in the paragraphs 1-17 as follows.

1. An antibody or antibody fragment for use in a method of reducing cholesterol level or maintaining previously reduced cholesterol level in a human in need thereof, wherein the antibody comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises an IGHG2*01 human heavy chain constant region gene segment, or the human expresses antibodies comprising human gamma-2 constant regions comprising such a Pro, Asn, Phe, Val and Ala.

In an embodiment, said mutation is I474V. In another embodiment, said mutation is E670G.

An example provides:—

An antibody or antibody fragment for use in a method of reducing cholesterol level or maintaining previously reduced cholesterol level in a human in need thereof, wherein the antibody comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44, and the antibody or fragment specifically binds a proprotein convertase subtilisin/kexin type 9 (PCSK9) amino acid sequence that comprises a C-terminal domain comprising a mutation I474V in SEQ ID NO:1, wherein the human comprises a nucleotide sequence encoding said amino acid sequence and comprises an IGHG2*01 human heavy chain constant region gene segment. Optionally, the antibody or fragment comprises an IGHG2*01 human heavy chain constant region.

Another example provides:—

An antibody or antibody fragment for use in a method of reducing cholesterol level or maintaining previously reduced cholesterol level in a human in need thereof, wherein the antibody comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44, and the antibody or fragment specifically binds a proprotein convertase subtilisin/kexin type 9 (PCSK9) amino acid sequence that comprises a C-terminal domain comprising a mutation E670G in SEQ ID NO:1, wherein the human comprises a nucleotide sequence encoding said amino acid sequence and comprises an IGHG2*01 human heavy chain constant region gene segment. Optionally, the antibody or fragment comprises an IGHG2*01 human heavy chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the antibody comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44.
3. The antibody or antibody fragment of paragraph 1 or 2, wherein the antibody comprises an IGHG2*01 human heavy chain constant region.
4. The antibody or antibody fragment of any one of paragraphs 1 to 3, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
5. The antibody or antibody fragment of any one of paragraphs 1 to 4, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

6. The antibody or antibody fragment of paragraph 5, wherein the step of determining comprises assaying a biological sample from the human for a nucleotide sequence encoding the PCSK9 that comprises the C-terminal domain comprising the mutation I474V or E670G in SEQ ID NO: 1.
7. The antibody or antibody fragment of paragraph 6, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.
8. The antibody or antibody fragment of paragraph 6 or 7, wherein the assaying comprises nucleic acid amplification and optionally one or more methods selected from sequencing, next generation sequencing, nucleic acid hybridization, and allele-specific amplification and/or wherein the assaying is performed in a multiplex format.
9. The antibody or antibody fragment of any one of paragraphs 1 to 8, wherein said antibody or antibody fragment is for administration to a human that is or has been further determined to be substantially resistant to statin treatment.
10. The antibody or antibody fragment of any one of paragraphs 1 to 9, wherein antibody or antibody fragment is for administration to a human that is receiving or has received statin treatment or has reduced responsiveness to statin treatment.
11. The antibody or antibody fragment of paragraph 9 or 10, wherein said antibody or antibody fragment is for administration to the human separately or simultaneously with said statin treatment.
12. The antibody or antibody fragment of any one of paragraphs 6 to 8, wherein said biological sample comprises serum, blood, faeces, tissue, a cell, urine and/or saliva of said human.
13. The antibody or antibody fragment of any one of paragraphs 1 to 12, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.
14. The antibody or antibody fragment of any one of paragraphs 1 to 13, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
15. The antibody or antibody fragment of any one of paragraphs 1 to 14, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The antibody or antibody fragment of any one of paragraphs 1 to 15, wherein the nucleotide sequence is SEQ ID NO: 29 or 30.
17. The antibody or antibody fragment of any one of paragraphs 1 to 16, wherein said antibody or antibody fragment is for administration by intravenous or subcutaneous administration and/or is comprised in an injectable preparation.

Further exemplary methods are in the paragraphs 1-18 as follows.

1. A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human gamma-2 heavy chain constant region that comprises an amino acid selected from the group consisting of a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment, or the human expresses antibodies comprising human gamma-2 heavy chain constant regions comprising such a Pro, Asn, Phe, Val and Ala and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

An example provides:—

A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises an IGHG2*01 human heavy chain constant region.

Another example provides:—

A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGHG2*01 human heavy chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human gamma-2 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44 and wherein said human comprises (i) an IGHG2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The method of paragraph 1, comprising, before said administering, selecting said human comprising said nucleotide sequence of (ii).

3. The method of paragraph 1 or 2, wherein the antibody comprises a human gamma-1 heavy chain constant region that comprises a Pro corresponding to position 72 of SEQ ID NO: 44, an Asn corresponding to position 75 of SEQ ID NO: 44, a Phe corresponding to position 76 of SEQ ID NO: 44, a Val corresponding to position 161 of SEQ ID NO: 44 and an Ala corresponding to position 257 of SEQ ID NO: 44.

4. The method of paragraph 1, 2 or 3, wherein the antibody comprises an IGHG2*01 human heavy chain constant region.

5. The method of any one of paragraphs 1 to 4, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

6. The method of any one of paragraphs 1 to 5, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

7. The method of paragraph 6, wherein the step of determining comprises assaying a biological sample from the human for a nucleotide sequence encoding the PCSK9 that comprises the C-terminal domain comprising the mutation I474V or E670G in SEQ ID NO: 1.

8. The method of paragraph 7, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.

9. The method of paragraph 7 or 8, wherein the assaying comprises nucleic acid amplification and optionally one or more methods selected from sequencing, next generation sequencing, nucleic acid hybridization, and allele-specific amplification and/or wherein the assaying is performed in a multiplex format.

10. The method of any one of paragraphs 1 to 9, wherein said human is or has been further determined to be substantially resistant to statin treatment.

11. The method of any one of paragraphs 1 to 10, wherein said human is receiving or has received statin treatment or has reduced responsiveness to statin treatment.

12. The method of paragraph 10 or 11, wherein said antibody or antibody fragment is administered to the human separately or simultaneously with said statin treatment.
13. The method of any one of paragraphs 7 to 9, wherein said biological sample comprises serum, blood, faeces, tissue, a cell, urine and/or saliva of said human.
14. The method of any one of paragraphs 1 to 13, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.
15. The method of any one of paragraphs 1 to 14, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The method of any one of paragraphs 1 to 15, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
17. The method of any one of paragraphs 1 to 16, wherein the nucleotide sequence is SEQ ID NO: 29 or 30.
18. The method of any one of paragraphs 1 to 17, wherein said antibody or antibody fragment is administered by intravenous or subcutaneous administration and/or is comprised in an injectable preparation.

Further exemplary ligands are in the paragraphs 1-17 as follows.

1. An antibody or antibody fragment for use in a method of reducing cholesterol level or maintaining previously reduced cholesterol level in a human in need thereof, wherein the antibody or fragment comprises a human kappa light chain constant region that comprises a Val corresponding to position 84 of SEQ ID NO: 50 or a Cys corresponding to position 87 of SEQ ID NO: 50, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises an IGKC*01 human light chain constant region gene segment, or the human expresses antibodies comprising human kappa light chain constant regions comprising such an Val and Cys.

In an embodiment, said mutation is I474V. In another embodiment, said mutation is E670G.

An example provides:—

An antibody or antibody fragment for use in a method of reducing cholesterol level or maintaining previously reduced cholesterol level in a human in need thereof, wherein the antibody or fragment comprises a human kappa light chain constant region that comprises a Val corresponding to position 84 of SEQ ID NO: 50 and a Cys corresponding to position 87 of SEQ ID NO: 50, and the antibody or fragment specifically binds a proprotein convertase subtilisin/kexin type 9 (PCSK9) amino acid sequence that comprises a C-terminal domain comprising a mutation I474V in SEQ ID NO:1, wherein the human comprises a nucleotide sequence encoding said amino acid sequence and comprises an IGKC*01 human light chain constant region gene segment. Optionally, the antibody or fragment comprises an IGKC*01 human light chain constant region.

Another example provides:—

An antibody or antibody fragment for use in a method of reducing cholesterol level or maintaining previously reduced cholesterol level in a human in need thereof, wherein the antibody or fragment comprises a human kappa light chain constant region that comprises a Val corresponding to position 84 of SEQ ID NO: 50 and a Cys corresponding to position 87 of SEQ ID NO: 50, and the antibody or fragment specifically binds a proprotein convertase subtilisin/kexin type 9 (PCSK9) amino acid sequence that comprises a C-terminal domain comprising a mutation E670G in SEQ ID NO:1, wherein the human comprises a nucleotide sequence encoding said amino acid sequence and comprises an IGKC*01 human light chain constant region gene segment. Optionally, the antibody or fragment comprises an IGKC*01 human light chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the antibody comprises a human kappa light chain constant region that comprises a Val corresponding to position 84 of SEQ ID NO: 50 or a Cys corresponding to position 87 of SEQ ID NO: 50.
3. The antibody or antibody fragment of paragraph 1 or 2, wherein the antibody comprises an IGKC*01 human kappa chain constant region.
4. The antibody or antibody fragment of any one of paragraphs 1 to 3, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
5. The antibody or antibody fragment of any one of paragraphs 1 to 4, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
6. The antibody or antibody fragment of paragraph 5, wherein the step of determining comprises assaying a biological sample from the human for a nucleotide sequence encoding the PCSK9 that comprises the C-terminal domain comprising the mutation I474V or E670G in SEQ ID NO: 1.

7. The antibody or antibody fragment of paragraph 6, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.
8. The antibody or antibody fragment of paragraph 6 or 7, wherein the assaying comprises nucleic acid amplification and optionally one or more methods selected from sequencing, next generation sequencing, nucleic acid hybridization, and allele-specific amplification and/or wherein the assaying is performed in a multiplex format.
9. The antibody or antibody fragment of any one of paragraphs 1 to 8, wherein said antibody or antibody fragment is for administration to a human that is or has been further determined to be substantially resistant to statin treatment.
10. The antibody or antibody fragment of any one of paragraphs 1 to 9, wherein antibody or antibody fragment is for administration to a human that is receiving or has received statin treatment or has reduced responsiveness to statin treatment.
11. The antibody or antibody fragment of paragraph 9 or 10, wherein said antibody or antibody fragment is for administration to the human separately or simultaneously with said statin treatment.
12. The antibody or antibody fragment of any one of paragraphs 6 to 10, wherein said biological sample comprises serum, blood, faeces, tissue, a cell, urine and/or saliva of said human.
13. The antibody or antibody fragment of any one of paragraphs 1 to 12, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.
14. The antibody or antibody fragment of any one of paragraphs 1 to 13, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
15. The antibody or antibody fragment of any one of paragraphs 1 to 14, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The antibody or antibody fragment of any one of paragraphs 1 to 15, wherein the nucleotide sequence is SEQ ID NO: 29 or 30.
17. The antibody or antibody fragment of any one of paragraphs 1 to 16, wherein said antibody or antibody fragment is for administration by intravenous or subcutaneous administration and/or is comprised in an injectable preparation.

Further exemplary methods are in the paragraphs 1-18 as follows.
1. A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human kappa light chain constant region that comprises a Val corresponding to position 84 of SEQ ID NO: 50 or a Cys corresponding to position 87 of SEQ ID NO: 50 and wherein said human comprises (i) an IGKC*01 human light chain constant region gene segment, or the human expresses antibodies comprising human kappa light chain constant regions comprising such an Val and Cys and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

An example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human light chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises an IGKC*01 human light chain constant region.

Another example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human light chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGKC*01 human light chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human kappa light chain constant region that comprises a Val corresponding to position 84 of SEQ ID NO: 50 and a Cys corresponding to position 87 of SEQ ID NO: 50 and wherein said human comprises (i) an IGKC*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The method of paragraph 1, comprising, before said administering, selecting said human comprising said nucleotide sequence of (ii).
3. The method of paragraph 1 or 2, wherein the antibody comprises a human kappa light chain constant region that comprises a Val corresponding to position 84 of SEQ ID NO: 50 or a Cys corresponding to position 87 of SEQ ID NO: 50.
4. The method of paragraph 1, 2 or 3, wherein the antibody comprises an IGKC*01 human kappa chain constant region.
5. The method of any one of paragraphs 1 to 4, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
6. The method of any one of paragraphs 1 to 5, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
7. The method of paragraph 6, wherein the step of determining comprises assaying a biological sample from the human for a nucleotide sequence encoding the PCSK9 that comprises the C-terminal domain comprising the mutation I474V or E670G in SEQ ID NO: 1.
8. The method of paragraph 7, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.
9. The method of paragraph 7 or 8, wherein the assaying comprises nucleic acid amplification and optionally one or more methods selected from sequencing, next generation sequencing, nucleic acid hybridization, and allele-specific amplification and/or wherein the assaying is performed in a multiplex format.
10. The method of any one of paragraphs 1 to 9, wherein said human is or has been further determined to be substantially resistant to statin treatment.
11. The method of any one of paragraphs 1 to 10, wherein said human is receiving or has received statin treatment or has reduced responsiveness to statin treatment.
12. The method of paragraph 10 or 11, wherein said antibody or antibody fragment is administered to the human separately or simultaneously with said statin treatment.
13. The method of any one of paragraphs 7 to 9, wherein said biological sample comprises serum, blood, faeces, tissue, a cell, urine and/or saliva of said human.
14. The method of any one of paragraphs 1 to 13, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.
15. The method of any one of paragraphs 1 to 14, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
16. The method of any one of paragraphs 1 to 15, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

17. The method of any one of paragraphs 1 to 16, wherein the nucleotide sequence is SEQ ID NO: 29 or 30.

18. The method of any one of paragraphs 1 to 17, wherein said antibody or antibody fragment is administered by intravenous or subcutaneous administration and/or is comprised in an injectable preparation.

Further exemplary ligands are in the paragraphs 1-15 as follows.

1. An antibody or antibody fragment for use in a method of reducing cholesterol level or maintaining previously reduced cholesterol level in a human in need thereof, wherein the antibody or fragment comprises a human IGLC2*01 lambda light chain constant region, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence and comprises a human IGLC2*01 lambda light chain constant region gene segment, or the human expresses antibodies comprising human IGLC2*01 lambda light chain constant regions.

In an embodiment, said mutation is I474V. In another embodiment, said mutation is E670G.

An example provides:—

An antibody or antibody fragment for use in a method of reducing cholesterol level or maintaining previously reduced cholesterol level in a human in need thereof, wherein the antibody or fragment comprises a human IGLC2*01 lambda light chain constant region, and the antibody or fragment specifically binds a proprotein convertase subtilisin/kexin type 9 (PCSK9) amino acid sequence that comprises a C-terminal domain comprising a mutation I474V in SEQ ID NO:1, wherein the human comprises a nucleotide sequence encoding said amino acid sequence and comprises a human IGLC2*01 lambda light chain constant region gene segment. Optionally, the antibody or fragment comprises a human IGLC2*01 lambda light chain constant region.

Another example provides:—

An antibody or antibody fragment for use in a method of reducing cholesterol level or maintaining previously reduced cholesterol level in a human in need thereof, wherein the antibody or fragment comprises a human IGLC2*01 lambda light chain constant region, and the antibody or fragment specifically binds a proprotein convertase subtilisin/kexin type 9 (PCSK9) amino acid sequence that comprises a C-terminal domain comprising a mutation E670G in SEQ ID NO:1, wherein the human comprises a nucleotide sequence encoding said amino acid sequence and comprises a human IGLC2*01 lambda light chain constant region gene segment. Optionally, the antibody or fragment comprises a human IGLC2*01 lambda light chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human IGLC2*01 lambda light chain constant region and wherein said human comprises (i) an IGLC2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1.

2. The antibody or antibody fragment of paragraph 1, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

3. The antibody or antibody fragment of paragraphs 1 or 2, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

4. The antibody or antibody fragment of paragraph 3, wherein the step of determining comprises assaying a biological sample from the human for a nucleotide sequence encoding the PCSK9 that comprises the C-terminal domain comprising the mutation I474V or E670G in SEQ ID NO: 1.

5. The antibody or antibody fragment of paragraph 4, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
   detecting the presence or absence of the complex, wherein detecting the presence of the complex determines that the human comprises the PCSK9 that comprises the C-terminal domain comprising the mutation I474V or E670G in SEQ ID NO: 1.

6. The antibody or antibody fragment of paragraph 4 or 5, wherein the assaying comprises nucleic acid amplification and optionally one or more methods selected from sequencing, next generation sequencing, nucleic acid hybridization, and allele-specific amplification and/or wherein the assaying is performed in a multiplex format.

7. The antibody or antibody fragment of any one of paragraphs 1 to 6, wherein said antibody or antibody fragment is for administration to a human that is or has been further determined to be substantially resistant to statin treatment.
8. The antibody or antibody fragment of any one of paragraphs 1 to 7, wherein antibody or antibody fragment is for administration to a human that is receiving or has received statin treatment or has reduced responsiveness to statin treatment.
9. The antibody or antibody fragment of paragraph 7 or 8, wherein said antibody or antibody fragment is for administration to the human separately or simultaneously with said statin treatment.
10. The antibody or antibody fragment of any one of paragraphs 4 to 8, wherein said biological sample comprises serum, blood, faeces, tissue, a cell, urine and/or saliva of said human.
11. The antibody or antibody fragment of any one of paragraphs 1 to 10, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.
12. The antibody or antibody fragment of any one of paragraphs 1 to 11, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
13. The antibody or antibody fragment of any one of paragraphs 1 to 12, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
14. The antibody or antibody fragment of any one of paragraphs 1 to 13, wherein the nucleotide sequence is SEQ ID NO: 29 or 30.
15. The antibody or antibody fragment of any one of paragraphs 1 to 14, wherein said antibody or antibody fragment is for administration by intravenous or subcutaneous administration and/or is comprised in an injectable preparation.

Further exemplary methods are in the paragraphs 1-16 as follows.
1. A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human IGLC2*01 lambda light chain constant region and wherein said human comprises (i) an IGLC2*01 human light chain constant region gene segment, or the human expresses antibodies comprising a human IGLC2*01 lambda light chain constant regions and (ii) a nucleotide sequence encoding said proprotein convertase subtilisin/kexin type 9 (PCSK9) that comprises a C-terminal domain comprising said mutation I474V or E670G in SEQ ID NO: 1.
In an embodiment, said mutation is I474V. In another embodiment, said mutation is E670G.

An example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 in SEQ ID NO: 1, wherein the antibody or fragment comprises a human IGLC2*01 lambda light chain constant region and wherein said human comprises (i) an IGLC2*01 human light chain constant region gene segment and (ii) a nucleotide sequence encoding said proprotein convertase subtilisin/kexin type 9 (PCSK9) that comprises a C-terminal domain comprising said mutation I474V in SEQ ID NO: 1. Optionally, the antibody or fragment comprises an IGLC2*01 human light chain constant region.

Another example provides:—
A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation E670G in SEQ ID NO: 1, wherein the antibody or fragment comprises a human IGLC2*01 lambda light chain constant region and wherein said human comprises (i) an IGLC2*01 human light chain constant region gene segment and (ii) a nucleotide sequence encoding said proprotein convertase subtilisin/kexin type 9 (PCSK9) that comprises a C-terminal domain comprising said mutation E670G in SEQ ID NO: 1. Optionally, the antibody or fragment comprises an IGLC2*01 human light chain constant region.

In an example, said antibody or antibody fragment has been determined to specifically bind a proprotein convertase subtilisin/kexin type 9 (PCSK9) that comprises a C-terminal domain comprising a mutation I474 or E670G in SEQ ID NO: 1, wherein the antibody or fragment comprises a human IGLC2*01 lambda light chain constant region and wherein said human comprises (i) an IGLC2*01 human heavy chain constant region gene segment and (ii) a nucleotide sequence encoding said proprotein convertase subtilisin/kexin type 9 (PCSK9) that comprises a C-terminal domain comprising said mutation I474V or E670G in SEQ ID NO: 1

2. The method of paragraph 1, comprising, before said administering, selecting said human comprising said nucleotide sequence of (ii).
3. The method of paragraph 1 or 2, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
4. The method of any one of paragraphs 1 to 3, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
5. The method of paragraph 4, wherein the step of determining comprises assaying a biological sample from the human for a nucleotide sequence encoding the PCSK9 that comprises the C-terminal domain comprising the mutation I474V or E670G in SEQ ID NO: 1.

6. The method of paragraph 5, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
   b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

7. The method of paragraph 5 or 6, wherein the assaying comprises nucleic acid amplification and optionally one or more methods selected from sequencing, next generation sequencing, nucleic acid hybridization, and allele-specific amplification and/or wherein the assaying is performed in a multiplex format.

8. The method of any one of paragraphs 1 to 7, wherein said human is or has been further determined to be substantially resistant to statin treatment.

9. The method of any one of paragraphs 1 to 8, wherein said human is receiving or has received statin treatment or has reduced responsiveness to statin treatment.

10. The method of paragraph 8 or 9, wherein said antibody or antibody fragment is administered to the human separately or simultaneously with said statin treatment.

11. The method of any one of paragraphs 5 to 7, wherein said biological sample comprises serum, blood, faeces, tissue, a cell, urine and/or saliva of said human.

12. The method of any one of paragraphs 1 to 11, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

13. The method of any one of paragraphs 1 to 12, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

14. The method of any one of paragraphs 1 to 13, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

15. The method of any one of paragraphs 1 to 14, wherein the nucleotide sequence is SEQ ID NO: 29 or 30.

16. The method of any one of paragraphs 1 to 15, wherein said antibody or antibody fragment is administered by intravenous or subcutaneous administration and/or is comprised in an injectable preparation.

Further exemplary ligands are in the paragraphs 1-15 as follows.

1. An antibody or antibody fragment for use in a method of reducing cholesterol level or maintaining previously reduced cholesterol level in a human in need thereof, wherein the antibody or fragment comprises a human variable domain that is derived from the recombination of a human VH gene segment, a human D gene segment and a human JH gene segment, wherein the VH gene segment is as defined in any one of clauses 80 to 90, and the antibody or fragment specifically binds a proprotein convertase subtilisin/kexin type 9 (PCSK9) amino acid sequence that comprises a C-terminal domain comprising a mutation I474V or E670G in SEQ ID NO:1, wherein the human comprises a nucleotide sequence encoding said amino acid sequence, and comprises said VH gene segment or expresses antibodies comprising VH domains that are derived from the recombination of said human VH gene segment, a human D gene segment and a human JH gene segment.

In an embodiment, said mutation is I474V. In another embodiment, said mutation is E670G.

2. The antibody or antibody fragment of paragraph 1, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

3. The antibody or antibody fragment of paragraphs 1 or 2, the method comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

4. The antibody or antibody fragment of paragraph 3, wherein the step of determining comprises assaying a biological sample from the human for a nucleotide sequence encoding the PCSK9 that comprises the C-terminal domain comprising the mutation I474V or E670G in SEQ ID NO: 1.

5. The antibody or antibody fragment of paragraph 4, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

6. The antibody or antibody fragment of paragraph 4 or 5, wherein the assaying comprises nucleic acid amplification and optionally one or more methods selected from sequencing, next generation sequencing, nucleic acid hybridization, and allele-specific amplification and/or wherein the assaying is performed in a multiplex format.

7. The antibody or antibody fragment of any one of paragraphs 1 to 6, wherein said antibody or antibody fragment is for administration to a human that is or has been further determined to be substantially resistant to statin treatment.

8. The antibody or antibody fragment of any one of paragraphs 1 to 7, wherein antibody or antibody fragment is for administration to a human that is receiving or has received statin treatment or has reduced responsiveness to statin treatment.

9. The antibody or antibody fragment of paragraph 7 or 8, wherein said antibody or antibody fragment is for administration to the human separately or simultaneously with said statin treatment.

10. The antibody or antibody fragment of any one of paragraphs 4 to 8, wherein said biological sample comprises serum, blood, faeces, tissue, a cell, urine and/or saliva of said human.

11. The antibody or antibody fragment of any one of paragraphs 1 to 10, wherein said human is indicated as heterozygous for a nucleotide sequence encoding the PCSK9 C-terminal domain comprising a mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising a mutation I474V or E670G in SEQ ID NO: 1.

12. The antibody or antibody fragment of any one of paragraphs 1 to 11, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

13. The antibody or antibody fragment of any one of paragraphs 1 to 12, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

14. The antibody or antibody fragment of any one of paragraphs 1 to 13, wherein the nucleotide sequence is SEQ ID NO: 29 or 30.

15. The antibody or antibody fragment of any one of paragraphs 1 to 14, wherein said antibody or antibody fragment is for administration by intravenous or subcutaneous administration and/or is comprised in an injectable preparation.

Further exemplary methods are in the paragraphs 1-16 as follows.

1. A method of reducing cholesterol level or maintaining previously reduced cholesterol level in a human in need thereof, the method comprising administering to said human an antibody or antibody fragment that specifically binds a proprotein convertase subtilisin/kexin type 9 (PCSK9) that comprises a C-terminal domain comprising a mutation I474 or E670G in SEQ ID NO: 1, wherein the antibody or fragment comprises a human variable domain that is derived from the recombination of a human VH gene segment, a human D gene segment and a human JH gene segment, wherein the VH gene segment is as defined in any one of clauses 80 to 90 and wherein said human comprises (i) comprises said VH gene segment or expresses antibodies comprising VH domains that are derived from the recombination of said human VH gene segment, a human D gene segment and a human JH gene segment and (ii) a nucleotide sequence encoding said proprotein convertase subtilisin/kexin type 9 (PCSK9) that comprises a C-terminal domain comprising said mutation I474V or E670G in SEQ ID NO: 1.

In an embodiment, said mutation is I474V. In another embodiment, said mutation is E670G.

2. The method of paragraph 1, comprising, before said administering, selecting said human comprising said nucleotide sequence of (ii).

3. The method of paragraph 1 or 2, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.

4. The method of any one of paragraphs 1 to 3, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.

5. The method of paragraph 4, wherein the step of determining comprises assaying a biological sample from the human for a nucleotide sequence encoding the PCSK9 that comprises the C-terminal domain comprising the mutation I474V or E670G in SEQ ID NO: 1.

6. The method of paragraph 5, wherein the assaying comprises contacting the biological sample with
   a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

7. The method of paragraph 5 or 6, wherein the assaying comprises nucleic acid amplification and optionally one or more methods selected from sequencing, next generation sequencing, nucleic acid hybridization, and allele-specific amplification and/or wherein the assaying is performed in a multiplex format.

8. The method of any one of paragraphs 1 to 7, wherein said human is or has been further determined to be substantially resistant to statin treatment.

9. The method of any one of paragraphs 1 to 8, wherein said human is receiving or has received statin treatment or has reduced responsiveness to statin treatment.

10. The method of paragraph 8 or 9, wherein said antibody or antibody fragment is administered to the human separately or simultaneously with said statin treatment.

11. The method of any one of paragraphs 5 to 7, wherein said biological sample comprises serum, blood, faeces, tissue, a cell, urine and/or saliva of said human.

12. The method of any one of paragraphs 1 to 11, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

13. The method of any one of paragraphs 1 to 12, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

14. The method of any one of paragraphs 1 to 13, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

15. The method of any one of paragraphs 1 to 14, wherein the nucleotide sequence is SEQ ID NO: 29 or 30.

16. The method of any one of paragraphs 1 to 15, wherein said antibody or antibody fragment is administered by intravenous or subcutaneous administration and/or is comprised in an injectable preparation.

Regimens

A: The invention further provides the following regimens, ligands and kits.

1. A method for treating a human PCSK9-mediated disease or condition in a human by targeting a rare variant human PCSK9, the method comprising administering to the human a ligand (eg, an antibody or fragment) that has been determined to specifically bind to said PCSK9 variant; wherein the human expresses said PCSK9 variant or the genome of the human comprises a nucleotide sequence encoding said PCSK9 variant; wherein said human is treated for said disease or condition.

The variant PCSK9 can, for example, be any rare variant as described herein.

For example, there is provided:

1a. A method for treating a PCSK9-mediated disease or condition in a human by targeting a PCSK9 that comprises a C-terminal domain amino acid polymorphism (compared to SEQ ID NO: 1), the method comprising administering to the human a ligand (eg, an antibody or fragment) that has been determined to specifically bind to a PCSK9 comprising a C-terminal domain comprising I474V or 670G (numbering according to SEQ ID NO:1); wherein the human expresses said PCSK9 or the genome of the human comprises a nucleotide sequence encoding said PCSK9; wherein said human is treated for said disease or condition.

In an embodiment, determination of said specific binding is by reference to binding assay data, eg, as determined using SPR or ELISA. Determination may, for example, be by reference to information in a printed publication, eg, with knowledge of data presented in the present or another patent application or in a journal article. Once armed with such knowledge (eg, in the absence of further testing of binding), the skilled person is able—by direction of the present invention—to treat a relevant human whose genotype or phenotype matches the binding specificity of the ligand.

The antibody or fragment can be according to any configuration, example, embodiment, aspect, clause or paragraph herein.

In an embodiment, the method comprises, before said administering, selecting a human comprising said nucleotide sequence encoding the PCSK9, wherein the human is said human in clause 1 (eg, 1a).

2. The method of clause 1, comprising before said administering the step of determining that the ligand specifically binds to said PCSK9, eg, using SPR or ELISA.

3. The method of clause 1 or 2, wherein the specific binding to said PCSK9 is binding with a dissociation constant (Kd) of 1 nM or less, eg, 100, 10 or 1 pM or less.

4. The method of any of clauses 1 to 3 (eg, clause 1a), wherein the condition is elevated LDL-cholesterol or is caused by elevated LDL-cholesterol.

5. The method of clause 4 (eg, when dependent from clause 1a), wherein the condition is selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
6. The method of any one of clauses 1 to 5 (eg, when dependent from clause 1a), wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
7. The method of any one of clauses 1 to 6 (eg, when dependent from clause 1a), comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
8. The method of clause 7, wherein the step of determining comprises assaying a biological sample from the human for a nucleotide sequence encoding the PCSK9 that comprises the C-terminal domain comprising the mutation I474V or E670G in SEQ ID NO: 1.
9. The method of clause 8, wherein the assaying comprises contacting the biological sample with
    a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or
    b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and
    detecting the presence or absence of the complex, wherein detecting the presence of the complex determines that the human comprises the PCSK9 that comprises the C-terminal domain comprising the mutation I474V or E670G in SEQ ID NO: 1.
10. The method of clause 8 or 9, wherein the assaying comprises nucleic acid amplification and optionally one or more methods selected from sequencing, next generation sequencing, nucleic acid hybridization, and allele-specific amplification and/or wherein the assaying is performed in a multiplex format.
11. The method of any one of clauses 1 to 10, wherein said human is or has been further determined to be substantially resistant to statin treatment.
12. The method of any one of clauses 1 to 11, wherein said human is receiving or has received statin treatment or has reduced responsiveness to statin treatment.
13. The method of clauses 11 or 12, wherein said antibody or antibody fragment is administered to the human separately or simultaneously with said statin treatment.
14. The method of any one of clauses 8 to 10, wherein said biological sample comprises serum, blood, faeces, tissue, a cell, urine and/or saliva of said human.
15. The method of any one of clauses 1 to 14, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.
16. The method of any one of clauses 1 to 15, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
17. The method of any one of clauses 1 to 16, wherein said antibody or antibody fragment treats or reduces the risk in said human of at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
18. The method of any one of clauses 1 to 17, wherein the nucleotide sequence is SEQ ID NO: 29 or 30.
19. The method of any one of clauses 1 to 18, wherein said antibody or antibody fragment is administered by intravenous or subcutaneous administration and/or is comprised in an injectable preparation.
20. A ligand (eg, an antibody or fragment) for use in the method of any one of clauses 1 to 19, wherein the ligand specifically binds the PCSK9.
21. A kit comprising the ligand of clause 20 and instructions for carrying out the method of any one of clauses 1 to 19.
    B: The invention further provides the following regimens, ligands and kits.
1. A method of reducing cholesterol level or maintaining a previously reduced cholesterol level in a human in need thereof, the method comprising:—
    a. Carrying out an initial treatment of said human for an initial treatment period by administering an anti-human PCSK9 ligand (eg, an antibody or fragment) to said human, wherein (i) the ligand has been determined to specifically bind to a PCSK9 comprising a C-terminal domain comprising I474V or 670G (numbering according to SEQ ID NO:1); (ii) the human expresses said PCSK9 or the genome of the human comprises a nucleotide sequence encoding said PCSK9 and (iii) the human has received or is receiving statin treatment to lower or maintain cholesterol level; wherein the initial treatment comprises the administration of a single or multiple doses of the ligand to the human;
    b. Determining to (i) terminate statin treatment (ii) keep the human off statin treatment; or (iii) reduce statin treatment after said initial treatment period; and c. Continuing to administer the ligand to said patient after said time period has expired, thereby reducing cholesterol level or maintaining a previously reduced cholesterol level in said human.

In an embodiment, determination of said specific binding is by reference to binding assay data, eg, as determined using SPR or ELISA. Determination may, for example, be by reference to information in a printed publication, eg, with knowledge of data presented in the present or another patent application or in a journal article. Once armed with such knowledge (eg, in the absence of further testing of binding), the skilled person is able—by direction of the present invention—to treat a relevant human whose genotype or phenotype matches the binding specificity of the ligand.

The antibody or fragment can be according to any configuration, example, embodiment, aspect, clause or paragraph herein.

A pharmaceutically-effective amount of said ligand is administered.

In an embodiment, the method comprises, before said administering, selecting a human comprising said nucleotide sequence encoding the PCSK9, wherein the human is said human recited in clause 1.

In an example, the initial treatment period is 7 days, 14 days, 21 days, 28 days, a month, two months, three months, four months, five months, six months, seven months, eight months, nine months or a year.

2. The method of clause 1, wherein the human has or is suffering from statin-associated memory loss or a statin-associated neurodegenerative condition, or has or is at increased risk of diabetes (eg, statin-associated diabetes).
3. The method of clause 1 or 2, comprising, before said initial treatment, the step of determining that the human has or is suffering from statin-associated memory loss or a statin-associated neurodegenerative condition, or has or is at increased risk of diabetes (eg, statin-associated diabetes).
4. The method of clause 2 or 3, comprising, after step (b) (eg, during step (c)) determining that the memory loss or said neurodegenerative condition has improved.
5. The method of any one of clauses 1 to 4, wherein said human is over 40 years of age (eg, 50 or over, 55 or over, 60 or over, 65 or over, or 70 or over).
6. The method of any one of clauses 1 to 5, wherein step (c) comprises determining to increase the doses of said ligand to be administered after said initial treatment period and administering said increased doses to said human.
7. The method of any one of clauses 1 to 6, wherein step (b) comprises determining that the human is intolerant or refactory to treatment by a statin.
8. The method of any one of clauses 1 to 7, wherein the initial treatment comprises the administration of a statin, fenofibrate (eg, Tricor™ or Lofibra™) or ezetimibe to the human in addition to the ligand.
9. The method of any one of clauses 1 to 8, wherein step (b) comprises terminating or reducing statin, fenofibrate (eg, Tricor™ or Lofibra™) or ezetimibe treatment during step (c).
10. The method of any one of clauses 1 to 9, comprising increasing (ie, increasing compared to the initial treatment dose) the ligand dose during step (c).
11. The method of any one of clauses 1 to 10, wherein the human has received high dose statin treatment prior to the initial treatment, and wherein step (c) comprises administering a lower (eg, a medium or low) dose statin treatment in addition to said ligand.

The skilled person is familiar with the meaning of high, medium and low dose treatments (and how to determine according to each patient, eg, the patient's body mass). For example, the statin is selected from rosuvastatin, atorvastatin and simvastatin.

For example daily statin doses are as follows:—Low 10 to 20 mg (eg, 10 mg); medium>20 and <60 mg (eg, 40 mg); high 60-100 mg (eg, 80 mg).

12. The method of any one of clauses 1 to 10, wherein the human has received medium dose statin treatment prior to the initial treatment, and wherein step (c) comprises administering a lower (eg, a low) dose statin treatment or no statin in addition to said ligand.
13. The method of any one of clauses 1 to 10, wherein the human has received low dose statin treatment prior to the initial treatment, and wherein step (c) comprises administering no statin in addition to said ligand.
14. The method of any one of clauses 1 to 13, comprising, before the initial treatment, the step of determining that the ligand specifically binds to said PCSK9, eg, using SPR or ELISA.
15. The method of any one of clauses 1 to 14, wherein the specific binding to said PCSK9 is binding with a dissociation constant (Kd) of 1 nM or less, eg, 100, 10 or 1 pM or less.
16. The method of any of clauses 1 to 15, wherein the human is at risk of or suffering from a condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.
17. The method of clause 16, wherein step (c) treats or reduces the risk of said condition in the human.
18. The method of any one of clauses 1 to 17, wherein the human has been determined to comprise the nucleotide sequence that encodes a PCSK9 comprising a C-terminal domain comprising said mutation I474V or E670G in SEQ ID NO: 1 and/or a proprotein convertase subtilisin/kexin type 9 (PCSK9) variant protein encoded by the nucleotide sequence of SEQ ID NO: 29 or 30.
19. The method of any one of clauses 1 to 18, comprising the step of determining that the human comprises the nucleotide sequence that encodes a PCSK9 comprising a C-terminal domain comprising said mutation I474V or E670G and/or a proprotein convertase subtilisin/kexin type 9 (PCSK9) variant protein comprising said mutation I474V or E670G, optionally, wherein the determining step is performed before administration of the antibody to the human.
20. The method of clause 19, wherein the step of determining comprises assaying a biological sample from the human for a nucleotide sequence encoding the PCSK9 that comprises the C-terminal domain comprising the mutation I474V or E670G in SEQ ID NO: 1.
21. The method of clause 20, wherein the assaying comprises contacting the biological sample with
    a. at least one oligonucleotide probe comprising a sequence of at least 10 contiguous nucleotides that can specifically hybridize to and identify in the biological sample a nucleotide sequence encoding the PCSK9 that comprises the C-terminal domain comprising the mutation I474V or E670G in SEQ ID NO: 1 or that specifically hybridizes to an antisense of said sequence, wherein said nucleic acid hybridizes to at least one nucleotide present in said selected sequence which is not present in SEQ ID NO: 28 or hybridizes to an antisense sequence thereby forming a complex when at least one nucleotide sequence encoding the PCSK9 that comprises the C-terminal domain comprising the mutation I474V or E670G in SEQ ID NO: 1 is present; and/or b. at least one oligonucleotide probe comprising a sequence of at least 10 contiguous nucleotides of a nucleotide sequence encoding the PCSK9 that comprises the C-terminal domain comprising the mutation I474V or E670G in SEQ ID NO: 1 or comprising an antisense sequence of said contiguous nucleotides, wherein said sequence of contiguous nucleotides comprises at least one nucleotide present in said selected sequence which is not present in SEQ ID NO: 28 thereby forming a complex when the nucleotide sequence encoding the PCSK9 that comprises a C-terminal domain comprising the mutation I474V or E670G in SEQ ID NO: 1 is present; and detecting the presence or absence of the complex, wherein detecting the presence of the complex determines that the human comprises the PCSK9 that comprises the C-terminal domain comprising the mutation I474V or E670G in SEQ ID NO: 1.

22. The method of clause 20 or 21, wherein the assaying comprises nucleic acid amplification and optionally one or more methods selected from sequencing, next generation sequencing, nucleic acid hybridization, and allele-specific amplification and/or wherein the assaying is performed in a multiplex format.

23. The method of any one of clauses 1 to 22, wherein said human is or has been further determined to be substantially resistant to statin treatment.

24. The method of any one of clauses 20 to 22, wherein said biological sample comprises serum, blood, faeces, tissue, a cell, urine and/or saliva of said human.

25. The method of any one of clauses 1 to 24, wherein said human is indicated as heterozygous for a nucleotide sequence encoding the PCSK9 C-terminal domain comprising said mutation I474V or E670G, optionally, wherein said human is further indicated as comprising the nucleotide sequence of SEQ ID NO: 28, or said human is indicated as homozygous for a nucleotide sequence encoding the PCSK9 C-terminal domain comprising said mutation I474V or E670G in SEQ ID NO: 1.

26. The method of any one of clauses 1 to 25, wherein said human has been diagnosed with at least one condition selected from a lipid disorder, hyperlipoproteinemia, hyperlipidemia, dyslipidemia, hypercholesterolemia, a heart attack, a stroke, coronary heart disease, atherosclerosis, peripheral vascular disease, claudication and high blood pressure.

27. The method of any one of clauses 1 to 26, wherein the nucleotide sequence is SEQ ID NO: 29 or 30.

28. The method of any one of clauses 1 to 27, wherein said ligand (eg, antibody or antibody fragment) is administered by intravenous or subcutaneous administration and/or is comprised in an injectable preparation.

29. A ligand (eg, an antibody or fragment) for use in the method of any one of clauses 1 to 28, wherein the ligand specifically binds the PCSK9.

30. A kit comprising the ligand of clause 29 and instructions for carrying out the method of any one of clauses 1 to 28.

In an example of any aspect of the invention, the ligand (eg, antibody or fragment, eg, alirocumab, bocovizumab or evolocumab, or an antibody or fragment comprising the variable domains of 316P or 31H4) is administered to the human at a two-weekly dose of from 75 to 150 mg (eg, from 75 to 150 mg administered once or twice over a two-week period). In an example, the ligand is for such administration to the human.

Determination of Specific Binding of Ligands of the Invention to PCSK9 Variants

Method of SPR Determination of Binding

Binding of the antibodies to the PCSK9 variants was carried out by SPR using the ProteOn XPR36™ Array system (BioRad). An anti-human IgG surface (Jackson Labs 109-005-008) was created on a GLC Biosensor chip by primary amine coupling. Test antibodies were captured on this surface as ligands. The PCSK9 variants were used as analytes and passed over the captured antibodies at 256 nM, 64 nM, 16 nM, 4 nM and 1 nM. Binding curves were double referenced using a buffer injection (i.e. 0 nM) to remove baseline drift and injection artefacts. Regeneration of the capture surface was with 100 mM phosphoric acid which removed the captured antibody allowing another cycle of capture and binding. The binding sensorgrams generated were analysed using the 1:1 model inherent to the ProteOn XPR36 Array system analysis software. The assay was performed at 25° C. and using 1×HBS-EP (Teknova) as running buffer.

Data

Three antibodies were tested and the resulting binding data are presented below (Table 3). Antibodies 316P and 31H4 are antibodies disclosed in US20110065902A1 (the sequences of these antibodies and their variable domains are incorporated herein by reference for possible use in the present invention and possible inclusion in claims herein). Antibody 316P comprises heavy chain variable domains derived from recombination of human VH3-23*04 and JH2*01 (with a D), and light chain variable domains derived from recombination of human Vκ4-1*01 and Jκ2*01.

Evolocumab comprises a human IGHG2*01 heavy chain and a human IGLC2*01 lambda light chain, a VH derived from recombination of human IGHV1-18*01 and IGHJ6*01 (with a D segment) and a Vλ derived from recombination of human IGLV2-14*01 and IGLJ2*01.

TABLE 3

SPR Determination of Ligand Binding Specificity for PCSK9 Variants

| Variant/Antibody | ka (1/Ms) | kd (1/s) | KD (nM) |
| --- | --- | --- | --- |
| PCSK9 a | | | |
| 316P | 1.37E+06 | 2.75E−04 | 0.201 |
| 31H4 | 1.14E+06 | 6.38E−05 | 0.056 |
| Evolocumab | 1.14E+05 | 2.62E−05 | 0.229 |
| PCSK9 a' | | | |
| 316P | 1.50E+06 | 2.72E−04 | 0.181 |
| 31H4 | 1.23E+06 | 6.06E−05 | 0.049 |
| Evolocumab | 1.24E+05 | 2.29E−05 | 0.185 |
| PCSK9 c | | | |
| 316P | 1.49E+06 | 2.75E−04 | 0.184 |
| 31H4 | 1.22E+06 | 5.69E−05 | 0.047 |
| Evolocumab | 1.20E+05 | 2.20E−05 | 0.183 |
| PCSK9 r | | | |
| 316P | 1.40E+06 | 2.76E−04 | 0.197 |
| 31H4 | 1.15E+06 | 5.82E−05 | 0.051 |
| Evolocumab | 1.16E+05 | 2.67E−05 | 0.230 |
| PCSK9 f | | | |
| 316P | 1.39E+06 | 2.82E−04 | 0.203 |
| 31H4 | 1.13E+06 | 5.95E−05 | 0.053 |
| Evolocumab | 1.16E+05 | 2.66E−05 | 0.229 |
| PCSK9 p | | | |
| 316P | 1.39E+06 | 2.73E−04 | 0.196 |
| 31H4 | 1.14E+06 | 6.12E−05 | 0.054 |
| Evolocumab | 1.14E+05 | 2.50E−05 | 0.219 |

Results

The results showed that all antibodies tested bound to PCSK9 variants equally, with any binding variation seen being within experimental error for such a strong affinity interaction.

Thus, the invention determines that an antibody with the following profile can specifically bind one or more variants of the invention:—

1. An antibody (eg, 316P or alirocumab) that comprises heavy chain variable domains derived from recombination of human IGHV3-23*04 and IGHJH2*01 (with a D), and light chain variable domains derived from recombination of human IGKV4-1*01 and IGKJ2*01; or 2. An antibody (eg, evolocumab) that comprises human heavy chain variable domains derived from recombination of human IGHV1-18*01 and IGHJ6*01 (with a D segment) and light chain variable domains derived from recombination of human IGLV2-14*01 and IGLJ2*01.

Thus, according to the invention, the skilled person is hereby provided with the required determination of specific binding of the ligand to PCSK9 variants. Applications of this determination are set out above in the context of methods and other aspects of the invention.

REFERENCES

Horton et al, Trends Biochem Sci. 2007 February; 32 (2):71-7. Epub 2007 Jan. 9, Molecular biology of PCSK9: its role in LDL metabolism.

Seidah and Prat, J Mol Med (Berl). 2007 July; 85(7):685-96. Epub 2007 Mar. 10, The proprotein convertases are potential targets in the treatment of dyslipidemia.

Benjannet et al, J Biol Chem. 2004 Nov. 19; 279(47):48865-75. Epub 2004 Sep. 9, NARC-1/PCSK9 and its natural mutants: zymogen cleavage and effects on the low density lipoprotein (LDL) receptor and LDL cholesterol.

Lagace et al, J Clin Invest. 2006 November; 116 (11):2995-3005, Secreted PCSK9 decreases the number of LDL receptors in hepatocytes and in livers of parabiotic mice.

Maxwell et al, Proc Natl Acad Sci USA. 2005 Feb. 8; 102(6): 2069-74. Epub 2005 Jan. 27, Overexpression of PCSK9 accelerates the degradation of the LDLR in a post-endoplasmic reticulum compartment.

Park et al, J Biol Chem. 2004 Nov. 26; 279(48):50630-8. Epub 2004 Sep. 22, Post-transcriptional regulation of low density lipoprotein receptor protein by proprotein convertase subtilisin/kexin type 9a in mouse liver.

Rashid et al, Proc Natl Acad Sci USA. 2005 Apr. 12; 102 (15):5374-9. Epub 2005 Apr. 1, Decreased plasma cholesterol and hypersensitivity to statins in mice lacking Pcsk9.

Kotowski et al, Am J Hum Genet. 2006 March; 78(3):410-22. Epub 2006 Jan. 20, A spectrum of PCSK9 alleles contributes to plasma levels of low-density lipoprotein cholesterol.

Chen et al, J Am Coll Cardiol. 2005 May 17; 45(10):1611-9. Epub 2005 Apr. 21, A common PCSK9 haplotype, encompassing the E670G coding single nucleotide polymorphism, is a novel genetic marker for plasma low-density lipoprotein cholesterol levels and severity of coronary atherosclerosis.

Pisciotta et al, Atherosclerosis. 2006 June; 186(2):433-40. Epub 2005 Sep. 23, Additive effect of mutations in LDLR and PCSK9 genes on the phenotype of familial hypercholesterolemia.

Zhao et al, Am J Hum Genet. 2006 September; 79(3):514-23. Epub 2006 Jul. 18, Molecular characterization of loss-of-function mutations in PCSK9 and identification of a compound heterozygote.

Seidah et al, Proc Natl Acad Sci USA. 2003 Feb. 4; 100(3): 928-33. Epub 2003 Jan. 27, The secretory proprotein convertase neural apoptosis-regulated convertase 1 (NARC-1): liver regeneration and neuronal differentiation.

TABLE 4

1000 GENOMES PROJECT HUMAN POPULATIONS
Below is a summary of the ethnic populations
as per the 1000 Genomes Project sequences.

| Population |
| --- |
| European ancestry |
| Utah residents (CEPH) with Northern and Western European ancestry (CEU) |
| Toscani in Italia (TSI) |
| British from England and Scotland (GBR) |
| Finnish from Finland (FIN) |
| Iberian populations in Spain (IBS) |
| East Asian ancestry |
| Han Chinese in Beijing, China (CHB) |
| Japanese in Toyko, Japan (JPT) |
| Han Chinese South (CHS) |
| Chinese Dai in Xishuangbanna (CDX) |
| Kinh in Ho Chi Minh City, Vietnam (KHV) |
| Chinese in Denver, Colorado (CHD) (pilot 3 only) |
| West African ancestry |
| Yoruba in Ibadan, Nigeria (YRI) |
| Luhya in Webuye, Kenya (LWK) |
| Gambian in Western Division, The Gambia (GWD) |
| Malawian in Blantyre, Malawi (MAB) |
| West African Population (TBD) |
| Americas |
| African Ancestry in Southwest US (ASW) |
| African American in Jackson , MS (AJM) |
| African Caribbean in Barbados (ACB) |
| Mexican Ancestry in Los Angeles, CA (MXL) |
| Puerto Rican in Puerto Rico (PUR) |
| Colombian in Medellin, Colombia (CLM) |
| Peruvian in Lima, Peru (PEL) |
| South Asian ancestry |
| Ahom in the State of Assam, India |
| Kayadtha in Calcutta, India |
| Reddy in Hyderabad, India |
| Maratha in Bombay, India |
| Punjabi in Lahore, Pakistan |

TABLE 5

TOIs & Related Diseases, Conditions and Example Ligands

| Human TOI | Example Disease or Condition | Example Ligand |
| --- | --- | --- |
| Il-17a | Inflammatory Disease | AIN457 |
| | Uveitis | Ixekizumab |
| | Rheumatoid Arthritis | |
| | Psoriasis | |

TABLE 5-continued

TOIs & Related Diseases, Conditions and Example Ligands

| Human TOI | Example Disease or Condition | Example Ligand |
|---|---|---|
| Angiotensin II Receptor Type 1 (AT$_1$) | Hypertension | LCZ696 |
| Neprilysin | Hypertension | LCZ696 |
| Metabotropic Glutamate Receptor 5 (Mglur5) | Fragile X Syndrome | AFQ056 Mavoglurant |
| A Histone Deacetylase | Cancer, Eg, Multiple Myeloma | LBH589 Panobinostat |
| Diacylglycerol acyltransferase-1 (DGAT-1) | Familial Chylomicronaemia Syndrome | LCQ908 Pradigastat |
| Smoothened (Smo) | Basal cell carcinoma Solid tumour Myelofibrosis Medulloblastoma Solid tumour | LDE225 |
| Smoothened (Smo) receptor | Basal cell carcinoma Solid tumors | LEQ506 |
| ALK | Non small cell lung carcinoma (NSCLC) | LDK378 |
| phosphatidylinositol-3-kinase (PI3K) mTOR AKT | Cancer, eg, solid tumour, breast cancer, Renal cell carcinoma (RCC), Endometrial cancer, Non-small cell lung cancer (NSCLC), prostate cancer, Glioblastoma multiforme (GBM) CRPC GIST Myelofibrosis | BKM120 |
| mTOR PI3K AKT | Cancer, eg, solid tumour, breast cancer, Renal cell carcinoma (RCC), Endometrial cancer, Non-small cell lung cancer (NSCLC), prostate cancer, Glioblastoma multiforme (GBM) CRPC GIST Myelofibrosis | BEZ235 |
| PI3Kα mTOR PI3K AKT | Cancer, eg, solid tumour, breast cancer, Renal cell carcinoma (RCC), Endometrial cancer, Non-small cell lung cancer (NSCLC), prostate cancer, Glioblastoma multiforme (GBM) CRPC GIST Myelofibrosis | BYL719 |
| Mitogen-activated ERK kinase 1 (MEK1) Mitogen-activated ERK kinase 2 (MEK2) | Cancer, eg, solid tumour, melanoma, pancreatic, colon, lung or thyroid cancer Metastasis | MEK162 |
| protein kinase protein kinase C FLT-3 c-KIT | Acute myeloid leukemia (AML) Myelodysplastic syndrome (MDS) Aggressive systemic mastocytosis (ASM) | PKC412 Midostaurin |
| ActRIIB | Sporadic inclusion body myositis (sIBM) | BYM338 bimagrumab |
| CD19 | Cancer, eg, Leukaemia, mast cell leukemia, Acute Lymphoblastic Leukemia, Chronic lymphocytic leukemia (CLL) or Hematological tumors | CTL019 (formerly CART-19) |

TABLE 5-continued

TOIs & Related Diseases, Conditions and Example Ligands

| Human TOI | Example Disease or Condition | Example Ligand |
|---|---|---|
| 11β-hydroxylase | Cushing's syndrome | LCI699 |
| BRAF | Cancer, eg, melanoma | LGX818 |
| Receptor Tyrosine Kinase | Cancer, eg, solid tumour | TKI258 (formerly CHIR-258) |
| FGFR | Breast Cancer | Dovitinib |
| | Endometrial cancer | |
| | Hepatocellular carcinoma | |
| | Renal cell carcinoma (RCC) | |
| | Bladder cancer | |
| | multiple myeloma (MM), | |
| | hepatocellular carcinoma | |
| | endometrial cancer | |
| DAC enzyme | hematologic malignancy | LBH589 |
| | Multiple myeloma | panobinostat |
| | Myel\odysplastic syndrome (MDS) | |
| | Myelofibrosis | |
| HSP90 | Cancer, eg, Breast Cancer, gastric cancer or Non-small cell lung cancer (NSCLC) | AUY922 |
| FGFR | Cancer, eg, solid tumour | BGJ398 |
| | Breast Cancer | |
| | Endometrial cancer | |
| | Hepatocellular carcinoma | |
| | Renal cell carcinoma (RCC) | |
| | Bladder cancer | |
| | multiple myeloma (MM), | |
| | hepatocellular carcinoma | |
| | endometrial cancer | |
| cIAP1 | Cancer, eg, solid tumour | LCL161 |
| cIAP2 | Breast Cancer | |
| | Endometrial cancer | |
| | Hepatocellular carcinoma | |
| | Renal cell carcinoma (RCC) | |
| | Bladder cancer | |
| | multiple myeloma (MM), | |
| | hepatocellular carcinoma | |
| | endometrial cancer | |
| Akt | Cancer, eg, Solid tumour, gastric cancer (eg, castration-resistant prostate cancer), prostate cancer, gastroesophageal junction cancer | GDC-0068 RG7440 |
| CD22 | Hematologic malignancies Non-Hodgkin's lymphoma (eg, relapsed or refractory follicular non-Hodgkin's lymphoma) Diffuse large B-cell lymphoma (eg, relapsed or refractory diffuse large B-cell lymphoma) | DCDT2980S RG7593 |
| CD79b | Hematologic malignancies Non-Hodgkin's lymphoma (eg, relapsed or refractory follicular non-Hodgkin's | DCDS4501A RG7596 |

TABLE 5-continued

TOIs & Related Diseases, Conditions and Example Ligands

| Human TOI | Example Disease or Condition | Example Ligand |
|---|---|---|
| | lymphoma) Diffuse large B-cell lymphoma (eg, relapsed or refractory diffuse large B-cell lymphoma) | |
| endothelin B receptor (ETBR) | Melanoma, eg, metastatic or unresectable melanoma | DEDN6526A RG7636 |
| HER3 | Cancer, eg, metastatic epithelial tumour, metastatic squamous cell carcinoma of the head and neck cancer, metastatic colorectal cancer | MEHD7945A RG7597 |
| EGFR | Cancer, eg, metastatic epithelial tumour, metastatic squamous cell carcinoma of the head and neck cancer, metastatic colorectal cancer | MEHD7945A RG7597 Necitumumab |
| MUC16 | Cancer, eg, ovarian cancer (eg, platinum-resistant ovarian cancer) | DMUC5754A RG7458 |
| sodium-dependent phosphate transport protein 2b (NaPi2b) | Cancer, eg, metastatic non-squamous non-small cell lung cancer, ovarian cancer (eg, platinum-resistant ovarian cancer) | DNIB0600A RG7599 |
| PDL1 (programmed death ligand 1) | Cancer, eg, solid tumour metastatic melanoma non-small cell lung cancer | MPDL3280A RG7446 |
| STEAP1 (six-transmembrane epithelial antigen of the prostate 1) | Cancer, eg, prostate cancer (eg, metastatic castration-resistant prostate cancer) | DSTP3086S RG7450 |
| Bcl-2 | Cancer, eg, leukaemia (eg, chronic lymphocytic leukaemia), non-Hodgkin's lymphoma | GDC-0199 RG7601 |
| Checkpoint kinase 1 (ChK1) | Cancer, eg, solid tumour, refractory solid tumour or lymphoma | GDC-0425 RG7602 GDC-0575 RG7741 |
| mitogen activated protein kinase kinase (MAPKK) MEK | Cancer, eg, solid tumour, melanoma (eg, metastatic melanoma) | GDC-0973 RG7421 Cobimetinib GDC-0623 RG7420 |
| epidermal growth factor domain-like-7 (EGFL7) | Cancer, eg, colorectal cancer (eg, metastatic colorectal cancer), NSCLC | Parsatuzumab MEGF0444A RG7414 |
| phosphatidylinositol-3-kinase (PI3K) | Cancer, eg, prostate cancer, renal cell carcinoma, endometrial cancer, breast cancer (eg, HER2-negative metastatic breast cancer, metastatic hormone receptor-positive breast cancer), solid tumour | GDC-0032 RG7604 GDC-0084 RG7666 Pictilisib GDC-0941 RG7321 |
| mTOR TORC1 TORC2 PI3K | Cancer, eg, prostate cancer, renal cell carcinoma, endometrial cancer, breast cancer (eg, HER2-negative metastatic breast cancer, metastatic hormone receptor-positive breast cancer), solid tumour | GDC-0980 RG7422 |
| IL17 | Autoimmune disease Ankylosing spondylitis; Asthma; Multiple myeloma; Multiple sclerosis; Polymyalgia rheumatica; Psoriasis; Psoriatic arthritis; Rheumatoid arthritis; Uveitis | Secukinumab ixekizumab |

TABLE 5-continued

TOIs & Related Diseases, Conditions and Example Ligands

| Human TOI | Example Disease or Condition | Example Ligand |
|---|---|---|
| M1 prime segment of membrane IgE | Allergic Asthma | Quilizumab<br>MEMP1972A<br>RG7449 |
| IFN alpha | Autoimmune disease<br>Systemic lupus erythematosus | Rontalizumab |
| PCSK9 (proprotein convertase subtilisin/kexin type 9) | coronary heart disease (CHD) or high risk of CHD<br>hyperlipidaemia<br>hypercholesterolaemia<br>stroke<br>atherosclerosis<br>a cardiovascular disease or condition<br>a condition associated with elevated LDL | MP SK3169A<br>RG7652 |
| Vascular Endothelial Growth Factor-A (VEGF-A) | Diabetic Macular Edema (DME), | EYLEA ®<br>Aflibercept |
| Placental Growth Factor (P1GF) | Branch Retinal Vein Occlusion (BRVO)<br>Wet age-related macular degeneration (Wet AMD) | AVASTIN ™<br>LUCENTIS ™ |
| IL-6 receptor | Inflammatory disease, eg, rheumatoid arthritis<br>Uveitis (eg, non-infectious uveitis)<br>Ankylosing spondylitis;<br>Cancer | Sarilumab<br>REGN88 |
| PCSK9 (proprotein convertase subtilisin/kexin type 9) | coronary heart disease (CHD) or high risk of CHD<br>hyperlipidaemia<br>hypercholesterolaemia<br>stroke<br>atherosclerosis<br>a cardiovascular disease or condition<br>a condition associated with elevated LDL | Alirocumab<br>REGN727<br>LY3015014 |
| NGF | Osteoarthritis<br>Pain | Fasinumab<br>REGN475 |
| IL-4 receptor alpha | Allergic asthma | Dupilumab |
| IL-13 receptor | eosinophilic asthma<br>Atopic dermatitis | REGN668 |
| delta-like ligand-4 (Dll4) | Cancer | Enoticumab<br>REGN421 |
| angiopoietin-2 (Ang2) | Cancer | Nesvacumab<br>REGN910 |
| GDF8 | Metabolic disorder<br>cancer, obesity, diabetes, arthritis, multiple sclerosis, muscular dystrophy, amyotrophic lateral sclerosis, Parkinson's disease, osteoporosis, osteoarthritis, osteopenia, metabolic syndromes (including, but not limited to diabetes, obesity, nutritional disorders, organ atrophy, chronic obstructive pulmonary disease and anorexia)<br>Disuse muscle atrophy<br>cancer-related cachexia | REGN1033<br>LY2495655 |
| ERBB3 | Cancer | REGN1400 |
| angiopoietin-1 (Ang1)<br>angiopoietin-1 (Ang2) | Cancer, eg, ovarian cancer | AMG386 |
| VEGF receptor | Cancer | Motesanib |
| PDGF receptor | NSCLC | AMG 706 |
| Stem cell factor receptor | Breast cancer<br>Thyroid cancer | |
| type 1 insulin-like growth factor receptor (IGF1R) | Cancer<br>Breast cancer<br>Pancreatic cancer | Ganitumab<br>Linsitinib<br>ASP7487 |

TABLE 5-continued

TOIs & Related Diseases, Conditions and Example Ligands

| Human TOI | Example Disease or Condition | Example Ligand |
|---|---|---|
| hepatocyte growth factor (HGF) | Cancer<br>Breast cancer<br>Pancreatic cancer | Rilotumumab |
| HER3 | Cancer | AMG 888 |
| ErbB3 | Breast cancer<br>Pancreatic cancer | U3-1287 |
| IL-17 receptor | Inflammatory disease<br>Asthma<br>Psoriasis | AMG 827<br>brodalumab |
| sclerostin | Bone-related condition<br>postmenopausal osteoporosis<br>fracture healing | AMG 785<br>CDP7851 |
| glucokinase | Diabetes | AMG 151<br>ARRY-403 |
| PCSK9 (proprotein convertase subtilisin/kexin type 9) | coronary heart disease (CHD) or high risk of CHD<br>hyperlipidaemia<br>hypercholesterolaemia<br>stroke<br>atherosclerosis<br>a cardiovascular disease or condition<br>a condition associated with elevated LDL | AMG 145<br>Evolocumab |
| VLA 2<br>Integrin α2β1 | Inflammatory bowel disease | SAR339658 |
| IL-4<br>IL-13 | Idiopathic pulmonary fibrosis | SAR156597 |
| lysophosphatidic acid receptor<br>LPA-1<br>LPA-3 | Systemic sclerosis<br>fibrosis | SAR100842 |
| Androgen receptor | Cancer, eg, prostate cancer, breast cancer | MDV3100<br>enzalutamide |
| HER1<br>EGFR | Cancer, eg, NSCLC | Erlotinib<br>ERBITUX ™<br>VECTIBIX ™ |
| VEGF receptor 1<br>VEGF receptor 2<br>VEGF receptor 3 | Cancer, eg, colorectal cancer, breast cancer | ASP4130<br>tivozanib |
| JAK<br>JAK1<br>JAK2 | Inflammatory disease, eg, rheumatoid arthritis<br>Diabetic nephropathy | ASP015K<br>Baricitinib |
| CD40 | Prevention of organ transplant rejection | ASP1240 |
| GnRH | Endometriosis<br>Cancer, eg, prostate cancer | ASP1707<br>degarelix |
| PDE9 | Lower urinary tract symptoms associated with benign prostatic hyperplasia | ASP4901 |
| TNF alpha | Inflammatory disease, eg, rheumatoid arthritis, psoriasis, chrohn's disease, IBD | Certolizumab pegol |
| Programmed cell death protein 1 | Cancer<br>Chronic myelocytic leukemia; Hepatitis C virus infection; Hepatocellular carcinoma; Hodgkins disease; Melanoma; Multiple myeloma; Non-Hodgkin lymphoma; Non-small-cell lung cancer; Renal cell carcinoma; Solid tumor; Stage IV melanoma | Nivolumab<br>MK-3475 |
| Hepatocyte growth factor<br>MET | Cancer<br>Glioblastoma; Hepatocellular carcinoma; Metastatic colorectal cancer; Metastatic non small cell lung cancer; Metastatic stomach cancer; Non-small-cell lung cancer | onartuzumab |

TABLE 5-continued

TOIs & Related Diseases, Conditions and Example Ligands

| Human TOI | Example Disease or Condition | Example Ligand |
|---|---|---|
| Angiopoietin ligand-1 Angiopoietin ligand-2 Tek tyrosine kinase receptor | Breast tumor; Cancer; Colorectal tumor; Fallopian tube cancer; Gastrointestinal tumor; Glioblastoma; Hepatocellular carcinoma; Metastatic esophageal cancer; Metastatic gastrointestinal cancer; Metastatic non small cell lung cancer; Metastatic ovary cancer; Metastatic renal cancer; Ovary tumor; Peritoneal tumor; Transitional cell carcinoma | trebananib |
| CD37 modulator Lymphocyte function antigen-3 receptor SLAM family member 7 | Cancer Multiple myeloma | elotuzumab |
| IL-2 IL-2 receptor alpha | Multiple sclerosis | daclizumab |
| EGFR | Cancer Metastatic non small cell lung cancer; Solid tumor | necitumumab |
| IL-5 | Asthma; Eosinophilic esophagitis | reslizumab |
| B-lymphocyte cell adhesion molecule CD22 | Cancer, eg Acute lymphoblastic leukemia; Follicle center lymphoma; Non-Hodgkin lymphoma; Systemic lupus erythematosus, hairy cell leukaemia | Inotuzumab inotuzumab ozogamicin epratuzumab moxetumomab moxetumomab pasudotox |
| IL1 beta | Acne vulgaris; Atherosclerosis; Behcets disease; Cardiovascular disease; Dermatomyositis; Insulin dependent diabetes; Multiple myeloma; Osteoarthritis; Paraproteinemia; Polymyositis; Pyoderma gangrenosum; Scleritis; Uveitis | gevokizumab |
| CD20 | Cancer Multiple sclerosis follicular lymphoma (eg, refractory or relapsed) diffuse large B cell lymphoma (eg, relapsed) chronic lymphocytic leukaemia (eg, first line therapy or relapsed) | Ocrelizumab ofatumumab |
| IL-23 | Crohns disease; Inflammatory disease; Psoriasis | tildrakizumab |
| BAFF Neutrokine alpha | Autoimmune disease systemic lupus erythematosus Multiple myeloma vasculitis | Belimumab Benlysta ™ Tabalumab |
| IL5 | Asthma | mepolizumab |
| IL6 | Inflammatory disease rheumatoid arthritis | sirukumab |
| Lp-PLA2 | Atherosclerosis diabetic macular oedema | darapladib |
| CCR9 chemokine receptor | Inflammatory disease rheumatoid arthritis Crohn's disease | Vercirnon |
| DOPA decarboxylase | Parkinson's Disease | Patrome |
| Her2 EGFR | Cancer, eg, gastric cancer, breast cancer, head and neck squamous cell cancer, | Tyverb ™ Tykerb ™ lapatinib |
| ADP receptor | Cardiovascular disease or condition | Brilinta Brilique |

TABLE 5-continued

TOIs & Related Diseases, Conditions and Example Ligands

| Human TOI | Example Disease or Condition | Example Ligand |
|---|---|---|
| | Thrombosis, eg, arterial thrombosis | |
| VEGFR | Cancer, eg, medullary thyroid cancer | Caprelsa |
| EGFR | | |
| LABA | Respiratory disease or condition, eg, COPD | PT003 GFF |
| LAMA | | |
| Factor Xa | thromboembolism | apixaban |
| Oxelumab | OX40 ligand | Asthma |
| | | Graft-versus-host disease |
| Tremelimumab | CTLA-4 | Cancer, eg, melanoma |
| Ticilimumab | CD152 | Autoimmune disease |
| ipilimumab | | |
| MPDL3280A | PD-L1 | Cancer, eg, solid tumour, kidney cancer, lung cancer, melanoma, NSCLC, multiple myeloma |
| MEDI4736 | | |
| | | Autoimmune disease |
| Nivolumab | PD-1 | Cancer, eg, solid tumour, kidney cancer, lung cancer, melanoma, NSCLC, multiple myeloma |
| AMP-514 | | |
| AMP-224 | | |
| | | Autoimmune disease |
| | LIGHT | |
| | TNFSF14 | |
| | CD40 ligand | |
| JAK | Inflammatory disease, eg, rheumatoid arthritis, psoriasis, chrohn's disease, IBD, ulcerative colitis, Psoriatic Arthritis | tofacitinib |
| Nerve Growth Factor | Pain | tanezumab |
| | Osteoarthritis pain | |
| Her1 receptor | Cancer, eg, Non-Small Cell Lung Cancer | dacomitinib |
| Her2 receptor | | |
| Her4 receptor | | |
| c-MET | Cancer, eg, Non-Small Cell Lung Cancer | crizotinib |
| ALK | | |
| Programmed cell death 1 receptor | Cancer, eg, renal cell carcinoma | Nivolumab |
| SLAMF7 | Cancer, eg, multiple myeloma | Elotuzumab |
| CD319 | | |
| CD30 | Cancer, eg, Hodgkin lymphoma, systemic anaplastic large cell lymphoma, T-cell lymphoma | Brentuximab Brentuximab vedotin |
| GPR40 | Diabetes, eg, diabetes mellitus | Fasiglifam |
| DPP-4 | | trelagliptin |
| VEFGR-1 receptor | Cancer, eg, non-squamous non-small cell lung cancer | Motesanib |
| VEFGR-2 receptor | | Motesanib diphosphate |
| VEFGR-3 receptor | | |
| PDGFR | | |
| cKit | | |
| amyloid β | Alzheimer's disease | Solanezumab |
| TNF alpha | Inflammatory disease, eg, rheumatoid arthritis, psoriasis, chrohn's disease, IBD, ulcerative colitis, Psoriatic Arthritis | SIMPONI ™ HUMIRA ™ REMICADE ™ ENBREL ™ Adalimumab |
| IL-21 | Autoimmune disease or condition Inflammatory disease or condition Rheumatoid arthritis Crohn's disease IBD Ulcerative colitis Systemic lupus erythematosus (SLE) Graft versus host disease Cancer Metastatic melanoma Renal cell carcinoma Melanoma Solid tumours | Agonist or antagonist antibody specific for human IL-21 NNC0114-0005 NNC0114-0006 NN8828 ATR-107 Said or an anti-IL-21 antibody in combination with an agent selected from the group consisting of ipilimumab (eg, to treat melanoma), an anti-PD1 antibody (eg, to treat solid tumours), sunitinib (eg, to treat renal cell carcinoma), |

TABLE 5-continued

TOIs & Related Diseases, Conditions and Example Ligands

| Human TOI | Example Disease or Condition | Example Ligand |
|---|---|---|
| | Acute myeloid leukaemia<br>Non-Hodgkin's lymphoma<br>Ovarian cancer<br>Colorectal cancer | rituximab (eg, to treat Non-Hodgkin's lymphoma), sorafenib (eg, to treat renal cell carcinoma), doxorubicin (eg, to treat ovarian cancer) and cetuximab (eg, to treat colorectal cancer). |

TABLE 6

PCSK9 SEQUENCES

AMINO ACID SEQUENCES

Italics = signal sequence 1-30
lowercase = catalytic domain 153-449
UPPERCASE = C-terminal domain 450-692
Underlined = residues changed from allele in other sequences (aaresidue number shown)

| FORM/ALLELE | VERSION | SEQUENCE | SEQ ID NO: |
|---|---|---|---|
| a | Pro-Form with Signal Sequence | *MGTVSSRRSWWPLPLLLLLLLLLGPAGARA* QEDEDGDYEELVLAL<u>R</u>S<sup>46</sup>EEDGLA<sup>53</sup>EAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQ sipwnleritppryradeyqppdggslvevylldtsiqsdhreiegrvmvtdfenvpeedgtrfhrqaskcdshg<br><br>thlagvvsgrdagvakgasmrslrvlncqgkgtvsgtligiefirksqivqpvgpivviipiaggysrvlnaacqrlaragvvivtaagnfrddacly<br>spasapevitvgatnaqdqpvtigtigtnfgrcvdifapgediigassdcstcfvsqsgtsqaaahvagiaammisaepeitlaelrqrlihfsak<br><br>dvi<u>n</u><sup>425</sup>eawfpedqrvltpnlva<u>a</u><sup>443</sup>lppsthGAGWQLFCRTVWSAHSGPTRMATA<u>I</u><sup>474</sup>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>HKPPVLRPRGQPNQCVGHREASIHASCCHAPGLECKVKEHGIPAPQ<u>E</u><sup>619</sup><u>E</u><sup>520</sup>QVTVACEEGWTLTGCSALPGTSHVLGAY<br><br>AVDNTCVVRSRDVSTTGSTSE<u>E</u><sup>670</sup>AVTAVAICCRSRHLAQASQELQ | 1 |
| a | Pro-Form | QEDEDGDYEELVLAL<u>R</u>S EEDGLA<u>E</u>APEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQ sipwnieritppryradeyqppdggslvevylldtsiqsdhreiegrvmvtdfenvpeedgtrfhrqaskcdshg<br><br>thlagvvsgrdagvakgasmrslrvlncqgkgtvsgtligiefirksqlvqpvgpivvllplaggysrvlnaacqrlaragvvlvtaagnfrddacly<br>spasapevitvgatnaqdqpvtigtigtnfgrcvdlfapgediigassdcstcfvsqsgtsqaaahvagiaammisaepeltlaepeltlaelrqrlihfsak<br><br>dvi<u>n</u><sup>425</sup>eawfpedqrvltpnlva<u>a</u><sup>443</sup>lppsthGAGWQLFCRTVWSAHSGPTRMATA<u>I</u><sup>474</sup>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>HKPPVLRPRGQPNQCVGHREASIHASCCHAPGLECKVKEHGIPAPQ<u>E</u><sup>519</sup><u>E</u><sup>520</sup>QVTVACEEGWTLTGCSALPGTSHVLGAY<br><br>AVDNTCVVRSRDVSTTGSTSE<u>E</u><sup>670</sup>AVTAVAICCRSRHLAQASQELQ | 2 |

TABLE 6-continued

PCSK9 SEQUENCES

| | | | |
|---|---|---|---|
| a | Mature form | sipwnieritppryradeyqppdggsivevyilldtsiqsdhreiegrvmvtdfenvpeedgtrfhrqaskcdshg<br>thlagvvsgrdagvakgasmrslrvincqgkgtvsgtliglefirksqlvqpvgplvvllplaggysrvlnaacqrlaragvvlvtaagnfrddacly<br>spasapevitvgatnaqdqpvtlgtlgtnfgrcvdlfapgedllgassdcstcfvsqsgtsqaaahvagiaammisaepeitiaeirqrlihfsak<br><br>    425      443          474<br>dvi<u>n</u>eawfpedqrvltpnlvaa<u>l</u>ppsthGAGWQLFCRTVWSAHSGPTRMATA<u>I</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                               619 520<br>HKPPVLRPRGQPNQCVGHREASIHASCCHAPGLECKVKEHGIPAP<u>QE</u>QVTVACEEGWTLTGCSALPGTSHVLGAY<br><br>        670<br>AVDNTCVVRSRDVSTTGSTSE<u>E</u>AVTAVAICCRSRHLAQASQELQ | 3 |
| f | Pro-<br><br>Form<br><br>with<br><br>Signal Se-<br><br>quence | *MGTVSSRRSWWPLPLLLLLLLGPAGARA*  QEDEDGDYEELVLALR<u>S</u>EEDGL<u>A</u>EAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnieritppryradeyqppdggslvevylldtsiqsdhreiegrvmvtdfenvpeedgtrfhrqaskcdshg<br><br>thlagvvsgrdagvakgasmrsirvincqgkgtvsgtliglefirksqlvqpvgplvvllplaggysrvlnaacqrlaragvvivtaagnfrddacly<br>spasapevitvgatnaqdqvtlgtlgtnfgrcvdlfapgediigassdcstcfvsqsgtsqaaahvagiaammlsaepeltlaelrqrlihfsak<br><br>    425      443          474<br>dvi<u>n</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAGNAFGGEGVYAIARCCLLPQANCSVHTAPPAEASMGTRVHCHQQGHVLTGCSSHWEVEDLGT<br><br>                               619 520<br>HKPPVLRPRGQPNQCVGHREASIHASCCHAPGLECKVKEHGIPAP<u>QE</u>QVTVACEEGWTLTGCSALPGTSHVLGAY<br><br>        670<br>AVDNTCVVRSRDVSTTGSTSE<u>E</u>AVTAVAICCRSRHLAQASQELQ | 4 |
| f | Pro-<br><br>Form | QEDEDGDYEELVLALR<u>S</u>EEDGL<u>A</u>EAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQsipwnieritppryradeyqppdggslvevylldtsiqsdhreiegrvmvtdfenvpeedgtrfhrqaskcdshg<br><br>thlagvvsgrdagvakgasmrslrvincqgkgtvsgtliglefirksqlvqpvgplvvllplaggysrvlnaacqrlaragvvlvtsaagnfrddacly<br>spasapevitvgatnaqdqpvtlgtlgtnfgrcvdlfapgediigassdcstcfvsqsgtsqaaahvagiaammisaepeitiaelrqrlihfsak<br><br>    425      443          474<br>dvi<u>n</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                               619 520<br>HKPPVLRPRGQPNQCVGHREASIHASCCHAPGLECKVKEHGIPAP<u>QE</u>QVTVACEEGWTLTGCSALPGTSHVLGAY<br><br>        670<br>AVDNTCVVRSRDVSTTGSTSE<u>E</u>AVTAVAICCRSRHLAQASQELQ | 5 |
| f, p, aj | Mature form | sipwnieritppryradeyqppdggsivevylldtsiqsdhreiegrvmvtdfenvpeedgtrfhrqaskcdshg<br>thlagvvsgrdagvakgasmrslrvincqgkgtvsgtliglefirksqlvqpvgplvvllplaggysrvlnaacqrlaragvvivtaagnfrddacly<br>spasapevitvgatnaqdqpvtigtlgtnfgrcvdlfapgediigassdcstcfvsqsgtsqaaahvagiaammlsaepeltlaelrqrlihfsak<br><br>    425      443          474<br>dvi<u>n</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                               619 620<br>HKPPVLRPRGQPNQCVGHREASIHASCCHAPGLECKVKEHGIPAP<u>QE</u>QVTVACEEGWTLTGCSALPGTSHVLGAY | 6 |

TABLE 6-continued

PCSK9 SEQUENCES

| | | | |
|---|---|---|---|
| | | 670<br>AVDNTCVVRSRDVSTTGSTSEEAVTAVAICCRSRHLAQASQELQ | 98 |
| c | Pro-<br>Form<br>with<br>Signal<br>Se-<br>quence |                                             46       53<br>MGTVSSRRSWWPLPLLLLLLLLGPAGARAQEDEDGDYEELVLALRSEEDGLAEAPEHGTTATFHRCAKDP<br>WRLPGTYVVVLKEETHLSQSERTARRLQAQAARRGYLTKILHVFHGLLPGFLVKMSGDLLELALKLPH<br>VDYIEEDSSVFAQsipwnieritppryradeyqppdggsivevyiidtsiqsdhreiegrvmvtdfenvpeedgtrfhrqaskcdshg<br>thlagvvsgrdagvakgasmrslrvincqgkgtvsgtliglefirksqlvqpvgpivvllplaggysrvlnaacqrlaragvvlvtaagnfrddacly<br>spasapevitvgatnaqdqpvtigtlgtnfgrcvdlfapgediigassdcstcfvsqsgtsqaaahvagiaammlsaepeltlaelrqrlihfsak<br>       425           443                    474<br>dvineawfpedqrvitpnivaaippsthGAGWQLFCRTVWSAHSGPTRMATAIARCAPDEELLSCSSFSRSGKRRGERM<br>EAQGGKLVCRAHNAFGGEGVYAIARCCLLPQANCSVHTAPPAEASMGTRVHCHQQGHVLTGCSSHWEVEDLGT<br>                                            619 620<br>HKPPVLRPRGQPNQCVGHREASIHASCCHAPGLECKVKEHGIPAPQEQVTVACEEGWTLTGCSALPGTSHVLGAY<br>                    670<br>AVDNTCVVRSRDVSTTGSTSEGAVTAVAICCRSRHLAQASQELQ | 7 |
| c | Pro-<br>Form | QEDEDGDYEELVLALRSEEDGLAEAPEHGTTATFHRCAKDP<br>WRLPGTYVVVLKEETHLSQSERTARRLQAQAARRGYLTKILHVFHGLLPGFLVKMSGDLLELALKLPH<br>VDYIEEDSSVFAQsipwnieritppryradeyqppdggsivevyiidtsiqsdhreiegrvmvtdfenvpeedgtrfhrqaskcdshg<br>thlagvvsgrdagvakasmrslrvlincqgkgtvsgtliglefirksqlvpqvgplvvllplaggysrvlnaacqrlaragvvivaagnfrddacly<br>spasapevitvgatnaqdqpvtlgtlgtnfgrcvdlfapgediigassdcstcfvsqsgtsqaaahvagiaammlsaepeltlaelrqrliihfsak<br>       425           443                    474<br>dvineawfpedqrvitpnivaaippsthGAGWQLFCRTVWSAHSGPTRMATAIARCAPDEELLSCSSFSRSGKRRGERM<br>EAQGGKLVCRAHNAFGGEGVYAIARCCLLPQANCSVHTAPPAEASMGTRVHCHQQGHVLTGCSSHWEVEDLGT<br>                    619 620<br>HKPPVLRPRGQPNQCVGHREASIHASCCHAPGLECKVKEHGIPAPQEQVTVACEEGWTLTGCSALPGTSHVLGAY<br>               670<br>AVDNTCVVRSRDVSTTGSTSEGAVTAVAICCRSRHLAQASQELQ | 8 |
| c, q | Mature<br>form | sipwnleritppryradeyqppdggslvevylldtsiqsdhreiegrvmvtdfenvpeedgtrfhrqaskcdshg<br>thlagvvsgrdagvakgasmrslrvlncqgkgtvsgtiiglefirksqlvqpvgplvvllplaggysrvlnaacqrlaragvvlvtaagnfrddacly<br>spasapevitvgatnaqdqpvtlgtlgtnfgrcvdlfapgediigassdcstcfvsqsgtsqaaahvagiaammlsaepeltiaelrqrlihfsak<br>       425           443                    474<br>dvineawfpedqrvitpnivaaippsthGAGWQLFCRTVWSAHSGPTRMATAIARCAPDEELLSCSSFSRSGKRRGERM<br>EAQGGKLVCRAHNAFGGEGVYAIARCCLLPQANCSVHTAPPAEASMGTRVHCHQQGHVLTGCSSHWEVEDLGT<br>                    619 620<br>HKPPVLRPRGQPNQCVGHREASIHASCCHAPGLECKVKEHGIPAPQEQVTVACEEGWTLTGCSALPGTSHVLGAY<br>               670<br>AVDNTCVVRSRDVSTTGSTSEGAVTAVAICCRSRHLAQASQELQ | 9 |
| r | Pro-<br>Form<br>with |                                             46       53<br>*MGTVSSRRSWWPLPLLLLLLLLLGPAGARA*QEDEDGDYEELVLALRSEEDGLAEAPEHGTTATFHRCAKDP<br>WRLPGTYVVVLKEETHLSQSERTARRLQAQAARRGYLTKILHVFHGLLPGFLVKMSGDLLELALKLPH<br>VDYIEEDSSVFAQsipwnieritppyryradeyqppdggsivevyiidtsiqsdhreiegrvmvtdfenvpeedgtrfhraskcdshg | 10 |

TABLE 6-continued

PCSK9 SEQUENCES

| | | | |
|---|---|---|---|
| | Signal Sequence | thlagvvsgrdagvakgasmrslrvlncqgkgtvsgtliglefirksqlvqpvgplvvlllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak   425         443                                474 dvineaawfpedqrvitpnivaaippsthGAGWQLFCRTVWSAHSGPTRMATAVARCAPDEELLSCSSFSRSGKRRGERM EAQGGKLVCRAHNAFGGEGVYAIARCCLLPQANCSVHTAPPAEASMGTRVHCHQQGHVLTGCSSHWEVEDLGT                                                              619 620 HKPPVLRPRGQPNQCVGHREASIHASCCHAPGLECKVKEHGIPAPQEQVTVACEEGWTLTGCSALPGTSHVLGAY                    670 AVDNTCVVRSRDVSTTGSTSEGAVTAVAICCRSRHLAQASQELQ | |
| r | Pro-Form | QEDEDGDYEELVLALRSEEDGLAEAPEHGTTATFHRCAKDP WRLPGTYVVVLKEETHLSQSERTARRLQAQAARRGYLTKILHVFHGLLPGFLVKMSGDLLELALKLPH VDYIEEDSSVFAQsipwnieritppryradeyqppdggsivevyiidtsiqsdhreiegrvmvtdfenvpeedgtrfhrqaskcdshg thlagvvsgrdagvakgasmrslrvlncqgkgtvsgtliglefirksqlvqpvgplvvlllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak   425         443                                474 dvineaawfpedqrvitpnivaaippsthGAGWQLFCRTVWSAHSGPTRMATAVARCAPDEELLSCSSFSRSGKRRGERM EAQGGKLVCRAHNAFGGEGVYAIARCCLLPQANCSVHTAPPAEASMGTRVHCHQQGHVLTGCSSHWEVEDLGT                                                              619 620 HKPPVLRPRGQPNQCVGHREASIHASCCHAPGLECKVKEHGIPAPQEQVTVACEEGWTLTGCSALPGTSHVLGAY                    670 AVDNTCVVRSRDVSTTGSTSEGAVTAVAICCRSRHLAQASQE | 11 |
| r | Mature form | sipwnleritppryradeyqppdggslvevylldtsiqsdhreiegrvmvtdfenvpeedgtrfhrqaskcdshg thlagvvsgrdagvakgasmrslrvlncqgkgtvsgtiiglefirksqlvqpvgplvvlllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak   425         443                                474 dvineaawfpedqrvitpnivaaippsthGAGWQLFCRTVWSAHSGPTRMATAVARCAPDEELLSCSSFSRSGKRRGERM EAQGGKLVCRAHNAFGGEGVYAIARCCLLPQANCSVHTAPPAEASMGTRVHCHQQGHVLTGCSSHWEVEDLGT                                                              619 520 HKPPVLRPRGQPNQCVGHREASIHASCCHAPGLECKVKEHGIPAPQEQVTVACEEGWTLTGCSALPGTSHVLGAY                    670 AVDNTCVVRSRDVSTTGSTSEGAVTAVAICCRSRHLAQASQELQ | 12 |
| p | Pro-Form with Signal Sequence | *MGTVSSRRSWWPLPLLLLLLLLL GPAGA*QEDEDGDYEELVLALRSEEDGLVEAPEHGTTATFHRCAKDP WRLPGTYVVLKEETHLSQSERTARRLQAQAARRGYLTKILHVFHGLIPGFLVKMSGDLLELALKLPH VDYIEEDSSVFAQslpwnleritppryradeyqppdggslvevylldtsiqsdhreiegrvmvtdfenvpeedgtrfhrqaskcdshg thlagvvsgrdagvakgasmrslrvlncqgkgtvsgtliglefirksqlvqpvgplvvlllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak   425         443                                474 dvineaawfpedqrvltpnlvaaIppsthGAGWQLFCRTVWSAHSGPTRMATAVARCAPDEELLSCSSFSRSGKRRGERM EAQGGKLVCRAHNAFGGEGVYAIARCCLLPQANCSVHTAPPAEASMGTRVHCHQQGHVLTGCSSHWEVEDLGT                                                              619 620 HKPPVLRPRGQPNQCVGHREASIHASCCHAPGLECKVKEHGIPAPQEQVTVACEEGWTLTGCSALPGTSHVLGAY                    670 AVDNTCVVRSRDVSTTGSTSEEAVTAVAICCRSRHLAQASQELQ | 13 |

TABLE 6-continued

PCSK9 SEQUENCES

| p | Pro-Form | QEDEDGDYEELVLAL<u>RS</u>EEDGL<u>V</u>EAPEHGTTATFHRCAKDP<br>WRLPGTYVVVLKEETHLSQSERTARRLQAQAARRGYLTKILHVFHGLLPGFLVKMSGDLLELALKLPH<br>VDYIEEDSSVFAQslpwnleritppryradeyqppdggslvevylldtsiqsdhreiegrvmvtdfenvpeedgtrfhrqaskcdshg<br>thlagvvsgrdagvakgasmrslrvlncqgkgtvsgtliglefirksqlvqpvgplvvllplaggysrvlnaacqrlaragvvivtaagnfrddacly<br>spasapevitvgatnaqdqpvtlgtlgtnfgrcvdlfapgediigassdcstcfvsqsgtsqaaahvagiaammlsaepeltiaelrqrlihfsak<br>     425        443        474<br>dvi<u>ne</u>awfpedqrvltpnlvaa<u>l</u>ppsthGAGWQLFCRTVWSAHSGPTRMATA<u>V</u>ARCAPDEELLSCSSFSRSGKRRGERM<br>EAQGGKLVCRAHNAFGGEGVYAIARCCLLPQANCSVHTAPPAEASMGTRVHCHQQGHVLTGCSSHWEVEDLGT<br>                      619 620<br>HKPPVLRPRGQPNQCVGHREASIHASCCHAPGLECKVKEHGIPAP<u>QE</u>QVTVACEEGWTLTGCSALPGTSHVLGAY<br>          670<br>AVDNTCVVRSRDVSTTGSTSE<u>E</u>AVTAVAICCRSRHLAQASQELQ | 14 |
| m | Pro-Form with Signal Sequence |                       46      53<br>MGTVSSRRSWWPLPLLLLLLLLLGPAGARAQEDEDGDYEELVLAL<u>RS</u>EEDGL<u>A</u>EAPEHGTTATFHRCAKDP<br>WRLPGTYVVVLKEETHLSQSERTARRLQAQAARRGYLTKILHVFHGLLPGFLVKMSGDLLELALKLPH<br>VDYIEEDSSVFAQslpwnleritppryradeyqppdggslvevylldtsiqsdhreiegrvmvtdfenvpeedgtrfhrqaskcdshg<br>thlagvvsgrdagvakgasmrslrvlncqgkgtvsgtliglefirksqlvqpvgplvvllplaggysrvlnaacqrlaragvvivtaagnfrddacly<br>spasapevitvgatnaqdqpvtlgtlgtnfgrcvdlfapgediigassdcstcfvsqsgtsqaaahvagiaammlsaepeltiaelrqrlihfsak<br>     425        443        474<br>dvi<u>ne</u>awfpedqrvltpnlvat<u>l</u>ppsthGAGWQLFCRTVWSAHSGPTRMATA<u>I</u>ARCAPDEELLSCSSFSRSGKRRGERM<br>EAQGGKLVCRAHNAFGGEGVYAIARCCLLPQANCSVHTAPPAEASMGTRVHCHQQGHVLTGCSSHWEVEDLGT<br>                      619 620<br>HKPPVLRPRGQPNQCVGHREASIHASCCHAPGLECKVKEHGIPAP<u>QE</u>QVTVACEEGWTLTGCSALPGTSHVLGAY<br>          670<br>AVDNTCVVRSRDVSTTGSTSE<u>E</u>AVTAVAICCRSRHLAQASQELQ | 15 |
| m | Pro-Form | QEDEDGDYEELVLAL<u>RS</u>EEDGL<u>A</u>EAPEHGTTATFHRCAKDP<br>WRLPGTYVVVLKEETHLSQSERTARRLQAQAARRGYLTKILHVFHGLLPGFLVKMSGDLLELALKLPH<br>VDYIEEDSSVFAQslpwnleritppryradeyqppdggslvevylldtsiqsdhreiegrvmvtdfenvpeedgtrfhrqaskcdshg<br>thlagvvsgrdagvakgasmrslrvlncqgkgtvsgtliglefirksqlvqpvgplvvllplaggysrvlnaacqrlaragvvivtaagnfrddacly<br>spasapevitvgatnaqdqpvtlgtlgtnfgrcvdlfapgediigassdcstcfvsqsgtsqaaahvagiaammlsaepeltiaelrqrlihfsak<br>     425        443        474<br>dvi<u>ne</u>awfpedqrvltpnlvat<u>l</u>ppsthGAGWQLFCRTVWSAHSGPTRMATA<u>I</u>ARCAPDEELLSCSSFSRSGKRRGERM<br>EAQGGKLVCRAHNAFGGEGVYAIARCCLLPQANCSVHTAPPAEASMGTRVHCHQQGHVLTGCSSHWEVEDLGT<br>                      619 620<br>HKPPVLRPRGQPNQCVGHREASIHASCCHAPGLECKVKEHGIPAP<u>QE</u>QVTVACEEGWTLTGCSALPGTSHVLGAY<br>                      619 620<br>HKPPVLRPRGQPNQCVGHREASIHASCCHAPGLECKVKEHGIPAP<u>QE</u>QVTVACEEGWTLTGCSALPGTSHVLGAY<br>          670<br>AVDNTCVVRSRDVSTTGSTSE<u>E</u>AVTAVAICCRSRHLAQASQELQ | 16 |

TABLE 6-continued

PCSK9 SEQUENCES

| | | | |
|---|---|---|---|
| m | Mature form | sipwnleritppryradeyqppdggslvevylldtsiqsdhreiegrvmvtdfenvpeedgtrfhrqaskcdshg thlagvvsgrdagvakgasmrslrvlncqgkgtvsgtiiglefirksqlvqpvgplvvllplaggysrvlnaacqrlaragvvlvtaagnfrddacly spasapevitvgatnaqdqpvtlgtlgtnfgrcvdlfapgediigassdcstcfvsqsgtsqaaahvagiaammlsaepeltiaelrqrlihfsak<br><br>           425           443                       474<br>dvi<u>n</u>eawfpedqrvltpnlvat<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                  619 620<br>HKPPVLRPRGQPNQCVGHREASIHASCCHAPGLECKVKEHGIPAP<u>QE</u>QVTVACEEGWTLTGCSALPGTSHVLGAY<br><br>                          670<br>AVDNTCVVRSRDVSTTGSTSE<u>E</u>AVTAVAICCRSRHLAQASQELQ | 17 |
| e | Pro-<br><br>Form<br><br>with<br><br>Signal Se-<br><br>quence |                                           46         53<br>MGTVSSRRSWWPLPLLLLLLLLLGPAGARAQEDEDGDYEELVLAL<u>R</u>SEEDGL<u>A</u>EAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQslpwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak<br><br>           425           443                       474<br>dvi<u>s</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                  619 620<br>HKPPVLRPRGQPNQCVGHREASIHASCCHAPGLECKVKEHGIPAP<u>QE</u>QVTVACEEGWTLTGCSALPGTSHVLGAY<br><br>                          670<br>AVDNTCVVRSRDVSTTGSTSE<u>E</u>AVTAVAICCRSRHLAQASQELQ | 18 |
| e | Pro-<br><br>Form | QEDEDGDYEELVLAL<u>R</u>SEEDGL<u>A</u>EAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQslpwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak<br><br>           425           443                       474<br>dvi<u>s</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                619 620<br>HKPPVLRPRGQPNQCVGHREASIHASCCHAPGLECKVKEHGIPAP<u>QE</u>QVTVACEEGWTLTGCSALPGTSHVLGAY<br><br>                          670<br>AVDNTCVVRSRDVSTTGSTSE<u>E</u>AVTAVAICCRSRHLAQASQELQ | 19 |
| e | Mature form | sipwnleritppryradeyqppdggslvevylldtsiqsdhreiegrvmvtdfenvpeedgtrfhrqaskcdshg thlagvvsgrdagvakgasmrslrvlncqgkgtvsgtiiglefirksqlvqpvgplvvllplaggysrvlnaacqrlaragvvlvtaagnfrddacly spasapevitvgatnaqdqpvtlgtlgtnfgrcvdlfapgediigassdcstcfvsqsgtsqaaahvagiaammlsaepeltiaelrqrlihfsak<br><br>           425           443                       474<br>dvi<u>s</u>eawfpedqrvltpnlvaa<u>l</u>ppsthGAGWQLFCRTVWSAHSGPTRMATA<u>V</u>ARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                                619 620<br>HKPPVLRPRGQPNQCVGHREASIHASCCHAPGLECKVKEHGIPAP<u>QE</u>QVTVACEEGWTLTGCSALPGTSHVLGAY | 20 |

TABLE 6-continued

PCSK9 SEQUENCES

|   |   |   |   |
|---|---|---|---|
| | | 670<br>AVDNTCVVRSRDVSTTGSTSEEAVTAVAICCRSRHLAQASQELQ | |
| h | Pro-<br>Form<br>with<br>Signal<br>Se-<br>quence | 46    53<br>MGTVSSRRSWWPLPLLLLLLLLLGPAGARAQEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQslpwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvivtaagnfrddacly<br>spasapevitvgatnaqdqpvtlgtlgtnfgrcvdlfapgediigassdcstcfvsqsgtsqaaahvagiaammlsaepeltiaelrqrlihfsak<br><br>425    443                474<br>dvineawfpedqrvltpnlvatlppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                         619 620<br>HKPPVLRPRGQPNQCVGHREASIHASCCHAPGLECKVKEHGIPAPPEQVTVACEEGWTLTGCSALPGTSHVLGAY<br><br>              670<br>AVDNTCVVRSRDVSTTGSTSEEAVTAVAICCRSRHLAQASQELQ | 21 |
| h | Pro-<br>Form | QEDEDGDYEELVLALRSEEDGLAEAPEHGTTATFHRCAKDP<br><br>WRLPGTYVVVLKEETHLSQSERTARRLQAQAARRGYLTKILHVFHGLLPGFLVKMSGDLLELALKLPH<br><br>VDYIEEDSSVFAQslpwnleritppryradeyqppdggslvevylldtsiqsdhreiegrvmvtdfenvpeedgtrfhrqaskcdshg<br><br>thlagvvsgrdagvakgasmrslrvlncqgkgtvsgtliglefirksqlvqpvgplvvllplaggysrvlnaacqrlaragvvivtaagnfrddacly<br>spasapevitvgatnaqdqpvtlgtlgtnfgrcvdlfapgediigassdcstcfvsqsgtsqaaahvagiaammlsaepeltiaelrqrlihfsak<br><br>425    443                474<br>dvineawfpedqrvltpnlvatlppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                         619 620<br>HKPPVLRPRGQPNQCVGHREASIHASCCHAPGLECKVKEHGIPAPPEQVTVACEEGWTLTGCSALPGTSHVLGAY<br><br>              670<br>AVDNTCVVRSRDVSTTGSTSEEAVTAVAICCRSRHLAQASQELQ | 22 |
| h | Mature<br>form | sipwnleritppryradeyqppdggslvevylldtsiqsdhreiegrvmvtdfenvpeedgtrfhrqaskcdshg<br>thlagvvsgrdagvakgasmrslrvlncqgkgtvsgtiiglefirksqlvqpvgplvvllplaggysrvlnaacqrlaragvvlvtaagnfrddacly<br>spasapevitvgatnaqdqpvtlgtlgtnfgrcvdlfapgediigassdcstcfvsqsgtsqaaahvagiaammlsaepeltiaelrqrlihfsak<br><br>425    443                474<br>dvineawfpedqrvltpnlvatlppsthGAGWQLFCRTVWSAHSGPTRMATAIARCAPDEELLSCSSFSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                         619 620<br>HKPPVLRPRGQPNQCVGHREASIHASCCHAPGLECKVKEHGIPAPPEQVTVACEEGWTLTGCSALPGTSHVLGAY<br><br>              670<br>AVDNTCVVRSRDVSTTGSTSEEAVTAVAICCRSRHLAQASQELQ | 23 |

TABLE 6-continued

PCSK9 SEQUENCES

| | | | |
|---|---|---|---|
| nj | Pro-Form with Signal Sequence | MGTVSSRRSWWPLPLLLLLLLLLGPAGARAQEDEDGDYEELVLAL<u>L</u>SEEDGL<u>A</u>EAPEHGTTATFHRCAKDP WRLPGTYVVVLKEETHLSQSERTARRLQAQAARRGYLTKILHVFHGLLPGFLVKMSGDLLELALKLPH VDYIEEDSSVFAQslpwnleritppryradeyqppdggslvevylldtsiqsdhreiegrvmvtdfenvpeedgtrfhrqaskcdshg thlagvvsgrdagvakgasmrslrvlncqgkgtvsgtliglefirksqlvqpvgplvvllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak dv<u>i</u>neawfpedqrvltpnlva<u>a</u>ippsthGAGWQLFCRTVWSAHSGPTRMATA<u>V</u>ARCAPDEELLSCSSFSRSGKRRGERM EAQGGKLVCRAHNAFGGEGVYAIARCCLLPQANCSVHTAPPAEASMGTRVHCHQQGHVLTGCSSHWEVEDLGT HKPPVLRPRGQPNQCVGHREASIHASCCHAPGLECKVKEHGIPAP<u>QE</u>QVTVACEEGWTLTGCSALPGTSHVLGAY AVDNTCVVRSRDVSTTGSTSE<u>E</u>AVTAVAICCRSRHLAQASQELQ | 24 |
| aj | Pro-Form | QEDEDGDYEELVLAL<u>L</u>SEEDGL<u>A</u>EAPEHGTTATFHRCAKDP WRLPGTYVVVLKEETHLSQSERTARRLQAQAARRGYLTKILHVFHGLLPGFLVKMSGDLLELALKLPH VDYIEEDSSVFAQsipwnieritppryradeyqppdggsivevyiidtsiqsdhreiegrvmvtdtenvpeedgtrthrqaskcdshg thlagvvsgrdagvakgasmrslrvlncqgkgtvsgtliglefirksqlvqpvgplvvllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak dv<u>i</u>neawfpedqrvitpniva<u>a</u>ippsthGAGWQLFCRTVWSAHSGPTRMATA<u>V</u>ARCAPDEELLSCSSFSRGKRRGERM EAQGGKLVCRAHNAFGGEGVYAIARCCLLPQANCSVHTAPPAEASMGTRVHCHQQGHVLTGCSSHWEVEDLGT HKPPVLRPRGQPNQCVGHREASIHASCCHAPGLECKVKEHIPAP<u>QE</u>QVTVACEEGWTLTGCSALPGTSHVLGAY AVDNTCVVRSRDVSTTGSTSE<u>E</u>AVTAVAICCRSRHLAQASQELQ | 25 |
| q | Pro-Form with Signal Sequence | *MGTVSSRRSWWPPLPLLLLLLLLLGPAGARA*QEDEDGDYEELVLALR<u>S</u>EEDGL<u>V</u>EAPEHGTTATFHRCAKDP WRLPGTYVVVLKEETHLSQSERTARRLQAQAARRGYLTKILHVFHGLLPGFLVKMSGDLLELALKLPH VDYIEEDSSVFAQsipwnieritppryradeyqppdggsivevyiidtsiqsdhreiegrvmtdfenvpeedgtrfhrqaskcdshg thlagvvsgrdagvakgasmrslrvlncqgkgtvsgtliglefirksqlvqpvgplvvllplaggysrvlnaacqrlaragvvivtaagnfrddacly spasapevitvgatnaqdqpvtlgtlgtnfgrcvdlfapgediigassdcstcfvsqsgtsqaaahvagiaammlsaepeltiaelrqrlihfsak dv<u>i</u>neawfpedqrvitpnlva<u>a</u>ippsthGAGWQLFCRTVWSAHSGPTRMATA<u>I</u>ARCAPDEELLSCSSFSRSGKRRGERM EAQGGKLVCRAHNAFGGEGVYAIARCCLLPQANCSVHTAPPAEASMGTRVHCHQQGHVLTGCSSHWEVEDLGT HKPPVLRPRGQPNQCVGHREASIHASCCHAPGLECKVKEHGIPAP<u>QE</u>QVTVACEEGWTLTGCSALPGTSHVLGAY AVDNTCVVRSRDVSTTGSTSE<u>GA</u>VTAVAICCRSRHLAQASQELQ | 26 |

TABLE 6-continued

PCSK9 SEQUENCES

| | | | |
|---|---|---|---|
| q | Pro-Form | QEDEDGDYEELVLALRSEEDGLVEAPEHGTTATFHRCAKDP WRLPGTYVVLKEETHLSQSERTARRLQAQAARRGYLTKILHVFHGLLPGFLVKMSGDLLELALKLPH<br><br>VDYIEEDSSVFAQsipwnieritppryradeyqppdggsivevyiidtsiqsdhreiegrvmvtdtenvpeedgtrfhrqaskcdshg<br><br>thlagvvsgrdagvakgasmrslrvlncqgkgtvsgtliglefirksqlvqpvgplvvllplaggysrvlnaacqrlaragvvivtaagnfrddacly<br>spasapevitvgatnaqdqpvtlgtlgtnfgrcvdlfapgediigassdcstcfvsqsgtsqaaahvagiaammlsaepeltiaelrqrlihfsak<br><br>        425                 443                       474<br>dvineawfpedqrvitpnivaaippsthGAGWQLFCRTVWSAHSGPTRMATAIARCAPDEELLSCSSPSRSGKRRGERM<br><br>EAQGGKLVCRAHNAFGGEGVYAIARCCLLPQANCSVHTAPPAEASMGTRVHCHQQGHVLTGCSSHWEVEDLGT<br><br>                                            619 620<br>HKPPVLRPRGQPNQCVGHREASIHASCCHAPGLECKVKEHGIPAPQEQVTVACEEGWTLTGCSALPGTSHVLGAY<br><br>        570<br>AVDNTCVVRSRDVSTTGSTSEGTAVAICCRSRHLAQASQELQ | 27 |

NUCLEOTIDE SEQUENCES

Italics = signal sequence 1-30
lowercase = catalytic domain 153-449
UPPERCASE = C-terminal domain 450-692

| | |   | |
|---|---|---|---|
| a | ATGGGCACCGTCACTCCAGGCGGTCCTGGTGGCCGCTGCCACTGCTGCTGCTGCTGCTCCTGGGTC<br><br>                                                                R46LCGT to CTT<br>*CCGCGGGCGCCCGTGCG*CAGGAGGACGAGGACGGCGACTACGAGGAGCTGGTGCTAGCCTTGCGTTCCG<br><br>           A53VGCC to GTC<br>AGGAGGACGGCCTGGCCGAAGCACCCGAGCACGGAACCACAGCCACCTTCCACCGCTGCGCCAAGGAT<br><br>CCGTGGAGGTTGCCTGGCACCTACGTGGTGGTGCTGAAGGAGGAGACCCACCTCTCGCAGTAGC<br><br>CACTGCCCGCCGCCTGCAGGCCCAGGCTGCCCGCCGGGGATACCTCACCAAGATCCTGCATGTCTTCC<br><br>ATGGCCTTCTTCCTGGCTTCCTGGTGAAGATGAGTGGCGACCTGCTGGAGCTGGCCTTGAAGTTGCCC<br><br>CATGTCGACTACATCGAGGAGGACTCCTCTGTCTTTGCCCAGagcatcccgtggaacctggagcggattaccctcca<br><br>cggtaccgggcggatgaataccagcccccgacggaggcagcctggtggaggtgtatctcctagacaccagcatacagagtgaccaccgggaa<br>atcgagggcagggtcatggtcaccgacttcgagaatgtgcccgaggaggacgggaccgcttccacagacaggccagcaagtgtgacagtcat<br>ggcacccacctggcagggggtggtcagagcggccgggatgccgaggccgccagcatgcgcagcctgcgcgtgctcaactgccaaggg<br>aagggcacggttagcggcaccctcataggcctggagtttattcggaaaagccagtcggtccagcctgtggggccactggtggtgctgctgcccct<br>ggcgggtgggtacagccgcgtcctcaacgccgcctgccagcgcctggcgaggcgtgggtcgtgctggtcaccgctgccggcaacttccgggac<br>gatgcctgcctctactcccagcctcagctcccgaggtcatcacagttgggcgccaccaatgccaagaccagccggtgaccctggggactttggg<br>gaccaactttggccgctgtgtggacctctttgccccaggggaggacatcattggtgcctccagcgactgcagcacctgctttgtgtcacagagtgg<br>gacatcacaggctgctgcccacgtggctggcattgcagccatgatgctgtctgccgagccggagctcaccctggccgagttgaggcagagactg<br><br>                        N4256 AAT to AGT                        A443T GCC to ACC<br>atccacttctctgccaaagatgtcatcaatgaggcctggttccctgaggaccagcggtactgacccccaacctggtggccgcctgccccccag<br><br>cacccatGGGGCAGGTTGGCAGCTGTTTTGCAGGACTGTATGGTCAGCACACTCGGGGCCTACACGGATGGCC<br><br>        I474V ATC to GTC<br>ACAGCCATCGCCCGCTGCGCCCCAGATGAGGAGCTGCTGAGCTGCTCCAGTTTCTCCAGGAGTGGGAAGCGG<br><br>CGGGGCGAGCGCATGGAGGCCCAAGGGGGCAAGCTGGTCTGCCGGGCCCACAACGCTTTTGGGGGTGAGGG<br>TGTCTACGCCATTGCCAGGTGCTGCCTGCTACCCCAGGCCAACTGCAGCGTCCACACAGCTCCACCAGCTGAG<br>GCCAGCATGGGGAACCCGTGTCCACTGCCACCAACAGGGCCACGTCCTCACAGGCTGCAGCTCCCACTGGGAG<br>GTGGAGGACCTTGGCACCCACAAGCCGCCTGTGCTGAGGCCACGAGGTCAGCCCAACCAGTGCGTGGGCCAC<br>AGGGAGGCCAGCATCCACGCTTCCTGCTGCCATGCCCCAGGTCTGGAATGCAAAGTCAAGGAGCATGGAA<br><br>        Q519P CAG to CCG   E620G GAG to GGG<br>TCCCGGCCCCTCAGGAGCAGGTGACCGTGGCCTGCGAGGAGGGCTGGACCCTGACTGGCTGCAGTGCCCTCC<br><br>CTGGGACCTCCCACGTCCTGGGGGCCTACGCCGTAGACAACACGTGTAGTCAGGAGCCGGGACGTCAGCA | 28 |

TABLE 6-continued

PCSK9 SEQUENCES

E670GGAG to GGG
CTACAGGCAGCACCAGCGAAGAGGCCGTGACAGCCGTTGCCATCTGCTGCCGGAGCCGGCACCTGGCGCAGG

CCTCCCAGGAGCTCCAGTGAC
f   *ATGGGCACCGTCACTCCAGGCGGTCCTGGTGGCCGCTGCCACTGCTGCTGCTGCTGCTGCTCCTGGGTC*   29

R46L CGT to CTT
CCGCGGGCGCCCGTGCGCAGGAGGACGAGGACGGCGACTACGAGGAGCTGGTGCTAGCCTTGCGTTCCG

A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCGACCTGCTGGAGCTGGCCTTGAAGTTGCCC

CATGTCGACTACATCGAGGAGGACTCCTCTGRCTTTGCCCAGagcatcccgtggaacctggagcggattaccctcca cggtaccgggcggatgaataccagccccccgacggaggcagcctggtggaggtgtatctcctagacaccagcatacagagtgaccaccgggaa
atcgagggcagggtcatggtcaccgacttcgagaatgtgcccgaggaggacggaccccgcttccacagacaggccagcaagtgtgacagtcat
ggcacccacctggcagggggtggtcagagcggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggccactggtggtgctgctgccct
ggcgggtgggtacagccgcgtcctcaacgccgcctgccagcgcctggcgagggctggggtcgtgctggtcaccgctgccggcaacttccgggac
gatgcctgcctctactccccagcctcagctcccgaggtcatcacagttggggccaccaatgccaagaccagccggtgaccctggggacttggg
gaccaacttttggccgctgtgtggacctctttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT                          A443T GCC to ACC
atccacttctctgccaaagatgtcatcaatgaggcctggttccctgaggaccagcgggtactgaccccaacctggtggccgccctgcccccag cacccatGGGGCAGGTTGGCAGCTGTTTTGCAGGACTGTATGGTCAGCACACTCGGGGCCTACACGGATGGCC I474V ATC to GTC
ACAGCCGTCGCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG   E620G GAG to GGG
TCCCGGCCCCTCAGGAGCAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAAGAGGCCGTGACAGCCGTTGCCATCTGCTGCCGGAGCCGGCACCTGGCGCAGG

CCTCCCAGGAGCTCCAGTGAC
c   *ATGGGCACCGTCACTCCAGGCGGTCCTGGTGGCCGCTGCCACTGCTGCTGCTGCTGCTGCTCCTGGGTC*   30

R46L CGT to CTT
CCGCGGGCGCCCGTGCGCAGGAGGACGAGGACGGCGACTACGAGGAGCTGGTGCTAGCCTTGCGTTCCG

A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCGACCTGCTGGAGCTGGCCTTGAAGTTGCCC

TABLE 6-continued

PCSK9 SEQUENCES

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggaccccgcttccacagacaggccagcaagtgtgacagtcat
ggcacccacctggcaggggtggtcagagcggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggccactggtggtgctgctgcccct
ggcgggtgggtacagccgcgtcctcaacgccgcctgccagcgcctggcgagggctggggtcgtgctggtcaccgctgccggcaacttccgggac
gatgcctgcctctactcccccagcctcagctcccgaggtcatcacagttggggccaccaatgcccaagaccagccggtgaccctggggactttggg
gaccaactttggccgctgtgtggacctcttttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT         A443T GCC to ACC
atccacttctctgccaaagatgtcatc<u>aat</u>gaggcctggttccctgaggaccagcgggtactgaccccccaacctggtggcc<u>gcc</u>ctgccccccag cacccatGGGGCAGGTTGGCAGCTGTTTTGCAGGACTGTATGGTCAGCACACTCGGGGCCTACACGGATGGCC I474V ATC to GTC
ACAGCC<u>ATC</u>GCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG  E620G GAG to GGG
TCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAA<u>GGG</u>GCCGTGACAGCCGTTGCCATCTGCTGCCGGAGCCGGCACCTGGCGCAGG

CCTCCCAGGAGCTCCAGTGAC r  *ATGGGCACCGTCACTCCAGGCGGTCCTGGTGGCCGCTGCCACTGCTGCTGCTGCTGCTCCTGGGTC*    31

R46L CGT to CTT
*CCGCGGGCGCCCGTGCG*CAGGAGGACGAGGACGGCGACTACGAGGAGCTGGTGCTAGCCTTGC<u>GTT</u>CCG

A53V GCC to GTC
AGGAGGACGGCCTGG<u>GCC</u>GAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggaccccgcttccacagacaggccagcaagtgtgacagtcat
ggcacccacctggcaggggtggtcagagcggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggccactggtggtgctgctgcccct
ggcgggtgggtacagccgcgtcctcaacgccgcctgccagcgcctggcgagggctggggtcgtgctggtcaccgctgccggcaacttccgggac
gatgcctgcctctactcccccagcctcagctcccgaggtcatcacagttggggccaccaatgcccaagaccagccggtgaccctggggactttggg
gaccaactttggccgctgtgtggacctcttttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT         A443T GCC to ACC
atccacttctctgccaaagatgtcatc<u>aat</u>gaggcctggttccctgaggaccagcgggtactgaccccccaacctggtggcc<u>gcc</u>ctgccccccag cacccatGGGGCAGGTTGGCAGCTGTTTTGCAGGACTGTATGGTCAGCACACTCGGGGCCTACACGGATGGCC I474V ATC to GTC
ACAGCC<u>GTC</u>GCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG

TABLE 6-continued

PCSK9 SEQUENCES

GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA

Q619P CAG to CCG    E620G GAG to GGG
TCCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAA<u>GGGG</u>CCGTGACAGCCGTTGCCATCTGCTGCCGGAGCCGGCACCTGGCGCAGG p    CCTCCCAGGAGCTCCAGTGAC
*ATGGGCACCGTCACTCCAGGCGGTCCTGGTGGCCGCTGCCACTGCTGCTGCTGCTGCTGCTCCTGGGTC*    32

R46L CGT to CTT
*CCGCGGGCGCCCGTGCG*caggaggacgaggacggcgactacgaggagctggtgctagccttg<u>c</u>gttccg A53V GCC to GTC
AGGAGGACGGCCTG<u>GTC</u>GAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

CATGTCGACTACATCGAGGAGGACTCCTCTGTCTTTGCCCAGagcatcccgtggaacctggagcggaattacccctcca cggtaccgggcggatgaataccagccccccgacggaggcagcctggtggaggtgtatctcctagacaccagcatacagagtgaccaccgggaa
atcgagggcagggtcatggtcaccgacttcgagaatgtgcccgaggaggacgggaccccgcttccacagacaggccagcaagtgtgacagtcat
ggcacccacctggcagggtggtcagagcggccggatgccggcgtggccaagggtgccagcatgcgcagcctgcgcgtgctcaactgccaaggg
aagggcacggttagcggcaccctcataggcctggagtttattcggaaaagccagctggtccagcctgtggggccactggtggtgctgctgcccct
ggcggtgggtacagccgcgtcctcaacgccgcctgccagcgcctggcgagggctggggtcgtgctggtcaccgctgccggcaacttccgggac
gatgcctgcctctactcccagcctcagctcccgaggtcatcacagttggggccaccaatgcccaagaccagccggtgaccctggggactttggg
gaccaactttggccgctgtgtggacctcttcgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT                                 A443T GCC to ACC
atccacttctctgccaaagatgtcatc<u>aat</u>gaggcctggttccctgaggaccagcgggtactgacccccaacctggtggcc<u>gcc</u>ctgccccccag cacccatGGGGCAGGTTGGCAGCTGTTTTGCAGGACTGTATGGTCAGCACACTCGGGGCCTACACGGATGGCC I474V ATC to GTC
ACAGCC<u>GTC</u>GCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG    E620G GAG to GGG
TCCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAA<u>GAG</u>GCCGTGACAGCCGTTGCCATCTGCTGCCGGAGCCGGCACCTGGCGCAGG m    CCTCCCAGGAGCTCCAGTGAC
*ATGGGCACCGTCACTCCAGGCGGTCCTGGTGGCCGCTGCCACTGCTGCTGCTGCTGCTGCTCCTGGGTC*    33

R46L CGT to CTT
*CCGCGGGCGCCCGTGCG*caggaggacgaggacggcgactacgaggagctggtgctagccttg<u>c</u>gttccg A53V GCC to GTC
AGGAGGACGGCCTG<u>GCC</u>GAAGCACCCGAGCACGGAACCACAGCCACCTTCCACCGCTGCGCCAAGGAT TABLE 6-continued

PCSK9 SEQUENCES

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggacccgcttccacagacaggccagcaagtgtgacagtcat
ggcacccacctggcaggggtggtcagagccggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggcacctggtggtgctgctgcccct
ggcgggtgggtacagccgcgtcctcaacgccgcctgccagcgcctggcgagggctggggtcgtgctggtcaccgctgccggcaacttccgggac
gatgcctgcctctactcccagcctcagctcccgaggtcatcacagttggggccaccaatgcccaagaccagccggtgaccctgggactttggg
gaccaacttggccgctgtgtggacctctttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT    A443T GCC to ACC
atccacttctctgccaaagatgtcatcaatgaggcctggttccctgaggaccagcgggtactgaccccccaacctggtggccacc ctgcccccccag cacccatGGGGCAGGTTGGCAGCTGTTTTGCAGGACTGTATGGTCAGCACACTCGGGGCCTACACGGATGGCC I474V ATC to GTC
ACAGCCATCGCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG  E620G GAG to GGG
TCCCGGCCCCTCAGGAGCAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAAGAGGCCGTGACAGCCGTTGCCATCTGCTGCCGGAGCCGGCACCTGGCGCAGG

CCTCCCAGGAGCTCCAGTGAC
e *ATGGGCACCGTCACTCCAGGCGGTCCTGGTGGCCGCTGCCACTGCTGCTGCTGCTGCTGCTCCTGGGTC*   34

R46L CGT to CTT
*CCGCGGGCGCCCGTGCG*caggaggacgaggacggcgactacgaggagctggtgctagccttgCGTTCCG A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggacccgcttccacagacaggccagcaagtgtgacagtcat
ggcacccacctggcaggggtggtcagagccggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggcacctggtggtgctgctgcccct
ggcgggtgggtacagccgcgtcctcaacgccgcctgccagcgcctggcgagggctggggtcgtgctggtcaccgctgccggcaacttccgggac
gatgcctgcctctactcccagcctcagctcccgaggtcatcacagttggggccaccaatgcccaagaccagccggtgaccctgggactttggg
gaccaacttggccgctgtgtggacctctttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg

TABLE 6-continued

PCSK9 SEQUENCES

N425S AAT to AGT          A443T GCC to ACC
atccacttctctgccaaagatgtcatca<u>agt</u>gaggcctggttccctgaggaccagcgggtactgaccccaacctggtggcc<u>gcc</u>ctgccccccag cacccatGGGGCAGGTTGGCAGCTGTTTTGCAGGACTGTATGGTCAGCACACTCGGGGCCTACACGGATGGCC I474V ATC to GTC
ACAGCC<u>GTC</u>GCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG     E620G GAG to GGG
TCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAA<u>GAG</u>GCCGTGACAGCCGTTGCCATCTGCTGCCGGAGCCGGCACCTGGCGCAGG

CCTCCCAGGAGCTCCAGTGAC
h    *ATGGGCACCGTCACTCCAGGCGGTCCTGGTGGCCGCTGCCACTGCTGCTGCTGCTGCTCCTGGGTC*        35

R46L CGT to CTT
*CCGCGGGCGCCCGTGCG*caggaggacgaggacggcgactacgaggagctggtgctagccttgc<u>gtt</u>ccg A53V GCC to GTC
AGGAGGACGGCCTGG<u>GCC</u>GAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggacccgcttccacagacaggccagcaagtgtgacagtcat
ggcacccacctggcagggggtggtcagagcggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggccactggtggtgctgctgcccct
ggcgggtgggtacagccgcgtcctcaacgccgcctgccagcgcctggcgagggctggggtcgtgctggtcaccgctgccggcaacttccgggac
gatgcctgcctctactcccagcctcagctcccgaggtcatcacagttggggccaccaatgcccaagaccagccggtgaccctggggactttggg
gaccaactttggccgctgtgtggacctctttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT          A443T GCC to ACC
atccacttctctgccaaagatgtcatc<u>aat</u>gaggcctggttccctgaggaccagcgggtactgaccccaacctggtggcc<u>acc</u>ctgccccccag cacccatGGGGCAGGTTGGCAGCTGTTTTGCAGGACTGTATGGTCAGCACACTCGGGGCCTACACGGATGGCC I474V ATC to GTC
ACAGCC<u>ATC</u>GCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG     E620G GAG to GGG
TCCCGGCCCCT<u>CCGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

TABLE 6-continued

PCSK9 SEQUENCES

E670G GAG to GGG
CTACAGGCAGCACCAGCGAAGAGGCCGTGACAGCCGTTGCCATCTGCTGCCGGAGCCGGCACCTGGCGCAGG

CCTCCCAGGAGCTCCAGTGAC aj *ATGGGCACCGTCACTCCAGGCGGTCCTGGTGGCCGCTGCCACTGCTGCTGCTGCTGCTCCTGGGTC* 36

R46L CGT to CTT
*CCGCGGGCGCCCGTGCG*CAGGAGGACGAGGACGGCGACTACGAGGAGCTGGTGCTAGCCTTGCTTTCCG

A53V GCC to GTC
AGGAGGACGGCCTGGCCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggaccgcttccacagacaggccagcaagtgtgacagtcat
ggcacccacctggcagggggtggtcagagcggccgggatgccggcgtggccaagggtgccagcatgcgcagcctgcgcgtgctcaactgccaaggg
aagggcacggttagcggcaccctcataggcctggagtttattcggaaaaagccagctggtccagcctgtggggccactggtggtgctgctgccct
ggcgggtgggtacagccgcgtcctcaacgccgcctgccagcgcctggcgagggctggggtcgtgctggtcaccgctgccggcaacttccgggac
gatgcctgcctctactcccagcctcagctcccgaggtcatcacagttggggccaccaatgcccaagaccagccggtgaccctggggactttggg
gaccaactttggccgctgtgtggacctctttgccccagggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT                                A443T GCC to ACC
atccacttctctgccaaagatgtcatcaatgaggcctggttccctgaggaccagcgggtactgaccccccaacctggtggccgccctgccccccag cacccatGGGGCAGGTTGGCAGCTGTTTTGCAGGACTGTATGGTCAGCACACTCGGGGCCTACACGGATGGCC I474V ATC to GTC
ACAGCCGTCGCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG E620G GAG to GGG
TCCCGGCCCCTCAGGAGCAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG
CTACAGGCAGCACCAGCGAAGAGGCCGTGACAGCCGTTGCCATCTGCTGCCGGAGCCGGCACCTGGCGCAGG

CCTCCCAGGAGCTCCAGTGAC q *ATGGGCACCGTCACTCCAGGCGGTCCTGGTGGCCGCTGCCACTGCTGCTGCTGCTGCTGCTCCTGGGTC* 37

R46L CGT to CTT
*CCGCGGGCGCCCGTGCG*CAGGAGGACGAGGACGGCGACTACGAGGAGCTGGTGCTAGCCTTGCGTTCCG

A53V GCC to GTC
AGGAGGACGGCCTGGTCGAAGCACCCGAGCACGGAACCACAGCCACCTTCCACCGCTGCGCCAAGGAT

CCGTGGAGGTTGCCTGGCACCTACGTGGTGGTGCTGAAGGAGGAGACCCACCTCTCGCAGTCAGAGCG

CACTGCCCGCCGCCTGCAGGCCCAGGCTGCCCGCCGGGGATACCTCACCAAGATCCTGCATGTCTTCC

ATGGCCTTCTTCCTGGCTTCCTGGTGAAGATGAGTGGCCGACCTGCTGGAGCTGGCCTTGAAGTTGCCC

TABLE 6-continued

PCSK9 SEQUENCES

CATGTCGACTACATCGAGGAGGACTCCTCTGTCTTTGCCCAGagcatcccgtggaacctggagcggaattacccctcca cggtaccgggcggatgaataccagcccccgacggaggcagcctggtggaggtgtatctcctagacaccagcatacagagtgaccaccgggaa
atcgagggcagggtcatggtcaccgacttcgagaatgtgcccgaggaggacgggacccgcttccacagacaggccagcaagtgtgacagtcat
ggcacccacctggcaggggtggtcagagcggccgggatgccggcgtggccaagggtgccagcatgcgcagcctgcgcgtgctcaactgccaaggg
aagggcacggttagcggcaccctcataggcctggagtttattcggaaaagccagctggtccagcctgtggggccactggtggtgctgctgcccct
ggcgggtgggtacagccgcgtcctcaacgccgcctgccagcgcctggcgagggctggggtcgtgctggtcaccgctgccggcaacttccgggac
gatgcctgcctctactcccagcctcagctcccgaggtcatcacagttggggccaccaatgcccaagaccagccggtgacccctggggactttggg
gaccaactttggccgctgtgtggacctctttgccccaggggaggacatcattggtgcctccagcgactgcagcacctgctttgtgtcacagagtgg
gacatcacaggctgctgcccacgtggctggcattgcagccatgatgctgtctgccgagccggagctcaccctggccgagttgaggcagagactg N425S AAT to AGT          A443T GCC to ACC atccacttctctgccaaagatgtcatc<u>aat</u>gaggcctggttccctgaggaccagccgggtactgacccccaacctggtggcc<u>gcc</u>ctgccccccag cacccatGGGGCAGGTTGGCAGCTGTTTTGCAGGACTGTATGGTCAGCACACTCGGGGCCTACACGGATGGCC I474V ATC to GTC ACAGCC<u>ATC</u>GCCCGCTGCGCCCCAGATGAGGAGCTGCTGAGCTGCTCCAGTTTCTCCAGGAGTGGGAAGCGG CGGGGCGAGCGCATGGAGGCCCAAGGGGGCAAGCTGGTCTGCCGGGCCCACAACGCTTTTGGGGGTGAGGG
TGTCTACGCCATTGCCAGGTGCTGCCTGCTACCCCAGGCCAACTGCAGCGTCCACACAGCTCCACCAGCTGAG
GCCAGCATGGGGAACCCGTGTCCACTGCCACCAACAGGGCCACGTCCTCACAGGCTGCAGCTCCCACTGGGAG
GTGGAGGACCTTGGCACCCACAAGCCGCCTGTGCTGAGGCCACGAGGTCAGCCCAACCAGTGCGTGGGCCAC
AGGGAGGCCAGCATCCACGCTTCCTGCTGCCATGCCCCAGGTCTGGAATGCAAAGTCAAGGAGCATGGAA Q619P CAG to CCG    E620G GAG to GGG TCCCGGCCCCT<u>CAGGAG</u>CAGGTGACCGTGGCCTGCGAGGAGGGCTGGACCCTGACTGGCTGCAGTGCCCTCC

CTGGGACCTCCCACGTCCTGGGGGCCTACGCCGTAGACAACACGTGTAGTCAGGAGCCGGGACGTCAGCA

E670G GAG to GGG

CTACAGGCAGCACCAGCGAA<u>GGG</u>GCCGTGACAGCCGTTGCCATCTGCTGCCGGAGCCGGCACCTGGCGCAGG

CCTCCCAGGAGCTCCAGTGAC

TABLE 7

Human VH3-23 Variant Alleles

| VH3-23 haplotype | Cumulative allele frequency | SNPs | | | |
|---|---|---|---|---|---|
| a (=VH3-23*04) | 0.0983 | rs56069819 | | | |
| d | 0.0087 | rs56069819 | rs61750837 | rs61752504 | |
| e | 0.0046 | rs56069819 | rs1064090 | rs1055799 | |
| j | 0.0009 | rs56069819 | rs1055799 | | |
| u | 0.0005 | rs56069819 | rs1064091 | | |
| s | 0.0005 | rs56069819 | rs1064091 | rs61752504 | rs61750837 |
| r | 0.0005 | rs56069819 | rs1064090 | | |
| TOTAL: | 0.114 | | | | |

TABLE 8

Exemplary anti-PCSK9 antibodies and/or antibody fragments

| SEQ ID NOs comprising an anti-PCSK9 monoclonal antibody or fragment thereof | Patent or patent Pblication |
|---|---|
| Light chain complementary determining regions (CDRL) SEQ ID NO: 5, 7, 9, 10, 12, 13, 14, 15, 16, 17, 18, 19, 20, 21, 22, 23, 24, 26, 28, 30, 31, 32, 33, 35, 36, 37, 38, 39, 40, 42, 44, 46, 270, 271, 272, 273, 275, 277, 286, 287, 288, 297, 299, 301, 405, 407, 409, 411, 413, 415, 417, 421, 425, 429, 433, 437, 441, 445, 449, 453, 457, 461, 465, 469, 473, 477, 481, 485; | US20120020975 A1 |
| Heavy chain complementary determining regions (CDRH) SEQ ID NO: 47, 48, 49, 50, 51, 52, 53, 54, 55, 56, 57, 58, 60, 61, 62, 64, 65, 67, 69, 71, 72, 74, 76, 77, 78, 79, 80, 81, 83, 85, 87, 89, 91, 278, 289, 290, 291, 292, 298, 300, 302, 401, 404, 406, 408, 410, 412, 414, 416, 419, 423, 427, 431, 435, 439, 443, 447, 451, 455, 459, 463, 467, 471, 475, 479, 483; | |

TABLE 8-continued

Exemplary anti-PCSK9 antibodies and/or antibody fragments

| SEQ ID NOs comprising an anti-PCSK9 monoclonal antibody or fragment thereof | Patent or patent Pblication |
|---|---|
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 465; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 463; | US20120027765A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 465; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 463; | US8168762B2 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 222, 229, 238, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 247, 256, 265, 404, 406, 408, 410, 412, 414, 416; | US20120020976A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; | US20130085265A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; | US20130079501A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 158, 162, 395, 473, 477; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 180, 175, 308, 368, 471, 475; | US20120213797A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416; | US20120251544A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; | US20130052201A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417, 461, 465, 485; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416, 459, 463, 483; | US20130058944A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416; | US20130079502A1 |
| CDRL SEQ ID NO: 5, 7, 9, 10, 12, 13, 15, 16, 17, 18, 19, 20, 21, 22, 23, 24, 26, 28, 30, 31, 32, 33, 35, 36, 37, 38, 39, 40, 42, 44, 46, 405, 407, 409, 411, 413, 415, 417; CDRH SEQ ID NO: 47, 48, 49, 50, 51, 52, 53, 54, 55, 56, 57, 58, 60, 62, 64, 65, 67, 69, 71, 72, 74, 76, 77, 78, 79, 80, 81, 83, 85, 87, 89, 91, 404, 406, 408, 410, 412, 414, 416; | US20130245235A1 |

TABLE 9

Human variable & constant variants distributed over several human ethnic populations - useful for ligand tailoring

| Human Gene Segment Type | Example Human Allele[1] | Amino Acid Position & Variation | Nucleotide Variation[2] (NCBI dbSNP reference number)[3] | Variant Nucleotide Position | Human Populations[4] | No. Individs[5] | Het Freq[6] | Hom Freq[7] (Het + Hom freq[8]) | Cum Freq[9] |
|---|---|---|---|---|---|---|---|---|---|
| IGHG1 | IGHG1*01 | 204D (CH3 variation) | GA<u>T</u> | 14:106208086 (forward strand) | A (European ancestry) | 153 | 0.400 | 0.096 (0.496) | 0.296 |
| | IGHG1*03 | 204E (CH3 variation) | GA<u>G</u> (rs1045853) | 14:106208086 (forward strand) | A (European ancestry) | 366 | 0.400 | 0.504 (0.904) | 0.704 |
| | IGHG1*01 | 206L (CH3 variation) | <u>C</u>TG | 14:106208082 (forward strand) | A (European ancestry) | | 0.358 | 0.104 (0.462) | 0.283 |
| | IGHG1*03 | 206M (CH3 variation) | <u>A</u>TG (rs11621259) | 14:106208082 (forward strand) | A (European ancestry) | | 0.358 | 0.538 (0.896) | 0.717 |
| IGHG2 | IGHG2*01 | 72P (CH1 variation) | CC<u>C</u> | 14:106110914 (forward strand) | B | | 0.336 | 0.540 (0.876) | 0.708 |

TABLE 9-continued

Human variable & constant variants distributed over several human ethnic populations - useful for ligand tailoring

| Human Gene Segment Type | Example Human Allele[1] | Amino Acid Position & Variation | Nucleotide Variation[2] (NCBI dbSNP reference number)[3] | Variant Nucleotide Position | Human Populations[4] | No. Individs[5] | Het Freq[6] | Hom Freq[7] (Het + Hom freq[8]) | Cum Freq[9] |
|---|---|---|---|---|---|---|---|---|---|
| | IGHG2*02 | 72T (CH1 variation) | ACC (rs11627594) | 14:106110914 (forward strand) | B | | 0.336 | 0.124 | 0.292 |
| | IGHG2*01 | 75N (CH1 variation) | AAC | 14:106110904 (forward strand) | A | | 0.007 | 0.993 | 0.997 |
| | IGHG2*04 | 75S (CH1 variation) | AGC (rs201590297) | 14:106110904 (forward strand) | A | | 0.007 | | 0.004 |
| | IGHG2*01 | 76F (CH1 variation) | TTC | | | | | | |
| | IGHG2*04 | 76L (CH1 variation) | TTG | | | | | | |
| | IGHG2*01 | 161V (CH2 variation) | GTG | 14:10611013 (forward strand) | B | | 0.342 | 0.539 (0.881) | 0.711 |
| | IGHG2*02 | 161M (CH2 variation) | ATG (rs8009156) | 14:10611013 (forward strand) | B | | 0.342 | 0.118 (0.46) | 0.289 |
| | IGHG2*01 | 257A (CH3 variation) | GCC | 14:106109752 (forward strand) | C | | 0.199 | 0.493 (0.692) | 0.592 |
| | | | | | D | | 0.007 | 0.992 (0.999) | 0.995 |
| | IGHG2*06 | 257S (CH3 variation) | TCC (rs4983499) | 14:106109752 (forward strand) | C | | 0.199 | 0.308 (0.507) | 0.408 |
| | | | | | D | | 0.007 | 0.002 (0.009) | 0.005 |

Table Footnotes:
[1]IMGT notation (ww.imgt.org); refer to figures for other alleles comprising this variation.
[2]SNP Underlined in Codon.
[3]NCBI dbSNP Build 138 released on Apr. 25, 2013.
[4]Human population used for representative variant frequency analysis.
Populations
A This population included 662 participants of European descent from the ClinSeq project, all of whom had undergone whole-exome sequencing using Agilent's 38 Mb or 50 Mb capture kit.
B 1000 Genomes database.
C ESP6500:African American.
D ESP6500:EuropeanAmerican.
[5]Number of individuals in representative population found to have the allele.
[6]Heterozygous human genotype frequency, ie, cumulative frequency of all genotypes having one occurrence of the variant allele and one occurrence of another allele (heterozygous state), eg, ac genotype in the population.
[7]Homozygous human genotype frequency, ie, cumulative frequency of two occurrences of the variant allele (homozygous state), eg, cc genotype in the population.
[8]Total human genotype frequency, ie, total of heterozygous plus homozygous human genotype frequencies.
[9]Cumulative human allele frequency of all occurrences of the variant allele in the population.

TABLE 10

FURTHER SEQUENCES

| SEQ ID NO: | Human Allele | Nucleotide/Amino Acid Sequence |
|---|---|---|

HEAVY CHAIN ALLELES

| 41 | IGHG1*01 (CH1 + Hinge + CH2 + CH3 + CH – S) | gcctccaccaagggcccatcggtcttccccctggcaccctcctccaaga gcacctctggg ggcacagcggccctgggctgcctggtcaaggactacttccccgaaccgg tgacggtgtcg tggaactcaggcgccctgaccagcggcgtgcacaccttcccggctgtcc tacagtcctca ggactctactccctcagcagcgtggtgaccgtgccctccagcagcttgg gcacccagacc tacatctgcaacgtgaatcacaagcccagcaacaccaaggtggacaaga agttgagccc aaatcttgtgacaaaactcacacatgcccaccgtgcccagcacctgaac tcctgggggga |

TABLE 10-continued

FURTHER SEQUENCES

| SEQ ID NO: | Human Allele | Nucleotide/Amino Acid Sequence |
|---|---|---|
| | | ccgtcagtcttcctcttcccccccaaaacccaaggacaccctcatgatct<br>cccggacccct<br>gaggtcacatgcgtggtggtggacgtgagccacgaagaccctgaggtca<br>agttcaactgg<br>tacgtggacggcgtggaggtgcataatgccaagacaaagccgcgggagg<br>agcagtacaac<br>agcacgtaccgggtggtcagcgtcctcaccgtcctgcaccaggactggc<br>tgaatggcaag<br>gagtacaagtgcaaggtctccaacaaagcctcccagccccatcgaga<br>aaaccatctcc<br>aaagccaaagggcagccccgagaaccacaggtgtacaccctgcccccat<br>cccgggatgag<br>ctgaccaagaaccaggtcagcctgacctgcctggtcaaaggcttctatc<br>ccagcgacatc<br>gccgtggagtgggagagcaatgggcagccggagaacaactacaagacca<br>cgcctcccgtg<br>ctggactccgacggctccttcttcctctacagcaagctcaccgtggaca<br>agagcaggtgg<br>cagcaggggaacgtcttctcatgctccgtgatgcatgaggctctgcaca<br>accactacacg<br>cagaagagcctctccctgtctccgggtaaa |
| 42 | | ASTKGPSVFPLAPSSKSTSGGTAALGCLVKDYFPEPVTVSWNSGALTSG<br>VHTFPAVLQSS<br>GLYSLSSVVTVPSSSLGTQTYICNVNHKPSNTKVDKKVEPKSCDKTHTC<br>PPCPAPELLGG<br>PSVFLFPPKPKDTLMISRTPEVTCVVVDVSHEDPEVKFNWYVDGVEVHN<br>AKTKPREEQYN<br>STYRVVSVLTVLHQDWLNGKEYKCKVSNKALPAPIEKTISKAKGQPREP<br>QVYTLPPSRDE<br>LTKNQVSLTCLVKGFYPSDIAVEWESNGQPENNYKTIPPVLDSDGSFFL<br>YSKLTVDKSRW<br>QQGNVFSCSVMHEALHNHYTQKSLSLSPGK<br>D = position 204<br>L = position 206 |
| 43 | IGHG2*01 (CH1 + Hinge + CH2 + CH3 + CH - S) | gcctccaccaagggcccatcggtcttccccctggcgccctgctccagga<br>gcacctccgag<br>agcacagccgccctgggctgcctggtcaaggactacttccccgaaccgg<br>tgacggtgtcg<br>tggaactcaggcgctctgaccagcggcgtgcacaccttcccagctgtcc<br>tacagtcctca<br>ggactctactccctcagcagcgtggtgaccgtgccctccagcaacttcg<br>gcacccagacc<br>tacacctgcaacgtagatcacaagcccagcaacaccaaggtggacaaga<br>cagttgagcgc<br>aaatgttgtgtcgagtgcccaccgtgcccagcaccacctgtggcaggac<br>cgtcagtcttc<br>ctcttcccccccaaaacccaaggacaccctcatgatctcccggacccctg<br>aggtcacgtgc<br>gtggtggtggacgtgagccacgaagaccccgaggtccagttcaactggt<br>acgtggacggc<br>gtggaggtgcataatgccaagacaaagccacgggaggagcagttcaaca<br>gcacgttccgt<br>gtggtcagcgtcctcaccgttgtgcaccaggactggctgaacggcaagg<br>agtacaagtgc<br>aaggtctccaacaaaggcctcccagccccatcgagaaaaccatctcca<br>aaaccaaaggg<br>cagccccgagaaccacaggtgtacaccctgcccccatcccgggaggaga<br>tgaccaagaac<br>caggtcagcctgacctgcctggtcaaaggcttctaccccagcgacatcg<br>ccgtggagtgg<br>gagagcaatgggcagccggagaacaactacaagaccacacctcccatgc<br>tggactccgac<br>ggctccttcttcctctacagcaagctcaccgtggacaagagcaggtggc<br>agcaggggaac<br>gtcttctcatgctccgtgatgcatgaggctctgcacaaccactacacgc<br>agaagagcctc<br>tccctgtctccgggtaaa |
| 44 | | ASTKGPSVFPLAPCSRSTSESTAALGCLVKDYFPEPVTVSWNSGALTSG<br>VHTFPAVLQSS<br>GLYSLSSVVTVPPSSNFGTQTYTCNVDHKPSNTKVDKTVERKCCVECPPC<br>PAPPVAGPSVF<br>LFPPKPKDTLMISRTPEVTCVVVDVSHEDPEVQFNWYVDGVEVHNAKTK<br>PREEQFNSTFR |

TABLE 10-continued

FURTHER SEQUENCES

| SEQ ID NO: | Human Allele | Nucleotide/Amino Acid Sequence |
|---|---|---|
| | | VVSVLTVVHQDWLNGKEYKCKVSNKGLPAPIEKTISKTKGQPREPQVYT LPPSREEMTKN<br>QVSLTCLVKGFYPSDIAVEWESNGQPENNYKTTPPMLDSDGSFFLYSKL TVDKSRWQQGN<br>VFSCSVMHEALHNHYTQKSLSLSPGK<br>P = position 72<br>N = position 75<br>F = position 76<br>V = position 161<br>A = position 257 |
| 45 | IGHV1-18*01 | caggttcagctggtgcagtctggagctgaggtgaagaagcctggggcct cagtgaaggtc<br>tcctgcaaggcttctggttacacctttaccagctatggtatcagctggg tgcgacaggcc<br>cctggacaagggcttgagtggatgggatggatcagcgcttacaatggta acacaaactat<br>gcacagaagctccagggcagagtcaccatgaccacagacacatccacga gcacagcctac<br>atggagctgaggagcctgagatctgacgacacggccgtgtattactgtg cgagaga |
| 46 | | QVQLVQSGAEVKKPGASVKVSCKASGYTFTSYGISWVRQAP GQGLEWMGWISAYNGNTNYAQKLQGRVTMTTDTSTSTAYMELRSLRSDD TAVYYCAR |
| 47 | IGHV1-46*01 | caggtgcagctggtgcagtctggggctgaggtgaagaagcctggggcct cagtgaaggtt<br>tcctgcaaggcatctggatacaccttcaccagctactatatgcactggg tgcgacaggcc<br>cctggacaagggcttgagtggatgggaataatcaaccctagtggtggta gcacaagctac<br>gcacagaagttccagggcagagtcaccatgaccagggacacgtccacga gcacagtctac<br>atggagctgagcagcctgagatctgaggacacggccgtgtattactgtg cgagaga |
| 48 | | QVQLVQSGAEVKKPGASVKVSCKASGYTFTSYYMHWVRQAP GQGLEWMGIINPSGGSTSYAQKFQGRVTMTRDTSTSTVYMELSSLRSED TAVYYCAR |

LIGHT CHAIN ALLELES

| 49 | IGKC*01 | cgaactgtggctgcaccatctgtcttcatcttcccgccatctgatgagc agttgaaatct<br>ggaactgcctctgttgtgtgcctgctgaataacttctatcccagagagg ccaaagtacag<br>tggaaggtggataacgccctccaatcgggtaactcccaggagagtgtca cagagcaggac<br>agcaaggacagcacctacagcctcagcagcaccctgacgctgagcaaag cagactacgag<br>aaacacaaagtctacgcctgcgaagtcacccatcagggcctgagctcgc ccgtcacaaag<br>agcttcaacaggggagagtgt |
| 50 | | RTVAAPSVFIFPPSDEQLKSGTASVVCLLNNFYPREAKVQWKVDNALQS GNSQESVTEQD<br>SKDSTYSLSSTLTLSKADYEKHKVYACEVTHQGLSSPVTKSFNRGEC<br>V = position 84<br>C = position 87 |
| 51 | IGLC2*01 | ggtcagcccaaggctgccccctcggtcactctgttcccgccctcctctg aggagcttcaa<br>gccaacaaggccacactggtgtgtctcataagtgacttctacccgggag ccgtgacagtg<br>gcttggaaagcagatagcagccccgtcaaggcgggagtggagaccacca caccctccaaa<br>caaagcaacaacaagtacgcggccagcagctatctgagcctgacgcctg agcagtggaag<br>tcccacagaagctacagctgccaggtcacgcatgaagggagcaccgtgg agaagacagtg<br>gcccctacagaatgttca |
| 52 | | GQPKAAPSVTLFPPSSEELQANKATLVCLISDFYPGAVTVAWKADSSPV KAGVETTTPSK<br>QSNNKYAASSYLSLTPEQWKSHRSYSCQVTHEGSTVEKTVAPTECS |

TABLE 10-continued

FURTHER SEQUENCES

| SEQ ID NO: | Human Allele | Nucleotide/Amino Acid Sequence |
|---|---|---|
| 53 | IGKV4-1*01 | atggtgttgcagacccaggtcttcatttctctgttgctctggatctctg gtgcctacggg gacatcgtgatgacccagtctccagactccctggctgtgtctctgggcg agagggccacc atcaactgcaagtccagccagagtgttttatacagctccaacaataaga actacttagct tggtaccagcagaaaccaggacagcctcctaagctgctcatttactggg catctacccgg gaatccggggtccctgaccgattcagtggcagcgggtctgggacagatt tcactctcacc atcagcagcctgcaggctgaagatgtggcagtttattactgtcagcaat attatagtact cctcc |
| 54 | | DIVMTQSPDSLAVSLGERATINCKSSQSVLYSSNNKNYLA WYQQKPGQPPKLLIYWASTRESGVPDRFSGSGSGTDFTLTISSLQAEDV AVYYCQQYYST P |
| 55 | IGKV1-13*02 | atggacatgagggtccccgctcagctcctggggcttctgctgctctggc tcccagcaggt gccagatgtgccatccagttgacccagtctccatcctccctgtctgcat ctgtaggagac agagtcaccatcacttgccgggcaagtcagggcattagcagtgctttag cctggtatcag cagaaaccagggaaagctcctaagctcctgatctatgatgcctccagtt tggaaagtggg gtcccatcaaggttcagcggcagtggatctgggacagatttcactctca ccatcagcagc ctgcagcctgaagattttgcaacttattactgtcaacagtttaatagtt accctcagtgc cagatgtgccatccagttgacccagtctccatcctccctgtctgcatct gtaggagacag agtcaccatcacttgccgggcaagtcagggcattagcagtgctttagcc tggtatcagca gaaaccagggaaagctcctaagctcctgatctatgatgcctccagtttg gaaagtggggt cccatcaaggttcagcggcagtggatctgggacagatttcactctcacc atcagcagcct gcagcctgaagattttgcaacttattactgtcaacagtttaatagttac cctca |
| 57 | IGKJ2*01 | tgtacacttttggccaggggaccaagctggagatcaaac |
| 58 | | YTFGQGTKLEIK |
| 59 | IGLJ2*01 | tgtggtattcggcggagggaccaagctgaccgtcctag |
| 60 | | VVFGGGTKLTVL |
| 61 | An IGHG1*01 Heavy Chain Constant Region | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELLGGPS VFLFPPKPKDTLMISRTPEVTCVVVDVSHEDPEVKFNWYVDGVEVHNAK TKPREEQYNST YRVVSVLTVLHQDWLNGKEYKCKVSNKALPAPIEKTISKAKGQPREPQV YTLPPSRDELT KNQVSLTCLVKGFYPSDIAVEWESNGQPENNYKTTPPVLDSDGSFFLYS KLTVDKSRWQQGNVFSCSVMHEALHNHYTQKSLSLSPG |
| 62 | An IGKC*01 Kappa Light Chain Constant Region | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC |
| 63 | An IGHG2*01 Heavy Chain Constant Region | ASTKGPSVFPLAPCSRSTSESTAALGCLVKDYFPEPVTVSWNSGALTSG VHTFPAVLQSSGLYSLSSVVTVPSSNFGTQTYTCNVDHKPSNTKVDKTV ERKCCVECPPCPAPPVAGPSVFLFPPKPKDTLMISRTPEVTCVVVDVSH EDPEVQFNWYVDGVEVHNAKTKPREEQFNSTFRVVSVLTVVHQDWLNGK EYKCKVSNKGLPAPIEKTISKTKGQPREPQVYTLPPSREEMTKNQVSLT CLVKGFYPSDIAVEWESNGQPENNYKTTPPMLDSDGSFFLYSKLTVDKS RWQQGNVFSCSVMHEALHNHYTQKSLSLSPGK |

TABLE 10-continued

FURTHER SEQUENCES

| SEQ ID NO: | Human Allele | Nucleotide/Amino Acid Sequence |
|---|---|---|
| 64 | An IGLC2*01 Lambda Light Chain Constant Region | QPKAAPSVTLEPPSSEELQANKATLVCLISDFYPGAVIVAWKADSSPVK AGVETTTPSKQSNNKYAASSYLSLTPEQWKSHRSYSCQVTHEGSTVEKT VAPTECS |
| 65 | An IGHG2*01 Heavy Chain Constant Region | ASTKGPSVFPLAPCSRSTSESTAALGCLVKDYFPEPVTVSWNSGALTSG VHTFPAVLQSSGLYSLSSVVTVPSSNFGTQTYTCNVDHKPSNTKVDKTV ERKCCVECPPCPAPPVAGPSVFLFPPKPKDTLMISRTPEVTCVVVDVSH EDPEVQFNWYVDGVEVHNAKTKPREEQFNSTFRVVSVLTVVHQDWLNGK EYKCKVSNKGLPSSIEKTISKTKGQPREPQVYTLPPSREEMTKNQVSLT CLVKGFYPSDIAVEWESNGQPENNYKTTPPMLDSDGSFFLYSKLTVDKS RWQQGNVFSCSVMHEALHNHYTQKSLSLSPGK |
| 66 | An IGKC*01 Kappa Light Chain Constant Region | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC |

The invention claimed is:

1. A method of treating diabetic macular edema (DME) or branch retinal vein occlusion (BRVO) in a human, the method comprising administering to said human an antibody, antibody fragment, or a trap that specifically binds to a human VEGF-A;
   wherein the antibody, antibody fragment, or trap comprises a human gamma-1 heavy chain constant region that comprises an Asp corresponding to position 204 of SEQ ID NO: 42 or a Leu corresponding to position 206 of SEQ ID NO: 42 and wherein
   (i) said human comprises and expresses an IGHG1*01 human heavy chain constant region gene segment, or the human expresses antibodies comprising human gamma-1 heavy chain constant regions comprising an Asp corresponding to position 204 of SEQ ID NO: 42 or a Leu corresponding to position 206 of SEQ ID NO: 42 and
   (ii) said human comprises a nucleotide sequence encoding said VEGF-A.

2. The method of claim 1, wherein the antibody, antibody fragment, or trap comprises a human gamma-1 heavy chain constant region that comprises an Asp corresponding to position 204 of SEQ ID NO: 42 and a Leu corresponding to position 206 of SEQ ID NO: 42.

3. The method of claim 1, wherein the antibody, antibody fragment, or trap comprises an IGHG1*01 human heavy chain constant region.

4. The method of claim 1, further comprising a step of selecting a human comprising said nucleotide sequence of (ii) before administering to said human the antibody, antibody fragment, or trap.

5. The method of claim 1, wherein the antibody, antibody fragment, or trap is administered by intravenous or subcutaneous administration and/or is comprised in an injectable preparation.

6. The method of claim 1, wherein the antibody or antibody fragment is a human antibody or human antibody fragment.

* * * * *

SEQUENCE LISTING

<160> NUMBER OF SEQ ID NOS: 77

<210> SEQ ID NO 1
<211> LENGTH: 692
<212> TYPE: PRT
<213> ORGANISM: Homo sapiens

<400> SEQUENCE: 1

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
```

-continued

```
            195                 200                 205
Pro Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Leu Leu Pro
                275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
    595                 600                 605

Lys Val Lys Glu His Gly Ile Pro Ala Pro Gln Glu Gln Val Thr Val
    610                 615                 620
```

```
Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
            645                 650                 655

Arg Ser Arg Asp Val Ser Thr Gly Ser Thr Ser Glu Glu Ala Val
        660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 2
<211> LENGTH: 662
<212> TYPE: PRT
<213> ORGANISM: Homo sapiens

<400> SEQUENCE: 2

Gln Glu Asp Glu Asp Gly Asp Tyr Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
        210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
```

```
            290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
                340                 345                 350
Ser Gly Thr Ser Gln Ala Ala Ala His Val Ala Gly Ile Ala Ala Met
                355                 360                 365
Met Leu Ser Ala Glu Pro Glu Leu Thr Leu Ala Glu Leu Arg Gln Arg
370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
                420                 425                 430
Ala His Ser Gly Pro Thr Arg Met Ala Thr Ala Ile Ala Arg Cys Ala
                435                 440                 445
Pro Asp Glu Glu Leu Leu Ser Cys Ser Ser Phe Ser Arg Ser Gly Lys
450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
                500                 505                 510
Glu Ala Ser Met Gly Thr Arg Val His Cys His Gln Gly His Val
                515                 520                 525
Leu Thr Gly Cys Ser Ser His Trp Glu Val Glu Asp Leu Gly Thr His
530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys His Ala Pro Gly Leu
                565                 570                 575
Glu Cys Lys Val Lys Glu His Gly Ile Pro Ala Pro Gln Glu Gln Val
                580                 585                 590
Thr Val Ala Cys Glu Glu Gly Trp Thr Leu Thr Gly Cys Ser Ala Leu
                595                 600                 605
Pro Gly Thr Ser His Val Leu Gly Ala Tyr Ala Val Asp Asn Thr Cys
610                 615                 620
Val Val Arg Ser Arg Asp Val Ser Thr Thr Gly Ser Thr Ser Glu Glu
625                 630                 635                 640
Ala Val Thr Ala Val Ala Ile Cys Cys Arg Ser Arg His Leu Ala Gln
                645                 650                 655
Ala Ser Gln Glu Leu Gln
                660

<210> SEQ ID NO 3
<211> LENGTH: 540
<212> TYPE: PRT
<213> ORGANISM: Homo sapiens

<400> SEQUENCE: 3
```

```
Ser Ile Pro Trp Asn Leu Glu Arg Ile Thr Pro Pro Arg Tyr Arg Ala
1               5                   10                  15
Asp Glu Tyr Gln Pro Pro Asp Gly Gly Ser Leu Val Glu Val Tyr Leu
            20                  25                  30
Leu Asp Thr Ser Ile Gln Ser Asp His Arg Glu Ile Glu Gly Arg Val
            35                  40                  45
Met Val Thr Asp Phe Glu Asn Val Pro Glu Glu Asp Gly Thr Arg Phe
50                  55                  60
His Arg Gln Ala Ser Lys Cys Asp Ser His Thr His Leu Ala Gly
65                  70                  75                  80
Val Val Ser Gly Arg Asp Ala Gly Val Ala Lys Gly Ala Ser Met Arg
                85                  90                  95
Ser Leu Arg Val Leu Asn Cys Gln Gly Lys Gly Thr Val Ser Gly Thr
                100                 105                 110
Leu Ile Gly Leu Glu Phe Ile Arg Lys Ser Gln Leu Val Gln Pro Val
                115                 120                 125
Gly Pro Leu Val Val Leu Leu Pro Leu Ala Gly Gly Tyr Ser Arg Val
            130                 135                 140
Leu Asn Ala Ala Cys Gln Arg Leu Ala Arg Ala Gly Val Val Leu Val
145                 150                 155                 160
Thr Ala Ala Gly Asn Phe Arg Asp Asp Ala Cys Leu Tyr Ser Pro Ala
                165                 170                 175
Ser Ala Pro Glu Val Ile Thr Val Gly Ala Thr Asn Ala Gln Asp Gln
                180                 185                 190
Pro Val Thr Leu Gly Thr Leu Gly Thr Asn Phe Gly Arg Cys Val Asp
                195                 200                 205
Leu Phe Ala Pro Gly Glu Asp Ile Ile Gly Ala Ser Ser Asp Cys Ser
            210                 215                 220
Thr Cys Phe Val Ser Gln Ser Gly Thr Ser Gln Ala Ala Ala His Val
225                 230                 235                 240
Ala Gly Ile Ala Ala Met Met Leu Ser Ala Glu Pro Glu Leu Thr Leu
                245                 250                 255
Ala Glu Leu Arg Gln Arg Leu Ile His Phe Ser Ala Lys Asp Val Ile
                260                 265                 270
Asn Glu Ala Trp Phe Pro Glu Asp Gln Arg Val Leu Thr Pro Asn Leu
            275                 280                 285
Val Ala Ala Leu Pro Pro Ser Thr His Gly Ala Gly Trp Gln Leu Phe
            290                 295                 300
Cys Arg Thr Val Trp Ser Ala His Ser Gly Pro Thr Arg Met Ala Thr
305                 310                 315                 320
Ala Ile Ala Arg Cys Ala Pro Asp Glu Glu Leu Leu Ser Cys Ser Ser
                325                 330                 335
Phe Ser Arg Ser Gly Lys Arg Gly Glu Arg Met Glu Ala Gln Gly
                340                 345                 350
Gly Lys Leu Val Cys Arg Ala His Asn Ala Phe Gly Gly Glu Gly Val
            355                 360                 365
Tyr Ala Ile Ala Arg Cys Cys Leu Leu Pro Gln Ala Asn Cys Ser Val
            370                 375                 380
His Thr Ala Pro Pro Ala Glu Ala Ser Met Gly Thr Arg Val His Cys
385                 390                 395                 400
His Gln Gln Gly His Val Leu Thr Gly Cys Ser Ser His Trp Glu Val
                405                 410                 415
Glu Asp Leu Gly Thr His Lys Pro Pro Val Leu Arg Pro Arg Gly Gln
```

```
                420             425             430
Pro Asn Gln Cys Val Gly His Arg Glu Ala Ser Ile His Ala Ser Cys
            435                 440                 445

Cys His Ala Pro Gly Leu Glu Cys Lys Val Lys Glu His Gly Ile Pro
        450                 455                 460

Ala Pro Gln Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
            500                 505                 510

Gly Ser Thr Ser Glu Glu Ala Val Thr Ala Val Ala Ile Cys Cys Arg
        515                 520                 525

Ser Arg His Leu Ala Gln Ala Ser Gln Glu Leu Gln
            530                 535                 540

<210> SEQ ID NO 4
<211> LENGTH: 692
<212> TYPE: PRT
<213> ORGANISM: Homo sapiens

<400> SEQUENCE: 4

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255
```

```
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
        275                 280                 285
Leu Ala Gly Gly Tyr Ser Arg Val Leu Asn Ala Ala Cys Gln Arg Leu
    290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
            340                 345                 350
Thr Asn Phe Gly Arg Cys Val Asp Leu Phe Ala Pro Gly Glu Asp Ile
        355                 360                 365
Ile Gly Ala Ser Ser Asp Cys Ser Thr Cys Phe Val Ser Gln Ser Gly
    370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
            420                 425                 430
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
    530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Glu Ala Val
            660                 665                 670
Thr Ala Val Ala Ile Cys Cys Arg Ser Arg His Leu Ala Gln Ala Ser
```

```
                    675                 680                 685

Gln Glu Leu Gln
    690

<210> SEQ ID NO 5
<211> LENGTH: 662
<212> TYPE: PRT
<213> ORGANISM: Homo sapiens

<400> SEQUENCE: 5

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350
```

```
Ser Gly Thr Ser Gln Ala Ala His Val Ala Gly Ile Ala Ala Met
            355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 6
<211> LENGTH: 540
<212> TYPE: PRT
<213> ORGANISM: Homo sapiens

<400> SEQUENCE: 6

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60
```

```
His Arg Gln Ala Ser Lys Cys Asp Ser His Gly Thr His Leu Ala Gly
 65                  70                  75                  80

Val Val Ser Gly Arg Asp Ala Gly Val Ala Lys Gly Ala Ser Met Arg
                 85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Val Ala Arg Cys Ala Pro Asp Glu Glu Leu Leu Ser Cys Ser Ser
                325                 330                 335

Phe Ser Arg Ser Gly Lys Arg Arg Gly Glu Arg Met Glu Ala Gln Gly
            340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
    370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
            420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
    450                 455                 460

Ala Pro Gln Glu Gln Val Thr Val Ala Cys Glu Glu Gly Trp Thr Leu
465                 470                 475                 480
```

```
Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
        500                 505                 510

Gly Ser Thr Ser Glu Glu Ala Val Thr Ala Val Ala Ile Cys Cys Arg
        515                 520                 525

Ser Arg His Leu Ala Gln Ala Ser Gln Glu Leu Gln
530                 535                 540

<210> SEQ ID NO 7
<211> LENGTH: 692
<212> TYPE: PRT
<213> ORGANISM: Homo sapiens

<400> SEQUENCE: 7

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320
```

```
Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 8
<211> LENGTH: 662
<212> TYPE: PRT
<213> ORGANISM: Homo sapiens
```

```
<400> SEQUENCE: 8

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
    370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415
```

Ser Thr His Gly Ala Gly Trp Gln Leu Phe Cys Arg Thr Val Trp Ser
            420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
            530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
            610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 9
<211> LENGTH: 540
<212> TYPE: PRT
<213> ORGANISM: Homo sapiens

<400> SEQUENCE: 9

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val

-continued

```
            115                 120                 125
Gly Pro Leu Val Val Leu Pro Leu Ala Gly Gly Tyr Ser Arg Val
        130                 135                 140
Leu Asn Ala Ala Cys Gln Arg Leu Ala Arg Ala Gly Val Val Leu Val
145                 150                 155                 160
Thr Ala Ala Gly Asn Phe Arg Asp Asp Ala Cys Leu Tyr Ser Pro Ala
                165                 170                 175
Ser Ala Pro Glu Val Ile Thr Val Gly Ala Thr Asn Ala Gln Asp Gln
            180                 185                 190
Pro Val Thr Leu Gly Thr Leu Gly Thr Asn Phe Gly Arg Cys Val Asp
                195                 200                 205
Leu Phe Ala Pro Gly Glu Asp Ile Ile Gly Ala Ser Ser Asp Cys Ser
210                 215                 220
Thr Cys Phe Val Ser Gln Ser Gly Thr Ser Gln Ala Ala Ala His Val
225                 230                 235                 240
Ala Gly Ile Ala Ala Met Met Leu Ser Ala Glu Pro Glu Leu Thr Leu
                245                 250                 255
Ala Glu Leu Arg Gln Arg Leu Ile His Phe Ser Ala Lys Asp Val Ile
            260                 265                 270
Asn Glu Ala Trp Phe Pro Glu Asp Gln Arg Val Leu Thr Pro Asn Leu
            275                 280                 285
Val Ala Ala Leu Pro Pro Ser Thr His Gly Ala Gly Trp Gln Leu Phe
290                 295                 300
Cys Arg Thr Val Trp Ser Ala His Ser Gly Pro Thr Arg Met Ala Thr
305                 310                 315                 320
Ala Ile Ala Arg Cys Ala Pro Asp Glu Glu Leu Leu Ser Cys Ser Ser
                325                 330                 335
Phe Ser Arg Ser Gly Lys Arg Arg Gly Glu Arg Met Glu Ala Gln Gly
            340                 345                 350
Gly Lys Leu Val Cys Arg Ala His Asn Ala Phe Gly Gly Glu Gly Val
            355                 360                 365
Tyr Ala Ile Ala Arg Cys Cys Leu Leu Pro Gln Ala Asn Cys Ser Val
370                 375                 380
His Thr Ala Pro Pro Ala Glu Ala Ser Met Gly Thr Arg Val His Cys
385                 390                 395                 400
His Gln Gln Gly His Val Leu Thr Gly Cys Ser Ser His Trp Glu Val
                405                 410                 415
Glu Asp Leu Gly Thr His Lys Pro Pro Val Leu Arg Pro Arg Gly Gln
            420                 425                 430
Pro Asn Gln Cys Val Gly His Arg Glu Ala Ser Ile His Ala Ser Cys
            435                 440                 445
Cys His Ala Pro Gly Leu Glu Cys Lys Val Lys Glu His Gly Ile Pro
            450                 455                 460
Ala Pro Gln Glu Gln Val Thr Val Ala Cys Glu Glu Gly Trp Thr Leu
465                 470                 475                 480
Thr Gly Cys Ser Ala Leu Pro Gly Thr Ser His Val Leu Gly Ala Tyr
                485                 490                 495
Ala Val Asp Asn Thr Cys Val Val Arg Ser Arg Asp Val Ser Thr Thr
            500                 505                 510
Gly Ser Thr Ser Glu Gly Ala Val Thr Ala Val Ala Ile Cys Cys Arg
            515                 520                 525
Ser Arg His Leu Ala Gln Ala Ser Gln Glu Leu Gln
            530                 535                 540
```

<210> SEQ ID NO 10
<211> LENGTH: 692
<212> TYPE: PRT
<213> ORGANISM: Homo sapiens

<400> SEQUENCE: 10

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
```

```
                  370                 375                 380
Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
                450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
                515                 520                 525

Leu Pro Gln Ala Asn Cys Ser Val His Thr Ala Pro Pro Ala Glu Ala
                530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
                595                 600                 605

Lys Val Lys Glu His Gly Ile Pro Ala Pro Gln Glu Gln Val Thr Val
                610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
                660                 665                 670

Thr Ala Val Ala Ile Cys Cys Arg Ser Arg His Leu Ala Gln Ala Ser
                675                 680                 685

Gln Glu Leu Gln
            690

<210> SEQ ID NO 11
<211> LENGTH: 662
<212> TYPE: PRT
<213> ORGANISM: Homo sapiens

<400> SEQUENCE: 11

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
                20                  25                  30

Thr Phe His Arg Cys Ala Lys Asp Pro Trp Arg Leu Pro Gly Thr Tyr
                35                  40                  45
```

```
Val Val Val Leu Lys Glu Glu Thr His Leu Ser Gln Ser Glu Arg Thr
             50              55                  60

Ala Arg Arg Leu Gln Ala Gln Ala Ala Arg Arg Gly Tyr Leu Thr Lys
 65                  70                  75                  80

Ile Leu His Val Phe His Gly Leu Leu Pro Gly Phe Leu Val Lys Met
                     85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
            115                 120                 125

Glu Arg Ile Thr Pro Pro Arg Tyr Arg Ala Asp Glu Tyr Gln Pro Pro
            130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                    165                 170                 175

Asn Val Pro Glu Glu Asp Gly Thr Arg Phe His Arg Gln Ala Ser Lys
                180                 185                 190

Cys Asp Ser His Gly Thr His Leu Ala Gly Val Val Ser Gly Arg Asp
                195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                    245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
                275                 280                 285

Arg Asp Asp Ala Cys Leu Tyr Ser Pro Ala Ser Ala Pro Glu Val Ile
                290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                    325                 330                 335

Asp Ile Ile Gly Ala Ser Ser Asp Cys Ser Thr Cys Phe Val Ser Gln
                340                 345                 350

Ser Gly Thr Ser Gln Ala Ala Ala His Val Ala Gly Ile Ala Ala Met
                355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                    405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Val Ala Arg Cys Ala
                435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
```

```
                465                 470                 475                 480
        Ala His Asn Ala Phe Gly Gly Glu Gly Val Tyr Ala Ile Ala Arg Cys
                        485                 490                 495

Cys Leu Leu Pro Gln Ala Asn Cys Ser Val His Thr Ala Pro Pro Ala
                        500                 505                 510

Glu Ala Ser Met Gly Thr Arg Val His Cys His Gln Gln Gly His Val
                        515                 520                 525

Leu Thr Gly Cys Ser Ser His Trp Glu Val Asp Leu Gly Thr His
                        530                 535                 540

Lys Pro Pro Val Leu Arg Pro Arg Gly Gln Pro Asn Gln Cys Val Gly
        545                 550                 555                 560

His Arg Glu Ala Ser Ile His Ala Ser Cys Cys His Ala Pro Gly Leu
                        565                 570                 575

Glu Cys Lys Val Lys Glu His Gly Ile Pro Ala Pro Gln Glu Gln Val
                        580                 585                 590

Thr Val Ala Cys Glu Glu Gly Trp Thr Leu Thr Gly Cys Ser Ala Leu
                        595                 600                 605

Pro Gly Thr Ser His Val Leu Gly Ala Tyr Ala Val Asp Asn Thr Cys
                        610                 615                 620

Val Val Arg Ser Arg Asp Val Ser Thr Thr Gly Ser Thr Ser Glu Gly
        625                 630                 635                 640

Ala Val Thr Ala Val Ala Ile Cys Cys Arg Ser Arg His Leu Ala Gln
                        645                 650                 655

Ala Ser Gln Glu Leu Gln
                        660

<210> SEQ ID NO 12
<211> LENGTH: 540
<212> TYPE: PRT
<213> ORGANISM: Homo sapiens

<400> SEQUENCE: 12

Ser Ile Pro Trp Asn Leu Glu Arg Ile Thr Pro Pro Arg Tyr Arg Ala
        1               5                   10                  15

Asp Glu Tyr Gln Pro Pro Asp Gly Gly Ser Leu Val Glu Val Tyr Leu
                        20                  25                  30

Leu Asp Thr Ser Ile Gln Ser Asp His Arg Glu Ile Glu Gly Arg Val
                        35                  40                  45

Met Val Thr Asp Phe Glu Asn Val Pro Glu Glu Asp Gly Thr Arg Phe
                50                  55                  60

His Arg Gln Ala Ser Lys Cys Asp Ser His Gly Thr His Leu Ala Gly
        65                  70                  75                  80

Val Val Ser Gly Arg Asp Ala Gly Val Ala Lys Gly Ala Ser Met Arg
                        85                  90                  95

Ser Leu Arg Val Leu Asn Cys Gln Gly Lys Gly Thr Val Ser Gly Thr
                        100                 105                 110

Leu Ile Gly Leu Glu Phe Ile Arg Lys Ser Gln Leu Val Gln Pro Val
                        115                 120                 125

Gly Pro Leu Val Val Leu Leu Pro Leu Ala Gly Tyr Ser Arg Val
                        130                 135                 140

Leu Asn Ala Ala Cys Gln Arg Leu Ala Arg Ala Gly Val Val Leu Val
        145                 150                 155                 160

Thr Ala Ala Gly Asn Phe Arg Asp Asp Ala Cys Leu Tyr Ser Pro Ala
                        165                 170                 175
```

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Val Ala Arg Cys Ala Pro Asp Glu Glu Leu Leu Ser Cys Ser Ser
                325                 330                 335

Phe Ser Arg Ser Gly Lys Arg Arg Gly Glu Arg Met Glu Ala Gln Gly
            340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
    370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
            420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
    450                 455                 460

Ala Pro Gln Glu Gln Val Thr Val Ala Cys Glu Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
            500                 505                 510

Gly Ser Thr Ser Glu Gly Ala Val Thr Ala Val Ala Ile Cys Cys Arg
        515                 520                 525

Ser Arg His Leu Ala Gln Ala Ser Gln Glu Leu Gln
    530                 535                 540

<210> SEQ ID NO 13
<211> LENGTH: 692
<212> TYPE: PRT
<213> ORGANISM: Homo sapiens

<400> SEQUENCE: 13

Met Gly Thr Val Ser Ser Arg Arg Ser Trp Trp Pro Leu Pro Leu Leu
1               5                   10                  15

-continued

```
Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
            35                  40                  45

Glu Asp Gly Leu Val Glu Ala Pro Glu His Gly Thr Thr Ala Thr Phe
50                      55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430
```

```
Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 14
<211> LENGTH: 662
<212> TYPE: PRT
<213> ORGANISM: Homo sapiens

<400> SEQUENCE: 14

Gln Glu Asp Glu Asp Gly Asp Tyr Glu Glu Leu Val Leu Ala Leu Arg
1               5                   10                  15

Ser Glu Glu Asp Gly Leu Val Glu Ala Pro Glu His Gly Thr Thr Ala
                20                  25                  30

Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
        50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110
```

```
Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525
```

-continued

```
Leu Thr Gly Cys Ser Ser His Trp Glu Val Glu Asp Leu Gly Thr His
        530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Gly Trp Thr Leu Thr Gly Cys Ser Ala Leu
        595                 600                 605

Pro Gly Thr Ser His Val Leu Gly Ala Tyr Ala Val Asp Asn Thr Cys
610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 15
<211> LENGTH: 692
<212> TYPE: PRT
<213> ORGANISM: Homo sapiens

<400> SEQUENCE: 15

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240
```

```
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
            260                 265                 270
Lys Ser Gln Leu Val Gln Pro Val Gly Pro Leu Val Val Leu Leu Pro
            275                 280                 285
Leu Ala Gly Gly Tyr Ser Arg Val Leu Asn Ala Ala Cys Gln Arg Leu
            290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
                340                 345                 350
Thr Asn Phe Gly Arg Cys Val Asp Leu Phe Ala Pro Gly Glu Asp Ile
                355                 360                 365
Ile Gly Ala Ser Ser Asp Cys Ser Thr Cys Phe Val Ser Gln Ser Gly
            370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
                420                 425                 430
Gln Arg Val Leu Thr Pro Asn Leu Val Ala Thr Leu Pro Pro Ser Thr
            435                 440                 445
His Gly Ala Gly Trp Gln Leu Phe Cys Arg Thr Val Trp Ser Ala His
450                 455                 460
Ser Gly Pro Thr Arg Met Ala Thr Ala Ile Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
                500                 505                 510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
            530                 535                 540
Ser Met Gly Thr Arg Val His Cys His Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
            610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
```

```
Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 16
<211> LENGTH: 662
<212> TYPE: PRT
<213> ORGANISM: Homo sapiens

<400> SEQUENCE: 16

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335
```

```
Asp Ile Ile Gly Ala Ser Ser Asp Cys Ser Thr Cys Phe Val Ser Gln
            340                 345                 350

Ser Gly Thr Ser Gln Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Thr Leu Pro Pro
                405                 410                 415

Ser Thr His Gly Ala Gly Trp Gln Leu Phe Cys Arg Thr Val Trp Ser
                420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
            450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
                500                 505                 510

Glu Ala Ser Met Gly Thr Arg Val His Cys His Gln Gln Gly His Val
            515                 520                 525

Leu Thr Gly Cys Ser Ser Trp Glu Val Glu Asp Leu Gly Thr His
530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
                580                 585                 590

Thr Val Ala Cys Glu Glu Gly Trp Thr Leu Thr Gly Cys Ser Ala Leu
                595                 600                 605

Pro Gly Thr Ser His Val Leu Gly Ala Tyr Ala Val Asp Asn Thr Cys
            610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 17
<211> LENGTH: 540
<212> TYPE: PRT
<213> ORGANISM: Homo sapiens

<400> SEQUENCE: 17

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
```

```
            35                  40                  45
Met Val Thr Asp Phe Glu Asn Val Pro Glu Glu Asp Gly Thr Arg Phe
 50                  55                  60

His Arg Gln Ala Ser Lys Cys Asp Ser His Gly Thr His Leu Ala Gly
 65                  70                  75                  80

Val Val Ser Gly Arg Asp Ala Gly Val Ala Lys Gly Ala Ser Met Arg
                 85                  90                  95

Ser Leu Arg Val Leu Asn Cys Gln Gly Lys Gly Thr Val Ser Gly Thr
                100                 105                 110

Leu Ile Gly Leu Glu Phe Ile Arg Lys Ser Gln Leu Val Gln Pro Val
                115                 120                 125

Gly Pro Leu Val Val Leu Leu Pro Leu Ala Gly Gly Tyr Ser Arg Val
                130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
                180                 185                 190

Pro Val Thr Leu Gly Thr Leu Gly Thr Asn Phe Gly Arg Cys Val Asp
                195                 200                 205

Leu Phe Ala Pro Gly Glu Asp Ile Ile Gly Ala Ser Ser Asp Cys Ser
210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
                260                 265                 270

Asn Glu Ala Trp Phe Pro Glu Asp Gln Arg Val Leu Thr Pro Asn Leu
                275                 280                 285

Val Ala Thr Leu Pro Pro Ser Thr His Gly Ala Gly Trp Gln Leu Phe
                290                 295                 300

Cys Arg Thr Val Trp Ser Ala His Ser Gly Pro Thr Arg Met Ala Thr
305                 310                 315                 320

Ala Ile Ala Arg Cys Ala Pro Asp Glu Glu Leu Leu Ser Cys Ser Ser
                325                 330                 335

Phe Ser Arg Ser Gly Lys Arg Arg Gly Glu Arg Met Glu Ala Gln Gly
                340                 345                 350

Gly Lys Leu Val Cys Arg Ala His Asn Ala Phe Gly Gly Glu Gly Val
                355                 360                 365

Tyr Ala Ile Ala Arg Cys Cys Leu Leu Pro Gln Ala Asn Cys Ser Val
                370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
                420                 425                 430

Pro Asn Gln Cys Val Gly His Arg Glu Ala Ser Ile His Ala Ser Cys
                435                 440                 445

Cys His Ala Pro Gly Leu Glu Cys Lys Val Lys Glu His Gly Ile Pro
                450                 455                 460
```

Ala Pro Gln Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
                500                 505                 510

Gly Ser Thr Ser Glu Glu Ala Val Thr Ala Val Ala Ile Cys Cys Arg
            515                 520                 525

Ser Arg His Leu Ala Gln Ala Ser Gln Glu Leu Gln
            530                 535                 540

<210> SEQ ID NO 18
<211> LENGTH: 692
<212> TYPE: PRT
<213> ORGANISM: Homo sapiens

<400> SEQUENCE: 18

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu

```
                290                 295                 300
Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
                355                 360                 365

Ile Gly Ala Ser Ser Asp Cys Ser Thr Cys Phe Val Ser Gln Ser Gly
                370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Ser Glu Ala Trp Phe Pro Glu Asp
                420                 425                 430

Gln Arg Val Leu Thr Pro Asn Leu Val Ala Ala Leu Pro Pro Ser Thr
                435                 440                 445

His Gly Ala Gly Trp Gln Leu Phe Cys Arg Thr Val Trp Ser Ala His
                450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
                515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys His Ala Pro Gly Leu Glu Cys
                595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
                660                 665                 670

Thr Ala Val Ala Ile Cys Cys Arg Ser Arg His Leu Ala Gln Ala Ser
                675                 680                 685

Gln Glu Leu Gln
    690

<210> SEQ ID NO 19
```

```
<211> LENGTH: 662
<212> TYPE: PRT
<213> ORGANISM: Homo sapiens

<400> SEQUENCE: 19

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

Met Leu Ser Ala Glu Pro Glu Leu Thr Leu Ala Glu Leu Arg Gln Arg
370                 375                 380

Leu Ile His Phe Ser Ala Lys Asp Val Ile Ser Glu Ala Trp Phe Pro
```

-continued

```
            385                 390                 395                 400
Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
        515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                645                 650                 655

Ala Ser Gln Glu Leu Gln
            660

<210> SEQ ID NO 20
<211> LENGTH: 540
<212> TYPE: PRT
<213> ORGANISM: Homo sapiens

<400> SEQUENCE: 20

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
        35                  40                  45

Met Val Thr Asp Phe Glu Asn Val Pro Glu Glu Asp Gly Thr Arg Phe
    50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95
```

-continued

```
Ser Leu Arg Val Leu Asn Cys Gln Gly Lys Gly Thr Val Ser Gly Thr
                100                 105                 110
Leu Ile Gly Leu Glu Phe Ile Arg Lys Ser Gln Leu Val Gln Pro Val
            115                 120                 125
Gly Pro Leu Val Val Leu Leu Pro Leu Ala Gly Gly Tyr Ser Arg Val
        130                 135                 140
Leu Asn Ala Ala Cys Gln Arg Leu Ala Arg Ala Gly Val Val Leu Val
145                 150                 155                 160
Thr Ala Ala Gly Asn Phe Arg Asp Asp Ala Cys Leu Tyr Ser Pro Ala
                165                 170                 175
Ser Ala Pro Glu Val Ile Thr Val Gly Ala Thr Asn Ala Gln Asp Gln
            180                 185                 190
Pro Val Thr Leu Gly Thr Leu Gly Thr Asn Phe Gly Arg Cys Val Asp
        195                 200                 205
Leu Phe Ala Pro Gly Glu Asp Ile Ile Gly Ala Ser Ser Asp Cys Ser
210                 215                 220
Thr Cys Phe Val Ser Gln Ser Gly Thr Ser Gln Ala Ala Ala His Val
225                 230                 235                 240
Ala Gly Ile Ala Ala Met Met Leu Ser Ala Glu Pro Glu Leu Thr Leu
                245                 250                 255
Ala Glu Leu Arg Gln Arg Leu Ile His Phe Ser Ala Lys Asp Val Ile
            260                 265                 270
Ser Glu Ala Trp Phe Pro Glu Asp Gln Arg Val Leu Thr Pro Asn Leu
        275                 280                 285
Val Ala Ala Leu Pro Pro Ser Thr His Gly Ala Gly Trp Gln Leu Phe
    290                 295                 300
Cys Arg Thr Val Trp Ser Ala His Ser Gly Pro Thr Arg Met Ala Thr
305                 310                 315                 320
Ala Val Ala Arg Cys Ala Pro Asp Glu Glu Leu Leu Ser Cys Ser Ser
                325                 330                 335
Phe Ser Arg Ser Gly Lys Arg Arg Gly Glu Arg Met Glu Ala Gln Gly
            340                 345                 350
Gly Lys Leu Val Cys Arg Ala His Asn Ala Phe Gly Gly Glu Gly Val
        355                 360                 365
Tyr Ala Ile Ala Arg Cys Cys Leu Leu Pro Gln Ala Asn Cys Ser Val
    370                 375                 380
His Thr Ala Pro Pro Ala Glu Ala Ser Met Gly Thr Arg Val His Cys
385                 390                 395                 400
His Gln Gln Gly His Val Leu Thr Gly Cys Ser Ser His Trp Glu Val
                405                 410                 415
Glu Asp Leu Gly Thr His Lys Pro Pro Val Leu Arg Pro Arg Gly Gln
            420                 425                 430
Pro Asn Gln Cys Val Gly His Arg Glu Ala Ser Ile His Ala Ser Cys
        435                 440                 445
Cys His Ala Pro Gly Leu Glu Cys Lys Val Lys Glu His Gly Ile Pro
    450                 455                 460
Ala Pro Gln Glu Gln Val Thr Val Ala Cys Glu Glu Gly Trp Thr Leu
465                 470                 475                 480
Thr Gly Cys Ser Ala Leu Pro Gly Thr Ser His Val Leu Gly Ala Tyr
                485                 490                 495
Ala Val Asp Asn Thr Cys Val Val Arg Ser Arg Asp Val Ser Thr Thr
            500                 505                 510
Gly Ser Thr Ser Glu Glu Ala Val Thr Ala Val Ala Ile Cys Cys Arg
```

```
                515                 520                 525
Ser Arg His Leu Ala Gln Ala Ser Gln Glu Leu Gln
    530                 535                 540

<210> SEQ ID NO 21
<211> LENGTH: 692
<212> TYPE: PRT
<213> ORGANISM: Homo sapiens

<400> SEQUENCE: 21

Met Gly Thr Val Ser Ser Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350
```

```
Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Thr Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 22
<211> LENGTH: 662
<212> TYPE: PRT
<213> ORGANISM: Homo sapiens

<400> SEQUENCE: 22

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30
```

-continued

```
Thr Phe His Arg Cys Ala Lys Asp Pro Trp Arg Leu Pro Gly Thr Tyr
        35                  40                  45
Val Val Val Leu Lys Glu Glu Thr His Leu Ser Gln Ser Glu Arg Thr
 50                  55                  60
Ala Arg Arg Leu Gln Ala Gln Ala Arg Arg Gly Tyr Leu Thr Lys
 65              70                  75                  80
Ile Leu His Val Phe His Gly Leu Leu Pro Gly Phe Leu Val Lys Met
                    85                  90                  95
Ser Gly Asp Leu Leu Glu Leu Ala Leu Lys Leu Pro His Val Asp Tyr
                100                 105                 110
Ile Glu Glu Asp Ser Ser Val Phe Ala Gln Ser Ile Pro Trp Asn Leu
                115                 120                 125
Glu Arg Ile Thr Pro Pro Arg Tyr Arg Ala Asp Glu Tyr Gln Pro Pro
            130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
            180                 185                 190
Cys Asp Ser His Gly Thr His Leu Ala Gly Val Val Ser Gly Arg Asp
            195                 200                 205
Ala Gly Val Ala Lys Gly Ala Ser Met Arg Ser Leu Arg Val Leu Asn
210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Val Leu Val Thr Ala Ala Gly Asn Phe
        275                 280                 285
Arg Asp Asp Ala Cys Leu Tyr Ser Pro Ala Ser Ala Pro Glu Val Ile
290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
            340                 345                 350
Ser Gly Thr Ser Gln Ala Ala Ala His Val Ala Gly Ile Ala Ala Met
        355                 360                 365
Met Leu Ser Ala Glu Pro Glu Leu Thr Leu Ala Glu Leu Arg Gln Arg
370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Thr Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Ile Ala Arg Cys Ala
        435                 440                 445
```

-continued

```
Pro Asp Glu Glu Leu Leu Ser Cys Ser Ser Phe Ser Arg Ser Gly Lys
    450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                    485                 490                 495
Cys Leu Leu Pro Gln Ala Asn Cys Ser Val His Thr Ala Pro Pro Ala
                500                 505                 510
Glu Ala Ser Met Gly Thr Arg Val His Cys His Gln Gln Gly His Val
            515                 520                 525
Leu Thr Gly Cys Ser Ser His Trp Glu Val Asp Leu Gly Thr His
    530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Pro Glu Gln Val
                580                 585                 590
Thr Val Ala Cys Glu Glu Gly Trp Thr Leu Thr Gly Cys Ser Ala Leu
            595                 600                 605
Pro Gly Thr Ser His Val Leu Gly Ala Tyr Ala Val Asp Asn Thr Cys
    610                 615                 620
Val Val Arg Ser Arg Asp Val Ser Thr Thr Gly Ser Thr Ser Glu Glu
625                 630                 635                 640
Ala Val Thr Ala Val Ala Ile Cys Cys Arg Ser Arg His Leu Ala Gln
                645                 650                 655
Ala Ser Gln Glu Leu Gln
            660

<210> SEQ ID NO 23
<211> LENGTH: 540
<212> TYPE: PRT
<213> ORGANISM: Homo sapiens

<400> SEQUENCE: 23

Ser Ile Pro Trp Asn Leu Glu Arg Ile Thr Pro Pro Arg Tyr Arg Ala
1               5                   10                  15
Asp Glu Tyr Gln Pro Pro Asp Gly Gly Ser Leu Val Glu Val Tyr Leu
            20                  25                  30
Leu Asp Thr Ser Ile Gln Ser Asp His Arg Glu Ile Glu Gly Arg Val
        35                  40                  45
Met Val Thr Asp Phe Glu Asn Val Pro Glu Glu Asp Gly Thr Arg Phe
    50                  55                  60
His Arg Gln Ala Ser Lys Cys Asp Ser His Gly Thr His Leu Ala Gly
65                  70                  75                  80
Val Val Ser Gly Arg Asp Ala Gly Val Ala Lys Gly Ala Ser Met Arg
                85                  90                  95
Ser Leu Arg Val Leu Asn Cys Gln Gly Lys Gly Thr Val Ser Gly Thr
                100                 105                 110
Leu Ile Gly Leu Glu Phe Ile Arg Lys Ser Gln Leu Val Gln Pro Val
            115                 120                 125
Gly Pro Leu Val Val Leu Leu Pro Leu Ala Gly Gly Tyr Ser Arg Val
    130                 135                 140
Leu Asn Ala Ala Cys Gln Arg Leu Ala Arg Ala Gly Val Val Leu Val
145                 150                 155                 160
```

```
Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260                 265                 270

Asn Glu Ala Trp Phe Pro Glu Asp Gln Arg Val Leu Thr Pro Asn Leu
        275                 280                 285

Val Ala Thr Leu Pro Pro Ser Thr His Gly Ala Gly Trp Gln Leu Phe
    290                 295                 300

Cys Arg Thr Val Trp Ser Ala His Ser Gly Pro Thr Arg Met Ala Thr
305                 310                 315                 320

Ala Ile Ala Arg Cys Ala Pro Asp Glu Glu Leu Leu Ser Cys Ser Ser
                325                 330                 335

Phe Ser Arg Ser Gly Lys Arg Gly Glu Arg Met Glu Ala Gln Gly
            340                 345                 350

Gly Lys Leu Val Cys Arg Ala His Asn Ala Phe Gly Gly Glu Gly Val
        355                 360                 365

Tyr Ala Ile Ala Arg Cys Cys Leu Leu Pro Gln Ala Asn Cys Ser Val
    370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                405                 410                 415

Glu Asp Leu Gly Thr His Lys Pro Pro Val Leu Arg Pro Arg Gly Gln
            420                 425                 430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
    450                 455                 460

Ala Pro Pro Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
                485                 490                 495

Ala Val Asp Asn Thr Cys Val Val Arg Ser Arg Asp Val Ser Thr Thr
            500                 505                 510

Gly Ser Thr Ser Glu Glu Ala Val Thr Ala Val Ala Ile Cys Cys Arg
        515                 520                 525

Ser Arg His Leu Ala Gln Ala Ser Gln Glu Leu Gln
    530                 535                 540

<210> SEQ ID NO 24
<211> LENGTH: 692
<212> TYPE: PRT
<213> ORGANISM: Homo sapiens
```

<400> SEQUENCE: 24

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Leu Ser Glu
        35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415
```

```
His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
        450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 25
<211> LENGTH: 662
<212> TYPE: PRT
<213> ORGANISM: Homo sapiens

<400> SEQUENCE: 25

Gln Glu Asp Glu Asp Gly Asp Tyr Glu Glu Leu Val Leu Ala Leu Leu
1               5                   10                  15

Ser Glu Glu Asp Gly Leu Ala Glu Ala Pro His Gly Thr Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
```

```
                85                  90                  95
Ser Gly Asp Leu Leu Glu Leu Ala Leu Lys Leu Pro His Val Asp Tyr
            100                 105                 110
Ile Glu Glu Asp Ser Ser Val Phe Ala Gln Ser Ile Pro Trp Asn Leu
            115                 120                 125
Glu Arg Ile Thr Pro Pro Arg Tyr Arg Ala Asp Glu Tyr Gln Pro Pro
130                 135                 140
Asp Gly Gly Ser Leu Val Glu Val Tyr Leu Leu Asp Thr Ser Ile Gln
145                 150                 155                 160
Ser Asp His Arg Glu Ile Glu Gly Arg Val Met Val Thr Asp Phe Glu
                165                 170                 175
Asn Val Pro Glu Glu Asp Gly Thr Arg Phe His Arg Gln Ala Ser Lys
            180                 185                 190
Cys Asp Ser His Gly Thr His Leu Ala Gly Val Val Ser Gly Arg Asp
            195                 200                 205
Ala Gly Val Ala Lys Gly Ala Ser Met Arg Ser Leu Arg Val Leu Asn
            210                 215                 220
Cys Gln Gly Lys Gly Thr Val Ser Gly Thr Leu Ile Gly Leu Glu Phe
225                 230                 235                 240
Ile Arg Lys Ser Gln Leu Val Gln Pro Val Gly Pro Leu Val Val Leu
                245                 250                 255
Leu Pro Leu Ala Gly Gly Tyr Ser Arg Val Leu Asn Ala Ala Cys Gln
            260                 265                 270
Arg Leu Ala Arg Ala Gly Val Val Leu Val Thr Ala Ala Gly Asn Phe
            275                 280                 285
Arg Asp Asp Ala Cys Leu Tyr Ser Pro Ala Ser Ala Pro Glu Val Ile
            290                 295                 300
Thr Val Gly Ala Thr Asn Ala Gln Asp Gln Pro Val Thr Leu Gly Thr
305                 310                 315                 320
Leu Gly Thr Asn Phe Gly Arg Cys Val Asp Leu Phe Ala Pro Gly Glu
                325                 330                 335
Asp Ile Ile Gly Ala Ser Ser Asp Cys Ser Thr Cys Phe Val Ser Gln
            340                 345                 350
Ser Gly Thr Ser Gln Ala Ala Ala His Val Ala Gly Ile Ala Ala Met
            355                 360                 365
Met Leu Ser Ala Glu Pro Glu Leu Thr Leu Ala Glu Leu Arg Gln Arg
            370                 375                 380
Leu Ile His Phe Ser Ala Lys Asp Val Ile Asn Glu Ala Trp Phe Pro
385                 390                 395                 400
Glu Asp Gln Arg Val Leu Thr Pro Asn Leu Val Ala Ala Leu Pro Pro
                405                 410                 415
Ser Thr His Gly Ala Gly Trp Gln Leu Phe Cys Arg Thr Val Trp Ser
            420                 425                 430
Ala His Ser Gly Pro Thr Arg Met Ala Thr Ala Val Ala Arg Cys Ala
            435                 440                 445
Pro Asp Glu Glu Leu Leu Ser Cys Ser Ser Phe Ser Arg Ser Gly Lys
            450                 455                 460
Arg Arg Gly Glu Arg Met Glu Ala Gln Gly Gly Lys Leu Val Cys Arg
465                 470                 475                 480
Ala His Asn Ala Phe Gly Gly Glu Gly Val Tyr Ala Ile Ala Arg Cys
                485                 490                 495
Cys Leu Leu Pro Gln Ala Asn Cys Ser Val His Thr Ala Pro Pro Ala
            500                 505                 510
```

-continued

Glu Ala Ser Met Gly Thr Arg Val His Cys His Gln Gln Gly His Val
            515                 520                 525
Leu Thr Gly Cys Ser Ser His Trp Glu Val Glu Asp Leu Gly Thr His
        530                 535                 540
Lys Pro Pro Val Leu Arg Pro Arg Gly Gln Pro Asn Gln Cys Val Gly
545                 550                 555                 560
His Arg Glu Ala Ser Ile His Ala Ser Cys Cys His Ala Pro Gly Leu
                565                 570                 575
Glu Cys Lys Val Lys Glu His Gly Ile Pro Ala Pro Gln Glu Gln Val
            580                 585                 590
Thr Val Ala Cys Glu Gly Trp Thr Leu Thr Gly Cys Ser Ala Leu
            595                 600                 605
Pro Gly Thr Ser His Val Leu Gly Ala Tyr Ala Val Asp Asn Thr Cys
        610                 615                 620
Val Val Arg Ser Arg Asp Val Ser Thr Thr Gly Ser Thr Ser Glu Glu
625                 630                 635                 640
Ala Val Thr Ala Val Ala Ile Cys Cys Arg Ser Arg His Leu Ala Gln
                645                 650                 655
Ala Ser Gln Glu Leu Gln
            660

<210> SEQ ID NO 26
<211> LENGTH: 692
<212> TYPE: PRT
<213> ORGANISM: Homo sapiens

<400> SEQUENCE: 26

Met Gly Thr Val Ser Ser Arg Arg Ser Trp Trp Pro Leu Pro Leu Leu
1               5                   10                  15
Leu Leu Leu Leu Leu Leu Gly Pro Ala Gly Ala Arg Ala Gln Glu
            20                  25                  30
Asp Glu Asp Gly Asp Tyr Glu Glu Leu Val Leu Ala Leu Arg Ser Glu
        35                  40                  45
Glu Asp Gly Leu Val Glu Ala Pro Glu His Gly Thr Thr Ala Thr Phe
    50                  55                  60
His Arg Cys Ala Lys Asp Pro Trp Arg Leu Pro Gly Thr Tyr Val Val
65                  70                  75                  80
Val Leu Lys Glu Glu Thr His Leu Ser Gln Ser Glu Arg Thr Ala Arg
                85                  90                  95
Arg Leu Gln Ala Gln Ala Ala Arg Arg Gly Tyr Leu Thr Lys Ile Leu
            100                 105                 110
His Val Phe His Gly Leu Leu Pro Gly Phe Leu Val Lys Met Ser Gly
        115                 120                 125
Asp Leu Leu Glu Leu Ala Leu Lys Leu Pro His Val Asp Tyr Ile Glu
    130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
            180                 185                 190
His Arg Glu Ile Glu Gly Arg Val Met Val Thr Asp Phe Glu Asn Val
        195                 200                 205
Pro Glu Glu Asp Gly Thr Arg Phe His Arg Gln Ala Ser Lys Cys Asp

```
            210                 215                 220
Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
        450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
            565                 570                 575

Pro Val Leu Arg Pro Arg Gly Gln Pro Asn Gln Cys Val Gly His Arg
        580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640
```

```
Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 27
<211> LENGTH: 662
<212> TYPE: PRT
<213> ORGANISM: Homo sapiens

<400> SEQUENCE: 27

Gln Glu Asp Glu Asp Gly Asp Tyr Glu Glu Leu Val Leu Ala Leu Arg
1               5                   10                  15

Ser Glu Glu Asp Gly Leu Val Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
```

```
            305                 310                 315                 320
        Leu Gly Thr Asn Phe Gly Arg Cys Val Asp Leu Phe Ala Pro Gly Glu
                        325                 330                 335

Asp Ile Ile Gly Ala Ser Ser Asp Cys Ser Thr Cys Phe Val Ser Gln
                        340                 345                 350

Ser Gly Thr Ser Gln Ala Ala His Val Ala Gly Ile Ala Ala Met
                    355                 360                 365

Met Leu Ser Ala Glu Pro Glu Leu Thr Leu Ala Glu Leu Arg Gln Arg
                370                 375                 380

Leu Ile His Phe Ser Ala Lys Asp Val Ile Asn Glu Ala Trp Phe Pro
        385                 390                 395                 400

Glu Asp Gln Arg Val Leu Thr Pro Asn Leu Val Ala Ala Leu Pro Pro
                        405                 410                 415

Ser Thr His Gly Ala Gly Trp Gln Leu Phe Cys Arg Thr Val Trp Ser
                        420                 425                 430

Ala His Ser Gly Pro Thr Arg Met Ala Thr Ala Ile Ala Arg Cys Ala
                        435                 440                 445

Pro Asp Glu Glu Leu Leu Ser Cys Ser Ser Phe Ser Arg Ser Gly Lys
                        450                 455                 460

Arg Arg Gly Glu Arg Met Glu Ala Gln Gly Gly Lys Leu Val Cys Arg
        465                 470                 475                 480

Ala His Asn Ala Phe Gly Gly Glu Gly Val Tyr Ala Ile Ala Arg Cys
                        485                 490                 495

Cys Leu Leu Pro Gln Ala Asn Cys Ser Val His Thr Ala Pro Pro Ala
                        500                 505                 510

Glu Ala Ser Met Gly Thr Arg Val His Cys His Gln Gln Gly His Val
                        515                 520                 525

Leu Thr Gly Cys Ser Ser His Trp Glu Val Glu Asp Leu Gly Thr His
                        530                 535                 540

Lys Pro Pro Val Leu Arg Pro Arg Gly Gln Pro Asn Gln Cys Val Gly
        545                 550                 555                 560

His Arg Glu Ala Ser Ile His Ala Ser Cys Cys His Ala Pro Gly Leu
                        565                 570                 575

Glu Cys Lys Val Lys Glu His Gly Ile Pro Ala Pro Gln Glu Gln Val
                        580                 585                 590

Thr Val Ala Cys Glu Glu Gly Trp Thr Leu Thr Gly Cys Ser Ala Leu
                        595                 600                 605

Pro Gly Thr Ser His Val Leu Gly Ala Tyr Ala Val Asp Asn Thr Cys
                        610                 615                 620

Val Val Arg Ser Arg Asp Val Ser Thr Thr Gly Ser Thr Ser Glu Gly
        625                 630                 635                 640

Ala Val Thr Ala Val Ala Ile Cys Cys Arg Ser Arg His Leu Ala Gln
                        645                 650                 655

Ala Ser Gln Glu Leu Gln
                    660

<210> SEQ ID NO 28
<211> LENGTH: 2080
<212> TYPE: DNA
<213> ORGANISM: Homo sapiens

<400> SEQUENCE: 28
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
```

```
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg aagggcacg    780
gttagcggca ccctcatagg cctggagttt attcggaaaa gccagctggt ccagcctgtg    840
gggccactgg tggtgctgct gccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact tggggaccca ctttggccg ctgtgtggac   1080
ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccatggg gcaggttggc agctgttttg caggactgta   1380
tggtcagcac actcggggcc tacacggatg ccacagccca tcgcccgctg cgccccagat   1440
gaggagctgc tgagctgctc cagtttctcc aggagtggga agcggcgggg cgagcgcatg   1500
gaggcccaag ggggcaagct ggtctgccgg gcccacaacg ctttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacaggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctccacg tcctggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctccagtgac                          2080
```

<210> SEQ ID NO 29
<211> LENGTH: 2080
<212> TYPE: DNA
<213> ORGANISM: Homo sapiens

<400> SEQUENCE: 29

```
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
```

| | |
|---|---:|
| ctggtgctag ccttgcgttc cgaggaggac ggcctggccg aagcacccga gcacggaacc | 180 |
| acagccacct tccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgg tgaagatgag tggcgacctg ctggagctgg ccttgaagtt gccccatgtc | 420 |
| gactacatcg aggaggactc ctctgtcttt gcccagagca tcccgtggaa cctggagcgg | 480 |
| attacccctc cacggtaccg gcggatgaa taccagcccc ccgacggagg cagcctggtg | 540 |
| gaggtgtatc tcctagacac cagcatacag agtgaccacc gggaaatcga gggcagggtc | 600 |
| atggtcaccg acttcgagaa tgtgcccgag gaggacggga cccgcttcca cagacaggcc | 660 |
| agcaagtgtg acagtcatgg cacccacctg gcagggtgg tcagcggccg ggatgccggc | 720 |
| gtggccaagg gtgccagcat gcgcagcctg cgcgtgctca actgccaagg gaagggcacg | 780 |
| gttagcggca ccctcatagg cctggagttt attcggaaaa gccagctggt ccagcctgtg | 840 |
| gggccactgg tggtgctgct gccccctggcg ggtgggtaca ccgcgtcct caacgccgcc | 900 |
| tgccagcgcc tggcgagggc tggggtcgtg ctggtcaccg ctgccggcaa cttccgggac | 960 |
| gatgcctgcc tctactcccc agcctcagct cccgaggtca tcacagttgg ggccaccaat | 1020 |
| gcccaagacc agccggtgac cctggggact tggggaccca actttggccg ctgtgtggac | 1080 |
| ctctttgccc caggggagga catcattggt gcctccagcg actgcagcac ctgctttgtg | 1140 |
| tcacagagtg ggacatcaca ggctgctgcc cacgtggctg gcattgcagc catgatgctg | 1200 |
| tctgccgagc cggagctcac cctggccgag ttgaggcaga gactgatcca cttctctgcc | 1260 |
| aaagatgtca tcaatgaggc ctggttccct gaggaccagc gggtactgac ccccaacctg | 1320 |
| gtggccgccc tgccccccag cacccatggg gcaggttggc agctgttttg caggactgta | 1380 |
| tggtcagcac actcggggcc tacacggatg ccacagccg tcgcccgctg cgccccagat | 1440 |
| gaggagctgc tgagctgctc cagtttctcc aggagtggga gcggcgggg cgagcgcatg | 1500 |
| gaggcccaag ggggcaagct ggtctgccgg gcccacaacg cttttgggggg tgagggtgtc | 1560 |
| tacgccattg ccaggtgctg cctgctaccc caggccaact gcagcgtcca cacagctcca | 1620 |
| ccagctgagg ccagcatggg gacccgtgtc cactgccacc aacagggcca cgtcctcaca | 1680 |
| ggctgcagct cccactggga ggtggaggac cttggcaccc acaagccgcc tgtgctgagg | 1740 |
| ccacgaggtc agcccaacca gtgcgtgggc cacagggagg ccagcatcca cgcttcctgc | 1800 |
| tgccatgccc caggtctgga atgcaaagtc aaggagcatg gaatcccggc ccctcaggag | 1860 |
| caggtgaccg tggcctgcga ggagggctgg accctgactg gctgcagtgc cctccctggg | 1920 |
| acctcccacg tcctggggc ctacgccgta gacaacacgt gtgtagtcag gagccgggac | 1980 |
| gtcagcacta caggcagcac cagcgaagag gccgtgacag ccgttgccat ctgctgccgg | 2040 |
| agccggcacc tggcgcaggc ctcccaggag ctccagtgac | 2080 |

<210> SEQ ID NO 30
<211> LENGTH: 2080
<212> TYPE: DNA
<213> ORGANISM: Homo sapiens

<400> SEQUENCE: 30

| | |
|---|---:|
| atgggcaccg tcagctccag gcggtcctgg tggccgctgc cactgctgct gctgctgctg | 60 |
| ctgctcctgg gtcccgcggg cgccgtgcg caggaggac aggacggcga ctacgaggag | 120 |
| ctggtgctag ccttgcgttc cgaggaggac ggcctggccg aagcacccga gcacggaacc | 180 |

```
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc cgacggagg cagcctggtg    540 gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact ttggggacca actttggccg ctgtgtggac   1080
ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgccccccag cacccatggg gcaggttggc agctgttttg caggactgta   1380
tggtcagcac actcggggcc tacacggatg gccacagcca tcgcccgctg cgccccagat   1440
gaggagctgc tgagctgctc cagtttctcc aggagtggga gcggcgggg cgagcgcatg   1500 gaggcccaag ggggcaagct ggtctgccgg gcccacaacg cttttgggg tgagggtgtc   1560 tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacaggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctgggggc ctacgccgta gacaacacgt gtgtagtcag gagccgggac   1980
gtcagcacta caggcagcac cagcgaaggg ccgtgacag ccgttgccat ctgctgccgg   2040
agccggcacc tggcgcaggc ctcccaggag ctccagtgac                          2080
```

<210> SEQ ID NO 31
<211> LENGTH: 2080
<212> TYPE: DNA
<213> ORGANISM: Homo sapiens

<400> SEQUENCE: 31

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
```

| | |
|---|---|
| acagccacct tccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgg tgaagatgag tggcgacctg ctggagctgg ccttgaagtt gccccatgtc | 420 |
| gactacatcg aggaggactc ctctgtcttt gcccagagca tcccgtggaa cctggagcgg | 480 |
| attacccctc cacggtaccg ggcggatgaa taccagcccc ccgacggagg cagcctggtg | 540 |
| gaggtgtatc tcctagacac cagcatacag agtgaccacc gggaaatcga gggcagggtc | 600 |
| atggtcaccg acttcgagaa tgtgcccgag gaggacggga cccgcttcca cagacaggcc | 660 |
| agcaagtgtg acagtcatgg cacccacctg gcaggggtgg tcagcggccg ggatgccggc | 720 |
| gtggccaagg gtgccagcat gcgcagcctg cgcgtgctca actgccaagg gaagggcacg | 780 |
| gttagcggca ccctcatagg cctggagttt attcggaaaa gccagctggt ccagcctgtg | 840 |
| gggccactgg tggtgctgct gcccctggcg ggtgggtaca gccgcgtcct caacgccgcc | 900 |
| tgccagcgcc tggcgagggc tggggtcgtg ctggtcaccg ctgccggcaa cttccggggac | 960 |
| gatgcctgcc tctactcccc agcctcagct cccgaggtca tcacagttgg ggccaccaat | 1020 |
| gcccaagacc agccggtgac cctggggact ttggggacca ctttggccg ctgtgtggac | 1080 |
| ctctttgccc caggggagga catcattggt gcctccagcg actgcagcac ctgctttgtg | 1140 |
| tcacagagtg gacatcaca ggctgctgcc cacgtggctg gcattgcagc catgatgctg | 1200 |
| tctgccgagc cggagctcac cctggccgag ttgaggcaga gactgatcca cttctctgcc | 1260 |
| aaagatgtca tcaatgaggc ctggttccct gaggaccagc gggtactgac ccccaacctg | 1320 |
| gtggccgccc tgccccccag cacccatggg gcaggttggc agctgttttg caggactgta | 1380 |
| tggtcagcac actcggggcc tacacggatg ccacagccg tcgcccgctg cgccccagat | 1440 |
| gaggagctgc tgagctgctc cagtttctcc aggagtggga agcggcgggg cgagcgcatg | 1500 |
| gaggcccaag ggggcaagct ggtctgccgg gcccacaacg cttttggggg tgagggtgtc | 1560 |
| tacgccattg ccaggtgctg cctgctaccc caggccaact gcagcgtcca cacagctcca | 1620 |
| ccagctgagg ccagcatggg gacccgtgtc cactgccacc aacagggcca cgtcctcaca | 1680 |
| ggctgcagct cccactggga ggtggaggac cttggcaccc acaagccgcc tgtgctgagg | 1740 |
| ccacgaggtc agcccaacca gtgcgtgggc cacaggagg ccagcatcca cgcttcctgc | 1800 |
| tgccatgccc caggtctgga atgcaaagtc aaggagcatg gaatcccggc ccctcaggag | 1860 |
| caggtgaccg tggcctgcga ggagggctgg accctgactg gctgcagtgc cctccctggg | 1920 |
| acctcccacg tcctgggggc ctacgccgta gacaacacgt gtgtagtcag gagccgggac | 1980 |
| gtcagcacta caggcagcac cagcgaaggg ccgtgacag ccgttgccat ctgctgccgg | 2040 |
| agccggcacc tggcgcaggc ctcccaggag ctccagtgac | 2080 |

<210> SEQ ID NO 32
<211> LENGTH: 2080
<212> TYPE: DNA
<213> ORGANISM: Homo sapiens

<400> SEQUENCE: 32

| | |
|---|---|
| atgggcaccg tcagctccag gcggtcctgg tggccgctgc cactgctgct gctgctgctg | 60 |
| ctgctcctgg gtcccgcggg cgcccgtgcg caggaggacg aggacggcga ctacgaggag | 120 |
| ctggtgctag ccttgcgttc cgaggaggac ggctggtcg aagcacccga gcacggaacc | 180 |
| acagccacct tccaccgctg cgccaaggat ccgtggaggt tgcctggcac ctacgtggtg | 240 |

```
gtgctgaagg aggagaccca cctctcgcag tcagagcgca ctgcccgccg cctgcaggcc    300
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg cagggtgg tcagcggccg ggatgccggc    720
gtggccaagg gtgccagcat gcgcagcctg cgcgtgctca actgccaagg aagggcacg    780 gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact ttggggacca ctttggccg ctgtgtggac   1080 ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga actgatcca cttctctgcc   1260 aaagatgtca tcaatgaggc ctggttccct gaggaccagc gggtactgac ccccaacctg   1320
gtggccgccc tgcccccag cacccatggg gcaggttggc agctgttttg caggactgta   1380
tggtcagcac actcggggcc tacacggatg ccacagccg tcgcccgctg cgccccagat   1440
gaggagctgc tgagctgctc cagtttctcc aggagtggga agcggcgggg cgagcgcatg   1500
gaggcccaag ggggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacaggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctccagtgac                          2080
```

<210> SEQ ID NO 33
<211> LENGTH: 2080
<212> TYPE: DNA
<213> ORGANISM: Homo sapiens

<400> SEQUENCE: 33

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc cgaggaggac ggcctggccg aagcacccga gcacggaacc    180
acagccacct tccaccgctg cgccaaggat ccgtggaggt tgcctggcac ctacgtggtg    240
```

```
gtgctgaagg aggagaccca cctctcgcag tcagagcgca ctgcccgccg cctgcaggcc      300
caggctgccc gccggggata cctcaccaag atcctgcatg tcttccatgg ccttcttcct      360
ggcttcctgg tgaagatgag tggcgacctg ctggagctgg ccttgaagtt gccccatgtc      420
gactacatcg aggaggactc ctctgtcttt gcccagagca tcccgtggaa cctggagcgg      480
attacccctc cacggtaccg gcggatgaa taccagcccc ccgacggagg cagcctggtg       540
gaggtgtatc tcctagacac cagcatacag agtgaccacc gggaaatcga gggcagggtc      600
atggtcaccg acttcgagaa tgtgcccgag gaggacggga cccgcttcca cagacaggcc      660
agcaagtgtg acagtcatgg cacccacctg gcagggtgg tcagcggccg ggatgccggc       720
gtggccaagg gtgccagcat gcgcagcctg cgcgtgctca actgccaagg gaagggcacg      780
gttagcggca ccctcatagg cctggagttt attcggaaaa gccagctggt ccagcctgtg      840
gggccactgg tggtgctgct gccctggcg ggtgggtaca ccgcgtcct caacgccgcc        900
tgccagcgcc tggcgagggc tggggtcgtg ctggtcaccg ctgccggcaa cttccgggac      960
gatgcctgcc tctactcccc agcctcagct cccgaggtca tcacagttgg ggccaccaat      1020
gcccaagacc agccggtgac ctggggact ttggggacca actttggccg ctgtgtggac       1080
ctctttgccc caggggagga catcattggt gcctccagcg actgcagcac ctgctttgtg      1140
tcacagagtg ggacatcaca ggctgctgcc cacgtggctg gcattgcagc catgatgctg      1200
tctgccgagc cggagctcac cctggccgag ttgaggcaga gactgatcca cttctctgcc      1260
aaagatgtca tcaatgaggc ctggttccct gaggaccagc gggtactgac ccccaacctg      1320
gtggccaccc tgcccccag cacccatggg gcaggttggc agctgttttg caggactgta      1380
tggtcagcac actcggggcc tacacggatg ccacagcca tcgcccgctg cgccccagat      1440
gaggagctgc tgagctgctc cagtttctcc aggagtggga gcggcgggg cgagcgcatg       1500
gaggcccaag ggggcaagct ggtctgccgg gcccacaacg cttttggggg tgagggtgtc      1560
tacgccattg ccaggtgctg cctgctaccc caggccaact gcagcgtcca cacagctcca      1620
ccagctgagg ccagcatggg gacccgtgtc cactgccacc aacagggcca cgtcctcaca      1680
ggctgcagct cccactggga ggtggaggac cttggcaccc acaagccgcc tgtgctgagg      1740
ccacgaggtc agcccaacca gtgcgtgggc acagggagg ccagcatcca cgcttcctgc      1800
tgccatgccc caggtctgga atgcaaagtc aaggagcatg gaatcccggc ccctcaggag      1860
caggtgaccg tggcctgcga ggagggctgg accctgactg gctgcagtgc cctccctggg      1920
acctcccacg tcctggggc ctacgccgta gacaacacgt gtgtagtcag gagccgggac       1980
gtcagcacta caggcagcac cagcgaagag gccgtgacag ccgttgccat ctgctgccgg      2040
agccggcacc tggcgcaggc ctcccaggag ctccagtgac                            2080
```

<210> SEQ ID NO 34
<211> LENGTH: 2080
<212> TYPE: DNA
<213> ORGANISM: Homo sapiens

<400> SEQUENCE: 34

```
atgggcaccg tcagctccag gcggtcctgg tggccgctgc cactgctgct gctgctgctg      60
ctgctcctgg gtcccgcggg cgcccgtgcg caggaggacg aggacggcga ctacgaggag      120
ctggtgctag ccttgcgttc gaggaggac ggcctggccg aagcacccga gcacggaacc       180
acagccacct tccaccgctg cgccaaggat ccgtggaggt tgcctggcac ctacgtggtg      240
gtgctgaagg aggagaccca cctctcgcag tcagagcgca ctgcccgccg cctgcaggcc      300
```

```
caggctgccc gccggggata cctcaccaag atcctgcatg tcttccatgg ccttcttcct    360
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat    1020
gcccaagacc agccggtgac cctggggact ttggggacca actttggccg ctgtgtggac    1080
ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcagtgaggc ctggttccct gaggaccagc gggtactgac ccccaacctg    1320
gtggccgccc tgcccccccag cacccatggg gcaggttggc agctgttttg caggactgta    1380
tggtcagcac actcggggcc tacacggatg gccacagccg tcgcccgctg cgccccagat    1440
gaggagctgc tgagctgctc cagtttctcc aggagtggga gcggcgggg cgagcgcatg    1500 gaggcccaag ggggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggagg ccagcatcca cgcttcctgc    1800
tgccatgccc caggtctgga atgcaaagtc aaggagcatg gaatcccggc ccctcaggag    1860
caggtgaccg tggcctgcga gagggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccagtgac                          2080
```

<210> SEQ ID NO 35
<211> LENGTH: 2080
<212> TYPE: DNA
<213> ORGANISM: Homo sapiens

<400> SEQUENCE: 35

```
atgggcaccg tcagctccag gcggtcctgg tggccgctgc cactgctgct gctgctgctg     60
ctgctcctgg gtcccgcggg cgcccgtgcg caggaggacg aggacggcga ctacgaggag    120
ctggtgctag ccttgcgttc gaggaggac ggcctggccg aagcacccga gcacggaacc    180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
```

-continued

```
caggctgccc gccggggata cctcaccaag atcctgcatg tcttccatgg ccttcttcct      360
ggcttcctgg tgaagatgag tggcgacctg ctggagctgg ccttgaagtt gccccatgtc      420
gactacatcg aggaggactc ctctgtcttt gcccagagca tcccgtggaa cctggagcgg      480
attacccctc cacggtaccg ggcggatgaa taccagcccc ccgacggagg cagcctggtg      540
gaggtgtatc tcctagacac cagcatacag agtgaccacc gggaaatcga gggcagggtc      600
atggtcaccg acttcgagaa tgtgcccgag gaggacggga cccgcttcca cagacaggcc      660
agcaagtgtg acagtcatgg cacccacctg gcaggggtgg tcagcggccg ggatgccggc      720
gtggccaagg gtgccagcat gcgcagcctg cgcgtgctca actgccaagg gaagggcacg      780
gttagcggca ccctcatagg cctggagttt attcggaaaa gccagctggt ccagcctgtg      840
gggccactgg tggtgctgct gcccctggcg ggtgggtaca gccgcgtcct caacgccgcc      900
tgccagcgcc tggcgagggc tggggtcgtg ctggtcaccg ctgccggcaa cttccgggac      960
gatgcctgcc tctactcccc agcctcagct cccgaggtca tcacagttgg ggccaccaat     1020
gcccaagacc agccggtgac cctggggact ttggggacca actttggccg ctgtgtggac     1080
ctctttgccc caggggagga catcattggt gcctccagcg actgcagcac ctgctttgtg     1140
tcacagagtg gacatcaca ggctgctgcc cacgtggctg gcattgcagc catgatgctg     1200
tctgccgagc cggagctcac cctggccgag ttgaggcaga gactgatcca cttctctgcc     1260
aaagatgtca tcaatgaggc ctggttccct gaggaccagg gggtactgac ccccaacctg     1320
gtggccaccc tgcccccccag cacccatggg gcaggttggc agctgttttg caggactgta     1380
tggtcagcac actcggggcc tacacggatg ccacagccca tcgcccgctg cgccccagat     1440
gaggagctgc tgagctgctc cagtttctcc aggagtggga gcggcgggg cgagcgcatg     1500 gaggcccaag ggggcaagct ggtctgccgg gcccacaacg cttttggggg tgagggtgtc     1560
tacgccattg ccaggtgctg cctgctaccc caggccaact gcagcgtcca cacagctcca     1620
ccagctgagg ccagcatggg gacccgtgtc cactgccacc aacagggcca cgtcctcaca     1680
ggctgcagct cccactggga ggtggaggac cttggcaccc acaagccgcc tgtgctgagg     1740
ccacgaggtc agcccaacca gtgcgtgggc cacaggagg ccagcatcca cgcttcctgc     1800
tgccatgccc caggtctgga atgcaaagtc aaggagcatg gaatcccggc ccctccggag     1860
caggtgaccg tggcctgcga ggagggctgg accctgactg gctgcagtgc cctccctggg     1920
acctcccacg tcctgggggc ctacgccgta gacaacacgt gtgtagtcag gagccgggac     1980
gtcagcacta caggcagcac cagcgaagag gccgtgacag ccgttgccat ctgctgccgg     2040
agccggcacc tggcgcaggc ctcccaggag ctccagtgac                           2080
```

<210> SEQ ID NO 36
<211> LENGTH: 2080
<212> TYPE: DNA
<213> ORGANISM: Homo sapiens

<400> SEQUENCE: 36

```
atgggcaccg tcagctccag gcggtcctgg tggccgctgc cactgctgct gctgctgctg       60
ctgctcctgg gtcccgcggg cgccgtgcg caggaggacg aggacggcga ctacgaggag      120
ctggtgctag ccttgctttc cgaggaggac ggcctggccg aagcacccga gcacggaacc      180
acagccacct tccaccgctg cgccaaggat ccgtggaggt tgcctggcac ctacgtggtg      240
gtgctgaagg aggagaccca cctctcgcag tcagagcgca ctgcccgccg cctgcaggcc      300
caggctgccc gccggggata cctcaccaag atcctgcatg tcttccatgg ccttcttcct      360
```

```
ggcttcctgg tgaagatgag tggcgacctg ctggagctgg ccttgaagtt gccccatgtc      420
gactacatcg aggaggactc ctctgtcttt gcccagagca tcccgtggaa cctggagcgg      480
attacccctc cacggtaccg ggcggatgaa taccagcccc ccgacggagg cagcctggtg      540
gaggtgtatc tcctagacac cagcatacag agtgaccacc gggaaatcga gggcagggtc      600
atggtcaccg acttcgagaa tgtgcccgag gaggacggga cccgcttcca cagacaggcc      660
agcaagtgtg acagtcatgg cacccacctg gcaggggtgg tcagcggccg ggatgccggc      720
gtggccaagg gtgccagcat gcgcagcctg cgcgtgctca actgccaagg gaagggcacg      780
gttagcggca ccctcatagg cctggagttt attcggaaaa gccagctggt ccagcctgtg      840
gggccactgg tggtgctgct gcccctggcg ggtgggtaca gccgcgtcct caacgccgcc      900
tgccagcgct ggcgagggc tggggtcgtg ctggtcaccg ctgccggcaa cttccgggac      960
gatgcctgcc tctactcccc agcctcagct cccgaggtca tcacagttgg ggccaccaat     1020
gcccaagacc agccggtgac cctggggact ttggggacca ctttggccg ctgtgtggac     1080 ctctttgccc caggggagga catcattggt gcctccagcg actgcagcac ctgctttgtg     1140
tcacagagtg ggacatcaca ggctgctgcc cacgtggctg gcattgcagc catgatgctg     1200
tctgccgagc cggagctcac cctggccgag ttgaggcaga gactgatcca cttctctgcc     1260
aaagatgtca tcaatgaggc ctggttccct gaggaccagc gggtactgac ccccaacctg     1320
gtggccgccc tgccccccag cacccatggg gcaggttggc agctgttttg caggactgta     1380
tggtcagcac actcggggcc tacacggatg ccacagccg tcgcccgctg cgccccagat     1440
gaggagctgc tgagctgctc cagtttctcc aggagtggga gcggcgggg cgagcgcatg     1500 gaggcccaag ggggcaagct ggtctgccgg gcccacaacg cttttggggg tgagggtgtc     1560
tacgccattg ccaggtgctg cctgctaccc caggccaact gcagcgtcca cacagctcca     1620
ccagctgagg ccagcatggg gacccgtgtc cactgccacc aacagggcca cgtcctcaca     1680
ggctgcagct cccactggga ggtggaggac cttggcaccc acaagccgcc tgtgctgagg     1740
ccacgaggtc agcccaacca gtgcgtgggc cacaggagg ccagcatcca cgcttcctgc     1800
tgccatgccc caggtctgga atgcaaagtc aaggagcatg gaatcccggc ccctcaggag     1860
caggtgaccg tggcctgcga ggagggctgg accctgactg gctgcagtgc cctccctggg     1920
acctcccacg tcctggggc ctacgccgta gacaacacgt gtgtagtcag gagccgggac     1980
gtcagcacta caggcagcac cagcgaagag gccgtgacag ccgttgccat ctgctgccgg     2040
agccggcacc tggcgcaggc ctcccaggag ctccagtgac                           2080
```

<210> SEQ ID NO 37
<211> LENGTH: 2080
<212> TYPE: DNA
<213> ORGANISM: Homo sapiens

<400> SEQUENCE: 37

```
atgggcaccg tcagctccag gcggtcctgg tggccgctgc cactgctgct gctgctgctg       60
ctgctcctgg gtcccgcggg cgcccgtgcg caggaggacg aggacggcga ctacgaggag      120
ctggtgctag ccttgcgttc cgaggaggac ggcctggtcg aagcacccga gcacggaacc      180
acagccacct tccaccgctg cgccaaggat ccgtggaggt tgcctggcac ctacgtggtg      240
gtgctgaagg aggagaccca cctctcgcag tcagagcgca ctgcccgccg cctgcaggcc      300
caggctgccc gccggggata cctcaccaag atcctgcatg tcttccatgg ccttcttcct      360
```

```
ggcttcctgg tgaagatgag tggcgacctg ctggagctgg ccttgaagtt gccccatgtc    420
gactacatcg aggaggactc ctctgtcttt gcccagagca tcccgtggaa cctggagcgg    480
attacccctc cacggtaccg ggcggatgaa taccagcccc ccgacggagg cagcctggtg    540
gaggtgtatc tcctagacac cagcatacag agtgaccacc gggaaatcga gggcagggtc    600
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gccctggcg gtgggtaca gccgcgtcct caacgccgcc    900
tgccagcgcc tggcgagggc tggggtcgtg ctggtcaccg ctgccggcaa cttccgggac    960
gatgcctgcc tctactcccc agcctcagct cccgaggtca tcacagttgg ggccaccaat   1020
gcccaagacc agccggtgac cctggggact tgggggacca actttggccg ctgtgtggac   1080
ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgccccccag cacccatggg gcaggttggc agctgttttg caggactgta   1380
tggtcagcac actcggggcc tacacggatg ccacagcca tcgcccgctg cgccccagat   1440
gaggagctgc tgagctgctc cagtttctcc aggagtggga gcggcgggg cgagcgcatg   1500 gaggcccaag ggggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc   1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctggggc ctacgccgta gacaacacgt gtgtagtcag gagccgggac   1980
gtcagcacta caggcagcac cagcgaaggg gccgtgacag ccgttgccat ctgctgccgg   2040
agccggcacc tggcgcaggc ctcccaggag ctccagtgac                         2080
```

<210> SEQ ID NO 38
<211> LENGTH: 98
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Lys

<210> SEQ ID NO 39
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 39 gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat        96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg       192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt       288
Leu Gln Met Asn Ser Leu Arg Ala Glu Asp Thr Ala Val Tyr Tyr Cys
                85                  90                  95 gcg aaa ga                                                             296
Ala Lys <210> SEQ ID NO 40
<211> LENGTH: 25
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 41
<211> LENGTH: 990
<212> TYPE: DNA
<213> ORGANISM: Homo sapiens

<400> SEQUENCE: 41
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga    360
```

```
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gggtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990
```

<210> SEQ ID NO 42
<211> LENGTH: 330
<212> TYPE: PRT
<213> ORGANISM: Homo sapiens

<400> SEQUENCE: 42

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 43
<211> LENGTH: 978
<212> TYPE: DNA
<213> ORGANISM: Homo sapiens

<400> SEQUENCE: 43
gcctccacca agggcccatc ggtcttcccc ctggcgccct gctccaggag cacctccgag    60
agcacagccg ccctgggctg cctggtcaag gactacttcc ccgaaccggt gacggtgtcg   120
tggaactcag gcgctctgac cagcggcgtg cacaccttcc cagctgtcct acagtcctca   180
ggactctact ccctcagcag cgtggtgacc gtgccctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
gtggaggtgc ataatgccaa gacaaagcca cgggaggagc agttcaacag cacgttccgt   540
gtggtcagcg tcctcaccgt tgtgcaccag gactggctga acggcaagga gtacaagtgc   600
aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
gtcttctcat gctccgtgat gcatgaggct ctgcacaacc actacacgca gaagagcctc   960
tccctgtctc cgggtaaa                                                 978

<210> SEQ ID NO 44
<211> LENGTH: 326
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80
```

-continued

```
Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130             135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 45
<211> LENGTH: 296
<212> TYPE: DNA
<213> ORGANISM: Homo sapiens

<400> SEQUENCE: 45
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat     180
gcacagaagc tccagggcag agtcaccatg accacagaca tccacgag cacagcctac      240 atggagctga ggagcctgag atctgacgac acggccgtgt attactgtgc gagaga        296

<210> SEQ ID NO 46
<211> LENGTH: 98
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Gly Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg

<210> SEQ ID NO 47
<211> LENGTH: 296
<212> TYPE: DNA
<213> ORGANISM: Homo sapiens

<400> SEQUENCE: 47
caggtgcagc tggtgcagtc tggggctgag gtgaagaagc ctggggcctc agtgaaggtt        60
tcctgcaagg catctggata caccttcacc agctactata tgcactgggt gcgacaggcc       120
cctggacaag gcttgagtg gatgggaata atcaaccota gtggtggtag cacaagctac       180
gcacagaagt tccagggcag agtcaccatg accagggaca cgtccacgag cacagtctac       240
atggagctga gcagcctgag atctgaggac acggccgtgt attactgtgc gagaga           296

<210> SEQ ID NO 48
<211> LENGTH: 98
<212> TYPE: PRT
<213> ORGANISM: Homo sapiens

<400> SEQUENCE: 48

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
            35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 49
<211> LENGTH: 321
<212> TYPE: DNA
<213> ORGANISM: Homo sapiens

<400> SEQUENCE: 49
cgaactgtgg ctgcaccatc tgtcttcatc ttcccgccat ctgatgagca gttgaaatct        60
ggaactgcct ctgttgtgtg cctgctgaat aacttctatc ccagagaggc caaagtacag       120
tggaaggtgg ataacgccct ccaatcgggt aactcccagg agagtgtcac agagcaggac       180
agcaaggaca gcacctacag cctcagcagc accctgacgc tgagcaaagc agactacgag       240
aaacacaaag tctacgcctg cgaagtcacc catcagggcc tgagctcgcc cgtcacaaag       300
```
agcttcaaca ggggagagtg t                                                      321

<210> SEQ ID NO 50
<211> LENGTH: 107
<212> TYPE: PRT
<213> ORGANISM: Homo sapiens

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
<211> LENGTH: 318
<212> TYPE: DNA
<213> ORGANISM: Homo sapiens

<400> SEQUENCE: 51
ggtcagccca aggctgcccc ctcggtcact ctgttcccgc cctcctctga ggagcttcaa     60
gccaacaagg ccacactggt gtgtctcata agtgacttct acccgggagc cgtgacagtg    120
gcttggaaag cagatagcag ccccgtcaag gcgggagtgg agaccaccac accctccaaa    180
caaagcaaca acaagtacgc ggccagcagc tatctgagcc tgacgcctga gcagtggaag    240
tcccacagaa gctacagctg ccaggtcacg catgaaggga gcaccgtgga agacagtgtg    300 gccccctacag aatgttca                                                 318

<210> SEQ ID NO 52
<211> LENGTH: 106
<212> TYPE: PRT
<213> ORGANISM: Homo sapiens

<400> SEQUENCE: 52

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 53
<211> LENGTH: 365
<212> TYPE: DNA
<213> ORGANISM: Homo sapiens

<400> SEQUENCE: 53

```
atggtgttgc agacccaggt cttcatttct ctgttgctct ggatctctgg tgcctacggg    60
gacatcgtga tgacccagtc tccagactcc ctggctgtgt ctctgggcga gagggccacc   120
atcaactgca gtccagcca gagtgtttta tacagctcca acaataagaa ctacttagct   180
tggtaccagc agaaaccagg acagcctcct aagctgctca tttactgggc atctacccgg   240
gaatccgggg tccctgaccg attcagtggc agcgggtctg ggacagattt cactctcacc   300
atcagcagcc tgcaggctga agatgtggca gtttattact gtcagcaata ttatagtact   360
cctcc                                                               365
```

<210> SEQ ID NO 54
<211> LENGTH: 101
<212> TYPE: PRT
<213> ORGANISM: Homo sapiens

<400> SEQUENCE: 54

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100
```

<210> SEQ ID NO 55
<211> LENGTH: 654
<212> TYPE: DNA
<213> ORGANISM: Homo sapiens

<400> SEQUENCE: 55

```
atggacatga gggtccccgc tcagctcctg gggcttctgc tgctctggct cccagcaggt    60
gccagatgtg ccatccagtt gacccagtct ccatcctccc tgtctgcatc tgtaggagac   120
agagtcacca tcacttgccg ggcaagtcag ggcattagca gtgctttagc ctggtatcag   180
cagaaaccag ggaaagctcc taagctcctg atctatgatg cctccagttt ggaaagtggg   240
gtcccatcaa ggttcagcgg cagtggatct gggacagatt tcactctcac catcagcagc   300
ctgcagcctg aagattttgc aacttattac tgtcaacagt ttaatagtta ccctcagtgc   360
cagatgtgcc atccagttga cccagtctcc atcctccctg tctgcatctg taggagacag   420
agtcaccatc acttgccggg caagtcaggg cattagcagt gctttagcct ggtatcagca   480
gaaaccaggg aaagctccta agctcctgat ctatgatgcc tccagtttgg aaagtggggt   540
cccatcaagg ttcagcggca gtggatctgg gacagatttc actctcacca tcagcagcct   600
```
gcagcctgaa gattttgcaa cttattactg tcaacagttt aatagttacc ctca        654

<210> SEQ ID NO 56

<400> SEQUENCE: 56

000

<210> SEQ ID NO 57
<211> LENGTH: 39
<212> TYPE: DNA
<213> ORGANISM: Homo sapiens

<400> SEQUENCE: 57
tgtacacttt tggccagggg accaagctgg agatcaaac        39

<210> SEQ ID NO 58
<211> LENGTH: 12
<212> TYPE: PRT
<213> ORGANISM: Homo sapiens

<400> SEQUENCE: 58

Tyr Thr Phe Gly Gln Gly Thr Lys Leu Glu Ile Lys
1               5                   10

<210> SEQ ID NO 59
<211> LENGTH: 38
<212> TYPE: DNA
<213> ORGANISM: Homo sapiens

<400> SEQUENCE: 59
tgtggtattc ggcggaggga ccaagctgac cgtcctag        38

<210> SEQ ID NO 60
<211> LENGTH: 12
<212> TYPE: PRT
<213> ORGANISM: Homo sapiens

<400> SEQUENCE: 60

Val Val Phe Gly Gly Gly Thr Lys Leu Thr Val Leu
1               5                   10

<210> SEQ ID NO 61
<211> LENGTH: 329
<212> TYPE: PRT
<213> ORGANISM: Homo sapiens

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys

```
                   100                 105                 110
Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 62
<211> LENGTH: 107
<212> TYPE: PRT
<213> ORGANISM: Homo sapiens

<400> SEQUENCE: 62

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 63
<211> LENGTH: 326
<212> TYPE: PRT
<213> ORGANISM: Homo sapiens
```

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 64
<211> LENGTH: 105
<212> TYPE: PRT
<213> ORGANISM: Homo sapiens

<400> SEQUENCE: 64

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

```
Tyr Pro Gly Ala Val Thr Val Ala Trp Lys Ala Asp Ser Ser Pro Val
             35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
                100                 105

<210> SEQ ID NO 65
<211> LENGTH: 326
<212> TYPE: PRT
<213> ORGANISM: Homo sapiens

<400> SEQUENCE: 65

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
             115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300
```

```
Ser Val Met His Glu Ala Leu His Asn His Tyr Thr Gln Lys Ser Leu
305                 310                 315                 320

Ser Leu Ser Pro Gly Lys
            325

<210> SEQ ID NO 66
<211> LENGTH: 107
<212> TYPE: PRT
<213> ORGANISM: Homo sapiens

<400> SEQUENCE: 66

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 67
<211> LENGTH: 7
<212> TYPE: PRT
<213> ORGANISM: Homo sapiens

<400> SEQUENCE: 67

Val Phe Ala Gln Ser Ile Pro
1               5

<210> SEQ ID NO 68
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 68 gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt     288
```

```
Leu Gln Met Asn Ser Leu Arg Ala Glu Asp Thr Ala Val Tyr Tyr Cys
                85                  90                  95 gcg aaa ga                                                          296
Ala Lys

<210> SEQ ID NO 69
<211> LENGTH: 98
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 70
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 70 gag gtg cag ctg ttg gag tct ggg gga ggc ttg gta cag cct ggg ggg    48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat    96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg    192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt    288
Leu Gln Met Asn Ser Leu Arg Ala Glu Asp Thr Ala Val Tyr Tyr Cys
                85                  90                  95 gcg aaa                                                             294
Ala Lys

<210> SEQ ID NO 71
<211> LENGTH: 296
<212> TYPE: DNA
<213> ORGANISM: Homo sapiens
<220> FEATURE:
<221> NAME/KEY: CDS
```

-continued

<222> LOCATION: (1)..(294)

<400> SEQUENCE: 71

```
gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca gct att agt ggt agt ggt ggt agc aca tac tac gga gac tcc gtg     192
Ser Ala Ile Ser Gly Ser Gly Gly Ser Thr Tyr Tyr Gly Asp Ser Val
    50                  55                  60 aag ggc cgg ttc acc atc tca aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt     288
Leu Gln Met Asn Ser Leu Arg Ala Glu Asp Thr Ala Val Tyr Tyr Cys
                85                  90                  95 gcg aaa ga                                                          296
Ala Lys
```

<210> SEQ ID NO 72
<211> LENGTH: 98
<212> TYPE: PRT
<213> ORGANISM: Homo sapiens

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 73
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 73

```
gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
```

```
Ala Met Ser Trp Val Arg Gln Ala Pro Gly Lys Gly Leu Glu Trp Val
        35                  40                  45 tca gtt att tat agc ggt ggt agt agc aca tac tat gca gac tcc gtg     192
Ser Val Ile Tyr Ser Gly Gly Ser Ser Thr Tyr Tyr Ala Asp Ser Val
 50                  55                  60 aag ggc cgg ttc acc atc tcc aga gat aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt     288
Leu Gln Met Asn Ser Leu Arg Ala Glu Asp Thr Ala Val Tyr Tyr Cys
                85                  90                  95 gcg aaa                                                              294
Ala Lys
```

<210> SEQ ID NO 74
<211> LENGTH: 98
<212> TYPE: PRT
<213> ORGANISM: Homo sapiens

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 75
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 75

```
gag gtg cag ctg ttg gag tct ggg gga ggc ttg gta cag cct ggg ggg      48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca gtt att tat agc ggt ggt agt agc aca tac tat gca gac tcc gtg     192
Ser Val Ile Tyr Ser Gly Gly Ser Ser Thr Tyr Tyr Ala Asp Ser Val
 50                  55                  60 aag ggc cgg ttc acc atc tcc aga gat aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt     288
Leu Gln Met Asn Ser Leu Arg Ala Glu Asp Thr Ala Val Tyr Tyr Cys
```

```
gcg aaa ga                                                          296
Ala Lys
```

<210> SEQ ID NO 76
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 76

```
gag gtg cag ctg ttg gag tct ggg gga ggc ttg gta cag cct ggg ggg    48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agc agc tat    96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc   144
Ala Met Ser Trp Val Arg Gln Ala Pro Gly Lys Gly Leu Glu Trp Val
        35                  40                  45 tca gct att tat agc agt ggt agt agc aca tac tat gca gac tcc gtg   192
Ser Ala Ile Tyr Ser Ser Gly Ser Ser Thr Tyr Tyr Ala Asp Ser Val
    50                  55                  60 aag ggc cgg ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt   288
Leu Gln Met Asn Ser Leu Arg Ala Glu Asp Thr Ala Val Tyr Tyr Cys
                85                  90                  95 gcg aaa                                                            294
Ala Lys
```

<210> SEQ ID NO 77
<211> LENGTH: 98
<212> TYPE: PRT
<213> ORGANISM: Homo sapiens

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Tyr Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```